(12) United States Patent
Wu et al.

(10) Patent No.: US 9,365,506 B2
(45) Date of Patent: Jun. 14, 2016

(54) COMPOUNDS AND COMPOSITIONS AS TLR2 AGONISTS

(71) Applicants: Tom Yao-Hsiang Wu, San Diego, CA (US); Yefen Zou, San Diego, CA (US); Timothy Z. Hoffman, San Diego, CA (US); Jianfeng Pan, San Diego, CA (US)

(72) Inventors: Tom Yao-Hsiang Wu, San Diego, CA (US); Yefen Zou, San Diego, CA (US); Timothy Z. Hoffman, San Diego, CA (US); Jianfeng Pan, San Diego, CA (US)

(73) Assignee: NOVARTIS AG, Basel (CH)

( * ) Notice: Subject to any disclaimer, the term of this patent is extended or adjusted under 35 U.S.C. 154(b) by 19 days.

(21) Appl. No.: 14/326,957

(22) Filed: Jul. 9, 2014

(65) Prior Publication Data

US 2014/0323390 A1  Oct. 30, 2014

Related U.S. Application Data

(63) Continuation of application No. 13/636,328, filed as application No. PCT/US2011/029661 on Mar. 23, 2011, now Pat. No. 8,808,703.

(60) Provisional application No. 61/316,551, filed on Mar. 23, 2010.

(51) Int. Cl.
| | |
|---|---|
| *C07C 53/00* | (2006.01) |
| *C07C 57/00* | (2006.01) |
| *C07C 59/00* | (2006.01) |
| *C08G 63/48* | (2006.01) |
| *A61K 31/21* | (2006.01) |
| *C07C 323/60* | (2006.01) |
| *C07F 9/38* | (2006.01) |
| *C07D 213/56* | (2006.01) |
| *C07K 5/00* | (2006.01) |

(52) U.S. Cl.
CPC ............ *C07C 323/60* (2013.01); *C07D 213/56* (2013.01); *C07F 9/3808* (2013.01); *C07K 5/00* (2013.01); *C07C 2101/02* (2013.01)

(58) Field of Classification Search
None
See application file for complete search history.

(56) References Cited

U.S. PATENT DOCUMENTS

| | | | |
|---|---|---|---|
| 4,666,886 A | 5/1987 | Baschang et al. | |
| 5,342,977 A | 8/1994 | Baschang et al. | |
| 5,478,809 A | 12/1995 | Tanida et al. | |
| 2005/0214359 A1 | 9/2005 | Stegmann | |
| 2006/0193873 A1 | 8/2006 | Stegmann et al. | |
| 2007/0004654 A1 | 1/2007 | Raz et al. | |
| 2009/0196916 A1 | 8/2009 | Ingale et al. | |
| 2011/0280899 A1 | 11/2011 | Jackson et al. | |
| 2012/0141409 A1 | 6/2012 | Seymour et al. | |

FOREIGN PATENT DOCUMENTS

| | | | | |
|---|---|---|---|---|
| DE | 3546150 A1 * | 1/1987 | ............ | A61K 9/1272 |
| DE | 4116256 A1 * | 11/1992 | ....... | C07K 14/70539 |
| EP | 0114787 | 8/1984 | | |
| EP | 0338437 | 10/1989 | | |
| EP | 0431327 | 6/1991 | | |
| EP | 0547681 | 6/1993 | | |
| EP | 0548024 | 6/1993 | | |
| EP | 0604957 | 7/1994 | | |
| EP | 1382352 A1 * | 1/2004 | ....... | A61K 47/48215 |
| EP | 2050455 | 4/2009 | | |
| WO | WO2007063421 | 6/2007 | | |
| WO | WO2009108762 | 9/2009 | | |

OTHER PUBLICATIONS

Metzger et al. Angewandte Chemie (1987), 99(4), 343-5.*
Metzger, J., et al., Int. J. Peptide Protein Res., 1991, vol. 37, pp. 46-57.
Reitermann, A., et al., Biol. Chem. Hoppe-Seyler, 1989, vol. 370, pp. 343-352.
Uhl, B., et al., Journal of Leukocyte Biology, 1991, vol. 50, pp. 10-18.
Bessler, W. G., et al., Lung, 1990, vol. 168 Suppl., pp. 707-715.
Jin, Ms et al., "Crystal Structure of the TLR1-TLR2 Heterodimer Induced by Binding of a Tri-Acylated Lipopeptide", Cell, 2007, pp. 1071-1082.
Buwitt-Beckmann, Ute et al., "Lipopeptide structure determines TLR2 dependent cell activation level", FEBS Journal 272 (2005) 6354-6364.
Zahringer, Ulrich et al., "TLR2—promiscuous or specific? A critical re-evaluation of a receptor expressing apparent broad specificity", Immunobiology 213 (2008) 205-224.
Muller, Silke D.C., et al., "Triacyl-lipopentapeptide adjuvants: TLR2-dependent activation of macrophages and modulation of receptor-mediated cell activation by altering acyl-moieties", International Immunopharmacology 4 (2004) 1287-1300.
Jin, Y.K. et al., "Recognition of Lipopeptide Patterns by Toll-like Receptor 2-Toll-like Receptor 6 Heterodimer", Immunity 31, 873-884,2009.

* cited by examiner

*Primary Examiner* — Jeffrey S Lundgren
*Assistant Examiner* — Michael Schmitt
(74) *Attorney, Agent, or Firm* — The Genomics Institute of the Novartis Research Foundation; Daniel E. Raymond

(57) ABSTRACT

The invention provides a novel class of compounds, immunogenic compositions and pharmaceutical compositions comprising such compounds and methods of using such compounds to treat or prevent diseases or disorders associated with Toll-Like Receptors 2. In one aspect, the compounds are useful as adjuvants for enhancing the effectiveness of a vaccine.

18 Claims, No Drawings

COMPOUNDS AND COMPOSITIONS AS TLR2 AGONISTS

CROSS-REFERENCE TO RELATED APPLICATIONS

This application is a continuation of prior application Ser. No. 13/636,328, filed Sep. 20, 2012, which was the National Stage of International Application No. PCT/US2011/029661, filed Mar. 23, 2011, which claims the benefit of priority under 35 U.S.C. §119(e) to U.S. Provisional Patent Application No. 61/316,551, filed Mar. 23, 2010, the disclosures of which are incorporated herein by reference in its entirety and for all purposes.

STATEMENT OF GOVERNMENT SUPPORT

This invention was made in part with Government support under DTRA Grant No. HDTRA1-07-9-0001 awarded by the Department of Defense. The Government has certain rights in the invention.

FIELD OF THE INVENTION

The invention relates to modulators of Toll-Like Receptors (TLRs), and methods of using such compounds.

BACKGROUND OF THE INVENTION

Early detection of specific classes of pathogens is accomplished by the innate immune system with the help of pattern recognition receptors (PRRs). The detected pathogens include viruses, bacteria, protozoa and fungi, and each constitutively expresses a set of class-specific, mutation-resistant molecules called pathogen-associated molecular patterns (PAMPs). These molecular markers may be composed of proteins, carbohydrates, lipids, nucleic acids or combinations thereof, and may be located internally or externally. Examples of PAMPs include bacterial carbohydrates (lipopolysaccharide or LPS, mannose), nucleic acids (bacterial or viral DNA or RNA), peptidoglycans and lipotechoic acids (from Gram positive bacteria), N-formylmethionine, lipoproteins and fungal glucans.

Pattern recognition receptors have evolved to take advantage of three PAMP qualities. First, constitutive expression allows the host to detect the pathogen regardless of its life cycle stage. Second, the PAMPs are class specific, which allows the host to distinguish between pathogens and thereby tailor its response. Third, mutation resistance allows the host to recognize the pathogen, regardless of its particular strain.

Pattern recognition receptors are involved in more than just recognition of pathogens via their PAMPs. Once bound, pattern recognition receptors tend to cluster, recruit other extracellular and intracellular proteins to the complex, and initiate signaling cascades that ultimately impact transcription. Additionally, pattern recognition receptors are involved in activation of complement, coagulation, phagocytosis, inflammation, and apoptosis functions in response to pathogen detection.

Pattern recognition receptors (PRRs) may be divided into endocytic PRRs or signaling PRRs. The signaling PRRs include the large families of membrane-bound Toll-like receptors (TLRs) and cytoplasmic NOD-like receptors, while the endocytic PRRs promote the attachment, engulfment and destruction of microorganisms by phagocytes without relaying an intracellular signal, are found on all phagocytes and mediate removal of apoptotic cells. In addition, endocytic PRRs recognize carbohydrates and include mannose receptors of macrophages, glucan receptors present on all phagocytes and scavenger receptors that recognize charged ligands.

SUMMARY OF THE INVENTION

Provided herein are compounds and pharmaceutical compositions thereof, which are agonists of toll-like receptor 2 (TLR2). In certain embodiments, such TLR2 agonists are immune potentiators that bind to aluminum-containing adjuvants, such as, by way of example only, aluminum hydroxide, aluminum oxyhydroxide and aluminum hydroxyphosphate. Thus, also provided herein are immunogenic compositions that contain an antigen and a TLR2 agonist provided herein that bind to aluminum-containing adjuvants. When such immunogenic compositions are administered to a subject in need thereof, such TLR2 agonists enhance the immune response to the immunogenic composition.

In one aspect provided herein such compounds, and the pharmaceutically acceptable salts, pharmaceutically acceptable solvates (e.g. hydrates), the N-oxide derivatives, prodrug derivatives, protected derivatives, individual isomers and mixture of isomers thereof, have a structure according to Formula (I):

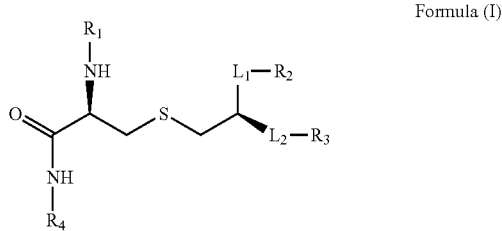

Formula (I)

wherein:
$R^1$ is H, —C(O)—$C_7$-$C_{18}$alkyl or —C(O)—$C_1$-$C_6$alkyl;
$R^2$ is $C_7$-$C_{18}$alkyl;
$R^3$ is $C_7$-$C_{18}$alkyl;
$L_1$ is —$CH_2$OC(O)—, —$CH_2$O—, —$CH_2NR^7C(O)$— or —$CH_2OC(O)NR^7$—;
$L_2$ is —OC(O)—, —O—, —$NR^7C(O)$— or —OC(O)$NR^7$—;
$R^4$ is -$L_3R^5$ or -$L_4R^5$;
$R^5$ is —$N(R^7)_2$, —$P(O)(OR^7)_2$, —$C(O)OR^7$, —$NR^7C(O)L_3R^8$, —$NR^7C(O)L_4R^8$, —$OL_3R^6$, —$C(O)NR^7L_3R^8$, —$C(O)NR^7L_4R^8$, —$S(O)_2OR^7$, —$OS(O)_2OR^7$, $C_1$-$C_6$alkyl, a $C_6$aryl, a $C_{10}$aryl, a $C_{14}$aryl, 5 to 14 ring membered heteroaryl containing 1 to 3 heteroatoms selected from O, S and N, $C_3$-$C_8$cycloalkyl or a 5 to 6 ring membered heterocycloalkyl containing 1 to 3 heteroatoms selected from O, S and N, wherein the aryl, heteroaryl, cycloalkyl and heterocycloalkyl of $R^5$ are each unsubstituted or the aryl, heteroaryl, cycloalkyl and heterocycloalkyl of $R^5$ are each substituted with 1 to 3 substituents independently selected from —$OR^9$, —$OL_3R^6$, —$OL_4R^6$, —$OR^7$, and —$C(O)OR^7$;
$L_3$ is a $C_1$-$C_{10}$alkylene, wherein the $C_1$-$C_{10}$alkylene of $L_3$ is unsubstituted, or the $C_1$-$C_{10}$alkylene of $L_3$ is substituted with 1 to 4 $R^6$ groups, or the $C_1$-$C_{10}$alkylene of $L_3$ is substituted with 2 $C_1$-$C_6$alkyl groups on the same carbon atom which together, along with the carbon atom they are attached to, form a $C_3$-$C_8$cycloalkyl;
$L_4$ is —$((CR^7R^7)_pO)_q(CR^{10}R^{10})_p$— or —$(CR^{11}R^{11})((CR^7R^7)_pO)_q(CR^{10}R^{10})_p$—, wherein each $R^{11}$ is a $C_1$-$C_6$alkyl groups which together, along with the carbon atom they are attached to, form a $C_3$-$C_8$cycloakyl;

each $R^6$ is independently selected from halo, $C_1$-$C_6$alkyl, $C_1$-$C_6$alkyl substituted with 1-2 hydroxyl groups, —$OR^7$, —$N(R^7)_2$, —C(O)OH, —C(O)N($R^7$)$_2$, —P(O)(OR$^7$)$_2$, a $C_6$aryl, a $C_{10}$aryl and a $C_{14}$aryl;

each $R^7$ is independently selected from H and $C_1$-$C_6$alkyl;

$R^8$ is selected from —$SR^7$, —C(O)OH, —P(O)(OR$^7$)$_2$, and a 5 to 6 ring membered heterocycloalkyl containing 1 to 3 heteroatoms selected from O and N;

$R^9$ is phenyl;

each $R^{10}$ is independently selected from H and halo;

each p is independently selected from 1, 2, 3, 4, 5 and 6, and q is 1, 2, 3 or 4.

In certain embodiments of such compounds and pharmaceutically acceptable salts thereof, $R^1$ is H, —C(O)—$C_{10}$-$C_{18}$alkyl;

$R^2$ is $C_{10}$-$C_{18}$alkyl;

$R^3$ is $C_{10}$-$C_{18}$alkyl;

$L_1$ is —CH$_2$O—, —CH$_2$OC(O)—, —CH$_2$NR$^7$C(O)— or —C(O)NR$^7$—;

$L_2$ is —O—, —OC(O)— or —NR$^7$C(O)—;

$R^4$ is -L$_3$R$^5$ or -L$_4$R$^5$;

$R^5$ is —N($R^7$)$_2$, —$OR^7$, —P(O)(OR$^7$)$_2$, —C(O)$OR^7$, —NR$^7$C(O)L$_3$R$^8$, —OL$_3$R$^6$, —C(O)NR$^7$L$_3$R$^8$, $C_1$-$C_6$alkyl, a $C_6$ aryl, a $C_{10}$ aryl, a $C_{14}$ aryl, 5 to 14 membered heteroaryl containing 1 to 3 heteroatoms selected from O, S and N, $C_3$-$C_8$cycloalkyl or a 5 to 6 membered heterocycloalkyl containing 1 to 3 heteroatoms selected from O, S and N, wherein the aryl, heteroaryl, cycloalkyl and heterocycloalkyl of R$^5$ are each optionally substituted with 1 to 3 substituents independently selected from —$OR^9$, —OL$_3$R$^6$, —OL$_4$R$^6$, —$OR^7$, and —C(O)$OR^7$;

$L_3$ is a $C_1$-$C_{10}$alkylene, wherein the $C_1$-$C_6$alkylene of L$_3$ is optionally substituted with 1 to 4 R$^6$ groups, or the $C_1$-$C_6$alkylene of L$_3$ is substituted with 2 $C_1$-$C_6$alkyl groups on the same carbon atom which together, along with the carbon atom they are attached to, form a $C_3$-$C_8$cycloalkyl;

$L_4$ is —((CR$^7$R$^7$)$_p$O)$_q$(CR$^{10}$R$^{10}$)$_p$— or —(CR$^{11}$R$^{11}$)((CR$^7$R$^7$)$_p$O)$_q$(CR$^{10}$R$^{10}$)$_p$—, wherein each R$^{11}$ is a $C_1$-$C_6$alkyl groups which together, along with the carbon atom they are attached to, form a $C_3$-$C_8$cycloalkyl;

each $R^6$ is independently selected from halo, $C_1$-$C_6$alkyl, —$OR^7$, —$N(R^7)_2$, —C(O)N($R^7$)$_2$, —P(O)(OR$^7$)$_2$, a $C_6$ aryl, a $C_{10}$ aryl and a $C_{14}$ aryl;

each $R^7$ is independently selected from H and $C_1$-$C_6$alkyl;

$R^8$ is selected from —$SR^7$, —C(O)OH and a 5 to 6 membered heterocycloalkyl containing 1 to 3 heteroatoms selected from O and N;

$R^9$ is phenyl;

each $R^{10}$ is independently selected from H and halo;

each p is independently selected from 1, 2, 3, 4, 5 and 6, and q is 1, 2, 3 or 4.

In certain embodiments of such compounds and pharmaceutically acceptable salts thereof, $R^1$ is H. In other embodiments of such compounds and pharmaceutically acceptable salts thereof, $R^1$ is —C(O)—$C_{15}$alkyl. In other embodiments of such compounds and pharmaceutically acceptable salts thereof, $R^1$ is —C(O)—$C_{10}$-$C_{18}$alkyl.

In certain embodiments of such compounds and pharmaceutically acceptable salts thereof, $L_1$ is —CH$_2$OC(O)— and $L_2$ is —OC(O)—, —O—, —NR$^7$C(O)— or —OC(O)NR$^7$—;

or $L_1$ is —CH$_2$O— and $L_2$ is —OC(O)—, —O—, —NR$^7$C(O)— or —OC(O)NR$^7$—;

or $L_1$ is —CH$_2$NR$^7$C(O)— and $L_2$ is —OC(O)—, —O—, —NR$^7$C(O)— or —OC(O)NR$^7$—;

or $L_1$ is —CH$_2$OC(O)NR$^7$— and $L_2$ is —OC(O)—, —O—, —NR$^7$C(O)— or —OC(O)NR$^7$—.

In certain embodiments of such compounds and pharmaceutically acceptable salts thereof, $L_1$ is —CH$_2$OC(O)— and $L_2$ is —OC(O)—. In other embodiments of such compounds and pharmaceutically acceptable salts thereof, $L_1$ is —CH$_2$O— and $L_2$ is —O—. In other embodiments of such compounds and pharmaceutically acceptable salts thereof, $L_1$ is —CH$_2$O— and $L_2$ is —NR$^7$C(O)—. In other embodiments of such compounds and pharmaceutically acceptable salts thereof, $L_1$ is —CH$_2$OC(O)NR$^7$— and $L_2$ is —OC(O)NR$^7$—. In other embodiments of such compounds and pharmaceutically acceptable salts thereof, $L_1$ is —CH$_2$NR$^7$C(O)— and $L_2$ is —NR$^7$C(O)—.

In certain embodiments of the aforementioned compounds and pharmaceutically acceptable salts thereof, $R^2$ is $C_{10}$-$C_{18}$alkyl. In certain embodiments of the aforementioned compounds and pharmaceutically acceptable salts thereof, $R^3$ is $C_{10}$-$C_{18}$alkyl. In certain embodiments of the aforementioned compounds and pharmaceutically acceptable salts thereof, $R^2$ is —$C_{11}$alkyl and $R^3$ is —$C_{11}$alkyl; or $R^2$ is —$C_{16}$alkyl and $R^3$ is —$C_{16}$alkyl; or $R^2$ is —$C_{16}$alkyl and $R^3$ is —$C_{11}$alkyl; or $R^2$ is —$C_{12}$alkyl and $R^3$ is —$C_{12}$alkyl; or $R^2$ is —$C_7$alkyl and $R^3$ is —$C_7$alkyl; or $R^2$ is —$C_9$alkyl and $R^3$ is —$C_9$alkyl; or $R^2$ is —$C_8$alkyl and $R^3$ is —$C_8$alkyl; or $R^2$ is —$C_{13}$alkyl and $R^3$ is —$C_{13}$alkyl; or $R^2$ is —$C_{12}$alkyl and $R^3$ is —$C_{11}$alkyl; or $R^2$ is —$C_{12}$alkyl and $R^3$ is —$C_{12}$alkyl; or $R^2$ is —$C_{10}$alkyl and $R^3$ is —$C_{10}$alkyl; or $R^2$ is —$C_{15}$alkyl and $R^3$ is —$C_{15}$alkyl.

In certain embodiments of the aforementioned compounds and pharmaceutically acceptable salts thereof, $R^2$ is —$C_{11}$alkyl and $R^3$ is —$C_{11}$alkyl.

In certain embodiments of the aforementioned compounds and pharmaceutically acceptable salts thereof, $R^5$ is —NH$_2$, —N(CH$_2$CH$_3$)$_2$, —OH, —OCH$_3$, —P(O)(OH)$_2$, —C(O)OH, —NHC(O)L$_3$R$^8$, —S(O)$_2$OH, —OS(O)$_2$OH, —OL$_3$R$^6$, —C(O)NHL$_4$R$^8$ or —C(O)NHL$_3$R$^8$. In certain embodiments of the aforementioned compounds and pharmaceutically acceptable salts thereof, $R^5$ is —NH$_2$, —N(CH$_2$CH$_3$)$_2$, —OH, —OCH$_3$, —P(O)(OH)$_2$, —C(O)OH, —NHC(O)L$_3$R$^8$, —S(O)$_2$OH, —OS(O)$_2$OH and —OL$_3$R$^6$.

In certain embodiments of the aforementioned compounds and pharmaceutically acceptable salts thereof, $R^5$ is —NH$_2$, —OH, —P(O)(OH)$_2$, —C(O)OH, —NHC(O)L$_3$R$^8$, —OL$_3$R$^6$, or —C(O)NHL$_3$R$^8$. While, in other embodiments of the aforementioned compounds and pharmaceutically acceptable salts thereof, $R^5$ is $C_1$-$C_6$alkyl, phenyl, pyridinyl, imidazolyl or morpholinyl, each of which is optionally substituted with 1 to 3 substituents independently selected from —$OR^9$, —OL$_3$R$^6$, —OL$_4$R$^6$, —OH and —C(O)OH.

In certain embodiments of the aforementioned compounds and pharmaceutically acceptable salts thereof, $R^8$ is selected from —SH, —C(O)OH, —P(O)(OH)$_2$, and a 5-6 membered heterocycloalkyl containing 1 to 2 heteroatoms selected from O. In certain embodiments of the aforementioned compounds and pharmaceutically acceptable salts thereof, $R^8$ is selected from —SH, —C(O)OH and a 5 to 6 membered heterocycloalkyl containing 1 to 2 heteroatoms selected from O.

In certain embodiments of the aforementioned compounds and pharmaceutically acceptable salts thereof, $L_3$ is a $C_1$-$C_{10}$alkylene, wherein the $C_1$-$C_{10}$alkylene of $L_3$ is optionally substituted with 1 to 4 R$^6$ groups.

In certain embodiments of the aforementioned compounds and pharmaceutically acceptable salts thereof, $L_4$ is —((CR$^7$R$^7$)$_p$O)$_q$(CR$^{10}$R$^{10}$)$_p$—, each R$^{10}$ is independently selected from H and F; each p is independently selected from 2, 3, and 4, and q is 1, 2, 3 or 4.

In certain embodiments of the aforementioned compounds and pharmaceutically acceptable salts thereof, each $R^6$ is independently selected from $C_1$-$C_6$alkyl, —OH, —NH$_2$, —C(O)NH$_2$, —P(O)(OH)$_2$ and phenyl.

In certain embodiments of the aforementioned compounds and pharmaceutically acceptable salts thereof, each $R^6$ is independently selected from methyl, ethyl, i-propyl, i-butyl, —CH$_2$OH, —OH, —F, —NH$_2$, —C(O)OH, —C(O)NH$_2$, —P(O)(OH)$_2$ and phenyl.

In certain embodiments of the aforementioned compounds and pharmaceutically acceptable salts thereof, each $R^7$ is independently selected from H, methyl and ethyl.

In certain embodiments of the aforementioned compounds and pharmaceutically acceptable salts thereof, are selected from: (R)-3-(((R)-2-amino-3-((1-(hydroxymethyl)cyclopropyl)amino)-3-oxopropyl)thio)propane-1,2-diyl didodecanoate; (3-((R)-2-amino-3-(((R)-2,3-bis(dodecanoyloxy)propyl)thio)propanamido)propyl)phosphonic acid; ((8R,12R)-8-amino-12-(dodecanoyloxy)-7,15-dioxo-3,14-dioxa-10-thia-6-azahexacosyl)phosphonic acid; ((12R,16R)-12-amino-16-(dodecanoyloxy)-1,1-difluoro-11,19-dioxo-4,7,18-trioxa-14-thia-10-azatriacontyl)phosphonic acid; ((11R,15R)-11-amino-15-(dodecanoyloxy)-10,18-dioxo-3,6,17-trioxa-13-thia-9-azanonacosyl)phosphonic acid; (R)-3-(((R)-2-amino-3-oxo-3-((2-(pyridin-2-yl)ethyl)amino)propyl)thio)propane-1,2-diyl didodecanoate; (R)-3-(((R)-2-amino-3-((5-aminopentyl)amino)-3-oxopropyl)thio)propane-1,2-diyl didodecanoate; (2R,6R)-6,20-diamino-7-oxo-12,17-dioxa-4-thia-8-azaicosane-1,2-diyl didodecanoate; (20R,24R)-2,20-diamino-1-mercapto-3,19-dioxo-8,11,14-trioxa-22-thia-4,18-diazapentacosane-24,25-diyl didodecanoate; (4R,7S,10R,14R)-10-amino-4-carbamoyl-7-ethyl-14-(hexadecyloxy)-6,9-dioxo-16-oxa-12-thia-5,8-diazadotriacontan-1-oic acid; N—((R)-1-(((R)-2-amino-3-((1-(hydroxymethyl)cyclopropyl)amino)-3-oxopropyl)thio)-3-(hexadecyloxy)propan-2-yl)dodecanamide; N,N'—(R)-3-(((R)-2-amino-3-((1-(hydroxymethyl)cyclopropyl)amino)-3-oxopropyl)thio)propane-1,2-diyl)didodecanamide; (5S,8R,12R)-8-amino-12-(dodecanoyloxy)-5-ethyl-7,15-dioxo-3,14-dioxa-10-thia-6-azahexacosan-1-oic acid; ((6S,9R,13R)-9-amino-13-(dodecanoyloxy)-6-methyl-8,16-dioxo-4,15-dioxxa-11-thia-7-azaheptacosyl)phosphonic acid; (3-((1-((R)-2-amino-3-(((R)-2,3-bis(dodecanoyloxy)propyl)thio)propanamido)cyclopropyl)methoxy)propyl)phosphonic acid; (3-(4-(2-((R)-2-amino-3-(((R)-2,3-bis(dodecanoyloxy)propyl)thio)propanamido)ethyl)phenoxy)propyl)phosphonic acid; 6-((R)-2-amino-3-(((R)-2,3-bis(dodecanoyloxy)propyl)thio)propanamido)hexanoic acid; ((14R,18R)-14-amino-18-(dodecanoyloxy)-13,21-dioxo-3,6,9,20-tetraoxa-16-thia-12-azadotriacontyl)phosphonic acid; (4-((R)-2-amino-3-(((R)-2,3-bis(dodecanoyloxy)propyl)thio)propanamido)-1,1-difluorobutyl)phosphonic acid; ((14R,18R)-14-amino-18-(dodecyloxy)-13-oxo-3,6,9,20-tetraoxa-16-thia-12-azadotriacontyl)phosphonic acid; ((9R,13R)-9-amino-13-(dodecanoyloxy)-1,1-difluoro-8,16-dioxo-4,15-dioxa-11-thia-7-azaheptacosyl)phosphonic acid; ((12R,16R)-12-amino-16-(dodecyloxy)-1,1-difluoro-11-oxo-4,7,18-trioxa-14-thia-10-azatriacontyl)phosphonic acid; ((14R,18R)-14-amino-18-(octanoyloxy)-13,21-dioxo-3,6,9,20-tetraoxa-16-thia-12-azaoctacosyl)phosphonic acid; ((14R,18R)-14-amino-18-(decanoyloxy)-13,21-dioxo-3,6,9,20-tetraoxa-16-thia-12-azatriacontyl)phosphonic acid; ((14R,18R)-14-amino-13,21-dioxo-18-(tetradecanoyloxy)-3,6,9,20-tetraoxa-16-thia-12-azatetratriacontyl)phosphonic acid; ((14R,18R)-14-amino-18-dodecanamido-13-oxo-3,6,9,20-tetraoxa-16-thia-12-azadotriacontyl)phosphonic acid; ((14R,18R)-14-amino-18-(dodecanoyloxy)-13-oxo-3,6,9,20-tetraoxa-16-thia-12-azadotriacontyl)phosphonic acid; ((11S,14R,18R)-14-amino-18-dodecanamido-11-methyl-13-oxo-3,6,9,20-tetraoxa-16-thia-12-azadotriacontyl)phosphonic acid; ((11S,14R,18R)-14-amino-18-(dodecyloxy)-11-methyl-13-oxo-3,6,9,20-tetraoxa-16-thia-12-azadotriacontyl) phosphonic acid; ((11S,14R,18R)-14-amino-18-(dodecyloxy)-11-methyl-10,13-dioxo-3,6,20-trioxa-16-thia-9,12-diazadotriacontyl)phosphonic acid; ((11S,14R,18R)-14-amino-18-dodecanamido-11-methyl-10,13-dioxo-3,6,20-trioxa-16-thia-9,12-diazadotriacontyl)phosphonic acid; (15R,19R)-15-amino-19-(dodecyloxy)-14-oxo-4,7,10,21-tetraoxa-17-thia-13-azatritriacontan-1-oic acid; (15R,19R)-15-amino-19-dodecanamido-14-oxo-4,7,10,21-tetraoxa-17-thia-13-azatritriacontan-1-oic acid; ((14R,18R)-18-(dodecanoyloxy)-13,21-dioxo-14-palmitamido-3,6,9,20-tetraoxa-16-thia-12-azadotriacontyl)phosphonic acid; ((12R,16R)-12-amino-16-dodecanamido-1,1-difluoro-11-oxo-4,7,18-trioxa-14-thia-10-azatriacontyl)phosphonic acid; ((14R,18R)-14-amino-18-((decylcarbamoyl)oxy)-13,21-dioxo-3,6,9,20-tetraoxa-16-thia-12,22-diazadotriacontyl) phosphonic acid; (15R,19R)-15-amino-19-((decylcarbamoyl)oxy)-14,22-dioxo-4,7,10,21-tetraoxa-17-thia-13,23-diazatritriacontan-1-oic acid; ((14R,18R)-14-amino-18-((octylcarbamoyl)oxy)-13,21-dioxo-3,6,9,20-tetraoxa-16-thia-12,22-diazatriacontyl)phosphonic acid; ((14R,18R)-18-((decylcarbamoyl)oxy)-13,21-dioxo-14-palmitamido-3,6,9,20-tetraoxa-16-thia-12,22-diazadotriacontyl)phosphonic acid; (20R,24R)-1-(1,3-dioxolan-2-yl)-3,19-dioxo-20-palmitamido-8,11,14-trioxa-22-thia-4,18-diazapentacosane-24,25-diyl didodecanoate; (R)-3-(((R)-2-amino-3-((4-(2-(2-hydroxyethoxy)ethoxy)phenethyl)amino)-3-oxopropyl)thio)propane-1,2-diyl didodecanoate; 10-((R)-2-amino-3-(((R)-2,3-bis(dodecanoyloxy)propyl)thio)propanamido)decanoic acid; (R)-3-(((R)-2-amino-3-((1-hydroxy-2-methylpropan-2-yl)amino)-3-oxopropyl)thio)propane-1,2-diyl didodecanoate; (R)-3-(((R)-2-amino-3-((4-(isopentyloxy)phenethyl)amino)-3-oxopropyl)thio)propane-1,2-diyl didodecanoate; (R)-3-(((R)-2-amino-3-(((R)-1-hydroxypropan-2-yl)amino)-3-oxopropyl)thio)propane-1,2-diyl didodecanoate; (R)-3-(((R)-2-amino-3-(((S)-1-hydroxypropan-2-yl)amino)-3-oxopropyl)thio)propane-1,2-diyl didodecanoate; (4R,7S,10R,14R)-4-carbamoyl-7-ethyl-6,9,17-trioxo-10-palmitamido-14-(palmitoyloxy)-16-oxa-12-thia-5,8-diazadotriacontan-1-oic acid; (4R,7S,10R,14R)-10-amino-4-carbamoyl-7-ethyl-6,9,17-trioxo-14-(palmitoyloxy)-16-oxa-12-thia-5,8-diazadotriacontan-1-oic acid; (R)-3-(((R)-2-amino-3-((3-hydroxyphenethyl)amino)-3-oxopropyl)thio)propane-1,2-diyl didodecanoate; (2R)-3-(((2R)-2-amino-3-((1-(4-hydroxyphenyl)ethyl)amino)-3-oxopropyl)thio)propane-1,2-diyl didodecanoate; (R)-3-(((R)-2-amino-3-((4-hydroxyphenethyl)amino)-3-oxopropyl)thio)propane-1,2-diyl didodecanoate; (2R)-3-(((2R)-2-amino-3-oxo-3-((1-phenylethyl)amino)propyl)thio)propane-1,2-diyl didodecanoate; (R)-3-(((R)-2-amino-3-oxo-3-(phenethylamino)propyl)thio)propane-1,2-diyl didodecanoate; (11R,15R)-1,11-diamino-10-oxo-3,6-dioxa-13-thia-9-azahexadecane-15,16-diyl didodecanoate; (R)-3-(((R)-2-amino-3-((2-aminoethyl)amino)-3-oxopropyl)thio)propane-1,2-diyl didodecanoate; (R)-3-(((R)-2-amino-3-((6-aminohexyl)amino)-3-oxopropyl)thio)propane-1,2-diyl didodecanoate; (R)-3-(((R)-2-amino-3-((4-aminobutyl)amino)-3-oxopropyl)thio)propane-1,2-diyl didodecanoate; (R)-3-(((R)-2-amino-3-oxo-3-((2-(pyridin-4-yl)ethyl)amino)propyl)thio)propane-1,2-diyl didodecanoate; (R)-3-(((R)-2-amino-3-((3-morpholinopropyl)amino)-3-oxopropyl)thio)propane-1,2-diyl didodecanoate; (R)-3-(((R)-3-((3-(1H-imidazol-1-yl)propyl)amino)-2-amino-3-oxopropyl)thio)propane-1,2-diyl didodecanoate; (R)-3-(((R)-2-amino-3-((3-aminopropyl)amino)-3-oxopropyl)thio)propane-1,2-diyl didodecanoate; (R)-3-(((R)-2-amino-3-oxo-3-((2-(pyridin-3-yl)ethyl)amino)propyl)thio)propane-1,2-diyl didodecanoate; (2R)-3-(((2R)-2-amino-3-((1-methoxybutan-2-yl)amino)-3-oxopropyl)thio)propane-1,2-diyl didodecanoate; (16R,20R)-1,16-diamino-15-oxo-4,7,10-trioxa-18-thia-14-azahenicosane-20,21-diyl didodecanoate; (R)-3-(((R)-2-amino-3-(((1R,2S)-1-hydroxy-1-phenylpropan-2-yl)amino)-3-oxopropyl)thio)propane-1,2-diyl didodecanoate; (2R)-3-(((2R)-2-amino-3-oxo-3-((4-phenylbutan-2-yl)amino)propyl)thio)propane-1,2-diyl didodecanoate; (2R)-3-(((2R)-2-amino-3-((1,2-diphenylethyl)amino)-3-oxopropyl)thio)propane-1,2-diyl didodecanoate; (R)-3-(((R)-2-amino-3-oxo-3-((4-phenoxyphenethyl)amino)propyl)thio)propane-1,2-diyl didodecanoate; (2R)-3-(((2R)-2-amino-3-((5-(diethylamino)pentan-2-yl)amino)-3-oxopropyl)thio)propane-1,2-diyl didodecanoate; (R)-3-(((R)-2-amino-3-((6-hydroxyhexyl)amino)-3-oxopropyl)thio)propane-1,2-diyl didodecanoate; (R)-3-(((R)-2-amino-3-((2-hydroxyethyl)amino)-3-oxopropyl)thio)propane-1,2-diyl didodecanoate; (R)-3-(((R)-2-amino-3-((5-hydroxy-4,4-dimethylpentyl)amino)-3-oxopropyl)thio)propane-1,2-diyl didodecanoate; (2R)-3-(((2R)-2-amino-3-oxo-3-((2-phenylpropyl)amino)propyl)thio)propane-1,2-diyl didodecanoate; (2R)-3-(((2R)-2-amino-3-((5-methylhexan-2-yl)amino)-3-oxopropyl)thio)propane-1,2-diyl didodecanoate; (4R,7S,10R,14R)-4-carbamoyl-14-(dodecanoyloxy)-7-methyl-6,9,17-trioxo-10-palmitamido-16-oxa-12-thia-5,8-diazaoctacosan-1-oic acid; ((14R,18R)-14-amino-18-(hexadecyloxy)-13-oxo-3,6,9,20-tetraoxa-16-thia-12-azahexatriacontyl)phosphonic acid; ((17R,21R)-17-amino-21-(dodecanoyloxy)-16,24-dioxo-3,6,9,12,23-pentaoxa-19-thia-15-azapentatriacontyl)phosphonic acid; ((17R,21R)-17-amino-21-(dodecyloxy)-16-oxo-3,6,9,12,23-pentaoxa-19-thia-15-azapentatriacontyl)phosphonic acid; ((17R,21R)-17-amino-21-dodecanamido-16-oxo-3,6,9,12,23-pentaoxa-19-thia-15-azapentatriacontyl)phosphonic acid; ((11S,14R,18R)-14-amino-18-(dodecyloxy)-11-(hydroxymethyl)-10,13-dioxo-3,6,20-trioxa-16-thia-9,12-diazadotriacontyl)phosphonic acid; ((11S,14R,18R)-14-amino-18-dodecanamido-11-(hydroxymethyl)-10,13-dioxo-3,6,20-trioxa-16-thia-9,12-diazadotriacontyl)phosphonic acid; ((14R,18R)-14-acetamido-18-((decylcarbamoyl)oxy)-13,21-dioxo-3,6,9,20-tetraoxa-16-thia-12,22-diazadotriacontyl)phosphonic acid; ((14R,18R)-14-amino-18-((decylcarbamoyl)oxy)-13,21-dioxo-3,6,9,20-tetraoxa-16-thia-12,22-diazadotriacontyl)phosphonic acid; 3-((R)-2-amino-3-(((R)-2,3-bis(dodecanoyloxy)propyl)thio)propanamido)propane-1-sulfonic acid; ((14R,18R)-18-((decylcarbamoyl)oxy)-14-heptanamido-13,21-dioxo-3,6,9,20-tetraoxa-16-thia-12,22-diazadotriacontyl)phosphonic acid; (15R,19R)-15-amino-19-(dodecanoyloxy)-14,22-dioxo-4,7,10,21-tetraoxa-17-thia-13-azatritriacontan-1-oic acid; (15R,19R)-19-(dodecanoyloxy)-14,22-dioxo-15-palmitamido-4,7,10,21-tetraoxa-17-thia-13-azatritriacontan-1-oic acid; (15S,18R,22R)-18-amino-22-(dodecanoyloxy)-15-(hydroxymethyl)-14,17,25-trioxo-4,7,10,24-tetraoxa-20-thia-13,16-diazahexatriacontan-1-oic acid; (15S,18R,22R)-22-(dodecanoyloxy)-15-(hydroxymethyl)-14,17,25-trioxo-18-palmitamido-4,7,10,24-tetraoxa-20-thia-13,16-diazahexatriacontan-1-oic acid; ((14R,18R)-14-amino-18-((dodecyloxy)methyl)-13,20-dioxo-3,6,9,19-tetraoxa-16-thia-12,21-diazahentriacontyl)phosphonic acid; (R)-3-(((R)-2-amino-3-oxo-3-((2-(2-(sulfooxy)ethoxy)ethyl)amino) propyl)thio)propane-1,2-diyl didodecanoate, and ((14R,18R)-18-((decylcarbamoyl)oxy)-14-hexanamido-13,21-dioxo-3,6,9,20-tetraoxa-16-thia-12,22-diazadotriacontyl) phosphonic acid.

Each of these compounds individually comprises a preferred embodiment of the compounds, compositions, and methods described herein.

Another aspect provided herein are pharmaceutical compositions comprising a therapeutically effective amount a compound of any one of the aforementioned compounds, and pharmaceutically acceptable salts thereof, and a pharmaceutically acceptable carrier. In certain embodiments of such pharmaceutical compositions, the pharmaceutical composition is formulated for intravenous administration, intravitrial administration, intramuscular administration, oral administration, rectal administration inhalation, nasal administration, topical administration, ophthalmic administration or otic administration. On other embodiments of such pharmaceutical compositions, the pharmaceutical compositions is in the form of a tablet, a pill, a capsule, a liquid, an inhalant, a nasal spray solution, a suppository, a solution, an emulsion, an ointment, eye drop or ear drop.

Another aspect provided herein is the use of a compound of Formula (I) of claim 1 in the manufacture of a medicament for treating a disease or disorder in a patient where modulation of a TLR2 receptor is implicated. In certain embodiments of this aspect, such a disease or condition is an infectious disease, an inflammatory disease, a respiratory disease, a dermatological disease or an autoimmune disease. In certain embodiments of this aspect, the disease or condition is asthma, chronic obstructive pulmonary disease (COPD), adult respiratory distress syndrome (ARDS), ulcerative colitis, Crohns disease, bronchitis, dermatitis, actinic keratosis, basal cell carcinoma, allergic rhinitis, psoriasis, scleroderma, urticaria, rheumatoid arthritis, multiple sclerosis, cancer, breast cancer, HIV or lupus.

Another aspect provided herein includes methods for activating a TLR2 receptor, wherein the method includes administering to a system or a subject in need thereof, a therapeutically effective amount of a compound of Formula (I), or pharmaceutically acceptable salts or pharmaceutical compositions thereof, thereby activating the TLR receptor. In such methods, the compound of Formula (I) is a TLR2 receptor agonist. In certain embodiments of such methods, the methods include administering the compound to a cell or tissue system or to a human or animal subject.

Another aspect provided herein is a method for treating a disease or disorder where modulation of TLR2 receptor is implicated, wherein the method comprises administering to a system or subject in need of such treatment an effective amount of a compound of Formula (I) of claim 1, wherein the compound of Formula (I) is a TLR2 receptor agonist. In certain embodiments of this aspect, such a disease or condition is an infectious disease, an inflammatory disease, a respiratory disease, a dermatological disease or an autoimmune disease. In certain embodiments of this aspect, the disease or condition is asthma, chronic obstructive pulmonary disease (COPD), adult respiratory distress syndrome (ARDS), ulcerative colitis, Crohns disease, bronchitis, dermatitis, actinic keratosis, basal cell carcinoma, allergic rhinitis, psoriasis, scleroderma, urticaria, rheumatoid arthritis, multiple sclerosis, cancer, breast cancer, HIV or lupus.

Another aspect provided herein is a compound for use in the treatment of a disease associated with TLR2 receptor activity, wherein the disease is an infectious disease, an inflammatory disease, a respiratory disease, a dermatological disease or an autoimmune disease. In certain embodiments of this aspect, the disease or condition is asthma, chronic obstructive pulmonary disease (COPD), adult respiratory distress syndrome (ARDS), ulcerative colitis, Crohns disease, bronchitis, dermatitis, actinic keratosis, basal cell carcinoma, allergic rhinitis, psoriasis, scleroderma, urticaria, rheumatoid arthritis, multiple sclerosis, cancer, breast cancer, HIV or lupus.

Another aspect provided herein are pharmaceutical compositions that include a therapeutically effective amount of a compound of Formula (I), an aluminum-containing adjuvant, an antigen and a pharmaceutically acceptable carrier. In such pharmaceutical compositions the compound of Formula (I) is present in an amount sufficient to produce an immunostimulatory effect when administered. In certain embodiments of such pharmaceutical compositions, the pharmaceutical composition is formulated for intravenous administration, intravitrial administration or intramuscular administration. In such compositions the aluminum-containing adjuvant is selected from aluminum hydroxide, aluminum oxyhydroxide and aluminum hydroxyphosphate. In certain embodiments of such compositions, the aluminum-containing adjuvant is aluminum oxyhydroxide or aluminum hydroxide.

Another aspect provided herein is a pharmaceutical composition that includes a therapeutically effective amount of a compound of Formula (I) bound to an aluminum-containing adjuvant and a pharmaceutically acceptable carrier. In certain embodiments, such a composition is a dried down solid. In certain embodiments, such a composition is a lyophilized solid. In such compositions the aluminum-containing adjuvant is selected from aluminum hydroxide, aluminum oxyhydroxide and aluminum hydroxyphosphate. In certain embodiments of such compositions, the aluminum-containing adjuvant is aluminum oxyhydroxide or aluminum hydroxide.

Another aspect provided herein are immunogenic compositions comprising a compound of Formula (I), an aluminum-containing adjuvant and an antigen. In certain embodiments, the compound of Formula (I) is present in an amount effective to elicit, induce or enhance an immune response to the antigen in a subject to whom the composition is administered. In such immunogenic compositions the compound of Formula (I) is present in an amount sufficient to produce an immunostimulatory effect when administered. In such immunogenic compositions the aluminum-containing adjuvant is selected from aluminum hydroxide, aluminum oxyhydroxide and aluminum hydroxyphosphate. In certain embodiments of such immunogenic compositions, the aluminum-containing adjuvant is aluminum oxyhydroxide or aluminum hydroxide. In certain embodiments of such immunogenic compositions, the antigen is a bacterial antigen. In other embodiments of such immunogenic compositions, the antigen is a viral antigen or a fungal antigen. In certain embodiments of such immunogenic compositions, the antigen is a polypeptide. In certain embodiments such immunogenic compositions further comprise an additional adjuvant. In certain embodiments, such an immunogenic composition is a dried down solid. In certain embodiments, such an immunogenic composition is a lyophilized solid.

Another aspect provided herein is a method for enhancing the effectiveness of an immunogenic composition, wherein the immunogenic composition comprises an aluminum-containing adjuvant, and the method comprises adding an effective amount of a compound of Formula (I) to the immunogenic composition. In such methods the aluminum-containing adjuvant is selected from aluminum hydroxide, aluminum oxyhydroxide and aluminum hydroxyphosphate. In certain embodiments of such methods, the aluminum-containing adjuvant is aluminum oxyhydroxide or aluminum hydroxide.

Another aspect provided herein are methods for eliciting or inducing an immune response in a vertebrate subject comprising administering to the vertebrate subject an effective amount of an immunogenic composition of the invention. In some embodiments, the present invention provides methods for eliciting or inducing a cytotoxic-T lymphocyte (CTL) response in a vertebrate subject comprising administering to the vertebrate subject an effective amount of an immunogenic composition of the invention. In other embodiments, the present invention provides methods of eliciting or inducing an antibody-mediated immune response in a vertebrate subject comprising administering to the vertebrate subject an effective amount of an immunogenic composition of the invention.

Another aspect provided herein are methods of making immunogenic compositions described herein. Another aspect provided herein are vaccine compositions that comprise an immunogenic composition of the invention.

Another aspect provided herein are medicaments for treating a patient with a disease or disorder associated with TLR2 receptor activity, and such medicaments include a therapeutically effective amount of a compound of Formula (I) wherein the compound of Formula (I) is a TLR2 receptor agonist.

Another aspect provided herein includes methods for treating a cell-proliferative disease, comprising administering to a system or subject in need of such treatment an effective amount of a compound of Formula (I), or pharmaceutically acceptable salts or pharmaceutical compositions thereof; wherein the cell-proliferative disease is lymphoma, osteosarcoma, melanoma, or a tumor of breast, renal, prostate, colorectal, thyroid, ovarian, pancreatic, neuronal, lung, uterine or gastrointestinal tumor.

Another aspect provided herein are pharmaceutical composition that include a compound of Formula (I), an antigen and a pharmaceutically acceptable carrier, wherein such pharmaceutical compositions are immunogenic compositions, and the compound is an immune potentiator and is present in an amount effective to enhance an immune response to the antigen, in a subject receiving the composition. In certain embodiments, such pharmaceutical compositions, further includes one or more immunoregulatory agents. In certain embodiments, the one or more immunoregulatory agents include one or more adjuvants. In certain embodiments, such adjuvants are selected from adjuvants that are a mineral-containing composition, an oil emulsion, a saponin formulation, a virosome, a virus-like particle, a bacterial derivative, a microbial derivative, a human immunomodulator, a bioadhesive, a mucoadhesive, a microparticle, a liposome, a polyoxyethylene ether formulation, a polyoxyethylene ester formulation, a polyphosphazene, a muramyl peptide, or an imidazoquinolone compound. In certain embodiments, the adjuvant is an oil emulsion. In certain embodiments the immunogenic compositions are useful as vaccines, and the compound is present in an amount sufficient to produce an immunostimulatory effect upon administration.

DETAILED DESCRIPTION OF THE INVENTION

Definitions

The term "alkyl," as used herein, refers to a saturated branched or straight chain hydrocarbon. In certain embodiments such alkyl groups are optionally substituted. As used herein, the terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. If not otherwise specified, an alkyl group generally is a $C_1$-$C_6$ alkyl. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "alkylene," as used herein, refers to a saturated branched or straight chain divalent hydrocarbon radical derived from an alkyl group. In certain embodiments such alkylene groups are optionally substituted. As used herein, the terms "$C_1$-$C_3$alkylene", "$C_1$-$C_4$alkylene", "$C_1$-$C_5$alkylene", "$C_1$-$C_6$alkylene", "$C_1$-$C_7$alkylene" and "$C_1$-$C_8$alkylene" refer to an alkylene group containing at least 1, and at most 3, 4, 5, 6, 7 or 8 carbon atoms respectively. If not otherwise specified, an alkylene group generally is a $C_1$-$C_6$ alkylene. Non-limiting examples of alkylene groups as used herein include, methylene, ethylene, n-propylene, isopropylene, n-butylene, isobutylene, sec-butylene, t-butylene, n-pentylene, isopentylene, hexylene and the like.

The term "alkoxy," as used herein, refers to the group —$OR_a$, where $R_a$ is an alkyl group as defined herein. An alkoxy group can be optionally substituted. As used herein, the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy" and "$C_1$-$C_8$alkoxy" refer to an alkoxy group wherein the alkyl moiety contains at least 1, and at most 3, 4, 5, 6, 7 or 8, carbon atoms. Non-limiting examples of alkoxy groups, as used herein, include methoxy, ethoxy, n-propoxy, isopropoxy, n-butyloxy, t-butyloxy, pentyloxy, hexyloxy, heptyloxy, octyloxy, nonyloxy, decyloxy and the like.

The term "aryl," as used herein, refers to monocyclic, bicyclic, and tricyclic ring systems having a total of five to fourteen ring members, wherein at least one ring in the system is aromatic and wherein each ring in the system contains 3 to 7 ring members. In certain embodiments such aryl groups are optionally substituted. Non-limiting examples of an aryl group, as used herein, include phenyl, naphthyl, fluorenyl, indenyl, azulenyl, anthracenyl and the like.

The term "arylene," as used herein means a divalent radical derived from an aryl group. In certain embodiments such arylene groups are optionally substituted.

The term "cycloalkyl," as used herein, refers to a saturated or partially unsaturated, monocyclic, fused bicyclic, fused tricyclic or bridged polycyclic ring assembly. As used herein, the terms "$C_3$-$C_8$cycloalkyl", "$C_3$-$C_6$cycloalkyl", "$C_3$-$C_7$cycloalkyl", "$C_3$-$C_8$cycloalkyl, "$C_3$-$C_9$cycloalkyl and "$C_3$-$C_{10}$cycloalkyl refer to a cycloalkyl group wherein the saturated or partially unsaturated, monocyclic, fused bicyclic or bridged polycyclic ring assembly contain at least 3, and at most 5, 6, 7, 8, 9 or 10, carbon atoms. In certain embodiments the cycloalkyl group is optionally substituted. Non-limiting examples of cycloalkyl groups, as used herein, include cyclopropyl, cyclobutyl, cyclopentyl, cyclohexyl, cycloheptyl, cyclooctyl, cyclononyl, cyclodecyl, cyclopentenyl, cyclohexenyl, decahydronaphthalenyl, 2,3,4,5,6,7-hexahydro-1H-indenyl and the like.

The term "halogen," as used herein, refers to fluorine (F), chlorine (Cl), bromine (Br), or iodine (I).

The term "halo," as used herein, refers to the halogen radicals: fluoro (—F), chloro (—Cl), bromo (—Br), and iodo (—I).

The terms "haloalkyl" or "halo-substituted alkyl," as used herein, refers to an alkyl group as defined herein, substituted with one or more halogen groups, wherein the halogen groups are the same or different. A haloalkyl group can be optionally substituted. Non-limiting examples of such branched or straight chained haloalkyl groups, as used herein, include methyl, ethyl, propyl, isopropyl, isobutyl and n-butyl substituted with one or more halogen groups, wherein the halogen groups are the same or different, including, but not limited to, trifluoromethyl, pentafluoroethyl, and the like.

The term "heteroaryl," as used herein, refers to monocyclic, bicyclic, and tricyclic ring systems having a total of five to fourteen ring members, wherein at least one ring in the system is aromatic, at least one ring in the system contains one or more heteroatoms selected from nitrogen, oxygen and sulfur, and wherein each ring in the system contains 3 to 7 ring members. In certain embodiments such heteroaryl groups are optionally substituted. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo[1,3]dioxole, benzo[b]furyl, benzo[b]thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl.

The term "heteroarylene," as used herein means a divalent radical derived from a heteroaryl group. In certain embodiments such heteroarylene groups are optionally substituted.

The term "heteroatom," as used herein, refers to one or more of oxygen, sulfur, nitrogen, phosphorus, or silicon.

The term "heterocycloalkyl," as used herein, refers to a cycloalkyl, as defined herein, wherein one or more of the ring carbons are replaced by a moiety selected from —O—, —N=, —NR—, —C(O)—, —S—, —S(O)— or —S(O)$_2$—, wherein R is hydrogen, $C_1$-$C_4$alkyl or a nitrogen protecting group, with the proviso that the ring of said group does not contain two adjacent O or S atoms. In certain embodiments the heterocycloalkyl group is optionally substituted. Non-limiting examples of heterocycloalkyl groups, as used herein, include morpholino, pyrrolidinyl, pyrrolidinyl-2-one, piperazinyl, piperidinyl, piperidinyl-2-one, piperidinyl-3-one, piperidinyl-4-one, 1,4-dioxa-8-aza-spiro[4.5]dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo[3.1.0]hexanyl, and 3-azabicyclo[4.1.0]heptanyl.

The term "hydroxyl," as used herein, refers to the group —OH.

The term "hydroxyalkyl," as used herein refers to an alkyl group as defined herein substituted with one or more hydroxyl group. Non-limiting examples of branched or straight chained "$C_1$-$C_6$ hydroxyalkyl groups as used herein include methyl, ethyl, propyl, isopropyl, isobutyl and n-butyl groups substituted with one or more hydroxyl groups.

The term "optionally substituted," as used herein, means that the referenced group may or may not be substituted with one or more additional group(s) individually and independently selected from alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof. Non-limiting examples of optional substituents include, halo, —CN, =O, =N—OH, =N—OR, =N—R, —OR, —C(O)R, —C(O)OR, —OC(O)R, —OC(O)OR, —C(O)NHR, —C(O)NR$_2$, —OC(O)NHR, —OC(O)NR$_2$, —SR—, —S(O)R, —S(O)$_2$R, —NHR, —N(R)$_2$, —NHC(O)R, —NRC(O)R, —NHC(O)OR, —NRC(O)OR, S(O)$_2$NHR, —S(O)$_2$N(R)$_2$, —NHS(O)$_2$NR$_2$, —NRS(O)$_2$NR$_2$, —NHS(O)$_2$R, —NRS(O)$_2$R, C$_1$-C$_8$alkyl, C$_1$-C$_8$alkoxy, aryl, heteroaryl, cycloalkyl, heterocycloalkyl, halo-substituted C$_1$-C$_8$alkyl, and halo-substituted C$_1$-C$_8$alkoxy, where each R is independently selected from H, halo, C$_1$-C$_8$alkyl, C$_1$-C$_8$alkoxy, aryl, heteroaryl, cycloalkyl, heterocycloalkyl, halo-substituted C$_1$-C$_8$alkyl, and halo-substituted C$_1$-C$_8$alkoxy. The placement and number of such substituent groups is done in accordance with the well-understood valence limitations of each group, for example =O is a suitable substituent for an alkyl group but not for an aryl group.

The term "solvate," as used herein, refers to a complex of variable stoichiometry formed by a solute (by way of example, a compound of Formula (I), or a salt thereof, as described herein) and a solvent. Non-limiting examples of a solvent are water, acetone, methanol, ethanol and acetic acid.

The term "acceptable" with respect to a formulation, composition or ingredient, as used herein, means having no persistent detrimental effect on the general health of the subject being treated.

The term "administration" or "administering" of the subject compound means providing a compound of Formula (I), a pharmaceutically acceptable salt, a pharmaceutically acceptable solvate, or prodrug thereof to a subject in need of treatment.

The term "antigen" refers to a molecule containing one or more epitopes (e.g., linear, conformational or both) that elicit an immunological response. The term may be used interchangeably with the term "immunogen." By "elicit" is meant to induce, promote, enhance or modulate an immune response or immune reaction. In some instances, the immune response or immune reaction is a humoral and/or cellular response. An antigen may induce, promote, enhance or modulate an immune response or immune reaction in cells in vitro and/or in vivo in a subject and/or ex vivo in a subject's cells or tissues. Such immune response or reaction may include, but is not limited to, eliciting the formation of antibodies in a subject, or generating a specific population of lymphocytes reactive with the antigen. Antigens are typically macromolecules (e.g., proteins, polysaccharides, polynucleotides) that are foreign to the host.

The term "antigen", as used herein, also denotes subunit antigens (i.e., antigens which are separate and discrete from a whole organism with which the antigen is associated in nature), as well as killed, attenuated or inactivated bacteria, viruses, parasites, parasites or other pathogens or tumor cells, including extracellular domains of cell surface receptors and intracellular portions containing T-cell epitopes. Antibodies such as anti-idiotype antibodies, or fragments thereof, and synthetic peptide mimotopes, which can mimic an antigen or antigenic determinant, are also encompassed by the definition of antigen as used herein. Similarly, an oligonucleotide or polynucleotide that expresses an immunogenic protein, antigen or antigenic determinant in vivo, such as in gene therapy or nucleic acid immunization applications, is also encompassed by the definition of antigen herein.

The term "epitope" refers to that portion of given species (e.g., an antigenic molecule or antigenic complex) that determines its immunological specificity. An epitope is within the scope of the present definition of antigen. Commonly, an epitope is a polypeptide or polysaccharide in a naturally occurring antigen. In artificial antigens, it can be a low molecular weight substance such as an arsanilic acid derivative. Normally, a B-cell epitope will include at least about 5 amino acids but can be as small as 3-4 amino acids. A T-cell epitope, such as a CTL epitope, will typically include at least about 7-9 amino acids, and a helper T-cell epitope will typically include at least about 12-20 amino acids.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to chemical compounds or agents that facilitate the incorporation of a compound described herein into cells or tissues.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, actinic keratosis, basal cell carcinoma and urticaria.

The term "diluent," as used herein, refers to chemical compounds that are used to dilute a compound described herein prior to delivery. Diluents can also be used to stabilize compounds described herein.

The terms "effective amount" or "therapeutically effective amount," as used herein, refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "excipient" refers to any essentially accessory substance that may be present in the finished dosage form. For example, the term "excipient" includes vehicles, binders, disontegrants, fillers (diluents), lubricants, suspending/dispersing agents, and the like.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "iatrogenic," as used herein, means a condition, disorder, or disease created or worsened by medical or surgical therapy.

The term "immunologically effective amount," as used herein, means that the administration of a sufficient amount to an individual, either in a single dose or as part of a series, that is effective for treatment or prevention of an immunological disease or disorder. This amount varies depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

An "immunological response" or "immune response" to an antigen or composition, as used herein, refers to the development in a subject of a humoral and/or cellular immune response to the antigen or composition.

Immune responses include innate and adaptive immune responses. Innate immune responses are fast-acting responses that provide a first line of defense for the immune system. In contrast, adaptive immunity uses selection and clonal expansion of immune cells having somatically rearranged receptor genes (e.g., T- and B-cell receptors) that recognize antigens from a given pathogen or disorder (e.g., a tumor), thereby providing specificity and immunological memory. Innate immune responses, among their many effects, lead to a rapid burst of inflammatory cytokines and activation of antigen-presenting cells (APCs) such as macrophages and dendritic cells. To distinguish pathogens from self-components, the innate immune system uses a variety of relatively invariable receptors that detect signatures from pathogens, known as pathogen-associated molecular patterns, or PAMPs. The addition of microbial components to experimental vaccines is known to lead to the development of robust and durable adaptive immune responses. The mechanism behind this potentiation of the immune responses has been reported to involve pattern-recognition receptors (PRRs), which are differentially expressed on a variety of immune cells, including neutrophils, macrophages, dendritic cells, natural killer cells, B cells and some nonimmune cells such as epithelial and endothelial cells. Engagement of PRRs leads to the activation of some of these cells and their secretion of cytokines and chemokines, as well as maturation and migration of other cells. In tandem, this creates an inflammatory environment that leads to the establishment of the adaptive immune response. PRRs include nonphagocytic receptors, such as Toll-like receptors (TLRs) and nucleotide-binding oligomerization domain (NOD) proteins, and receptors that induce phagocytosis, such as scavenger receptors, mannose receptors and 3-glucan receptors. Dendritic cells are recognized as some of the most important cell types for initiating the priming of naive CD4$^+$ helper T ($T_H$) cells and for inducing CD8$^+$ T cell differentiation into killer cells. TLR signaling has been reported to play an important role in determining the quality of these helper T cell responses, for instance, with the nature of the TLR signal determining the specific type of $T_H$ response that is observed (e.g., $T_H1$ versus $T_H2$ response). A combination of antibody (humoral) and cellular immunity are produced as part of a $T_H1$-type response, whereas a $T_H2$-type response is predominantly an antibody response.

A "humoral immune response" refers to an immune response mediated by antibody molecules, while a "cellular immune response" refers to an immune response mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, non-specific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition such as an as an immunogenic composition or a vaccine that elicits a cellular immune response may thus serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen or composition to stimulate a cell-mediated immunological response may be determined by a number of assays known in the art, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al. (1993) *J. Immunol.* 151:4189-4199; Doe et al. (1994) *Eur. J. Immunol.* 24:2369-2376. Thus, an immunological response as used herein may be one which stimulates the production of CTLs and/or the production or activation of helper T-cells. The antigen of interest may also elicit an antibody-mediated immune response. Hence, an immunological response may include, for example, one or more of the following effects among others: the production of antibodies by, for example, B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

The immunogenic compositions of the invention display "enhanced immunogenicity" for a given antigen when they possess a greater capacity to elicit an immune response than the immune response elicited by an equivalent amount of the antigen in a differing composition (e.g., wherein the antigen is administered as a soluble protein). Thus, a composition may display "enhanced immunogenicity," for example, because the composition generates a stronger immune response, or because a lower dose or fewer doses of antigen is necessary to achieve an immune response in the subject to which it is administered. Such enhanced immunogenicity can be determined, for example, by administering the compositions of the invention, and antigen controls, to animals and comparing assay results of the two.

The term "inflammatory disorders," as used herein, refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arthritis); joints (arthritis: crystalline, osteo-, psoriatic, reactive, rheumatoid, Reiter's); gastrointestinal tract (Disease,); skin (dermatitis); or multiple organs and tissues (systemic lupus erythematosus).

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist or an antagonist.

The terms "ocular disease" or "ophthalmic disease," as used herein, refer to diseases which affect the eye or eyes and potentially the surrounding tissues as well. Ocular or ophthalmic diseases include, but are not limited to, conjunctivitis, retinitis, scleritis, uveitis, allergic conjunctivitis, vernal conjunctivitis, papillary conjunctivitis and cytomegalovirus (CMV) retinitis.

The term "oligonucleotide", as used herein, refers to a polynucleotide having in the range of 5 to 100 nucleotides, typically 5 to 30 nucleotides in size.

The term "pharmaceutically acceptable," as used herein, refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable salt," as used herein, refers to a formulation of a compound that does not cause significant irritation to an organism to which it is administered and does not abrogate the biological activity and properties of the compounds described herein.

The terms "combination" or "pharmaceutical combination," as used herein mean a product that results from the mixing or combining of more than one active ingredient and includes both fixed and non-fixed combinations of the active ingredients. The term "fixed combination" means that the active ingredients, by way of example, a compound of Formula (I) and an additional therapeutic agent, are both administered to a patient simultaneously in the form of a single entity or dosage. The term "non-fixed combination" means that the active ingredients, by way of example, a compound of Formula (I) and an additional therapeutic agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The terms "composition" or "pharmaceutical composition," as used herein, refers to a mixture of at least one compound, such as the compounds of Formula (I) provided herein, with at least one and optionally more than one other pharmaceutically acceptable chemical components, such as carriers, stabilizers, diluents, dispersing agents, suspending agents, thickening agents, and/or excipients.

By "physiological pH" or a "pH in the physiological range" is meant a pH in the range of approximately 7.2 to 8.0 inclusive, more typically in the range of approximately 7.2 to 7.6 inclusive.

The term "prodrug," as used herein, refers to an agent that is converted into the parent drug in vivo. A non-limiting example of a prodrug of the compounds described herein is a compound described herein administered as an ester which is then metabolically hydrolyzed to a carboxylic acid, the active entity, once inside the cell. A further example of a prodrug is a short peptide bonded to an acid group where the peptide is metabolized to reveal the active moiety.

The terms "polynucleotide" and "nucleic acid" are used interchangeably, and refer to a single- or double-stranded polymer of deoxyribonucleotide or ribonucleotide bases. Single-stranded polynucleotides include coding strands and antisense strands. Polynucleotides include RNA and DNA, and may be isolated from natural sources, synthesized in vitro, or prepared from a combination of natural and synthetic molecules. Examples of polynucleotides include, but are not limited to, genes, cDNAs, mRNAs, self-replicating RNA molecules, self-replicating DNA molecules, genomic DNA sequences, genomic RNA sequences, oligonucleotides. Self-replicating RNA molecules and self-replicating DNA molecules are able to self amplify when introduced into a host cell.

A polynucleotide can be linear or non-linear (e.g., comprising circular, branched, etc. elements). The terms "polynucleotide" and "nucleic acid" encompass modified variants (e.g., sequences with a deletion, addition and/or substitution). Modified variants may be deliberate, such as through site-directed mutagenesis, or may be accidental, such as through natural mutations.

A polynucleotide can be composed of monomers that are naturally-occurring nucleotides (such as DNA and RNA), or analogs of naturally-occurring nucleotides, or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Polynucleotide monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The terms "polynucleotide" and "nucleic acid" also include so-called "peptide nucleic acids", which comprise naturally-occurring or modified nucleic acid bases attached to a polyamide backbone.

The term "polynucleotide-containing species", as used herein, refers to a molecule, at least a portion of which is a polynucleotide.

The terms "polypeptide", "protein" and "peptide", as used herein, refer to any polymer formed from multiple amino acids, regardless of length or posttranslational modification (e.g., phosphorylation or glycosylation), associated, at least in part, by covalent bonding (e.g., "protein" as used herein refers both to linear polymers (chains) of amino acids associated by peptide bonds as well as proteins exhibiting secondary, tertiary, or quaternary structure, which can include other forms of intramolecular and intermolecular association, such as hydrogen and van der Waals bonds, within or between peptide chain(s)). Examples of polypeptides include, but are not limited to, proteins, peptides, oligopeptides, dimers, multimers, variants, and the like. In some embodiments, the polypeptide can be unmodified such that it lacks modifications such as phosphorylation and glycosylation. A polypeptide can contain part or all of a single naturally-occurring polypeptide, or can be a fusion or chimeric polypeptide containing amino acid sequences from two or more naturally-occurring polypeptides.

The term "polypeptide-containing species" refers to a molecule, at least a potion of which is a polypeptide. Examples include polypeptides, glycoproteins, metalloproteins, lipoproteins, saccharide antigens conjugated to carrier proteins, and so forth.

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "subject" or "patient," as used herein, encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like. Frequently the subject is a human, and may be a human who has been diagnosed as in need of treatment for a disease or disorder disclosed herein.

The term "TLR2 modulator," as used herein, refers to a compound which modulates a TLR2 receptor.

The term "TLR2 disease" or a "disease or disorder associated with TLR2 activity," as used herein, refers to any disease state associated with a toll-like receptor. Such diseases or disorders include, but are not limited to, infectious diseases, inflammatory diseases, respiratory diseases and autoimmune diseases, such as, by way of example only, asthma, chronic obstructive pulmonary disease (COPD), adult respiratory distress syndrome (ARDs), Crohns disease, bronchitis, dermatitis, allergic rhinitis, psoriasis, scleroderma, urticaria, rheumatoid arthritis, multiple sclerosis, cancer, HIV and lupus.

The term "therapeutically effective amount," as used herein, refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The term "vector construct" generally refers to any assembly that is capable of directing the expression of a nucleic acid sequence(s) or gene(s) of interest. A "DNA vector construct" refers to a DNA molecule that is capable of directing the expression of a nucleic acid sequence(s) or gene(s) of interest. One specific type of DNA vector construct is a plasmid, which is a circular episomal DNA molecule capable of autonomous replication within a host cell. Typically, a plasmid is a circular double stranded DNA loop into which additional DNA segments can be ligated. pCMV is one specific plasmid that is well known in the art. Other DNA vector constructs are known, which are based on RNA viruses. These DNA vector constructs typically comprise a promoter that functions in a eukaryotic cell, 5' of a cDNA sequence for which the transcription product is an RNA vector construct (e.g., an alphavirus RNA vector replicon), and a 3' termination region. Other examples of vector constructs include RNA vector constructs (e.g., alphavirus vector constructs) and the like. As used herein, "RNA vector construct", "RNA vector replicon" and "replicon" refer to an RNA molecule that is capable of directing its own amplification or self-replication in vivo, typically within a target cell. The RNA vector construct is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently.

The compound names provided herein were obtained using ChemDraw Ultra 10.0 (CambridgeSoft®) or JChem version 5.0.3 (ChemAxon).

Other objects, features and advantages of the methods, compositions and combinations described herein will become apparent from the following detailed description. It should be understood, however, that the detailed description and the specific examples, while indicating specific embodiments, are given by way of illustration only.

DESCRIPTION OF THE PREFERRED EMBODIMENTS

Provided herein are compounds and pharmaceutical compositions thereof, which are agonists of toll-like receptor-2 (TLR2). Also provided herein are compounds, pharmaceutical compositions and methods for the treatment of diseases and/or disorders associated with TLR2 activity.

The TLR2 agonists provided herein are compounds having the structure of Formula (I), and pharmaceutically acceptable salts, pharmaceutically acceptable solvates (e.g. hydrates), the N-oxide derivatives, prodrug derivatives, protected derivatives, individual isomers and mixture of isomers thereof:

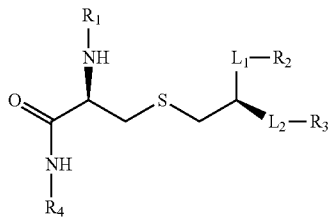

Formula (I)

wherein:
- $R^1$ is H, —C(O)—$C_7$-$C_{18}$alkyl or —C(O)—$C_1$-$C_6$alkyl;
- $R^2$ is $C_7$-$C_{15}$alkyl;
- $R^3$ is $C_7$-$C_{18}$alkyl;
- $L_1$ is —$CH_2$OC(O)—, —$CH_2$O—, —$CH_2$$NR^7$C(O)— or —$CH_2$OC(O)$NR^7$—;
- $L_2$ is —OC(O)—, —O—, —$NR^7$C(O)— or —OC(O)$NR^7$—;
- $R^4$ is -$L_3R^5$ or -$L_4$R;
- $R^5$ is —N($R^7$)$_2$, —$OR^7$, —P(O)(O$R^7$)$_2$, —C(O)$OR^7$, —$NR^7$C(O)$L_3R^8$, —$NR^7$C(O)$L_4R^8$, —$OL_3R^6$, —C(O)$NR^7L_3R^8$, —C(O)$NR^7L_4$R, —S(O)$_2OR^7$, —OS(O)$_2OR^7$, $C_1$-$C_6$alkyl, a $C_6$aryl, a $C_{10}$aryl, a $C_{14}$aryl, 5 to 14 ring membered heteroaryl containing 1 to 3 heteroatoms selected from O, S and N, $C_3$-$C_8$cycloalkyl or a 5 to 6 ring membered heterocycloalkyl containing 1 to 3 heteroatoms selected from O, S and N, wherein the aryl, heteroaryl, cycloalkyl and heterocycloalkyl of $R^5$ are each unsubstituted or the aryl, heteroaryl, cycloalkyl and heterocycloalkyl of $R^5$ are each substituted with 1 to 3 substituents independently selected from —$OR^9$, —$OL_3R^6$, —$OL_4R^6$, —$OR^7$, and —C(O)$OR^7$;
- $L_3$ is a $C_1$-$C_{10}$alkylene, wherein the $C_1$-$C_{10}$alkylene of $L_3$ is unsubstituted, or the $C_1$-$C_{10}$alkylene of $L_3$ is substituted with 1 to 4 $R^6$ groups, or the $C_1$-$C_{10}$alkylene of $L_3$ is substituted with 2 $C_1$-$C_6$alkyl groups on the same carbon atom which together, along with the carbon atom they are attached to, form a $C_3$-$C_8$cycloalkyl;
- $L_4$ is —(($CR^7R^7$)$_p$O)$_q$($CR^{10}R^{10}$)$_p$— or —($CR^{11}R^{11}$)(($CR^7R^7$)$_p$O)$_q$($CR^{10}R^{10}$)$_p$—, wherein each $R^{11}$ is a $C_1$-$C_6$alkyl groups which together, along with the carbon atom they are attached to, form a $C_3$-$C_8$cycloalkyl;
- each $R^6$ is independently selected from halo, $C_1$-$C_6$alkyl, $C_1$-$C_6$alkyl substituted with 1-2 hydroxyl groups, —$OR^7$, —N($R^7$)$_2$, —C(O)OH, —C(O)N($R^7$)$_2$, —P(O)(O$R^7$)$_2$, a $C_6$aryl, a $C_{10}$aryl and a $C_{14}$aryl;
- each $R^7$ is independently selected from H and $C_1$-$C_6$alkyl;
- $R^8$ is selected from —$SR^7$, —C(O)OH, —P(O)(O$R^7$)$_2$, and a 5 to 6 ring membered heterocycloalkyl containing 1 to 3 heteroatoms selected from O and N;
- $R^9$ is phenyl;
- each $R^{10}$ is independently selected from H and halo;
- each p is independently selected from 1, 2, 3, 4, 5 and 6, and
- q is 1, 2, 3 or 4.

In certain embodiments, compounds of Formula (I) are compounds having the structure of Formula (II):

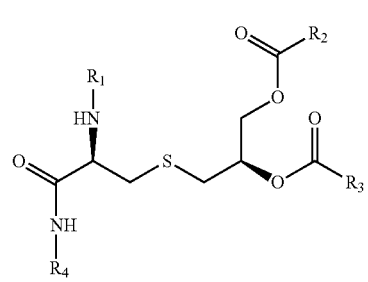

Formula (II)

In certain embodiments, compounds of Formula (I) are compounds having the structure of Formula (III):

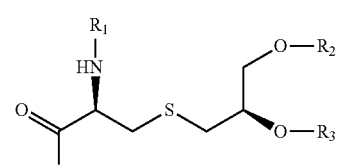

Formula (III)

In certain embodiments, compounds of Formula (I) are compounds having the structure of Formula (IV):

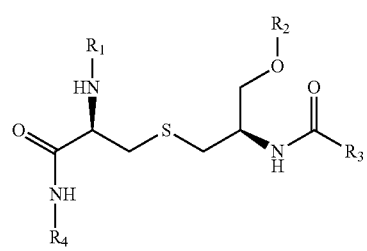

Formula (IV)

In certain embodiments, compounds of Formula (I) are compounds having the structure of Formula (V):

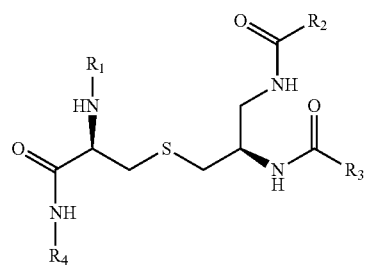

Formula (V)

In certain embodiments, compounds of Formula (I) are compounds having the structure of Formula (V):

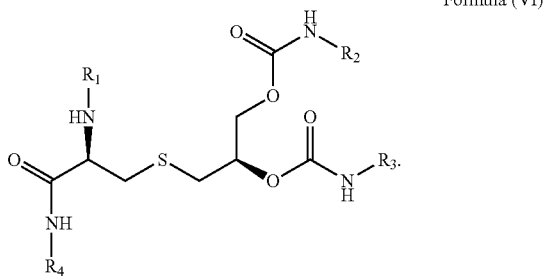

Formula (VI)

In certain embodiments of such compounds having a structure of Formula (I), Formula (II), Formula (III), Formula (IV), Formula (V) and Formula (VI), $R^1$ is H. In other embodiments of such compounds having a structure of Formula (I), Formula (II), Formula (III), Formula (IV), Formula (V) and Formula (VI), $R^1$ is —C(O)—$C_{1-15}$alkyl. In other embodiments of such compounds having a structure of Formula (I), Formula (II), Formula (III), Formula (IV), Formula (V) and Formula (VI), $R^1$ is —C(O)—$C_{10}$-$C_{15}$alkyl.

In certain embodiments of such compounds having a structure of Formula (I), $L_1$ is —$CH_2OC(O)$— and $L_2$ is —OC(O)—, —O—, —$NR^7C(O)$— or —$OC(O)NR^7$—; or $L_1$ is —$CH_2O$— and $L_2$ is —OC(O)—, —O—, —$NR^7C(O)$— or —$OC(O)NR^7$—; or $L_1$ is —$CH_2NR^7C(O)$— and $L_2$ is —OC(O)—, —O—, —$NR^7C(O)$— or —$OC(O)NR^7$—; or $L_1$ is —$CH_2OC(O)NR^7$— and $L_2$ is —OC(O)—, —O—, $NR^7C(O)$— or —$OC(O)NR^7$—.

In certain embodiments of such compounds having a structure of Formula (I), $L_1$ is —$CH_2OC(O)$— and $L_2$ is —OC(O)—. In certain embodiments of such compounds having a structure of Formula (I), $L_1$ is —$CH_2O$— and $L_2$ is —O—. In certain embodiments of such compounds having a structure of Formula (I), $L_1$ is —$CH_2O$— and $L_2$ is —$NR^7C(O)$—. In certain embodiments of such compounds having a structure of Formula (I), $L_1$ is —$CH_2OC(O)NR^7$— and $L_2$ is —OC(O)$NR^7$—. In other embodiments of such compounds having a structure of Formula (I), $L_1$ is —$CH_2NR^7C(O)$— and $L_2$ is —$NR^7C(O)$—.

In certain embodiments of such compounds having a structure of Formula (I), Formula (II), Formula (III), Formula (IV), Formula (V) and Formula (VI), $R^2$ is $C_{10}$-$C_{18}$alkyl. In certain embodiments of such compounds having a structure of Formula (I), Formula (II), Formula (III), Formula (IV), Formula (V) and Formula (VI), $R^3$ is $C_{10}$-$C_{18}$alkyl. In certain embodiments of such compounds having a structure of Formula (I), Formula (II), Formula (III), Formula (IV), Formula (V) and Formula (VI), $R^2$ is —$C_{11}$alkyl and $R^3$ is —$C_{11}$alkyl; or $R^2$ is —$C_{16}$alkyl and $R^3$ is —$C_{16}$alkyl; or $R^2$ is —$C_{16}$alkyl and $R^3$ is —$C_1$alkyl; or $R^2$ is —$C_{12}$alkyl and $R^3$ is —$C_2$alkyl; or $R^2$ is —$C_7$alkyl and $R^3$ is —$C_7$alkyl; or $R^2$ is —$C_9$alkyl and $R^3$ is —$C_9$alkyl; or $R^2$ is —$C_8$alkyl and $R^3$ is —$C_8$alkyl; or $R^2$ is —$C_3$alkyl and $R^3$ is —$C_3$alkyl; or $R^2$ is —$C_{12}$alkyl and $R^3$ is —$C_{11}$alkyl; or $R^2$ is —$C_{12}$alkyl and $R^3$ is —$C_{12}$alkyl; or $R^2$ is —$C_{10}$alkyl and $R^3$ is —$C_{10}$alkyl; or $R^2$ is —$C_{15}$alkyl and $R^3$ is —$C_{15}$alkyl.

In certain embodiments of such compounds having a structure of Formula (I), Formula (II), Formula (III), Formula (IV), Formula (V) and Formula (VI), $R^2$ is —$C_{11}$alkyl and $R^3$ is —$C_{11}$alkyl.

In certain embodiments of such compounds having a structure of Formula (I), Formula (II), Formula (III), Formula (IV), Formula (V) and Formula (VI), $R^5$ is —$NH_2$, —$N(CH_2CH_3)_2$, —OH, —$OCH_3$, —$P(O)(OH)_2$, —C(O)OH, —NHC(O)$L_3R^8$, —$S(O)_2OH$, —$OS(O)_2OH$, —$OL_3R^6$, —C(O)$NHL_4R^8$ or —C(O)$NHL_3R^8$. While in other embodiments of such compounds having a structure of Formula (I), Formula (II), Formula (III), Formula (IV), Formula (V) and Formula (VI), $R^5$ is —$NH_2$, —$N(CH_2CH_3)_2$, —OH, —$OCH_3$, —P(O)(OH)$_2$, —C(O)OH, —NHC(O)$L_3R^8$, —$S(O)_2OH$, —$OS(O)_2OH$ and —$OL_3R^6$.

In certain embodiments of such compounds having a structure of Formula (I), Formula (II), Formula (III), Formula (IV), Formula (V) and Formula (VI), $R^5$ is —$NH_2$, —$N(CH_2CH_3)_2$, —OH, —$OCH_3$, —P(O)(OH)$_2$, —C(O)OH, —NHC(O)$L_3R^8$, —$OL_3R^6$, —C(O)$NHL_4R^8$ or —C(O)$NHL_3R^8$.

In certain embodiments of such compounds having a structure of Formula (I), Formula (II), Formula (III), Formula (IV), Formula (V) and Formula (VI), $R^5$ is —$NH_2$, —OH, —P(O)(OH)$_2$, —C(O)OH, —NHC(O)$L_3R^8$, —$OL_3R^6$, or —C(O)$NHL_3R^8$. While, in other embodiments of such compounds having a structure of Formula (I), Formula (II), Formula (III), Formula (IV), Formula (V) and Formula (VI), $R^5$ is $C_1$-$C_6$alkyl, phenyl, pyridinyl, imidazolyl or morpholinyl, each of which is optionally substituted with 1 to 3 substituents independently selected from —$OR^9$, —$OL_3R^6$, —$OL_4R^6$, —OH and —C(O)OH.

In certain embodiments of such compounds having a structure of Formula (I), Formula (II), Formula (III), Formula (IV), Formula (V) and Formula (VI), $R^8$ is selected from —SH, —C(O)OH, —P(O)(OH)$_2$, and a 5-6 membered heterocycloalkyl containing 1 to 2 heteroatoms selected from O. In certain embodiments of such compounds having a structure of Formula (I), Formula (II), Formula (III), Formula (IV), Formula (V) and Formula (VI), $R^8$ is selected from —SH, —C(O)OH and a 5 to 6 membered heterocycloalkyl containing 1 to 2 heteroatoms selected from O.

In certain embodiments of such compounds having a structure of Formula (I), Formula (II), Formula (III), Formula (IV), Formula (V) and Formula (VI), $L_3$ is a $C_1$-$C_{10}$alkylene, wherein the $C_1$-$C_{10}$alkylene of $L_3$ is optionally substituted with 1 to 4 $R^6$ groups.

In certain embodiments of such compounds having a structure of Formula (I), Formula (II), Formula (III), Formula (IV), Formula (V) and Formula (VI), $L_4$ is —$((CR^7R^7)_pO)_q(CR^{10}R^{10})_p$—, each $R^{10}$ is independently selected from H and F; each p is independently selected from 2, 3, and 4, and q is 1, 2, 3 or 4.

In certain embodiments of such compounds having a structure of Formula (I), Formula (II), Formula (III), Formula (IV), Formula (V) and Formula (VI), each $R^6$ is independently selected from $C_1$-$C_6$alkyl, —OH, —$NH_2$, —C(O)$NH_2$, —P(O)(OH)$_2$ and phenyl.

In certain embodiments of such compounds having a structure of Formula (I), Formula (II), Formula (III), Formula (IV), Formula (V) and Formula (VI), each $R^6$ is independently selected from methyl, ethyl, i-propyl, i-butyl, —$CH_2OH$, —OH, —F, —$NH_2$, —C(O)OH, —C(O)$NH_2$, —P(O)(OH)$_2$ and phenyl.

In certain embodiments of such compounds having a structure of Formula (I), Formula (II), Formula (III), Formula (IV), Formula (V) and Formula (VI), each $R^7$ is independently selected from H, methyl and ethyl.

In such embodiments of compounds having a structure of Formula (II), Formula (III), Formula (IV), Formula (V) and Formula (VI), $R^1$ is H, —C(O)—$C_{10}$-$C_{15}$alkyl;
$R^2$ is $C_{10}$-$C_{18}$alkyl;
$R^3$ is $C_{10}$-$C_{18}$alkyl;
$R^4$ is -$L_3R^5$ or -$L_4R^5$;

$R^5$ is —N($R^7$)$_2$, —OR$^7$, —P(O)(OR$^7$)$_2$, —C(O)OR$^7$, —NR$^7$C(O)L$_3$R$^8$, —OL$_3$R$^6$, —C(O)NR$^7$L$_3$R$^8$, $C_1$-$C_6$alkyl, a $C_6$ aryl, a $C_{10}$ aryl, a $C_{14}$ aryl, 5 to 14 membered heteroaryl containing 1 to 3 heteroatoms selected from O, S and N, $C_3$-$C_8$cycloalkyl or a 5 to 6 membered heterocycloalkyl containing 1 to 3 heteroatoms selected from O, S and N, wherein the aryl, heteroaryl, cycloalkyl and heterocycloalkyl of $R^5$ are each optionally substituted with 1 to 3 substituents independently selected from —OR$^9$, —OL$_3$R$^6$, —OL$_4$R$^6$, —OR$^7$, and —C(O)OR$^7$;

$L_3$ is a $C_1$-$C_{10}$alkylene, wherein the $C_1$-$C_6$alkylene of $L_3$ is optionally substituted with 1 to 4 $R^6$ groups, or the $C_1$-$C_6$alkylene of $L_3$ is substituted with 2 $C_1$-$C_6$alkyl groups on the same carbon atom which together, along with the carbon atom they are attached to, form a $C_3$-$C_8$cycloalkyl;

$L_4$ is —((CR$^7$R$^7$)$_p$O)$_q$(CR$^{10}$R$^{10}$)$_p$— or —(CR$^{11}$R$^{11}$)((CR$^7$R$^7$)$_p$O)$_q$(CR$^{10}$R$^{10}$)$_p$—, wherein each $R^{11}$ is a $C_1$-$C_6$alkyl groups which together, along with the carbon atom they are attached to, form a $C_3$-$C_8$cycloalkyl;

each $R^6$ is independently selected from halo, $C_1$-$C_6$alkyl, —OR$^7$, —N(R$^7$)$_2$, —C(O)N(R$^7$)$_2$, —P(O)(OR$^7$)$_2$, a $C_6$ aryl, a $C_{10}$ aryl and a $C_{14}$ aryl;

each $R^7$ is independently selected from H and $C_1$-$C_6$alkyl;

$R^8$ is selected from —SR$^7$, —C(O)OH and a 5 to 6 membered heterocycloalkyl containing 1 to 3 heteroatoms selected from O and N;

$R^9$ is phenyl;

each $R^{10}$ is independently selected from H and halo;

each p is independently selected from 1, 2, 3, 4, 5 and 6, and q is 1, 2, 3 or 4.

In certain embodiments of compounds of Formulas (I)-(V), $R^5$ is —P(O)(O$^-$X$^+$)$_2$ or —P(O)(O$^-$)$_2$X$^{2+}$; wherein X$^+$ and X$^{2+}$ are pharmaceutically acceptable cations. In certain embodiments, such pharmaceutically acceptable cations are selected from sodium, potassium, calcium, zinc, and magnesium.

In certain embodiments of compounds of Formula (I), $R^5$ is —PO$_3$—X$^{3+}$; wherein X$^{3+}$ is Al$^{3+}$.

Aluminum-containing adjuvants, such as aluminum hydroxide, aluminum oxyhydroxide and aluminum hydroxyphosphate, are used in vaccines to bind antigens. A discussion of aluminum-containing adjuvants and their uses in vaccines is given in *Expert Rev. Vaccines,* 46(5), 2007, 685-698 and *Vaccines,* 25, 2007, 6618-6624, the disclosures of which are herein incorporated by references in their entirety.

In certain embodiment, compounds of Formula (I) provided herein are TLR2 agonists that bind to aluminum-containing adjuvants, such as, by way of example only, aluminum hydroxide, aluminum oxyhydroxide and aluminum hydroxyphosphate. In certain embodiments, such compounds of Formula (I) have a phosphate, a phosphonic acid, a phosphonate, a fluorinated phosphonic acid or a fluorinated phosphonate group. While in other embodiments, such compounds of Formula (I) have a phosphate, a phosphonic acid, a phosphonate, a fluorinated phosphonic acid or fluorinated phosphonate group, and one or more additional ionizable groups selected from a carboxylic acid and sulphate.

In certain embodiments compounds of Formula (I) provided herein are combined with an antigen, an aluminum-containing adjuvant, and optionally a carrier, pharmaceutically acceptable excipient, to provide an immunogenic composition. In other embodiments, such immunogenic composition comprise a compound of Formula (I) and an antigen, wherein the antigen includes, but is not limited to, a bacterial antigen, a viral antigen, a fungal antigen, a tumor antigen, or an antigen associated with an STD, Alzheimer's, respiratory disorders, autoimmune disorders such as, by way of example only, rheumatoid arthritis or lupus, pediatric disorders and obesity, and wherein the amount of the compound is an amount effective to enhance an immune response to the antigen in a subject to whom the composition is administered. Suitable antigens for use in such immunogenic compositions are described herein.

In certain embodiments, such immunogenic compositions include a bacterial antigen of a strain of *Neisseria meningitides*, such as serogroup A, C, W135, Y and/or B. Specific antigens for use in these compositions are described herein. In other embodiments, such immunogenic compositions, and others provided herein, are used as vaccines; their use in the treatment of disorders associated with the antigen included in the composition is described herein.

The compounds of Formula (I), pharmaceutically acceptable salts, solvates, N-oxides, prodrugs and isomers thereof, and pharmaceutical compositions provided herein also includes all suitable isotopic variations of such compounds, and pharmaceutically acceptable salts, solvates, N-oxides, prodrugs and isomers thereof, and pharmaceutical compositions. An isotopic variation of a compound provided herein or a pharmaceutically acceptable salt thereof is defined as one in which at least one atom is replaced by an atom having the same atomic number but an atomic mass different from the atomic mass usually found in nature. Examples of isotopes that may be incorporated into the compounds provided herein and pharmaceutically acceptable salts thereof include but are not limited to isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds provided herein and pharmaceutically acceptable salts thereof, for example, those in which a radioactive isotope such as $^3$H or $^{14}$C is incorporated, are useful in drug and/or substrate tissue distribution studies. In particular examples, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds, and pharmaceutically acceptable salts, solvates, N-oxides, prodrugs and isomers thereof, and pharmaceutical compositions provided herein are prepared by conventional procedures using appropriate isotopic variations of suitable reagents.

Processes for Making Compounds of Formula (I)

General procedures for preparing compounds of Formula (I) are described in the Examples, infra. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry," John Wiley and Sons, 1991).

In certain embodiments, the compounds of Formula (I) provided herein are prepared as a pharmaceutically acceptable acid addition salt by reacting the free base form of the compound of Formula (I) with a pharmaceutically acceptable organic acid or inorganic acid. In other embodiments, a pharmaceutically acceptable base addition salt of compounds of Formula (I) provided herein is prepared by reacting the free acid form of the compound of Formula (I) with a pharmaceutically acceptable organic base or inorganic base. Alternatively, the salt forms of the compounds of Formula (I) provided herein are prepared using salts of the starting materials or intermediates. In certain embodiments, the compounds of Formula (I) provided herein are in the form of other salts including, but not limited to, oxalates and trifluoroacetates. In certain embodiments, hemisalts of acids and bases are formed, for example, hemisulphate and hemicalcium salts.

Such pharmaceutically acceptable acid addition salts of compounds of Formula (I) include, but are not limited to, a hydrobromide, hydrochloride, sulfate, nitrate, succinate, maleate, formate, acetate, adipate, besylatye, bicarbonate/carbonate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate), hexanoate salt, bisulphate/sulphate, borate, camsylate, cyclamate, edisylate, esylate, gluceptate, gluconate, glucuronate, hexafluorophosphate, hibenzate, hydrochloride/chloride, hydrobromide/bromide, hydroiodide/iodide, isethionate, lactate, malate, malonate, mesylate, methylsulphate, naphthylate, 2-napsylate, nicotinate, orotate, oxalate, palmitate, pamoate, phosphate/hydrogen phosphate/dihydrogen phosphate, pyroglutamate, saccharate, stearate, tannate, tosylate, trifluoroacetate and xinofoate salts.

The organic acid or inorganic acids used to form certain pharmaceutically acceptable acid addition salts of compounds of Formula (I) include, but are not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid.

Such pharmaceutically acceptable base addition salt of a compound of Formula (I) include, but are not limited to, aluminium, arginine, benzathine, calcium, choline, diethylamine, diolamine, glycine, lysine, magnesium, meglumine, olamine, potassium, sodium, tromethamine and zinc salts.

In certain embodiments, the free acid or free base forms of the compounds of Formula (I) provided herein are prepared from the corresponding base addition salt or acid addition salt from, respectively. For example a compound Formula (I) in an acid addition salt form is converted to the corresponding free base by treating with a suitable base (by way of example only, an ammonium hydroxide solution, a sodium hydroxide, and the like). For example, a compound of Formula (I) in a base addition salt form is converted to the corresponding free acid by treating with a suitable acid (by way of example only, hydrochloric acid).

In certain embodiments, compounds of Formula (I) in unoxidized form are prepared from N-oxides of compounds Formula (I) by treating with a reducing agent (by way of example only, sulfur, sulfur dioxide, triphenyl phosphine, lithium borohydride, sodium borohydride, phosphorus trichloride, tribromide, or the like) in a suitable inert organic solvent (by way of example only, acetonitrile, ethanol, aqueous dioxane, or the like) at 0 to 80° C.

In certain embodiments, prodrug derivatives of compounds Formula (I) are prepared using methods known to those of ordinary skill in the art (e.g., for further details see Saulnier et al., (1994), Bioorganic and Medicinal Chemistry Letters, Vol. 4, p. 1985). For example, appropriate prodrugs are prepared by reacting a non-derivatized compound of Formula (I) with a suitable carbamylating agent (by way of example only, 1,1-acyloxyalkylcarbanochloridate, para-nitrophenyl carbonate, or the like).

In certain embodiments, compounds of Formula (I) are prepared as protected derivatives using methods known to those of ordinary skill in the art. A detailed description of the techniques applicable to the creation of protecting groups and their removal can be found in T. W. Greene, "Protecting Groups in Organic Chemistry," 3$^{rd}$ edition, John Wiley and Sons, Inc., 1999.

In certain embodiments, compounds of Formula (I) are prepared or formed, as solvates (e.g., hydrates). In certain embodiments, hydrates of compounds of Formula (I) are prepared by recrystallization from an aqueous/organic solvent mixture, using organic solvents such as dioxin, tetrahydrofuran or methanol.

In certain embodiments, compounds of Formula (I) are prepared as their individual stereoisomers. In other embodiments, the compounds of Formula (I) provided herein are prepared as their individual stereoisomers by reacting a racemic mixture of the compound with an optically active resolving agent to form a pair of diastereoisomeric compounds, separating the diastereomers and recovering the optically pure enantiomers. In certain embodiments, resolution of enantiomers is carried out using covalent diastereomeric derivatives of the compounds of Formula (I), or by using dissociable complexes (e.g., crystalline diastereomeric salts). Diastereomers have distinct physical properties (e.g., melting points, boiling points, solubility, reactivity, etc.) and are readily separated by taking advantage of these dissimilarities. In certain embodiments, the diastereomers are separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981.

Compounds of Formula (I) are made by processes described herein and as illustrated in the Examples. In certain embodiments, compounds of Formula (I) are made by:
  (a) optionally converting a compound of Formula (I) into a pharmaceutically acceptable salt;
  (c) optionally converting a salt form of a compound of Formula (I) to a non-salt form;
  (d) optionally converting an unoxidized form of a compound of Formula (I) into a pharmaceutically acceptable N-oxide;
  (e) optionally converting an N-oxide form of a compound of Formula (I) to its unoxidized form;
  (f) optionally resolving an individual isomer of a compound of Formula (I) from a mixture of isomers;
  (g) optionally converting a non-derivatized compound of Formula (I) into a pharmaceutically acceptable prodrug derivative; and
  (h) optionally converting a prodrug derivative of a compound of Formula (I) to its non-derivatized form.

Non-limiting examples of synthetic schemes used to make compounds of Formula (I) provided herein are illustrated in reaction schemes (I)-(II).

Scheme (I) illustrates the synthesis compounds of Formula (I), wherein lipopeptide I-4 is prepared by coupling the substituted N-protected-(R)-cysteine (1-1) with various amines (1-2) in the presence of a coupling reagent and then followed by deprotection. Further reaction of the primary amine of lipopeptide I-4 leads to lipopeptide I-5. The substituents $L_1$, $L_2$, $R_1$, $R_2$, $R_3$ and $R_4$ are as defined herein. "Prot." refers to an amine protecting group, such as, by way of example only, Fmoc, Boc and Cbz.

Scheme (I)

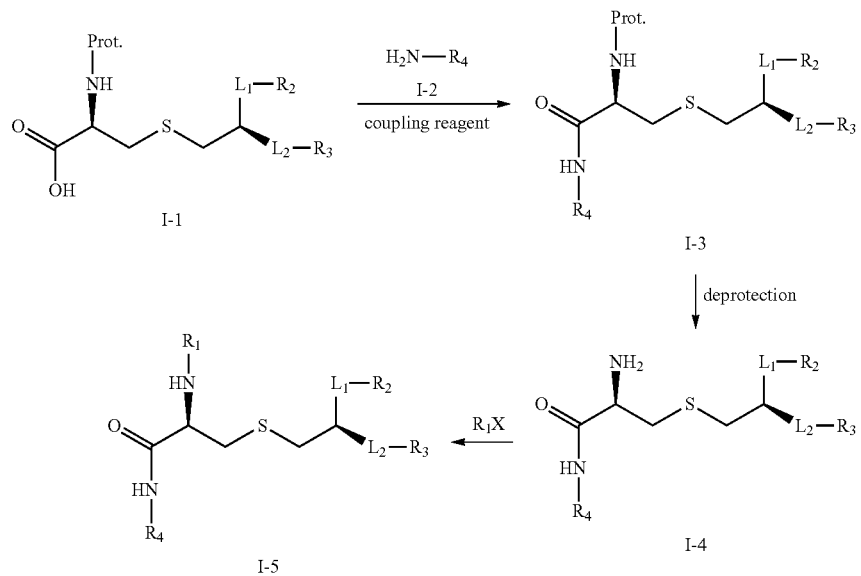

Scheme (II) illustrates the synthesis of compounds of Formula (I), wherein $L_1$ is —$CH_2OC(O)$— and $L_2$ is —OC(O)—. Here, the reduction of (N-Fmoc-OtBu-Cys)$_2$ (II-1) gives N-Fmoc-OtBu-cysteine (II-2), and the thiol of N-Fmoc-OtBu-cysteine (II-2) is alkylated with epoxide ester resulting in N-Fmoc-OtBu-[2(R),3-dihydroxylpropyl]-(R)-cysteine (II-3). Acylation of (II-3) gives (II-4), and subsequent hydrolysis of the tert-butyl ester leads to the substituted N-Fmoc-(R)-cysteine (II-5). Lipopeptide (II-7) is obtained by coupling the substituted N-Fmoc-(R)-cysteine (II-5) with various amines (II-6) in the presence of a coupling reagent. Fmoc deprotection then gives the lipopeptide (II-8), and further reaction of the primary amine of lipopeptide (II-8) leads to lipopeptide (II-9). The substituents $R_1$, $R_2$, $R_3$ and $R_4$ are as defined herein.

Scheme (II)

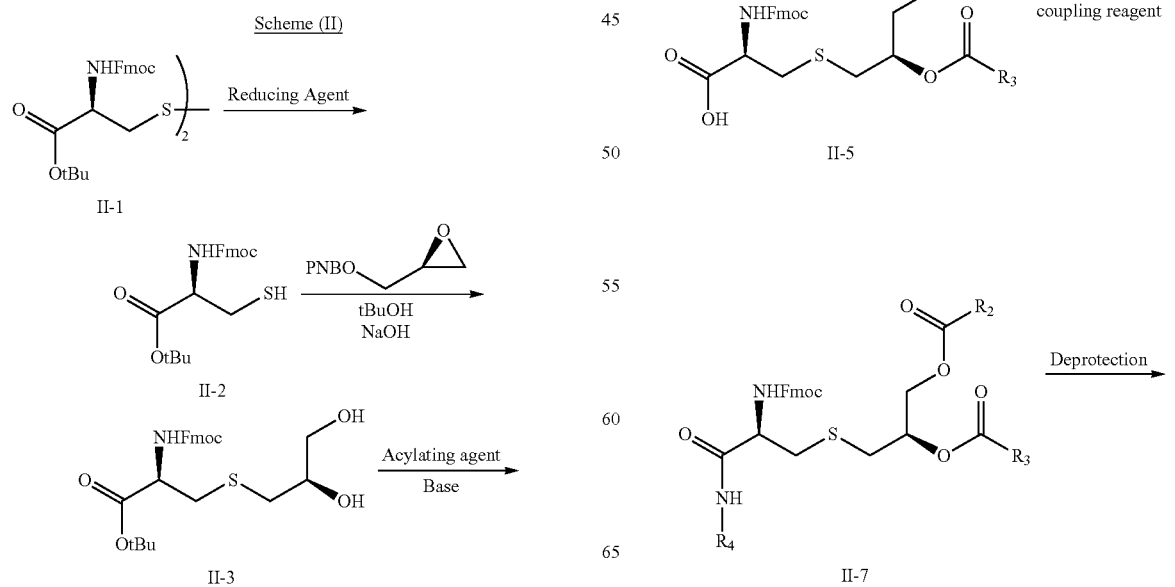

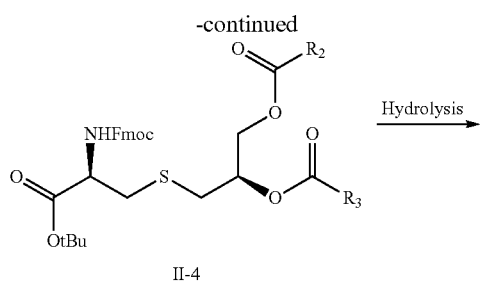

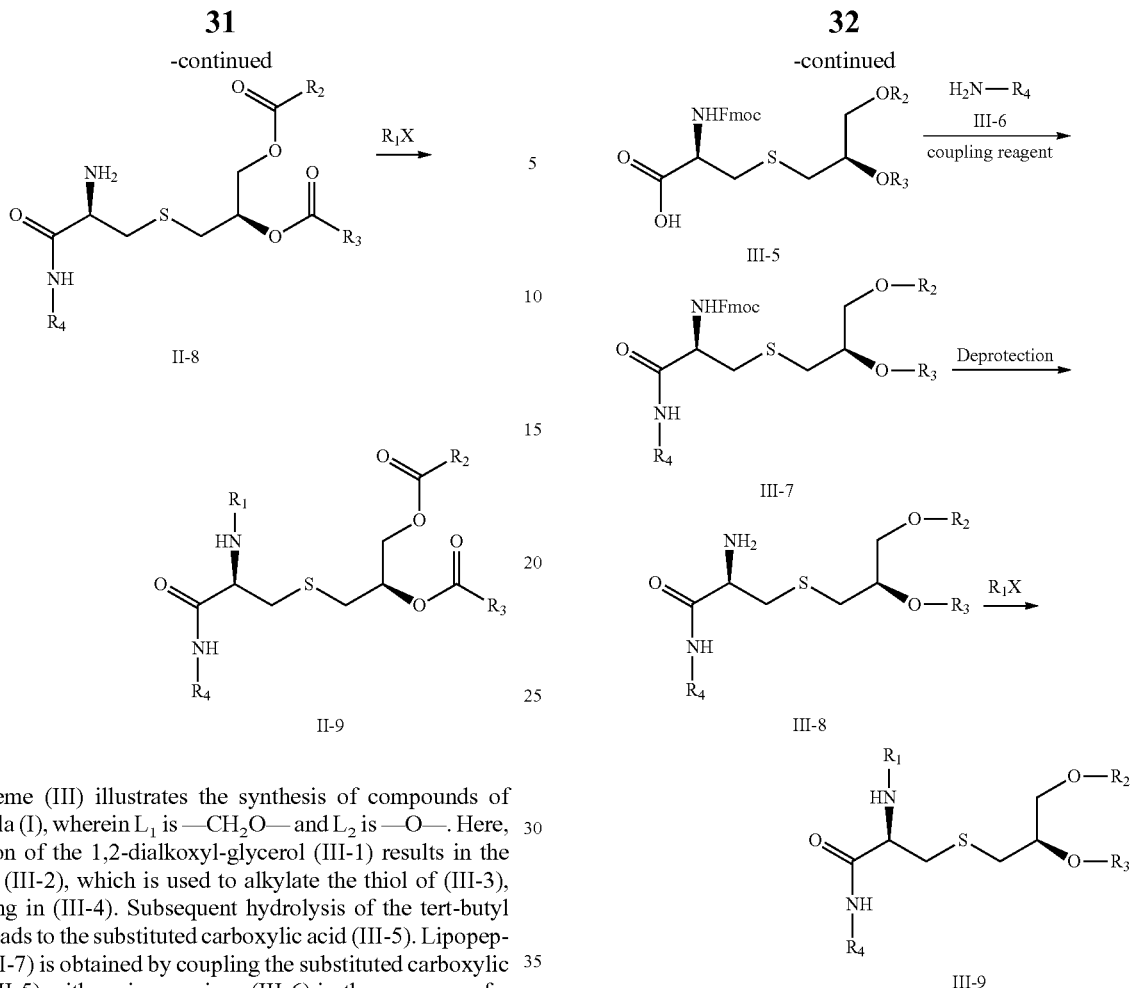

Scheme (III) illustrates the synthesis of compounds of Formula (I), wherein $L_1$ is —CH$_2$O— and $L_2$ is —O—. Here, triflation of the 1,2-dialkoxyl-glycerol (III-1) results in the triflate (III-2), which is used to alkylate the thiol of (III-3), resulting in (III-4). Subsequent hydrolysis of the tert-butyl ester leads to the substituted carboxylic acid (III-5). Lipopeptide (III-7) is obtained by coupling the substituted carboxylic acid (III-5) with various amines (III-6) in the presence of a coupling reagent. Fmoc deprotection then gives the lipopeptide (III-8), and further reaction of the primary amine of lipopeptide (III-8) leads to lipopeptide (III-9). The substituents $R_1$, $R_2$, $R_3$ and $R_4$ are as defined herein.

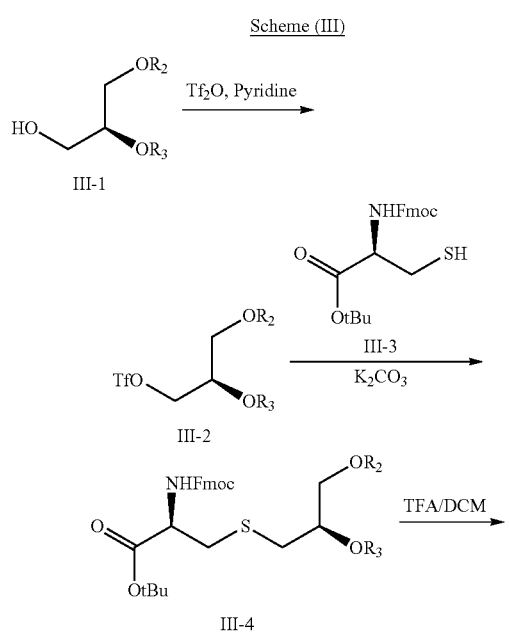

Scheme (IV) illustrates the synthesis of compounds of Formula (I), wherein $L_1$ is —CH$_2$O— and $L_2$ is —NR$_7$C(O)—. Here, Selective protection of primary alcohol in 3-alkoxyl-glycerol (IV-1) gives (IV-2). Mesylation of the secondary alcohol of glycerol (IV-2) gives (IV-3) and then treatment with NaN$_3$ results in azide (IV-4). Deprotection of the silyl group of (IV-4) followed by triflation of the resulting alcohol (IV-5) leads to triflated glycerol (IV-6). The thiol of (IV-7) is alkylated with triflate (IV-6), resulting in azide (IV-8). Azide (IV-8) is reduced to the corresponding amine, which is acylated to give amide (IV-9). Hydrolysis of tert-butyl ester of (IV-9) leads to the substituted carboxylic acid (IV-10). Lipopeptide (IV-12) is obtained by coupling the substituted carboxylic acid (IV-10) with various amines (IV-11) in the presence of a coupling reagent. Fmoc deprotection then gives the lipopeptide (IV-13), and further reaction of the primary amine of lipopeptide (IV-13) leads to lipopeptide (IV-14). The substituents $R_1$, $R_2$, $R_3$, $R_4$ and $R_7$ are as defined herein.

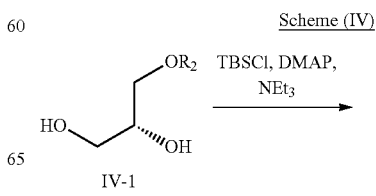

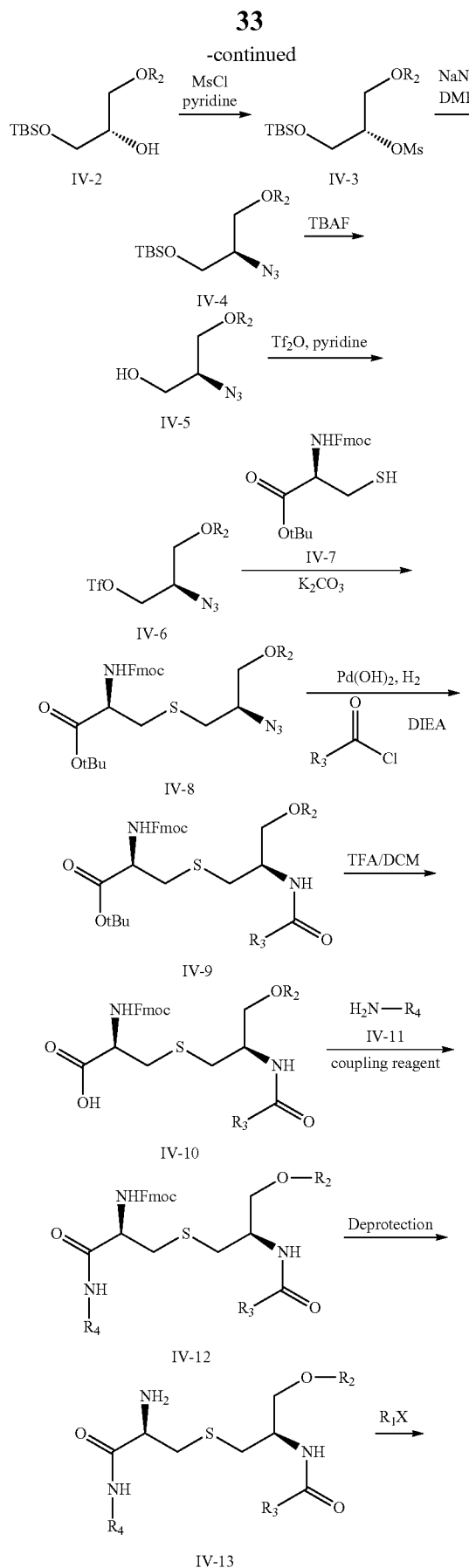

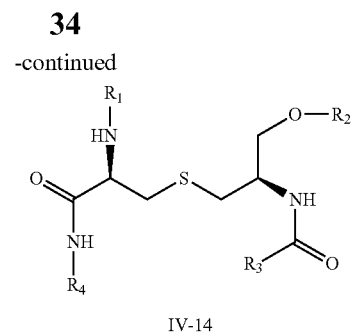

Scheme (V) illustrates the synthesis of compounds of Formula (I), wherein $L_1$ is —$CH_2NR^7C(O)$— and $L_2$ is —$NR_7C(O)$—. Here, the reduction of disulfide (V-2) gives thiol (V-3), which is alkylated with R-epoxide ester, resulting in diol (V-4). Mesylation of the diol (V-4) gives (V-5) which is treated with $NaN_3$ resulting in diazide (V-6). Diazide (V-6) is reduced to the diamine (V-7) by $Pd(OH)_2$, and then is acylated to give diamide (V-8). Hydrolysis of tert-butyl ester of (V-8) leads to substituted carboxylic acid (V-9). Lipopeptide (V-11) is obtained by coupling the substituted carboxylic acid (V-9) with various amines (V-10) in the presence of a coupling reagent. Cbz deprotection then gives the lipopeptide (V-12), and further reaction of the primary amine of lipopeptide (V-12) leads to lipopeptide (V-13). The substituents $R_1$, $R_2$, $R_3$ and $R_4$ are as defined herein.

Scheme (V)

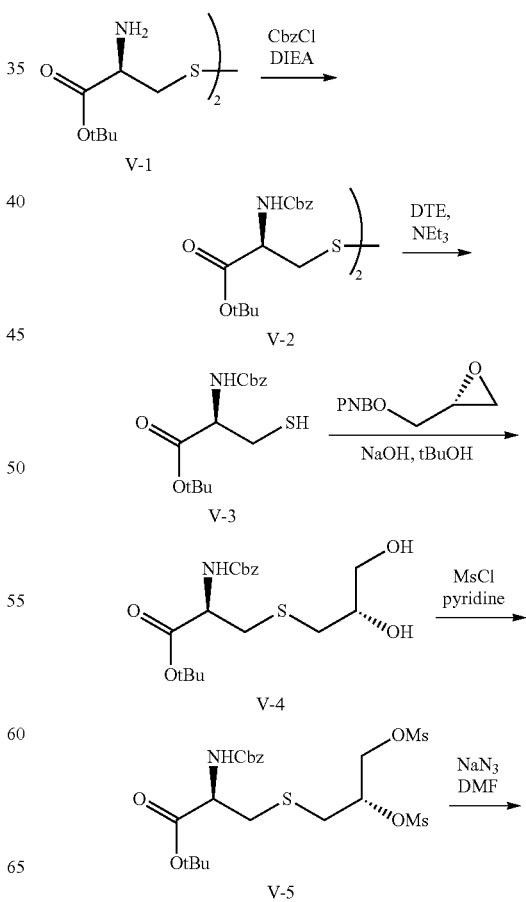

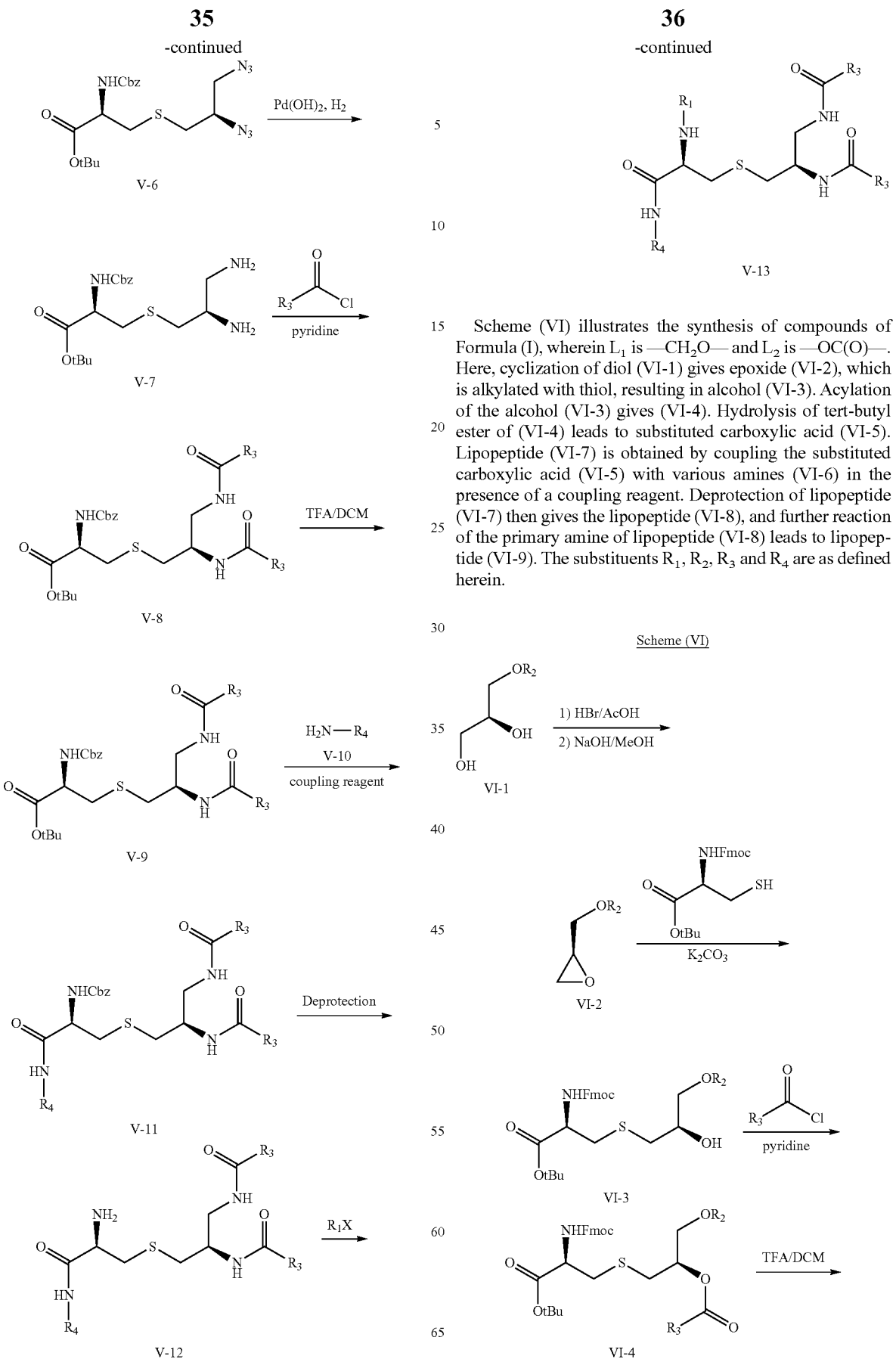

Scheme (VI) illustrates the synthesis of compounds of Formula (I), wherein $L_1$ is —$CH_2O$— and $L_2$ is —OC(O)—. Here, cyclization of diol (VI-1) gives epoxide (VI-2), which is alkylated with thiol, resulting in alcohol (VI-3). Acylation of the alcohol (VI-3) gives (VI-4). Hydrolysis of tert-butyl ester of (VI-4) leads to substituted carboxylic acid (VI-5). Lipopeptide (VI-7) is obtained by coupling the substituted carboxylic acid (VI-5) with various amines (VI-6) in the presence of a coupling reagent. Deprotection of lipopeptide (VI-7) then gives the lipopeptide (VI-8), and further reaction of the primary amine of lipopeptide (VI-8) leads to lipopeptide (VI-9). The substituents $R_1$, $R_2$, $R_3$ and $R_4$ are as defined herein.

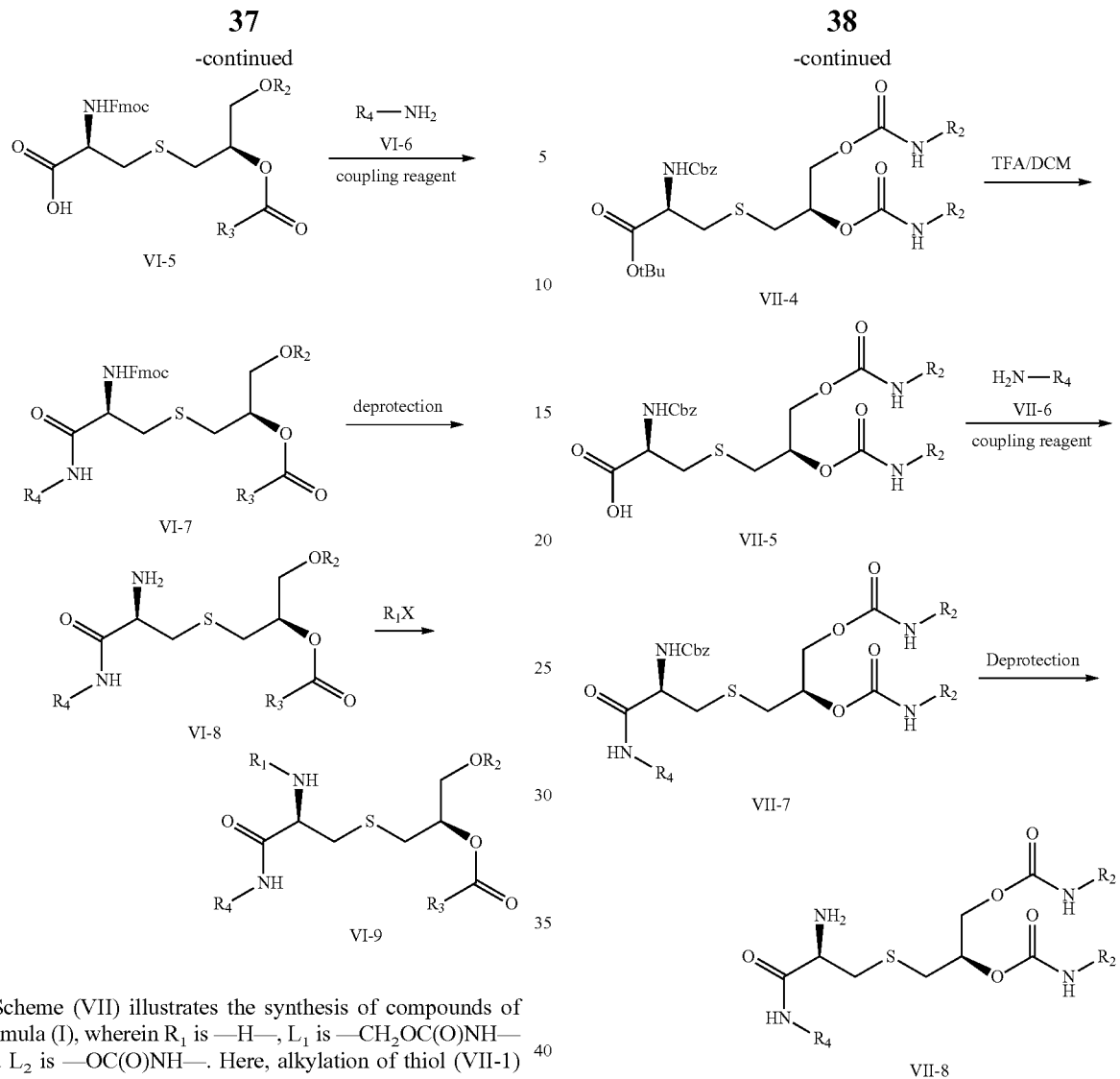

Scheme (VII) illustrates the synthesis of compounds of Formula (I), wherein $R_1$ is —H—, $L_1$ is —$CH_2OC(O)NH$— and $L_2$ is —$OC(O)NH$—. Here, alkylation of thiol (VII-1) with epoxide gives the diol (VII-2), which is acylated with isocyanate (VII-3), resulting in bis-carbamate (VII-4). Hydrolysis of tert-butyl ester of (VII-4) leads to substituted carboxylic acid (VII-5). Lipopeptide (VII-7) is obtained by coupling the substituted carboxylic acid (VII-5) with various amines (VII-6) in the presence of a coupling reagent. Deprotection of lipopeptide (VII-7) then gives the lipopeptide (VII-8). The substituents $R_1$, $R_2$, $R_3$ and $R_4$ are as defined herein.

Scheme (VIII) illustrates the synthesis of compounds of Formula (I), wherein $R_1$ is —C(O)—$C_8$-$C_{18}$ alkyl-, $L_1$ is —$CH_2OC(O)NH$— and $L_2$ is —$OC(O)NH$—. Here, reduction of VIII-1 gives the free amine (VIII-2), which is reacted with $RX_1$ (VIII-3), resulting in VIII-4. Hydrolysis of tert-butyl ester of VIII-4 leads to substituted carboxylic acid (VIII-5). Lipopeptide (VIII-7) is obtained by coupling the substituted carboxylic acid (VIII-5) with various amines (VIII-6) in the presence of a coupling reagent. The substituents $R_1$, $R_2$, $R_3$ and $R_4$ are as defined herein.

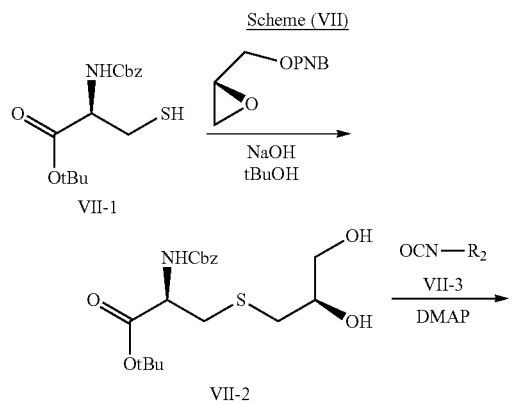

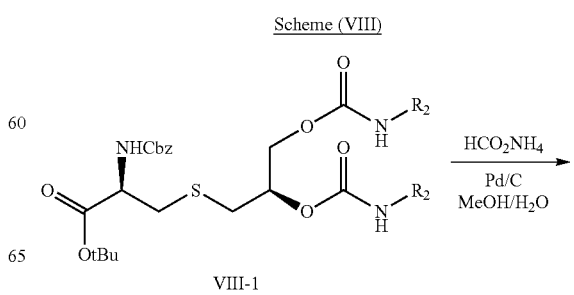

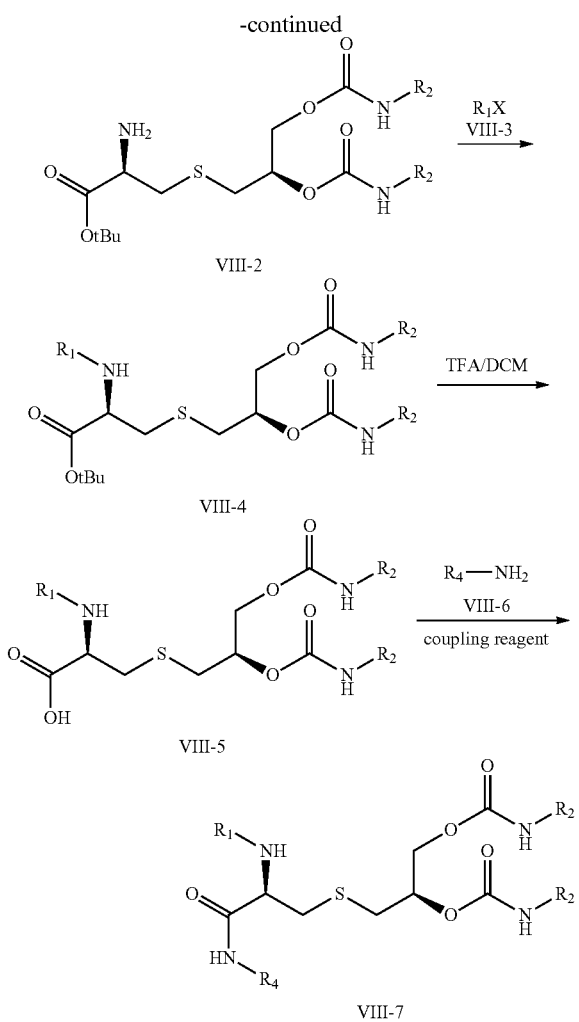

The examples provided herein are offered to illustrate, but not to limit, the compounds of Formula (I) provided herein, and the preparation of such compounds.

Pharmacology and Utility

When a foreign antigen challenges the immune system it responds by launching a protective response that is characterized by the coordinated interaction of both the innate and acquired immune systems. These two interdependent systems fulfill two mutually exclusive requirements: speed (contributed by the innate system) and specificity (contributed by the adaptive system).

The innate immune system serves as the first line of defense against invading pathogens, holding the pathogen in check while the adaptive responses are matured. It is triggered within minutes of infection in an antigen-independent fashion, responding to broadly conserved patterns in the pathogens (though it is not non-specific, and can distinguish between self and pathogens). Crucially, it also generates the inflammatory and co-stimulatory milieu (sometimes referred to as the danger signal) that potentiates the adaptive immune system and steers (or polarizes it) towards the cellular or humoral responses most appropriate for combating the infectious agent. The development of TLR modulators for therapeutic targeting of innate immunity has been reviewed (see *Nature Medicine*, 2007, 13, 552-559; *Drug Discovery Today: Therapeutic Stategies*, 2006, 3, 343-352 and *Journal of Immunology*, 2005, 174, 1259-1268).

The adaptive response becomes effective over days or weeks, but ultimately provides the fine antigenic specificity required for complete elimination of the pathogen and the generation of immunologic memory. It is mediated principally by T and B cells that have undergone germline gene rearrangement and are characterized by specificity and long-lasting memory. However, it also involves the recruitment of elements of the innate immune system, including professional phagocytes (macrophages, neutrophils etc.) and granulocytes (basophils, eosinophils etc.) that engulf bacteria and even relatively large protozoal parasites. Once an adaptive immune response has matured, subsequent exposure to the pathogen results in its rapid elimination due to highly specific memory cells have been generated that are rapidly activated upon subsequent exposure to their cognate antigen.

Autoimmune diseases, are defined by (i) humoral or autoantibody response to a self antigen (by way of example only, Graves' primary hyperthyroidism with antibodies to the TSH receptor), or (ii) cellular response wherein immune cells destroy nonimmune cells from which the self-antigen is derived (by way of example only, the thyrocyte (Hashimoto's thyroiditis) or pancreatic-islet cell (Type 1 diabetes). Many autoimmune diseases are a combination of both phenomena, for instance, Hashimoto's and Type 1 diabetes also have auto-antibodies, anti-thyroid peroxidase (TPO) or anti-glutamic acid decarboxylase (GAD)/Islet Cell. Autoimmune diseases often have an inflammatory component including, but not limited to, increases in adhesion molecules (by way of example only, vascular cell adhesion molecule-1 (VCAM-1), and altered leukocyte adhesion to the vasculature such as, by way of example only, colitis, systemic lupus, systemic sclerosis, and the vascular complications of diabetes.

Toll-like receptors (TLRs) are type-I transmembrane proteins characterized by an extracellular N-terminal leucine-rich repeat (LRR) domain, followed by a cysteine-rich region, a TM domain, and an intracellular (cytoplasmic) tail that contains a conserved region named the Toll/IL-1 receptor (TIR) domain. TLRs are pattern recognition receptors (PRR) that are expressed predominantly on immune cells including, but not limited to, dendritic cells, T lymphocytes, macrophages, monocytes and natural killer cells. The LLR domain is important for ligand binding and associated signaling and is a common feature of PRRs. The TIR domain is important in protein-protein interactions and is associated with innate immunity. The TIR domain also unites a larger IL-R/TLR superfamily that is composed of three subgroups. Members of the first group possess immunoglobin domains in their extracellular regions and include IL-1 and IL-18 receptors and accessory proteins as well as ST2. The second group encompasses the TLRs. The third group includes intracellular adaptor proteins important for signaling.

TLRs are a group of pattern recognition receptors which bind to pathogen-associated molecular patterns (PAMPS) from bacteria, fungi, protozoa and viruses, and act as a first line of defense against invading pathogens. TLRs are essential to induce expression of genes involved in inflammatory responses, and TLRs and the innate immune system are a critical step in the development of antigen-specific acquired immunity.

Adaptive (humoral or cell-mediated) immunity is associated with the TLR signal mechanism of innate immunity. Innate immunity is a protective immune cell response that functions rapidly to fight environmental insults including, but not limited to, bacterial or viral agents. Adaptive immunity is a slower response, which involves differentiation and activation of naive T lymphocytes into T helper 1 (Th1) or T helper 2 (Th2) cell types. Th1 cells mainly promote cellular immunity, whereas Th2 cells mainly promote humoral immunity. Though primarily a host protective system, pathologic expression of the innate immunity signals emanating from the TLR pathway are implicated in initiating autoimmune-inflammatory diseases.

All TLRs appear to function as either a homodimer or heterodimer in the recognition of a specific, or set of specific, molecular determinants present on pathogenic organisms including bacterial cell-surface lipopolysaccharides, lipoproteins, bacterial flagellin, DNA from both bacteria and viruses and viral RNA. The cellular response to TLR activation involves activation of one or more transcription factors, leading to the production and secretion of cytokines and co-stimulatory molecules such as interferons, TNF-, interleukins, MIP-1 and MCP-1 which contribute to the killing and clearance of the pathogenic invasion.

TLR spatial expression is coincident with the host's environmental interface. While only a few other Toll-like proteins have been cloned in $Drosophila$, the human TLR family is composed of at least 11 members, TLR1 through TLR11, that elicit overlapping yet distinct biological responses due to differences in cellular expression and signaling pathways they initiate. Each of the TLRs is expressed on a different subset of leukocytes and each of the TLRs is specific in its expression patterns and PAMP sensitivities and detects different subsets of pathogens allowing vigilant surveillance by the immune system.

TLR Signaling Pathways.

TLRs are distributed throughout the cell. TLR1, TLR2, TLR3 and TLR4 are expressed on the cell surface, whereas, TLR3, TLR2, TLR8 and TLR9 are expressed in intracellular compartments such as endosomes. TLR3-, TLR2- or TLR9-mediated recognition of their ligands require endosomal maturation and processing. When macrophages, monocytes, dendritic cells or nonimmune cells that become antigen presenting cells engulf bacteria by phagocytosis, the bacteria degrade and CpG DNA is release into phagosomes-lysosomes or in endosomes-lysosomes wherein they can interact with TLR9 that has been recruited from the endoplasmic reticulum upon non-specific uptake of CpG DNA. Furthermore, when viruses invade cells by receptor-mediated endocytosis, the viral contents are exposed to the cytoplasm by fusion of the viral membrane with the endosomal membrane. This results in exposure of TLR ligands such as dsRNA, ssRNA and CpG DNA to TLR9 in the phagosomal/lysosomal or endosomal/lysosomal compartments.

In the signaling pathways downstream of the TIR domain, a TIR domain-containing adaptor, MyD88, is essential for induction of inflammatory cytokines such as TNF-α and IL-12 through all TLRs. Although TIR domain-containing adaptor molecules (MyD88) are common to all TLRs, individual TLR signaling pathways are divergent and activation of specific TLRs leads to slightly different patterns of gene expression profiles. By way of example only, activation of TLR3 and TLR4 signaling pathways results in induction of type I interferons (IFNs), while activation of TLR2- and TLR5-mediated pathways do not. However, activation of TLR2, TLR8 and TLR9 signaling pathways also leads to induction of Type I IFNs, although this occurs through mechanisms distinct from TLR3/4-mediated induction.

Once engaged, TLRs initiate a signal transduction cascade leading to activation of NF B via the adapter protein myeloid differentiation primary response gene 88 (MyD88) and recruitment of the IL-1 receptor associated kinase (IRAK). The MyD88-dependent pathway is analogous to signaling by the IL-1 receptors, and it is regarded that MyD88, harboring a C-terminal TIR domain and an N-terminal death domain, associates with the TIR domain of TLRs. Upon stimulation, MyD88 recruits IRAK-4 to TLRs through interaction of the death domains of both molecules, and facilitates IRAK-4-mediated phosphorylation of IRAK-1. Phosphorylation of IRAK-1 then leads to recruitment of TNF-receptor associated factor 6 (TRAF6), leading to the activation of two distinct signaling pathways. One pathway leads to activation of AP-1 transcription factors through activation of MAP kinases. Another pathway activates the TAK1/TAB complex, which enhances activity of the IκB kinase (IKK) complex. Once activated, the IKK complex induces phosphorylation and subsequent degradation of the NFκB inhibitor IκB, which leads to nuclear translocation of transcription factor NFκB and the initiation of transcription of genes whose promoters contain NF B binding sites, such as cytokines. The MyD88-dependent pathway plays a crucial role and is essential for inflammatory cytokine production through all TLRs.

Stimulation of TLR8-expressing cells, such as PBMCs results in production of high levels of IL-12, IFN-γ, IL-1, TNF-α, IL-6 and other inflammatory cytokines. Similarly, stimulation of TLR2-expressing cells, such as plasmacytoid dendritic cells, results in production of high levels of interferon-α (IFNα) and low levels of inflammatory cytokines. Thus, through activation of dendritic cells and other antigen-presenting cells, TLR2, TLR8 or TLR9 engagement and cytokine production is expected to activate diverse innate and acquired immune response mechanisms leading to the destruction of pathogens, infected cells or tumor cells.

Toll-Like Receptor 2 (TLR2)

TLR2 is highly expressed on the membrane of dendritic cells, which are considered as the most potent cell type for antigen presentation (Wetzler, L. M., "The role of Toll-like receptor 2 in microbial disease and immunity", Vaccine 2003, 21, 55-60; Iwasaki, A., Medzhitov, R., "Toll-like receptor control of the adaptive immune Responses", Nat. Immunol., 2004, 5, 987-995; Schmitt, A., $L_1$, L., Giannopoulos, K., Greiner, J., Reinhardt, P., Wiesneth, M., Schmitt, M., "Quantitative expression of Toll-like receptor-2, -4, and -9 in dendritic cells generated from blasts of patients with acute myeloid leukemia", Transfusion, 2008, 48, 861-870). TLR2 maps to chromosome 4q31-32 and encodes a putative 784 (aa) protein with 19 N-terminal LLRs and a calculated molecular weight of 84 kDa. TLR2 is most closely related to TLR6 with 31% overall (aa) sequence identity. TLR2 mRNA expression is observed in brain, heart, lung, and spleen tissues and is highest in PBLs, specifically those of myelomonocytic origin. In vivo, two different sized transcripts for TLR2 are observed suggesting that the mRNA is alternatively spliced. In vitro, TLR2 mRNA and protein expression is upregulated in monocytic leukemic (THP-1) cells upon PMA-induced differentiation. TLR2 is upregulated by autocrine IL-6 and TNF-α, IL-1β, and IL-10. TLR2 mRNA expression is elevated after exposure to both Gram-positive and Gram-negative bacteria.

TLR2 recognizes its ligands as heterodimer either in combination with TLR-1 or TLR-6. TLR2 forms heterodimers with TLR1, TLR6, and possibly TLR10, where each complex is particularly sensitive to subsets of TLR2-associated PAMPs. A major difference between both heterodimer types is that TLR-1/TLR2 enables recognition of triacylated lipoproteins, whereas TLR2/TLR-6 detects diacylated lipoproteins and peptidoglycans (Wetzler, L. M., "The role of Toll-like receptor 2 in microbial disease and immunity", Vaccine 2003, 21, 55-60).

Among all TLRs, TLR2 recognizes the broadest repertoire of pathogen-associated molecular patterns (PAMPs) from a large variety of pathogens, mostly from bacteria. These include, but are not limited to, lipoarabinomannan (LAM), lipopolysaccharide (LPS), lipoteichoic acid (LTA), peptidoglycan (PGN), and other glycolipids, glycoproteins, and lipoproteins. TLR2 complexes are also capable of detecting viruses, including but not limited to, measles virus (MV), human cytomegalovirus (HCMV), and hepatitis C virus (HCV) and fungal PAMPs, including but not limited to, zymosan. TLR2 recognizes a variety of lipoproteins/lipopeptides from various pathogens such as, by way of example only, Gram-positive bacteria, mycobacteria, *Trypanosoma cruzi*, fungi and *Treponema*. In addition, TLR2 recognizes LPS preparations from non-enterobacteria such as, by way of example only, *Leptospira interrogans, Porphyromonas gingivalis* and *Helicobacter pylori*. TLR2 complexes are capable of both detection of non-self patterns and detecting altered self patterns, such as those displayed by necrotic cells. TLR2 is recruited to phagosomes and is involved in the internalization of microbial products by cells.

Compounds of Formula (I), pharmaceutically acceptable salts, solvates, N-oxides, prodrugs and isomers thereof, pharmaceutical compositions, and/or combinations provided herein are agonists of toll-like receptor 2 activity, and are used in the treatment of diseases and/or disorders associated with such TLR2 receptors.

In certain embodiments, the compounds of Formula (I), pharmaceutically acceptable salts, solvates, N-oxides, prodrugs and isomers thereof, pharmaceutical compositions, and/or combinations provided herein are used in the treatment of respiratory diseases and/or disorders including, but not limited to, asthma, bronchial asthma, allergic asthma, intrinsic asthma, extrinsic asthma, exercise-induced asthma, drug-induced asthma (including aspirin and NSAID-induced) and dust-induced asthma, chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

In certain embodiments, the compounds of Formula (I), pharmaceutically acceptable salts, solvates, N-oxides, prodrugs and isomers thereof, pharmaceutical compositions, and/or combinations provided herein are used in the treatment of dermatological disorders including, but not limited to, psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, basal cell carcinoma, actinic keratosis, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

In certain embodiments, the compounds of Formula (I), pharmaceutically acceptable salts, solvates, N-oxides, prodrugs and isomers thereof, pharmaceutical compositions, and/or combinations provided herein are used in the treatment of ocular diseases and/or disorders including, but not limited to, blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial.

In certain embodiments, the compounds of Formula (I), pharmaceutically acceptable salts, solvates, N-oxides, prodrugs and isomers thereof, pharmaceutical compositions, and/or combinations provided herein are used in the treatment of genitourinary diseases and/or disorders including, but not limited to, nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female).

In certain embodiments, the compounds of Formula (I), pharmaceutically acceptable salts, solvates, N-oxides, prodrugs and isomers thereof, pharmaceutical compositions, and/or combinations provided herein are used in the treatment of allograft rejection including, but not limited to, acute and chronic following, for example, transplantation of kidney, heart, liver, lung, bone marrow, skin or cornea or following blood transfusion; or chronic graft versus host disease.

In certain embodiments, the compounds of Formula (I), pharmaceutically acceptable salts, solvates, N-oxides, prodrugs and isomers thereof, pharmaceutical compositions, and/or combinations provided herein are used in the treatment of other auto-immune and allergic disorders including, but not limited to, rheumatoid arthritis, irritable bowel syndrome, systemic lupus erythematosus, multiple sclerosis, Hashimoto's thyroiditis, Crohns disease, inflammatory bowel disease (IBD), Graves' disease, Addison's disease, diabetes mellitus, idiopathic thrombocytopaenic purpura, eosinophilic fasciitis, hyper-IgE syndrome, antiphospholipid syndrome and Sazary syndrome.

In certain embodiments, the compounds of Formula (I), pharmaceutically acceptable salts, solvates, N-oxides, prodrugs and isomers thereof, and pharmaceutical compositions provided herein are used in the treatment of cancer including, but not limited to, prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumor recurrences, and paraneoplastic syndromes. In certain embodiments, the compounds of Formula (I), pharmaceutically acceptable salts, solvates, N-oxides, prodrugs and isomers thereof, and pharmaceutical compositions provided herein are useful as modulators of toll-like receptor activity, and are used in the treatment of neoplasias including, but not limited to, basal cell carcinoma, squamous cell carcinoma, actinic keratosis, melanoma, carcinomas, sarcomas, leukemias, renal cell carcinoma, Kaposi's sarcoma, myelogeous leukemia, chronic lymphocytic leukemia and multiple myeloma.

In certain embodiments, the compounds of Formula (I), pharmaceutically acceptable salts, solvates, N-oxides, prodrugs and isomers thereof, pharmaceutical compositions, and/or combinations provided herein are used in the treatment of infectious diseases including, but not limited to, viral diseases such as genital warts, common warts, plantar warts, respiratory syncytial virus (RSV), hepatitis B, hepatitis C, Dengue virus, herpes simplex virus (by way of example only, HSV-I, HSV-II, CMV, or VZV), molluscum contagiosum, vaccinia, variola, lentivirus, human immunodeficiency virus (HIV), human papilloma virus (HPV), cytomegalovirus (CMV), varicella zoster virus (VZV), rhinovirus, enterovirus, adenovirus, coronavirus (e.g., SARS), influenza, parainfluenza, mumps virus, measles virus, papovavirus, hepadnavirus, flavivirus, retrovirus, arenavirus (by way of example only, LCM, Junin virus, Machupo virus, Guanarito virus and Lassa Fever) and filovirus (by way of example only, ebola virus or marbug virus).

In certain embodiments, the compounds of Formula (I), pharmaceutically acceptable salts, solvates, N-oxides, prodrugs and isomers thereof, pharmaceutical compositions, and/or combinations provided herein are used in the treatment of bacterial, fungal, and protozoal infections including, but not limited to, tuberculosis and *mycobacterium avium*, leprosy; *pneumocystis carnii*, cryptosporidiosis, histoplasmosis, toxoplasmosis, trypanosome infection, leishmaniasis, infections caused by bacteria of the genus *Escherichia, Enterobacter, Salmonella, Staphylococcus, Klebsiella, Proteus, Pseudomonas, Streptococcus*, and *Chlamydia*, and fungal infections such as candidiasis, aspergillosis, histoplasmosis, cryptococcal meningitis.

In certain embodiments, the compounds of Formula (I), pharmaceutically acceptable salts, solvates, N-oxides, prodrugs and isomers thereof, are used as immune potentiators. In certain embodiments, the compounds provided herein are included in immunogenic compositions or are used in combination with immunogenic compositions. In certain embodiments, the immunogenic compositions are useful as vaccines, and the compound is present in an amount sufficient to enhance an immune response to the vaccine, or to an antigen admixed with the compound. The vaccine comprises at least one antigen, which may be a bacterial antigen or a cancer-associated antigen, or a viral antigen. In certain embodiments, the compounds of Formula (I), pharmaceutically acceptable salts, solvates, N-oxides, prodrugs and isomers thereof, and pharmaceutical compositions provided herein are included in therapeutic vaccines or are used in combination with therapeutic vaccines. In certain embodiments, the compounds of Formula (I), pharmaceutically acceptable salts, solvates, N-oxides, prodrugs and isomers thereof, and pharmaceutical compositions provided herein are included in prophylactic vaccines or used in combination with prophylactic vaccines. In certain embodiments, the compounds of Formula (I), pharmaceutically acceptable salts, solvates, N-oxides, prodrugs and isomers thereof, and pharmaceutical compositions provided herein are included in, or are used in combination with, therapeutic viral vaccines. In certain embodiments, the compounds of Formula (I), pharmaceutically acceptable salts, solvates, N-oxides, prodrugs and isomers thereof, and pharmaceutical compositions provided herein are included in, or are used in combination with, with cancer vaccines.

In other embodiments, the compounds of Formula (I), or a pharmaceutically acceptable salt or solvate thereof, described herein are useful for the treatment of damaged or ageing skin such as scarring and wrinkles.

Administration and Pharmaceutical Compositions

For the therapeutic uses of compounds of Formula (I), or pharmaceutically acceptable salts, solvates, N-oxides, prodrugs and isomers thereof, described herein, such compounds are administered in therapeutically effective amounts either alone or as part of a pharmaceutical composition. Accordingly, provided herein are pharmaceutical compositions, which comprise at least one compound of Formula (I) provided herein, pharmaceutically acceptable salts and/or solvates thereof, and one or more pharmaceutically acceptable carriers, diluents, or excipients. In addition, such compounds and compositions are administered singly or in combination with one or more additional therapeutic agents. The method of administration of such compounds and compositions include, but are not limited to, oral administration, rectal administration, parenteral, intravenous administration, intravitreal administration, intramuscular administration, inhalation, intranasal administration, topical administration, ophthalmic administration or otic administration.

The therapeutically effective amount will vary depending on, among others, the disease indicated, the severity of the disease, the age and relative health of the subject, the potency of the compound administered, the mode of administration and the treatment desired. In certain embodiments, the daily dosage of a compound of Formula (I), satisfactory results are indicated to be obtained systemically at daily dosages of from about 0.03 to 2.5 mg/kg per body weight. In certain embodiments, the daily dosage of a compound of Formula (I), administered by inhalation, is in the range from 0.05 micrograms per kilogram body weight (µg/kg) to 100 micrograms per kilogram body weight (µg/kg). In other embodiments, the daily dosage of a compound of Formula (I), administered orally, is in the range from 0.01 micrograms per kilogram body weight (µg/kg) to 100 milligrams per kilogram body weight (mg/kg). An indicated daily dosage in the larger mammal, e.g. humans, is in the range from about 0.5 mg to about 100 mg of a compound of Formula (I), conveniently administered, e.g. in divided doses up to four times a day or in controlled release form. In certain embodiment, unit dosage forms for oral administration comprise from about 1 to 50 mg of a compound of Formula (I).

Other aspects provided herein are processes for the preparation of pharmaceutical composition which comprise at least one compound of Formula (I) provided herein, or pharmaceutically acceptable salts and/or solvates thereof. In certain embodiments, such processes include admixing a compound of the Formula (I) provided herein, and pharmaceutically acceptable salts and solvates thereof, with one or more pharmaceutically acceptable carriers, diluents or excipients. In certain embodiments, the pharmaceutical compositions comprising a compound of Formula (I) in free form or in a pharmaceutically acceptable salt or solvate form, in association with at least one pharmaceutically acceptable carrier, diluent or excipient are manufactured by mixing, granulating and/or coating methods. In other embodiments, such compositions are optionally contain excipients, such as preserving, stabilizing, wetting or emulsifying agents, solution promoters, salts for regulating the osmotic pressure and/or buffers. In other embodiments, such compositions are sterilized.

Oral Dosage Forms

In certain embodiments, the pharmaceutical compositions containing at least one compound of Formula (I) are administered orally as discrete dosage forms, wherein such dosage forms include, but are not limited to, capsules, gelatin capsules, caplets, tablets, chewable tablets, powders, granules, syrups, flavored syrups, solutions or suspensions in aqueous or non-aqueous liquids, edible foams or whips, and oil-in-water liquid emulsions or water-in-oil liquid emulsions.

The capsules, gelatin capsules, caplets, tablets, chewable tablets, powders or granules, used for the oral administration of at least one compound of Formula (I) are prepared by admixing at least one compound of Formula (I) (active ingredient) together with at least one excipient using conventional pharmaceutical compounding techniques. Non-limiting examples of excipients used in oral dosage forms described herein include, but are not limited to, binders, fillers, disintegrants, lubricants, absorbents, colorants, flavors, preservatives and sweeteners.

Non-limiting examples of such binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof.

Non-limiting examples of such fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions provided herein are present in from about 50 to about 99 weight percent of the pharmaceutical composition or dosage form.

Non-limiting examples of such disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain embodiments, the amount of disintegrant used in the pharmaceutical compositions provided herein is from about 0.5 to about 15 weight percent of disintegrant, while in other embodiments the amount is from about 1 to about 5 weight percent of disintegrant.

Non-limiting examples of such lubricants include, but are not limited to, sodium stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and combinations thereof. In certain embodiments, the amount of lubricants used in the pharmaceutical compositions provided herein is in an amount of less than about 1 weight percent of the pharmaceutical compositions or dosage forms.

Non-limiting examples of such diluents include, but are not limited to, lactose, dextrose, sucrose, mannitol, sorbitol, cellulose, glycine or combinations thereof.

In certain embodiments, tablets and capsules are prepared by uniformly admixing at least one compound of Formula (I) (active ingredients) with liquid carriers, finely divided solid carriers, or both, and then shaping the product into the desired presentation if necessary. In certain embodiments, tablets are prepared by compression. In other embodiments, tablets are prepared by molding.

In certain embodiments, at least one compound of Formula (I) is orally administered as a controlled release dosage form.

Such dosage forms are used to provide slow or controlled-release of one or more compounds of Formula (I). Controlled release is obtained using, for example, hydroxypropylmethyl cellulose, other polymer matrices, gels, permeable membranes, osmotic systems, multilayer coatings, microparticles, liposomes, microspheres, or a combination thereof. In certain embodiments, controlled-release dosage forms are used to extend activity of the compound of Formula (I), reduce dosage frequency, and increase patient compliance.

Administration of compounds of Formula (I) as oral fluids such as solution, syrups and elixirs are prepared in unit dosage forms such that a given quantity of solution, syrups or elixirs contains a predetermined amount of a compound of Formula (I). Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

Parenteral Dosage Forms

In certain embodiments pharmaceutical compositions containing at least one compound of Formula (I) are administered parenterally by various routes including, but not limited to, subcutaneous, intravenous (including bolus injection), intramuscular, and intraarterial.

Such parenteral dosage forms are administered in the form of sterile or sterilizable injectable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Transdermal Dosage Forms

In certain embodiments pharmaceutical compositions containing at least one compound of Formula (I) are administered transdermally. Such transdermal dosage forms include "reservoir type" or "matrix type" patches, which are applied to the skin and worn for a specific period of time to permit the penetration of a desired amount of a compound of Formula (I). By way of example only, such transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In other embodiments, matrix transdermal formulations are used.

Formulations for transdermal delivery of a compound of Formula (I) include an effective amount of a compound of Formula (I), a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof.

In certain embodiments, such transdermal delivery systems include penetration enhancers to assist in delivering one or more compounds of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other embodiments, the pH of such a transdermal pharmaceutical composition or dosage form, or of the tissue to which the pharmaceutical composition or dosage form is applied, is adjusted to improve delivery of one or more compounds of Formula (I). In other embodiments, the polarity of a solvent carrier, its ionic strength, or tonicity are adjusted to improve delivery. In other embodiments, compounds such as stearates are added to advantageously alter the hydrophilicity or lipophilicity of one or more compounds of Formula (I) so as to improve delivery. In certain embodiments, such stearates serve as a lipid vehicle for the formulation, as an emulsifying agent or surfactant, and as a delivery-enhancing or penetration-enhancing agent. In other embodiments, different salts, hydrates or solvates of the compounds of Formula (I) are used to further adjust the properties of the resulting composition.

Topical Dosage Forms

In certain embodiments at least one compound of Formula (I) is administered by topical application of pharmaceutical composition containing at least one compound of Formula (I) in the form of lotions, gels, ointments solutions, emulsions, suspensions or creams. Suitable formulations for topical application to the skin are aqueous solutions, ointments, creams or gels, while formulations for ophthalmic administration are aqueous solutions. Such formulations optionally contain solubilizers, stabilizers, tonicity enhancing agents, buffers and preservatives.

Such topical formulations include at least one carrier, and optionally at least one diluent. Such carriers and diluents include, but are not limited to, water, acetone, ethanol, ethylene glycol, propylene glycol, butane-1,3-diol, isopropyl myristate, isopropyl palmitate, mineral oil, and combinations thereof.

In certain embodiments, such topical formulations include penetration enhancers to assist in delivering one or more compounds of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In certain embodiments pharmaceutical compositions containing at least one compound of Formula (I) are administered by inhalation. Dosage forms for inhaled administration are formulated as aerosols or dry powders. Aerosol formulations for inhalation administration comprise a solution or fine suspension of at least one compound of Formula (I) in a pharmaceutically acceptable aqueous or non-aqueous solvent. In addition, such pharmaceutical compositions optionally comprise a powder base such as lactose, glucose, trehalose, mannitol or starch, and optionally a performance modifier such as L-leucine or another amino acid, and/or metals salts of stearic acid such as magnesium or calcium stearate.

In certain embodiments, compounds of Formula (I) are be administered directly to the lung by inhalation using a Metered Dose Inhaler ("MDI"), which utilizes canisters that contain a suitable low boiling propellant, e.g., dichlorodifluoromethane, trichlorofluoromethane, dichlorotetrafluoroethane, carbon dioxide or other suitable gas, or a Dry Powder Inhaler (DPI) device which uses a burst of gas to create a cloud of dry powder inside a container, which is then be inhaled by the patient. In certain embodiments, capsules and cartridges of gelatin for use in an inhaler or insufflator are formulated containing a powder mixture of a compound of Formula (I) and a powder base such as lactose or starch. In certain embodiments, compounds of Formula (I) are delivered to the lung using a liquid spray device, wherein such devices use extremely small nozzle holes to aerosolize liquid drug formulations that can then be directly inhaled into the lung. In other embodiments, compounds of Formula (I) are delivered to the lung using a nebulizer device, wherein a nebulizers creates an aerosols of liquid drug formulations by using ultrasonic energy to form fine particles that can be readily inhaled. In other embodiments, compounds of Formula (I) are delivered to the lung using an electrohydrodynamic ("EHD") aerosol device wherein such EHD aerosol devices use electrical energy to aerosolize liquid drug solutions or suspensions.

In certain embodiments, the pharmaceutical composition containing at least one compound of Formula (I), or pharmaceutically acceptable salts and solvates thereof, described herein, also contain one or more absorption enhancers. In certain embodiments, such absorption enhancers include, but are not limited to, sodium glycocholate, sodium caprate, N-lauryl-1-D-maltopyranoside, EDTA, and mixed micelles.

In certain embodiments pharmaceutical compositions containing at least one compound of Formula (I) are administered nasally. The dosage forms for nasal administration are formulated as aerosols, solutions, drops, gels or dry powders.

In certain embodiments pharmaceutical compositions containing at least one compound of Formula (I) are administered rectally in the form of suppositories, enemas, ointment, creams rectal foams or rectal gels. In certain embodiments such suppositories are prepared from fatty emulsions or suspensions, cocoa butter or other glycerides.

In certain embodiments pharmaceutical compositions containing at least one compound of Formula (I) are administered opthamically as eye drops. Such formulations are aqueous solutions that optionally contain solubilizers, stabilizers, tonicity enhancing agents, buffers and preservatives.

In certain embodiments pharmaceutical compositions containing at least one compound of Formula (I) are administered otically as ear drops. Such formulations are aqueous solutions that optionally contain solubilizers, stabilizers, tonicity enhancing agents, buffers and preservatives.

In certain embodiments pharmaceutical compositions containing at least one compound of Formula (I) are formulated as a depot preparation. Such formulations are administered by implantation (for example subcutaneously or intramuscularly) or by intramuscular injection. In certain embodiments, such formulations include polymeric or hydrophobic materials (for example, as an emulsion in an acceptable oil) or ion exchange resins, or as sparingly soluble derivatives, for example, as a sparingly soluble salt.

In a further embodiment, the pharmaceutical compositions comprising at least one compound of Formula (I) are adapted for oral administration for the treatment of viral diseases and/or disorders associated with TLR2 activity.

In a further embodiment, the pharmaceutical compositions comprising at least one compound of Formula (I) are adapted for oral administration for the treatment of infectious diseases and/or disorders associated with TLR2.

In a further embodiment, the pharmaceutical compositions comprising at least one compound of Formula (I) are adapted for oral administration for the treatment of bacterial diseases and/or disorders associated with TLR2.

In a further embodiment, the pharmaceutical compositions comprising at least one compound of Formula (I) are adapted for oral administration for the treatment of fungal diseases and/or disorders associated with TLR2.

In a further embodiment, the pharmaceutical compositions comprising at least one compound of Formula (I) are adapted for oral administration for the treatment of cancer associated with TLR2.

In a further embodiment, the pharmaceutical compositions comprising at least one compound of Formula (I) are adapted for intravenous administration for the treatment of cancer associated with TLR2.

In a further embodiment, the pharmaceutical compositions comprising at least one compound of Formula (I) are adapted for oral administration for the treatment of allograft rejection diseases and/or disorders associated with TLR2.

In a further embodiment, the pharmaceutical compositions comprising at least one compound of Formula (I) are adapted for oral administration for the treatment of genitourinary diseases and/or disorders associated with TLR2.

In a further embodiment, the pharmaceutical compositions comprising at least one compound of Formula (I) are adapted for administration as eye drops for the treatment of ophthalmic diseases and/or disorders associated with TLR2.

In a further embodiment, the pharmaceutical compositions comprising at least one compound of Formula (I) are adapted for topical administration for the treatment of dermatological diseases and/or disorders associated with TLR2.

In a further embodiment, the pharmaceutical compositions comprising at least one compound of Formula (I) are adapted for topical administration for the treatment of actinic keratosis. In a further embodiment, the pharmaceutical compositions comprising at least one compound of Formula (I) are adapted for topical administration as a cream for the treatment of actinic keratosis.

In a further embodiment, the pharmaceutical compositions comprising at least one compound of Formula (I) are adapted for topical administration for the treatment of basal cell carcinoma. In a further embodiment, the pharmaceutical compositions comprising at least one compound of Formula (I) are adapted for topical administration as a cream for the treatment of basal cell carcinoma.

In a further embodiment, the pharmaceutical compositions comprising at least one compound of Formula (I) are adapted for administration by inhalation for the treatment of respiratory diseases and/or disorders associated with TLR2. In certain embodiments, the respiratory disease is allergic asthma.

Provided herein are compounds of Formula (I), pharmaceutically acceptable salts and solvates thereof, and pharmaceutical compositions containing at least one compound of Formula (I) and/or pharmaceutically acceptable salts and solvates thereof, for use in activating TLR2 activity, and thereby are used to in the prevention or treatment of diseases and/or disorders associated with TLR2 activity. Such compounds of Formula (I), pharmaceutically acceptable salts and solvates thereof, and pharmaceutical compositions are agonists of TLR2.

Also provided herein are methods for the treatment of a subject suffering from a disease and/or disorder associated with TLR2 activity, wherein the methods include administering to the subject an effective amount of a compound of Formula (I) or a pharmaceutically acceptable salt, solvate, either alone or as part of a pharmaceutical composition as described herein.

Provided herein is the use of a compound of Formula (I), or a pharmaceutically acceptable salt or solvate thereof, in the preparation of a medicament for the treatment of a disease or disorder associated with TLR2 activity.

Combination Treatment

In certain embodiments, a compound of Formula (I) provided herein, or a pharmaceutically acceptable salt or solvate thereof, or a pharmaceutical composition containing at least one compound of Formula (I) provided herein, is administered alone (without an additional therapeutic agent) for the treatment of one or more of the disease and/or disorders associated with TLR activity described herein.

In other embodiments, a compound of Formula (I) provided herein, or a pharmaceutically acceptable salt or solvate thereof, or a pharmaceutical composition containing at least one compound of Formula (I) provided herein, is administered in combination with one or more additional therapeutic agents, for the treatment of one or more of the disease and/or disorders associated with TLR2 activity described herein.

In other embodiments, a compound of Formula (I) provided herein, or a pharmaceutically acceptable salt or solvate thereof, or a pharmaceutical composition containing at least one compound of Formula (I) provided herein, is formulated in combination with one or more additional therapeutic agents and administered for the treatment of one or more of the disease and/or disorders associated with TLR2 activity described herein.

In a compound of Formula (I) provided herein, or a pharmaceutically acceptable salt or solvate thereof, or a pharmaceutical composition containing at least one compound of Formula (I) provided herein, is administered sequentially with one or more additional therapeutic agents, for the treatment of one or more of the disease and/or disorders associated with TLR2 activity described herein.

In other embodiments, the combination treatments provided herein include administration of a compound of Formula (I) provided herein, or a pharmaceutically acceptable salt or solvate thereof, or a pharmaceutical composition containing a compound of Formula (I), prior to administration of one or more additional therapeutic agents, for the treatment of one or more of the disease and/or disorders associated with TLR2 activity described herein.

In other embodiments, the combination treatments provided herein include administration of a compound of Formula (I) provided herein, or a pharmaceutically acceptable salt or solvate thereof, or a pharmaceutical composition containing a compound of Formula (I), subsequent to administration of one or more additional therapeutic agents, for the treatment of one or more of the disease and/or disorders associated with TLR2 activity described herein.

In certain embodiments, the combination treatments provided herein include administration of a compound of Formula (I) provided herein, or a pharmaceutically acceptable salt or solvate thereof, or a pharmaceutical composition containing a compound of Formula (I), concurrently with one or more additional therapeutic agents, for the treatment of one or more of the disease and/or disorders associated with TLR2 activity described herein.

In certain embodiments, the combination treatments provided herein include administration of a compound of Formula (I) provided herein, or a pharmaceutically acceptable salt or solvate thereof, or a pharmaceutical composition containing a compound of Formula (I) formulated with one or more additional therapeutic agents, for the treatment of one or more of the disease and/or disorders associated with TLR2 activity described herein.

In certain embodiments of the combination treatments described herein the compounds of Formula (I), or a pharmaceutically acceptable salts or solvates thereof, are agonists of TLR2 activity.

In certain embodiments of the combination therapies described herein, the compounds of Formula (I) provided herein, or a pharmaceutically acceptable salts or solvates thereof, and the additional therapeutics agent(s) act additively. In certain embodiments of the combination therapies described herein, the compounds of Formula (I) provided herein, or a pharmaceutically acceptable salts or solvates thereof, and the additional therapeutics agent(s) act synergistically.

In other embodiments, a compound of Formula (I) provided herein, or a pharmaceutically acceptable salts or solvates thereof, or a pharmaceutical composition containing a compound of Formula (I), is administered to a patient who has not previously undergone or is not currently undergoing treatment with another therapeutic agent.

The additional therapeutic agents used in combination with at least one compound of Formula (I) provided herein, or a pharmaceutically acceptable salt or solvate thereof, include, but are not limited to antibiotics or antibacterial agents, antiemetic agents, antifungal agents, anti-inflammatory agents, antiviral agents, immunomodulatory agents, cytokines, antidepressants, hormones, alkylating agents, antimetabolites, antitumour antibiotics, antimitotic agents, topoisomerase inhibitors, cytostatic agents, anti-invasion agents, antiangiogenic agents, inhibitors of growth factor function inhibitors of viral replication, viral enzyme inhibitors, anticancer agents, α-interferons, β-interferons, ribavirin, hormones, cytokines, and other toll-like receptor modulators.

The antibiotics or antibacterial agents used in combination with at least one compound of Formula (I) provided herein, or a pharmaceutically acceptable salt or solvate thereof, include, but are not limited to, valganciclovir hydrochloride, metronidazole, a beta-lactam, macrolides (such as, by way of example only, azithromycin, tobramycin (TOBI™)), cephalosporins (such as, by way of example only, cefaclor, cefadroxil, cephalexin, cephradine, cefamandole, cefatrizine, cefazedone, cefixime, cefozopran, cefpimizole, cefuroxime, cefpiramide, cefprozil, cefpirome, KEFLEX™, VELOSEF™, CEFTIN™, CEFZIL™, CECLOR™, SUPRAX™ and DURICEF™), a clarithromycin (such as, by way of example only, clarithromycin and BIAXIN™), an erythromycin (such as, by way of example only, erythromycin and EMYCIN™), ciprofloxacin, CIPRO™, a norfloxacin (such as, by way of example only, NOROXIN™), aminoglycoside antibiotics (such as, by way of example only, apramycin, arbekacin, bambermycins, butirosin, dibekacin, neomycin, neomycin, undecylenate, netilmicin, paromomycin, ribostamycin, sisomicin, and spectinomycin), amphenicol antibiotics (such as, by way of example only, azidamfenicol, chloramphenicol, florfenicol, and thiamphenicol), ansamycin antibiotics (such as, by way of example only, rifamide and rifampin), carbacephems (such as, by way of example only, loracarbef), carbapenems (such as, by way of example only, biapenem and imipenem), cephamycins (such as, by way of example only, cefbuperazone, cefmetazole, and cefminox), monobactams (such as, by way of example only, aztreonam, carumonam, and tigemonam), oxacephems (such as, by way of example only, flomoxef, and moxalactam), penicillins (such as, by way of example only, amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, phencihicillin potassium, V-CILLIN K™ and PEN VEE K™), lincosamides (such as, by way of example only, clindamycin, and lincomycin), amphomycin, bacitracin, capreomycin, colistin, enduracidin, enviomycin, tetracyclines (such as, by way of example only, apicycline, chlortetracycline, clomocycline, and demeclocycline), 2,4-diaminopyrimidines (such as, by way of example only, brodimoprim), nitrofurans (such as, by way of example only, furaltadone, and furazolium chloride), quinolones and analogs thereof (such as, by way of example only, a fluoroquinolone, ofloxacin, cinoxacin, clinafloxacin, flumequine, grepagloxacin and FLOXIN™), sulfonamides (such as, by way of example only, acetyl sulfamethoxypyrazine, benzylsulfamide, noprylsulfamide, phthalylsulfacetamide, sulfachrysoidine, and sulfacytine), sulfones (such as, by way of example only, diathymosulfone, glucosulfone sodium, and solasulfone), cycloserine, mupirocin, tuberin and combinations thereof.

The antiemetic agents used in combination with at least one compound of Formula (I) provided herein, or a pharmaceutically acceptable salt or solvate thereof, include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and combinations thereof.

The antifungal agents used in combination with at least one compound of Formula (I) provided herein, or a pharmaceutically acceptable salt or solvate thereof, include, but are not limited to, amphotericin B, itraconazole, ketoconazole, fluconazole, fosfluconazole, intrathecal, flucytosine, miconazole, butoconazole, itraconazole, clotrimazole, nystatin, terconazole, tioconazole, voriconazole, ciclopirox, econazole, haloprogrin, naftifine, terbinafine, undecylenate, and griseofulvin.

The anti-inflammatory agents used in combination with at least one compound of Formula (I) provided herein, or a pharmaceutically acceptable salt or solvate thereof, include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide, leukotriene antagonists including, but not limited to, zileuton, aurothioglucose, gold sodium thiomalate and auranofin, steroids including, but not limited to, alclometasone diproprionate, amcinonide, beclomethasone dipropionate, betametasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide and other anti-inflammatory agents including, but not limited to, methotrexate, colchicine, allopurinol, probenecid, thalidomide or a derivative thereof, 5-aminosalicylic acid, retinoid, dithranol or calcipotriol, sulfinpyrazone and benzbromarone.

The antiviral agents used in combination with at least one compound of Formula (I) provided herein, or a pharmaceutically acceptable salt or solvate thereof, include, but are not limited to, protease inhibitors, nucleoside/nucleotide reverse transcriptase inhibitors (NRTIs), non-nucleoside reverse transcriptase inhibitors (NNRTIs), CCR1 antagonist, CCR5 antagonists, and nucleoside analogs. The antiviral agents include but are not limited to fomivirsen, didanosine, lamivudine, stavudine, zalcitabine, zidovudine, acyclovir, famciclovir, valaciclovir, ganciclovir, gangcyclovir, cidofovir, zanamivir, oseltamavir, vidarabine, idoxuridine, trifluridine, levovirin, viramidine and ribavirin, as well as foscarnet, amantadine, rimantadine, saquinavir, indinavir, nelfinavir, amprenavir, lopinavir, ritonavir, the α-interferons; β-interferons; adefovir, clevadine, entecavir, pleconaril, HCV-086, EMZ702, emtricitabine, celgosivir, valopicitabine, inhibitors of HCV protease, such as BILN 2061, SCH-503034, ITMN-191 or VX-950, inhibitors of NS5B polymerase such as NM107 (and its prodrug NM283), R1626, R7078, BILN1941, GSK625433, GILD9128 or HCV-796, efavirenz, HBY-097, nevirapine, TMC-120 (dapivirine), TMC-125, BX-471, etravirine, delavirdine, DPC-083, DPC-961, capravirine, rilpivirine, 5-{[3,5-diethyl-1-(2-hydroxyethyl)-1H-pyrazol-4-yl]oxy}isophthalonitrile, GW-678248, GW-695634, MIV-150, calanolide, TAK-779, SC-351125, ancriviroc, vicriviroc, maraviroc, PRO-140, aplaviroc 40, Ono-4128, AK-602), AMD-887 CMPD-167, methyl 1-endo-{8-[(3S)-3-(acetylamino)-3-(3-fluorophenyl)propyl]-8-azabicyclo[3.-2.1]oct-3-yl}-2-methyl-4,5,6,7-tetrahydro-1H-imidazo[4,5-c]pyridine-5-carboxylate, methyl 3-endo-{8-[(3S)-3-(acetamido)-3-(3-fluorophenyl)propyl]-8-azabicyclo[3.2.-1]oct-3-yl}-2-methyl-4,5,6,7-tetrahydro-3H-imidazo[4,5-c]pyridine-5-carboxylate, ethyl 1-endo-{8-[(3S)-3-(acetylamino)-3-(3-fluorophenyl)propyl]-8-azabicyclo[3.-2.1]oct-3-yl}-2-methyl-4,5,6,7-tetrahydro-1H-imidazo[4,5-c]pyridine-5-carboxylate, and N-{(1S)-3-[3-endo-(5-Isobutyryl-2-methyl-4,5,6,7-tetrahydro-1H-imidazo[4,-5-c]pyridin-1-yl)-8-azabicyclo[3.2.1]oct-8-yl]-1-(3-fluorophenyl)propyl}acetamide), BMS-806, BMS-488043, 5-{(1S)-2-[(2R)-4-benzoyl-2-methyl-piperazin-1-yl]-1-methyl-2-oxo-ethoxy}-4-methoxy-pyridine-2-carboxylic acid methylamide and 4-{(1S)-2-[(2R)-4-benzoyl-2-methyl-piperazin-1-yl]-1-methyl-2-oxo-ethoxy}-3-methoxy-N-methyl-benzamide, enfuvirtide (T-20), sifuvirtide SP-01A, T1249, PRO542, AMD-3100, soluble CD4, HMG CoA reductase inhibitors, atorvastatin, 3-O-(3'3'-dimethylsuccinyl) betulic acid (otherwise known as PA-457) and aHGA.

The immunomodulatory agents used in combination with at least one compound of Formula (I) provided herein, or a pharmaceutically acceptable salt or solvate thereof, include, but are not limited to, azathioprine, tacrolimus, cyclosporin methothrexate, leflunomide, corticosteroids, cyclophosphamide, cyclosporine A, cyclosporin G, mycophenolate mofetil, ascomycin, rapamycin (sirolimus), FK-506, mizoribine, deoxyspergualin, brequinar, mycophenolic acid, malononitriloaminides (such as, by way of example only, leflunamide), T cell receptor modulators, and cytokine receptor modulators, peptide mimetics, and antibodies (such as, by way of example only, human, humanized, chimeric, monoclonal, polyclonal, Fvs, ScFvs, Fab or F(ab)$_2$ fragments or epitope binding fragments), nucleic acid molecules (such as, by way of example only, antisense nucleic acid molecules and triple helices), small molecules, organic compounds, and inorganic compounds. Examples of T cell receptor modulators include, but are not limited to, anti-T cell receptor antibodies (such as, by way of example only, anti-CD4 antibodies (such as, by way of example only, cM-T412 (Boehringer), IDEC-CE9.1™ (IDEC and SKB), mAB 4162W94, Orthoclone and OKTcdr4a (Janssen-Cilag)), anti-CD3 antibodies (such as, by way of example only, Nuvion (Product Design Labs), OKT3 (Johnson & Johnson), or Rituxan (IDEC)), anti-CD5 antibodies (such as, by way of example only, an anti-CD5 ricin-linked immunoconjugate), anti-CD7 antibodies (such as, by way of example only, CHH-380 (Novartis)), anti-CD8 antibodies, anti-CD40 ligand monoclonal antibodies (such as, by way of example only, IDEC-131 (IDEC)), anti-CD52 antibodies (such as, by way of example only, CAMPATH 1H (Ilex)), anti-CD2 antibodies, anti-CD11a antibodies (such as, by way of example only, Xanelim (Genentech)), anti-B7 antibodies (such as, by way of example only, IDEC-114 (IDEC)), CTLA4-immunoglobulin, and other toll receptor-like (TLR) modulators. Examples of cytokine receptor modulators include, but are not limited to, soluble cytokine receptors (such as, by way of example only, the extracellular domain of a TNF-receptor or a fragment thereof, the extracellular domain of an IL-1β receptor or a fragment thereof, and the extracellular domain of an IL-6 receptor or a fragment thereof), cytokines or fragments thereof (such as, by way of example only, interleukin (IL)-2, IL-3, IL-4, IL-5, IL-6, IL-7, IL-8, IL-9, IL-10, IL-11, IL-12, IL-15, TNF-α, interferon (IFN)-α, IFN-β, IFN-γ, and GM-CSF), anti-cytokine receptor antibodies (such as, by way of example only, anti-IFN receptor antibodies, anti-IL-2 receptor antibodies (such as, by way of example only, Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (such as, by way of example only, anti-IFN antibodies, anti-TNF-α antibodies, anti-IL-1β antibodies, anti-IL-6 antibodies, and anti-IL-8 antibodies (such as, by way of example only, ABX-IL-8 (Abgenix)), and anti-IL-12 antibodies).

The cytokines or modulator of cytokine function used in combination with at least one compound of Formula (I) provided herein, or a pharmaceutically acceptable salt or solvate thereof, include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, alpha-, beta-, and gamma-interferon, interferon β-1a, interferon β-1b, interferon α-1, interferon α-2a (roferon), interferon α-2b, pegylated interferons (by way of example only, peginterferon α-2a and peginterferon α-2b), intron, Peg-Intron, Pegasys, consensus interferon (infergen), albumin-interferon α and albuferon.

The antidepressants used in combination with at least one compound of Formula (I) provided herein, or a pharmaceutically acceptable salt or solvate thereof, include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, echinopsidine iodide, etryptamine, iproclozide, iproniazid, isocarboxazid, mebanazine, metfendrazine, nialamide, pargyline, octamoxin, phenelzine, pheniprazine, phenoxypropazine, pivhydrazine, safrazine, selegiline, 1-deprenyl, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

In certain embodiments, the antidepressants used in combination with at least one compound of Formula (I) provided herein, or a pharmaceutically acceptable salt or solvate thereof, are MAO-inhibitors including, but are not limited to, benmoxin, echinopsidine iodide, etryptamine, iproclozide, iproniazid, isocarboxazid, mebanazine, metfendrazine, moclobamide, nialamide, pargyline, phenelzine, pheniprazine, phenoxypropazine, pivhydrazine, safrazine, selegiline, 1-deprenyl, toloxatone and tranylcypromine.

The hormones used in combination with at least one compound of Formula (I) provided herein, or a pharmaceutically acceptable salt or solvate thereof, include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, thymostimulin, synthetic and natural opioids, insulin thyroid stimulating hormones, and endorphins.

The alkylating agents used in combination with at least one compound of Formula (I) provided herein, or a pharmaceutically acceptable salt or solvate thereof, include, but are not limited to, nitrogen mustards, ethylenimines, methylmelamines, alkyl sulfonates, nitrosoureas, carmustine, lomustine, triazenes, melphalan, mechlorethamine, cis-platin, oxaliplatin, carboplatin, cyclophosphamide, ifosfamide, melphalan, chlorambucil, hexamethylmelaine, thiotepa, busulfan, carmustine, streptozocin, dacarbazine and temozolomide.

The antimetabolites used in combination with at least one compound of Formula (I) provided herein, or a pharmaceutically acceptable salt or solvate thereof, include, but are not limited to, cytarabile, gemcitabine and antifolates such as, by way of example only, fluoropyrimidines (by way of example only, 5-fluorouracil and tegafur), raltitrexed, methotrexate, cytosine arabinoside, and hydroxyurea.

The antitumour antibiotics in combination with at least one compound of Formula (I) provided herein, or a pharmaceutically acceptable salt or solvate thereof, include, but are not limited to, anthracyclines, bleomycin, doxorubicin, daunomycin, epirubicin, idarubicin, mitomycin-C, dactinomycin and mithramycin.

The antimitotic agents used in combination with at least one compound of Formula (I) provided herein, or a pharmaceutically acceptable salt or solvate thereof, include, but are not limited to, vinca alkaloids (by way of example only, vincristine, vinblastine, vindesine and vinorelbine), taxoids (by way of example only, taxol, paclitaxel and taxotere) and polokinase inhibitors.

The topoisomerase inhibitors used in combination with at least one compound of Formula (I) provided herein, or a pharmaceutically acceptable salt or solvate thereof, include, but are not limited to, epipodophyllotoxins by way of example only, etoposide and teniposide, amsacrine, topotecan, irinotecan and camptothecin.

The cytostatic agents used in combination with at least one compound of Formula (I) provided herein, or a pharmaceutically acceptable salt or solvate thereof, include, but are not limited to, antioestrogens (such as, by way of example only, tamoxifen, fulvestrant, toremifene, raloxifene, droloxifene and iodoxyfene), antiandrogens (such as, by way of example only, bicalutamide, flutamide, nilutamide and cyproterone acetate), LHRH antagonists or LHRH agonists (such as, by way of example only, goserelin, leuprorelin, leuprolide and buserelin), progestogens (such as, by way of example only, megestrol acetate), aromatase inhibitors (such as, by way of example only, as anastrozole, letrozole, vorazole and exemestane) and inhibitors of 5α-reductase (such as, by way of example only, finasteride).

The anti-invasion agents used in combination with at least one compound of Formula (I) provided herein, or a pharmaceutically acceptable salt or solvate thereof, include, but are not limited to, c-Src kinase family inhibitors (such as, by way of example only, 4-(6-chloro-2,3-methylenedioxyanilino)-7-[2-(4-methylpiperazin-1-yl)ethoxy]-5-tetrahydropyran-4-yloxyquinazoline (AZD0530) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825)), and metalloproteinase inhibitors (such as, by way of example only, marimastat, inhibitors of urokinase plasminogen activator receptor function and antibodies to Heparanase).

The antiangiogenic agents used in combination with at least one compound of Formula (I) provided herein, or a pharmaceutically acceptable salt or solvate thereof, include, but are not limited to, those which inhibit the effects of vascular endothelial growth factor such as, by way of example only, anti-vascular endothelial cell growth factor antibody bevacizumab (AVASTIN™) and VEGF receptor tyrosine kinase inhibitors such as 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787) and SUI 1248 (sunitinib), linomide, and inhibitors of integrin αvβ3 function and angiostatin.

The inhibitors of growth factor function used in combination with at least one compound of Formula (I) provided herein, or a pharmaceutically acceptable salt or solvate thereof, include, but are not limited to, growth factor antibodies and growth factor receptor antibodies (such as, by way of example only, the anti-erbB2 antibody trastuzumab (HERCEPTIN™), the anti-EGFR antibody panitumumab, the anti-erbB1 antibody cetuximab (Erbitux, C225), tyrosine kinase inhibitors, such as, by way of example only, inhibitors of the epidermal growth factor family (for example EGFR family tyrosine kinase inhibitors such as, by way of example only, N-(3-chloro-4-fluorophenyl)-7-methoxy-6-(3-orpholinopropoxy)quinazolin-4-amine (gefitinib, ZDI 839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as, by way of example only, lapatinib, inhibitors of the hepatocyte growth factor family, inhibitors of the platelet-derived growth factor family such as imatinib, GLEEVEC™, inhibitors of serine/threonine kinases (such as, by way of example only, Ras/Raf signaling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1 152, PH739358, VX-680, MLv8054, R763, MP235, MP529, VX-528 AND AX39459) and cyclin dependent kinase inhibitors such as CDK2 and/or CDK4 inhibitors.

In other embodiments, at least one compound of Formula (I) provided herein, or a pharmaceutically acceptable salt or solvate thereof, is used in combination with vascular damaging agents such as, by way of example only, Combretastatin A4.

In other embodiments, at least one compound of Formula (I) provided herein, or a pharmaceutically acceptable salt or solvate thereof, is used in combination with antisense therapies, such as, by way of example only, ISIS 2503, an anti-ras antisense.

In other embodiments, at least one compound of Formula (I) provided herein, or a pharmaceutically acceptable salt or solvate thereof, is used in combination with gene therapy approaches, including for example approaches to replace aberrant genes such as aberrant p53 or aberrant BRCA1 or BRCA2, GDEPT (gene-directed enzyme pro-drug s therapy) approaches such as those using cytosine deaminase, thymidine kinase or a bacterial nitroreductase enzyme and approaches to increase patient tolerance to chemotherapy or radiotherapy such as multi-drug resistance gene therapy.

In other embodiments, at least one compound of Formula (I) provided herein, or a pharmaceutically acceptable salt or solvate thereof, is used in combination with immunotherapy approaches, including for example ex-vivo and in-vivo approaches to increase the immunogenicity of patient tumor cells, such as transfection with cytokines such o as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies.

In other embodiments, at least one compound of Formula (I) provided herein, or a pharmaceutically acceptable salt or solvate thereof, is used in combination with other treatment methods including, but not limited to, surgery and radiotherapy (γ-radiation, neutron beam radiotherapy, electron beam radiotherapy, proton therapy, brachytherapy, and systemic radioactive isotopes).

In certain embodiments, the compounds of Formula (I) provided herein, or pharmaceutically acceptable salts and solvates thereof, are administered or formulated in combination with an absorption enhancer, including, but not limited to, sodium glycocholate, sodium caprate, N-lauryl-D-maltopyranoside, EDTA, and mixed micelles. In certain embodiments, such absorption enhancers target the lymphatic system.

In certain embodiments, the additional therapeutic agent(s) used in the combination therapies described herein include, but are not limited to, agents such as tumor necrosis factor alpha (TNF-α) inhibitors (such as anti-TNF monoclonal antibodies (by way of example only, Remicade, CDP-870 and adalimumab) and TNF receptor immunoglobulin molecules (by way of example only, Enbrel)); non-selective cyclo-oxygenase COX-1/COX-2 inhibitors (by way of example only, piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (by way of example only, meloxicam, celecoxib, rofecoxib, valdecoxib, lumarocoxib, parecoxib and etoricoxib); glucocorticosteroids; methotrexate, lefunomide; hydroxychloroquine, d-penicillamine, auranofin or other parenteral or oral gold preparations.

In other embodiments, the combinations described herein include combination of a compound of Formula (I) provided herein, or a pharmaceutically acceptable salt or solvate thereof, with a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAYx1005.

In other embodiments, the combinations described herein include combination of a compound of Formula (I) provided herein, or a pharmaceutically acceptable salt or solvate thereof, with a receptor antagonist for leukotrienes (LT B4, LTC4, LTD4, and LTE4) selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, SINGULAIR™, pranlukast, verlukast (MK-679), RG-12525, Ro-245913, iralukast (CGP 45715A), and BAYx7195.

In other embodiments, the combinations described herein include combination of a compound of Formula (I) provided herein, or a pharmaceutically acceptable salt or solvate thereof, with a phosphodiesterase (PDE) inhibitor such as a methylxanthanine including theophylline and aminophylline; a selective PDE isoenzyme inhibitor including a PDE4 inhibitor, including, but not limited to, cilomilast or roflumilast, an inhibitor of the isoform PDE4D, or an inhibitor of PDE5.

In other embodiments, the combinations described herein include combination of a compound of Formula (I) provided herein, or a pharmaceutically acceptable salt or solvate thereof, with a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine.

In other embodiments, the combinations described herein include combination of a compound of Formula (I) provided herein, or a pharmaceutically acceptable salt or solvate thereof, with a gastroprotective histamine type 2 receptor antagonist. In other embodiments, the combinations described herein include combination of a compound of Formula (I), or a pharmaceutically acceptable salt or solvate thereof, described herein, with an antagonist of the histamine type 4 receptor.

In other embodiments, the combinations described herein include combination of a compound of Formula (I) provided herein, or a pharmaceutically acceptable salt or solvate thereof, with an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

In other embodiments, the combinations described herein include combination of a compound of Formula (I) provided herein, or a pharmaceutically acceptable salt or solvate thereof, with an anticholinergic agent including muscarinic receptor (M1, M2, and M3) antagonists such as atropine, hyoscine, glycopyrrrolate, ipratropium bromide, tiotropium bromide, oxitropium bromide, pirenzepine or telenzepine.

In other embodiments, the combinations described herein include combination of a compound of Formula (I) provided herein, or a pharmaceutically acceptable salt or solvate thereof, with a beta-adrenoceptor agonist (including beta receptor subtypes 1-4) such as isoprenaline, salbutamol, albuterol, formoterol, salmeterol, terbutaline, orciprenaline, bitolterol mesylate, and pirbuterol.

In other embodiments, the combinations described herein include combination of a compound of Formula (I) provided herein, or a pharmaceutically acceptable salt or solvate thereof, with a chromone, such as sodium cromoglycate or nedocromil sodium.

In other embodiments, the combinations described herein include combination of a compound of Formula (I) provided herein, or a pharmaceutically acceptable salt or solvate thereof, with an insulin-like growth factor type I (IGF-I) mimetic.

In other embodiments, the combinations described herein include combination of a compound of Formula (I) provided herein, or a pharmaceutically acceptable salt or solvate thereof, with a glucocorticoid, such as flunisolide, triamcinolone acetonide, beclomethasone dipropionate, budesonide, fluticasone propionate, ciclesonide or mometasone furoate.

In other embodiments, the combinations described herein include combination of a compound of Formula (I) provided herein, or a pharmaceutically acceptable salt or solvate thereof, with an inhibitor of matrix metalloproteases (MMPs), i.e., the stromelysins, the collagenases, and the gelatinases, as well as aggrecanase; especially collagenase-1 (MMP-I), collagenase-2 (MMP-8), collagenase-3 (MMP-13), stromelysin-1 (MMP-3), stromelysin-2 (MMP-IO), and stromelysin-3 (MMP-I1) and MMP-9 and MMP-12.

In other embodiments, the combinations described herein include combination of a compound of Formula (I) provided herein, or a pharmaceutically acceptable salt or solvate thereof, with modulators of chemokine receptor function such as antagonists of CCR1, CCR2, CCR2A, CCR2B, CCR3, CCR4, CCR5, CCR6, CCR7, CCR8, CCR9, CCR100 and CCR11 (for the C—C family); CXCR1, CXCR2, CXCR3, CXCR4 and CXCR5 (for the C—X—C family) and CX3CR1 for the C—X3-C family.

In other embodiments, the combinations described herein include combination of a compound of Formula (I) provided herein, or a pharmaceutically acceptable salt or solvate thereof, with an immunoglobulin (Ig), gamma globulin, Ig preparation or an antagonist or antibody modulating Ig function such as anti-IgE (omalizumab).

Compounds of Formula (I) as Immune Potentiators

In certain embodiments, pharmaceutical compositions containing at least one compound of Formula (I) provided herein, or a pharmaceutically acceptable salt or solvate thereof, are immunogenic compositions. In certain embodiments, such immunogenic compositions are useful as vaccines. In certain embodiments, such vaccines are prophylactic (i.e. to prevent infection), while in other embodiments, such vaccines are therapeutic (i.e. to treat infection).

In other embodiments, the compound(s) of Formula (I) provided herein, or a pharmaceutically acceptable salt or solvate thereof, are immune potentiators and impart an immunostimulatory effect upon administration when compared to immunogenic formulations that do not contain compound(s) of Formula (I). In certain embodiments, compounds of Formula (I) impart an immunostimulatory effect upon administration when included in an immunogenic composition having one or more immunoregulatory agents, while in other embodiments, compounds of Formula (I) impart an immunostimulatory effect upon administration when included in an immunogenic composition without the presence of other immunoregulatory agents.

The immunostimulatory effect referred to herein is often an enhancement of the immunogenic composition's effect. In certain embodiments the enhancement of the efficacy of the immunogenic composition is by at least 10% relative to the effect of the immunogenic composition in the absence of the immune potentiator. In certain embodiments the enhancement of the efficacy of the immunogenic composition is by at least 20% relative to the effect of the immunogenic composition in the absence of the immune potentiator. In certain embodiments the enhancement of the efficacy of the immunogenic composition is by at least 30% relative to the effect of the immunogenic composition in the absence of the immune potentiator. In certain embodiments the enhancement of the efficacy of the immunogenic composition is by at least 40% relative to the effect of the immunogenic composition in the absence of the immune potentiator. In certain embodiments the enhancement of the efficacy of the immunogenic composition is by at least 50% relative to the effect of the immunogenic composition in the absence of the immune potentiator. In certain embodiments the enhancement of the efficacy of the immunogenic composition is by at least 60% relative to the effect of the immunogenic composition in the absence of the immune potentiator. In certain embodiments the enhancement of the efficacy of the immunogenic composition is by at least 70% relative to the effect of the immunogenic composition in the absence of the immune potentiator. In certain embodiments the enhancement of the efficacy of the immunogenic composition is by at least 80% relative to the effect of the immunogenic composition in the absence of the immune potentiator. In certain embodiments the enhancement of the efficacy of the immunogenic composition is by at least 90% relative to the effect of the immunogenic composition in the absence of the immune potentiator. In certain embodiments the enhancement of the efficacy of the immunogenic composition is by at least 100% relative to the effect of the immunogenic composition in the absence of the immune potentiator.

In certain embodiments, the enhancement of the immunogenic composition's effect is measured by the increased effectiveness of the immunogenic composition for achieving its protective effects. In certain embodiments, this increased effectiveness is measured as a decreased probability that a subject receiving the immunogenic composition will experience a condition for which the immunogenic composition is considered protective, or a decrease in duration or severity of the effects of such condition. In other embodiments, this increased effectiveness is measured as an increase in a titer of an antibody elicited by the immunogenic composition in a treated subject.

Along with one or more compounds of Formula (I) provided herein, or a pharmaceutically acceptable salt or solvate thereof, such immunogenic compositions include an effective amount of one or more antigens, and a pharmaceutically acceptable carrier. Such carriers are include, but are not limited to, proteins, polysaccharides, polylactic acids, polyglycolic acids, polymeric amino acids, amino acid copolymers, sucrose, trehalose, lactose, lipid aggregates (such as oil droplets or liposomes), and inactive virus particles. The immunogenic compositions typically also contain diluents, such as water, saline, and glycerol, and optionally contain other excipients, such as wetting or emulsifying agents, and pH buffering substances.

In certain embodiments, immunogenic compositions optionally include one or more immunoregulatory agents. In certain embodiments, one or more of the immunoregulatory agents include one or more adjuvants. Such adjuvants include, but are not limited to, a TH1 adjuvant and/or a TH2 adjuvant, further discussed below. In certain embodiments, the adjuvants used in immunogenic compositions provide herein include, but are not limited to:

A. Mineral-Containing Compositions;
B. Oil Emulsions;
C. Saponin Formulations;
D. Virosomes and Virus-Like Particles;
E. Bacterial or Microbial Derivatives;
F. Human Immunomodulators;
G. Bioadhesives and Mucoadhesives;
H. Microparticles;
I. Liposomes;
J. Polyoxyethylene Ether and Polyoxyethylene Ester Formulations;
K. Polyphosphazene (PCPP);
L. Muramyl Peptides, and
M. Imidazoquinolone Compounds.

Mineral-containing compositions suitable for use as adjuvants include, but are not limited to, mineral salts, such as aluminium salts and calcium salts. By way of example only, such mineral salts include, hydroxides (e.g. oxyhydroxides, including aluminium hydroxides and aluminium oxyhydroxides), phosphates (e.g. hydroxyphosphates and orthophosphates, including aluminium phosphates, aluminium hydroxyphosphates, aluminium orthophosphates and calcium phosphate), sulfates (e.g. aluminium sulfate), or mixtures of different mineral compounds. Such mineral salts are in any suitable form, such as, by way of example only, gel, crystalline, and amorphous forms. In certain embodiments, such mineral containing compositions are formulated as a particle of the metal salt. In certain embodiments, components of the immunogenic compositions described herein are adsorbed to such mineral salts. In certain embodiments, an aluminium hydroxide and/or aluminium phosphate adjuvant is used in the immunogenic compositions described herein. In other embodiments, antigens used in an immunogenic composition described herein are adsorbed to such aluminium hydroxide and/or aluminium phosphate adjuvants. In certain embodiments, a calcium phosphate adjuvant is used in the immunogenic compositions described herein. In other embodiments, antigens used in an immunogenic composition described herein are adsorbed to such calcium phosphate adjuvants.

In certain embodiments, aluminum phosphates are used as an adjuvant in the immunogenic compositions described herein. In other embodiments, aluminum phosphates are used as an adjuvant in the immunogenic compositions described herein, wherein such compositions include a H. influenzae saccharide antigen. In certain embodiments, the adjuvant is amorphous aluminium hydroxyphosphate with a $PO_4$/Al molar ratio between 0.84 and 0.92, included at 0.6 mg $Al^{3+}$/ml. In other embodiments, adsorption with a low dose of aluminium phosphate is used, by way of example only, between 50 and 100 μg $Al^{3+}$ per conjugate per dose. Where there is more than one conjugate in a composition, not all conjugates need to be adsorbed.

Oil emulsions suitable for use as adjuvants include, but are not limited to, squalene-water emulsions (such as MF59 (5% Squalene, 0.5% Tween 80, and 0.5% Span 85, formulated into submicron particles using a microfluidizer), Complete Freund's adjuvant (CFA) and incomplete Freund's adjuvant (IFA).

Saponins are a heterologous group of sterol glycosides and triterpenoid glycosides that are found in the bark, leaves, stems, roots and even flowers of a wide range of plant species. Saponin formulations suitable for use as adjuvants include, but are not limited to, saponins from the bark of the *Quillaia saponaria* Molina tree, from *Smilax ornata* (sarsaprilla), *Gypsophilla paniculata* (brides veil), and *Saponaria officianalis* (soap root). In certain embodiments, saponin formulations suitable for use as adjuvants include, but are not limited to, purified formulations including, but are not limited to, QS7, QS17, QS18, QS21, QH-A, QH-B and QH-C. QS21 is marketed as STIMULOM™. In other embodiments, saponin formulations include sterols, cholesterols and lipid formulations, such as unique particles formed by the combinations of saponins and cholesterols called immunostimulating complexes (ISCOMs). In certain embodiments, the ISCOMs also include a phospholipid such as phosphatidylethanolamine or phosphatidylcholine. Any known saponin can be used in ISCOMs. In certain embodiments, the ISCOM includes one or more of QuilA, QHA & QHC. In other embodiments, the ISCOMS are optionally devoid of an additional detergent.

Virosomes and virus-like particles (VLPs) suitable for use as adjuvants include, but are not limited to, one or more proteins from a virus optionally combined or formulated with a phospholipid. Such virosomes and VLPs are generally non-pathogenic, non-replicating and generally do not contain any of the native viral genome. In certain embodiments, the viral proteins are recombinantly produced, while in other embodiments the viral proteins are isolated from whole viruses.

The viral proteins suitable for use in virosomes or VLPs include, but are not limited to, proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Q-phage (such as coat proteins), GA-phage, fr-phage, AP205 phage, and Ty (such as retrotransposon Ty protein p1).

Bacterial or microbial derivatives suitable for use as adjuvants include, but are not limited to, bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. Such non-toxic derivatives of LPS include, but are not limited to, monophosphoryl lipid A (MPL) and 3-O-deacylated MPL (3dMPL). 3dMPL is a mixture of 3 de-O-acylated monophosphoryl lipid A with 4, 5 or 6 acylated chains. Other non-toxic LPS derivatives include monophosphoryl lipid A mimics, such as aminoalkyl glucosaminide phosphate derivatives (e.g. RC-529). Lipid A derivatives include, but are not limited to, derivatives of lipid A from *Escherichia coli* (e.g. OM-174).

Immunostimulatory oligonucleotides used as adjuvants include, but are not limited to, nucleotide sequences containing a CpG motif (a dinucleotide sequence containing an unmethylated cytosine linked by a phosphate bond to a guanosine). Such CpG sequences can be double-stranded or single-stranded. In certain embodiments, such nucleotide sequences are double-stranded RNAs or oligonucleotides containing palindromic or poly(dG) sequences. In other embodiments, the CpG's include nucleotide modifications/analogs such as phosphorothioate modifications.

In certain embodiments the CpG sequence are directed to TLR9, and in certain embodiments the motif is GTCGTT or TTCGTT. In certain embodiments the CpG sequence is specific for inducing a Th1 immune response, such as, by way of example only, a CpG-A ODN, or in other embodiments the CpG sequence is more specific for inducing a B cell response, such as, by way of example only, a CpG-B ODN. In certain embodiments the CpG is a CpG-A ODN.

In certain embodiments the CpG oligonucleotide is constructed so that the 5' end is accessible for receptor recognition. In other embodiments two CpG oligonucleotide sequences are optionally attached at their 3' ends to form "immunomers".

A particularly useful adjuvant based around immunostimulatory oligonucleotides is known as IC-31™. In certain embodiments, an adjuvant used with immunogenic compositions described herein, includes a mixture of (i) an oligonucleotide (such as, by way of example only, between 15-40 nucleotides) including at least one (and preferably multiple) CpI motifs (such as, by way of example only, a cytosine linked to an inosine to form a dinucleotide), and (ii) a polycationic polymer, such as, by way of example only, an oligopeptide (such as, by way of example only, between 5-20 amino acids) including at least one (and preferably multiple) Lys-Arg-Lys tripeptide sequence(s). In certain embodiments, the oligonucleotide is a deoxynucleotide comprising 26-mer sequence 5'-(IC)$_{13}$-3'. In other embodiments, the polycationic polymer is a peptide comprising 11-mer amino acid sequence KLKLLLLLKLK.

In certain embodiments, bacterial ADP-ribosylating toxins and detoxified derivatives thereof are used as adjuvants in the immunogenic compositions described herein. In certain embodiments, such proteins are derived from E. coli (E. coli heat labile enterotoxin "LT"), cholera ("CT"), or pertussis ("PT"). In other embodiments, the toxin or toxoid is in the form of a holotoxin, comprising both A and B subunits. In other embodiments, the A subunit contains a detoxifying mutation; whereas the B subunit is not mutated. In other embodiments, the adjuvant is a detoxified LT mutant such as LT-K63, LT-R72, and LT-G192.

The human immunomodulators suitable for use as adjuvants include, but are not limited to, cytokines, such as, by way of example only, interleukins (IL-1, IL-2, IL-4, IL-5, IL-6, IL-7, IL-12), interferons (such as, by way of example only, interferon-γ), macrophage colony stimulating factor, and tumor necrosis factor.

The bioadhesives and mucoadhesives used as adjuvants in the immunogenic compositions described herein include, but are not limited to, esterified hyaluronic acid microspheres, and cross-linked derivatives of poly(acrylic acid), polyvinyl alcohol, polyvinyl pyrollidone, polysaccharides and carboxymethylcellulose. In certain embodiments, chitosan and derivatives thereof are used as in the vaccine compositions described herein adjuvants.

The microparticles suitable for use as adjuvants include, but are not limited to, microparticles formed from materials that are biodegradable and non-toxic (e.g. a poly(.alpha.-hydroxy acid), a polyhydroxybutyric acid, a polyorthoester, a polyanhydride, a polycaprolactone, etc.), with poly(lactide-co-glycolide). In certain embodiments, such microparticles are treated to have a negatively-charged surface (e.g. with SDS) or a positively-charged surface (e.g. with a cationic detergent, such as CTAB). The microparticles suitable for use as adjuvants have a particle diameter of about. 100 nm to about 150 µm in diameter. In certain embodiments, the particle diameter is about 200 nm to about 30 µm, and in other embodiments the particle diameter is about 500 nm to 10 µm.

The polyoxyethylene ether and polyoxyethylene ester formulations suitable for use as adjuvants include, but are not limited to, polyoxyethylene sorbitan ester surfactants in combination with an octoxynol, and polyoxyethylene alkyl ethers or ester surfactants in combination with at least one additional non-ionic surfactant such as an octoxynol. In certain embodiments, the polyoxyethylene ethers are selected from polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

The muramyl peptides suitable for use as adjuvants include, but are not limited to, N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-s-n-glycero-3-hydroxyphosphoryloxy)-ethylamine MTP-PE).

In certain embodiments, one or more compounds of Formula (I) used as an immune potentiator are included in compositions having combinations of one or more of the adjuvants identified above. Such combinations include, but are not limited to, (1) a saponin and an oil-in-water emulsion;
(2) a saponin (e.g. QS21)+a non-toxic LPS derivative (e.g. 3dMPL);
(3) a saponin (e.g. QS21)+a non-toxic LPS derivative (e.g. 3dMPL)+a cholesterol;
(4) a saponin (e.g. QS21)+3dMPTL+IL-12 (optionally including a sterol);
(5) combinations of 3dMPL with, for example, QS21 and/or oil-in-water emulsions;
(6) SAF, containing 10% squalane, 0.4% Tween 80™, 5% pluronic-block polymer $L_{121}$, and thr-MDP, either microfluidized into a submicron emulsion or vortexed to generate a larger particle size emulsion.
(7) RIBI™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and
(8) one or more mineral salts (such as an aluminum salt)+a non-toxic derivative of LPS (such as 3dMPL).

In other embodiments, the adjuvant combinations used in the immunogenic combinations provided herein include combinations of Th1 and Th2 adjuvants such as, by way of example only, CpG and alum or resiquimod and alum.

In certain embodiments, the immunogenic compositions provided herein elicit both a cell mediated immune response as well as a humoral immune response. In other embodiments, the immune response induces long lasting (e.g. neutralising) antibodies and a cell mediated immunity that quickly responds upon exposure to the infectious agent.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class 1 molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-β), an increase in activated macrophages, an increase in NK activity, or an increase in the production of IgG2a. Preferably, the enhanced TH1 immune response will include an increase in IgG2a production.

TH1 adjuvants can be used to elicit a TH1 immune response. A TH1 adjuvant will generally elicit increased levels of IgG2a production relative to immunization of the antigen without adjuvant. TH1 adjuvants suitable for use in immunogenic compositions provided herein include, but are not limited to, saponin formulations, virosomes and virus like particles, non-toxic derivatives of enterobacterial lipopolysaccharide (LPS), immunostimulatory oligonucleotides. In certain embodiments, the immunostimulatory oligonucleotides used as TH1 adjuvants in the immunogenic compositions provided herein contain a CpG motif.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

TH2 adjuvants can be used to elicit a TH2 immune response. A TH2 adjuvant will generally elicit increased levels of IgG1 production relative to immunization of the antigen without adjuvant. TH2 adjuvants suitable for use in immunogenic compositions provided herein include, but are not limited to, mineral containing compositions, oil-emulsions, and ADP-ribosylating toxins and detoxified derivatives thereof. In certain embodiments, the mineral containing compositions used as TH2 adjuvants in the immunogenic compositions provided herein are aluminium salts.

In certain embodiments, the immunogenic compositions provided herein include a TH1 adjuvant and a TH2 adjuvant. In other embodiments, such compositions elicit an enhanced TH1 and an enhanced TH2 response, such as, an increase in the production of both IgG1 and IgG2a production relative to immunization without an adjuvant. In still other embodiments, such compositions comprising a combination of a TH1 and a TH2 adjuvant elicit an increased TH1 and/or an increased TH2 immune response relative to immunization with a single adjuvant (i.e., relative to immunization with a TH1 adjuvant alone or immunization with a TH2 adjuvant alone).

In certain embodiments, the immune response is one or both of a TH1 immune response and a TH2 response. In other embodiments, the immune response provides for one or both of an enhanced TH1 response and an enhanced TH2 response.

In certain embodiments, the enhanced immune response is one or both of a systemic and a mucosal immune response. In other embodiments, the immune response provides for one or both of an enhanced systemic and an enhanced mucosal immune response. In certain embodiments, the mucosal immune response is a TH2 immune response. In certain embodiments, the mucosal immune response includes an increase in the production of IgA.

In certain embodiments the immunogenic compositions provided herein are used as vaccines, wherein such compositions include an immunologically effective amount of one or more antigen).

Antigens for use in the immunogenic compositions provided herein may be provided in an effective amount (e.g., an amount effective for use in therapeutic, prophylactic or diagnostic methods). For example, immunogenic compositions of the invention may be used to treat or prevent infections caused by any of the below-listed pathogens.

Antigens for use in the immunogenic compositions provided herein are typically macromolecules (e.g., polypeptides, polysaccharides, polynucleotides) that are foreign to the host, and include, but are not limited to, one or more of the antigens set forth below, or antigens derived from one or more of the pathogens set forth below.

Bacterial Antigens

Bacterial antigens suitable for use in immunogenic compositions provided herein include, but are not limited to, proteins, polysaccharides, lipopolysaccharides, polynucleotides, and outer membrane vesicles which are isolated, purified or derived from a bacteria. In certain embodiments, the bacterial antigens include bacterial lysates and inactivated bacteria formulations. In certain embodiments, the bacterial antigens are produced by recombinant expression. In certain embodiments, the bacterial antigens include epitopes which are exposed on the surface of the bacteria during at least one stage of its life cycle. Bacterial antigens are preferably conserved across multiple serotypes. In certain embodiments, the bacterial antigens include antigens derived from one or more of the bacteria set forth below as well as the specific antigens examples identified below:

*Neisseria meningitidis*: Meningitidis antigens include, but are not limited to, proteins, saccharides (including a polysaccharide, oligosaccharide, lipooligosaccharide or lipopolysaccharide), or outer-membrane vesicles purified or derived from *N. meningitides* serogroup such as A, C, W135, Y, X and/or B. In certain embodiments meningitides protein antigens are be selected from adhesions, autotransporters, toxins, Fe acquisition proteins, and membrane associated proteins (preferably integral outer membrane protein).

*Streptococcus pneumoniae*: *Streptococcus pneumoniae* antigens include, but are not limited to, a saccharide (including a polysaccharide or an oligosaccharide) and/or protein from *Streptococcus pneumoniae*. The saccharide may be a polysaccharide having the size that arises during purification of the saccharide from bacteria, or it may be an oligosaccharide achieved by fragmentation of such a polysaccharide. In the 7-valent PREVNAR™ product, for instance, 6 of the saccharides are presented as intact polysaccharides while one (the 18C serotype) is presented as an oligosaccharide. In certain embodiments saccharide antigens are selected from one or more of the following pneumococcal serotypes 1, 2, 3, 4, 5, 6A, 6B, 7F, 8, 9N, 9V, 10A, 11A, 12F, 14, 15B, 17F, 18C, 19A, 19F, 20, 22F, 23F, and/or 33F. An immunogenic composition may include multiple serotypes e.g. 2, 3, 4, 5, 6, 7, 8, 9, 10, 11, 12, 13, 14, 15, 16, 17, 18, 19, 20, 21, 22, 23 or more serotypes. 7-valent, 9-valent, 10-valent, 11-valent and 13-valent conjugate combinations are already known in the art, as is a 23-valent unconjugated combination. For example, an 10-valent combination may include saccharide from serotypes 1, 4, 5, 6B, 7F, 9V, 14, 18C, 19F and 23F. An 11-valent combination may further include saccharide from serotype 3. A 12-valent combination may add to the 10-valent mixture: serotypes 6A and 19A; 6A and 22F; 19A and 22F; 6A and 15B; 19A and 15B; r 22F and 15B; A 13-valent combination may add to the 11-valent mixture: serotypes 19A and 22F; 8 and 12F; 8 and 15B; 8 and 19A; 8 and 22F; 12F and 15B; 12F and 19A; 12F and 22F; 15B and 19A; 15B and 22F. etc. In certain embodiments, protein antigens may be selected from a protein identified in WO98/18931, WO98/18930, U.S. Pat. No. 6,699,703, U.S. Pat. No. 6,800,744, WO97/43303, WO97/37026, WO 02/079241, WO 02/34773, WO 00/06737, WO 00/06738, WO 00/58475, WO 2003/082183, WO 00/37105, WO 02/22167, WO 02/22168, WO 2003/104272, WO 02/08426, WO 01/12219, WO 99/53940, WO 01/81380, WO 2004/092209, WO 00/76540, WO 2007/116322, LeMieux et al., Infect. Imm. (2006) 74:2453-2456, Hoskins et al., J. Bacteriol. (2001) 183: 5709-5717, Adamou et al., Infect. Immun. (2001) 69(2): 949-958, Briles et al., J. Infect. Dis. (2000) 182:1694-1701, Talkington et al., Microb. Pathog. (1996) 21(1): 17-22, Bethe et al., FEMS Microbiol. Lett. (2001) 205 (1):99-104, Brown et al., Infect. Immun. (2001) 69:6702-6706, Whalen et al., FEMS Immunol. Med. Microbiol. (2005) 43:73-80, Jomaa et al., Vaccine (2006) 24(24):5133-5139. In other embodiments, *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125, Sp133, pneumococcal pilus sub-units.

*Streptococcus pyogenes* (Group A *Streptococcus*): Group A *Streptococcus* antigens include, but are not limited to, a protein identified in WO 02/34771 or WO 2005/032582 (including GAS 40), fusions of fragments of GAS M proteins (including those described in WO 02/094851, and Dale, Vaccine (1999) 17:193-200, and Dale, Vaccine 14(10): 944-948), fibronectin binding protein (Sfb1), Streptococcal heme-associated protein (Shp), and Streptolysin S (SagA).

*Moraxella catarrhalis: Moraxella* antigens include, but are not limited to, antigens identified in WO 02/18595 and WO 99/58562, outer membrane protein antigens (HMW-OMP), C-antigen, and/or LPS.

*Bordetella pertussis*: Pertussis antigens include, but are not limited to, pertussis holotoxin (PT) and filamentous haemagglutinin (FHA) from *B. pertussis*, optionally also combination with pertactin and/or agglutinogens 2 and 3.

*Burkholderia: Burkholderia* antigens include, but are not limited to *Burkholderia mallei*, *Burkholderia pseudomallei* and *Burkholderia cepacia*.

*Staphylococcus aureus*: Staph aureus antigens include, but are not limited to, a polysaccharide and/or protein from *S. aureus*. *S. aureus* polysaccharides include, but are not limited to, type 5 and type 8 capsular polysaccharides (CP5 and CP8) optionally conjugated to nontoxic recombinant *Pseudomonas aeruginosa* exotoxin A, such as StaphVAX™, type 336 polysaccharides (336PS), polysaccharide intercellular adhesions (PIA, also known as PNAG). *S. aureus* proteins include, but are not limited to, antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin). In certain embodiments, *S. aureus* antigens may be selected from a protein identified in WO 02/094868, WO 2008/019162, WO 02/059148, WO 02/102829, WO 03/011899, WO 2005/079315, WO 02/077183, WO 99/27109, WO 01/70955, WO 00/12689, WO 00/12131, WO 2006/032475, WO 2006/032472, WO 2006/032500, WO 2007/113222, WO 2007/113223, WO 2007/113224. In other embodiments, *S. aureus* antigens may be selected from IsdA, IsdB, IsdC, SdrC, SdrD, SdrE, ClfA, ClfB, SasF, SasD, SasH (AdsA), Spa, EsaC, EsxA, EsxB, Emp, HlaH35L, CP5, CP8, PNAG, 336PS.

*Staphylococcus epidermis*: *S. epidermidis* antigens include, but are not limited to, slime-associated antigen (SAA).

*Clostridium tetani* (Tetanus): Tetanus antigens include, but are not limited to, tetanus toxoid (TT). In certain embodiments such antigens are used as a carrier protein in conjunction/conjugated with the immunogenic compositions provided herein.

*Clostridium perfringens*: Antigens include, but are not limited to, Epsilon toxin from *Clostridium perfringen*.

*Clostridium botulinums* (Botulism): Botulism antigens include, but are not limited to, those derived from *C. botulinum*.

*Cornynebacterium diphtheriae* (Diphtheria): Diphtheria antigens include, but are not limited to, diphtheria toxin, preferably detoxified, such as $CRM_{197}$. Additionally antigens capable of modulating, inhibiting or associated with ADP ribosylation are contemplated for combination/co-administration/conjugation with the immunogenic compositions provided herein. In certain embodiments, the diphtheria toxoids are used as carrier proteins.

*Haemophilus influenzae* B (Hib): Hib antigens include, but are not limited to, a Hib saccharide antigen.

*Pseudomonas aeruginosa*: Pseudomonas antigens include, but are not limited to, endotoxin A, Wzz protein, *P. aeruginosa* LPS, LPS isolated from PAO1 (05 serotype), and/or Outer Membrane Proteins, including Outer Membrane Proteins F (OprF).

*Legionella pneumophila*. Bacterial antigens derived from *Legionella pneumophila*.

*Coxiella burnetii*. Bacterial antigens derived from *Coxiella burnetii*.

*Brucella*. Bacterial antigens derived from *Brucella*, including but not limited to, *B. abortus*, *B. canis*, *B. melitensis*, *B. neotomae*, *B. ovis*, *B. suis* and *B. pinnipediae*.

*Francisella*. Bacterial antigens derived from *Francisella*, including but not limited to, *F. novicida*, *F. philomiragia* and *F. tularensis*.

*Streptococcus agalactiae* (Group B *Streptococcus*): Group B *Streptococcus* antigens include, but are not limited to, a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes 1a, 1b, Ia/c, II, III, IV, V, VI, VII and VIII).

*Neiserria gonorrhoeae*: Gonorrhoeae antigens include, but are not limited to, Por (or porin) protein, such as PorB (see Zhu et al., Vaccine (2004) 22:660-669), a transferring binding protein, such as TbpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al, J Infectious Disease (2000) 182:848-855), also see, e.g., WO99/24578, WO99/36544, WO99/57280, WO02/079243).

*Chlamydia trachomatis*: *Chlamydia trachomatis* antigens include, but are not limited to, antigens derived from serotypes A, B, Ba and C (agents of trachoma, a cause of blindness), serotypes $L_1$, $L_2$ & $L_3$ (associated with Lymphogranuloma venereum), and serotypes, D-K. In certain embodiments, chlamydia trachomas antigens include, but are not limited to, an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), $L_7/L_{12}$ (CT316), OmcA (CT444), AtosS (CT467), CT547, Eno (CT587), HrtA (CT823), and MurG (CT761).

*Treponema pallidum* (Syphilis): Syphilis antigens include, but are not limited to, TmpA antigen.

*Haemophilus ducreyi* (causing chancroid): *Ducreyi* antigens include, but are not limited to, outer membrane protein (DsrA).

*Enterococcus faecalis* or *Enterococcus faecium*: Antigens include, but are not limited to, a trisaccharide repeat or other *Enterococcus* derived antigens.

*Helicobacter pylori*: *H pylori* antigens include, but are not limited to, Cag, Vac, Nap, HopX, HopY and/or urease antigen.

*Staphylococcus saprophyticus*: Antigens include, but are not limited to, the 160 kDa hemagglutinin of *S. saprophyticus* antigen.

*Yersinia enterocolitica* Antigens include, but are not limited to, LPS.

*E. coli*: *E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC antigens include, but are not limited to, accessory colonization factor (orf3526), orf353, bacterial Ig-like domain (group 1) protein (orf405), orf1364, NodT-family outer-membrane-factor-lipoprotein efflux transporter (orf1767), gspK (orf3515), gspJ (orf3516), tonB-dependent siderophore receptor (orf3597), fimbrial protein (orf3613), upec-948, upec-1232, A chain precursor of the type-1 fimbrial protein (upec-1875), yap H homolog (upec-2820), and hemolysin A (recp-3768).

*Bacillus anthracis* (anthrax): *B. anthracis* antigens include, but are not limited to, A-components (lethal factor (LF) and edema factor (EF)), both of which can share a common B-component known as protective antigen (PA). In certain embodiments, *B. anthracis* antigens are optionally detoxified.

*Yersinia pestis* (plague): Plague antigens include, but are not limited to, F1 capsular antigen, LPS, *Yersinia pestis* V antigen.

*Mycobacterium tuberculosis*: Tuberculosis antigens include, but are not limited to, lipoproteins, LPS, BCG antigens, a fusion protein of antigen 85B (Ag85B), ESAT-6 optionally formulated in cationic lipid vesicles, *Mycobacterium tuberculosis* (Mtb) isocitrate dehydrogenase associated antigens, and MPT51 antigens.

*Rickettsia*: Antigens include, but are not limited to, outer membrane proteins, including the outer membrane protein A and/or B (OmpB), LPS, and surface protein antigen (SPA).

*Listeria monocytogenes*: Bacterial antigens include, but are not limited to, those derived from *Listeria monocytogenes*.

*Chlamydia pneumoniae*: Antigens include, but are not limited to, those identified in WO 02/02606.

*Vibrio cholerae*: Antigens include, but are not limited to, proteinase antigens, LPS, particularly lipopolysaccharides of *Vibrio cholerae* II, 01 Inaba O-specific polysaccharides, *V. cholera* 0139, antigens of IEM108 vaccine and Zonula occludens toxin (Zot).

*Salmonella typhi* (typhoid fever): Antigens include, but are not limited to, capsular polysaccharides preferably conjugates (Vi, i.e. vax-TyVi).

*Borrelia burgdorferi* (Lyme disease): Antigens include, but are not limited to, lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, VlsE Antigenic Variation Protein.

*Porphyromonas gingivalis*: Antigens include, but are not limited to, *P. gingivalis* outer membrane protein (OMP).

*Klebsiella*: Antigens include, but are not limited to, an OMP, including OMP A, or a polysaccharide optionally conjugated to tetanus toxoid.

Other bacterial antigens used in the immunogenic compositions provided herein include, but are not limited to, capsular antigens, polysaccharide antigens, protein antigens or polynucleotide antigens of any of the above. Other bacterial antigens used in the immunogenic compositions provided herein include, but are not limited to, an outer membrane vesicle (OMV) preparation. Additionally, other bacterial antigens used in the immunogenic compositions provided herein include, but are not limited to, live, attenuated, and/or purified versions of any of the aforementioned bacteria. In certain embodiments, the bacterial antigens used in the immunogenic compositions provided herein are derived from gram-negative bacteria, while in other embodiments they are derived from gram-positive bacteria. In certain embodiments, the bacterial antigens used in the immunogenic compositions provided herein are derived from aerobic bacteria, while in other embodiments they are derived from anaerobic bacteria.

In certain embodiments, any of the above bacterial-derived saccharides (polysaccharides, LPS, LOS or oligosaccharides) are conjugated to another agent or antigen, such as a carrier protein (for example $CRM_{197}$). In certain embodiments, such conjugations are direct conjugations effected by reductive amination of carbonyl moieties on the saccharide to amino groups on the protein. In other embodiments, the saccharides are conjugated through a linker, such as, with succinamide or other linkages provided in *Bioconjugate Techniques,* 1996 and CRC, *Chemistry of Protein Conjugation and Cross-Linking,* 1993.

In certain embodiments useful for the treatment or prevention of *Neisseria* infection and related diseases and disorders, recombinant proteins from *N. meningitidis* for use in the immunogenic compositions provided herein may be found in WO99/24578, WO99/36544, WO99/57280, WO00/22430, WO96/29412, WO01/64920, WO03/020756, WO2004/048404, and WO2004/032958. Such antigens may be used alone or in combinations. Where multiple purified proteins are combined then it is helpful to use a mixture of 10 or fewer (e.g. 9, 8, 7, 6, 5, 4, 3, 2) purified antigens.

A particularly useful combination of antigens for use in the immunogenic compositions provided herein is disclosed in Giuliani et al. (2006) *Proc Natl Acad Sci USA* 103(29):10834-9 and WO2004/032958, and so an immunogenic composition may include 1, 2, 3, 4 or 5 of: (1) a 'NadA' protein (aka GNA1994 and NMB1994); (2) a 'fHBP' protein (aka '741', LP2086, GNA1870, and NMB1870); (3) a '936' protein (aka GNA2091 and NMB2091); (4) a '953' protein (aka GNA1030 and NMB1030); and (5) a '287' protein (aka GNA2132 and NMB2132). Other possible antigen combinations may comprise a transferrin binding protein (e.g. TbpA and/or TbpB) and an Hsf antigen. Other possible purified antigens for use in the immunogenic compositions provided herein include proteins comprising one of the following amino acid sequences: SEQ ID NO:650 from WO99/24578; SEQ ID NO:878 from WO99/24578; SEQ ID NO:884 from WO99/24578; SEQ ID NO:4 from WO99/36544; SEQ ID NO:598 from WO99/57280; SEQ ID NO:818 from WO99/57280; SEQ ID NO:864 from WO99/57280; SEQ ID NO:866 from WO99/57280; SEQ ID NO:1196 from WO99/57280; SEQ ID NO:1272 from WO99/57280; SEQ ID NO: 1274 from WO99/57280; SEQ ID NO:1640 from WO99/57280; SEQ ID NO: 1788 from WO99/57280; SEQ ID NO:2288 from WO99/57280; SEQ ID NO:2466 from WO99/57280; SEQ ID NO:2554 from WO99/57280; SEQ ID NO:2576 from WO99/57280; SEQ ID NO:2606 from WO99/57280; SEQ ID NO:2608 from WO99/57280; SEQ ID NO:2616 from WO99/57280; SEQ ID NO:2668 from WO99/57280; SEQ ID NO:2780 from WO99/57280; SEQ ID NO:2932 from WO99/57280; SEQ ID NO:2958 from WO99/57280; SEQ ID NO:2970 from WO99/57280; SEQ ID NO:2988 from WO99/57280 (each of the forgoing amino acid sequences is hereby incorporated by reference from the cited document), or a polypeptide comprising an amino acid sequence which: (a) has 50% or more identity (e.g., 60%, 70%, 80%, 90%, 95%, 99% or more) to said sequences; and/or (b) comprises a fragment of at least n consecutive amino acids from said sequences, wherein n is 7 or more (e.g., 8, 10, 12, 14, 16, 18, 20, 25, 30, 35, 40, 50, 60, 70, 80, 90, 100, 150, 200, 250 or more). Preferred fragments for (b) comprise an epitope from the relevant sequence. More than one (e.g., 2, 3, 4, 5, 6) of these polypeptides may be included in the immunogenic compositions.

The fHBP antigen falls into three distinct variants (WO2004/048404). An *N. meningitidis* serogroup vaccine based upon the immunogenic compositions disclosed herein utilizing one of the compounds disclosed herein may include a single fHBP variant, but is will usefully include an fHBP from each of two or all three variants. Thus the immunogenic composition may include a combination of two or three different purified fHBPs, selected from: (a) a first protein, comprising an amino acid sequence having at least a % sequence identity to SEQ ID NO: 1 and/or comprising an amino acid sequence consisting of a fragment of at least x contiguous amino acids from SEQ ID NO: 1; (b) a second protein, comprising an amino acid sequence having at least b % sequence identity to SEQ ID NO: 2 and/or comprising an amino acid sequence consisting of a fragment of at least y contiguous amino acids from SEQ ID NO: 2; and/or (c) a third protein, comprising an amino acid sequence having at least c % sequence identity to SEQ ID NO: 3 and/or comprising an amino acid sequence consisting of a fragment of at least z contiguous amino acids from SEQ ID NO: 3

```
                                              SEQ ID NO: 1
VAADIGAGLADALTAPLDHKDKGLQSLTLDQSVRKNEKLKLAAQGAEKT

YGNGDSLNTGKLKNDKVSRFDFIRQIEVDGQLITLESGEFQVYKQSHSA

LTAFQTEQIQDSEHSGKMVAKRQFRIGDIAGEHTSFDKLPEGGRATYRG

TAFGSDDAGGKLTYTIDFAAKQGNGKIEHLKSPELNVDLAAADIKPDGK

RHAVISGSVLYNQAEKGSYSLGIFGGKAQEVAGSAEVKTVNGIRHIGLA

AKQ

SEQ ID NO: 2
VAADIGAGLADALTAPLDHKDKSLQSLTLDQSVRKNEKLKLAAQGAEK

TYGNGDSLNTGKLKNDKVSRFDFIRQIEVDGQLITLESGEFQIYKQDH

SAVVALQIEKINNPDKIDSLINQRSFLVSGLGGEHTAFNQLPDGKAEY

HGKAFSSDDAGGKLTYTIDFAAKQGHGKIEHLKTPEQNVELAAAELKA

DEKSHAVILGDTRYGSEEKGTYHLALFGDRAQEIAGSATVKIGEKVHE

IGIAGKQ

SEQ ID NO: 3
VAADIGTGLADALTAPLDHKDKGLKSLTLEDSIPQNGTLTLSAQGAEK

TFKAGDKDNSLNTGKLKNDKISRFDFVQKIEVDGQTITLASGEFQIYK

QNHSAVVALQIEKINNPDKTDSLINQRSFLVSGLGGEHTAFNQLPGGK

AEYHGKAFSSDDPNGRLHYSIDFTKKQGYGRIEHLKTLEQNVELAAAE

LKADEKSHAVILGDTRYGSEEKGTYHLALFGDRAQEIAGSATVKIGEK

VHEIGIAGKQ.
```

The value of a is at least 85, e.g., 86, 87, 88, 89, 90, 91, 92, 93, 94, 95, 96, 97, 98, 99, 99.5, or more. The value of b is at least 85, e.g., 86, 87, 88, 89, 90, 91, 92, 93, 94, 95, 96, 97, 98, 99, 99.5, or more. The value of c is at least 85, e.g., 86, 87, 88, 89, 90, 91, 92, 93, 94, 95, 96, 97, 98, 99, 99.5, or more. The values of a, b and c are not intrinsically related to each other.

The value of x is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7, e.g., 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z are not intrinsically related to each other.

In some embodiments, the immunogenic compositions as disclosed herein will include fHBP protein(s) that are lipidated, e.g., at a N-terminal cysteine. In other embodiments they will not be lipidated A useful immunogenic composition as disclosed herein includes purified proteins comprises a mixture of: (i) a first polypeptide having amino acid sequence SEQ ID NO: 4; (ii) a second polypeptide having amino acid sequence SEQ ID NO: 5; and (iii) a third polypeptide having amino acid sequence SEQ ID NO: 6. See Giuliani et al. (2006) *Proc Natl Acad Sci USA* 103(29):10834-9 and WO2004/032958. A useful immunogenic composition as disclosed herein includes purified proteins comprises a mixture of: (i) a first polypeptide having at least a % sequence identity to amino acid sequence SEQ ID NO: 4; (ii) a second polypeptide having at least b % sequence identity to amino acid sequence SEQ ID NO: 5; and (iii) a third polypeptide having at least a % sequence identity to amino acid sequence SEQ ID NO: 6.

SEQ ID NO: 4
MASPDVKSADTLSKPAAPVVSEKETEAKEDAPQAGSQGQGAPSAQG
GQDMAAVSEENTGNGGAAATDKPKNEDEGAQNDMPQNAADTDSLTP
NHTPASNMPAGNMENQAPDAGESEQPANQPDMANTADGMQGDDPSA
GGENAGNTAAQGTNQAENNQTAGSQNPASSTNPSATNSGGDFGRTN
VGNSVVIDGPSQNITLTHCKGDSCSGNNFLDEEVQLKSEFEKLSDA
DKISNYKKDGKNDGKNDKFVGLVADSVQMKGINQYIIFYKPKPTSF
ARFRRSARSRRSLPAEMPLIPVNQADTLIVDGEAVSLTGHSGNIFA
PEGNYRYLTYGAEKLPGGSYALRVQGEPSKGEMLAGTAVYNGEVLH
FHTENGRPSPSRGRFAAKVDFGSKSVDGIIDSGDGLHMGTQKFKAA
IDGNGFKGTWTENGGGDVSGKFYGPAGEEVAGKYSYRPTDAEKGGF
GVFAGKKEQDGSGGGATYKVDEYHANARFAIDHFNTSTNVGGFYG
LTGSVEFDQAKRDGKIDITIPVANLQSGSQHFTDHLKSADIFDAAQ
YPDIRFVSTKFNFNGKKLVSVDGNLTMHGKTAPVKLKAEKFNCYQS
PMAKTEVCGGDFSTTIDRTKWGVDYLVNVGMTKSVRIDIQIEAAKQ

SEQ ID NO: 5
MVSAVIGSAAVGAKSAVDRRTTGAQTDDNVMALRIETTARSYLRQ
NNQTKGYTPQISVVGYNRHLLLLGQVATEGEKQFVGQIARSEQAA
EGVYNYITVASLPRTAGDIAGDTWNTSKVRATLLGISPATQARVK
IVTYGNVTYVMGILTPEEQAQITQKVSTTVGVQKVITLYQNYVQR
GSGGGGVAADIGAGLADALTAPLDHKDKGLQSLTLDQSVRKNEKL
KLAAQGAEKTYGNGDSLNTGKLKNDKVSRFDFIRQIEVDGQLITL
ESGEFQVYKQSHSALTAFQTEQIQDSEHSGKMVAKRQFRIGDIAG
EHTSFDKLPEGGRATYRGTAFGSDDAGGKLTYTIDFAAKQGNGKI
EHLKSPELNVDLAAADIKPDGKRHAVISGSVLYNQAEKGSYSLGI
FGGKAQEVAGSAEVKTVNGIRHIGLAAKQ

SEQ ID NO: 6
ATNDDDVKKAATVAIAAAYNNGQEINGFKAGETIYDIDEDGTIT
KKDATAADVEADDFKGLGLKKVVTNLTKTVNENKQNVDAKVKAA
ESEIEKLTTKLADTDAALADTDAALDATTNALNKLGENITTFAE
ETKTNIVKIDEKLEAVADTVDKHAEAFNDIADSLDETNTKADEA
VKTANEAKQTAEETKQNVDAKVKAAETAAGKAEAAAGTANTAAD
KAEAVAAKVTDIKADIATNKDNIAKKANSADVYTREESDSKFVR
IDGLNATTEKLDTRLASAEKSIADHDTRLNGLDKTVSDLRKETR
QGLAEQAALSGLFQPYNVG.

Bacterial Vesicle Antigens

The immunogenic compositions as disclosed herein may include outer membrane vesicles. Such outer membrane vesicles may be obtained from a wide array of pathogenic bacteria and used as antigenic components of the immunogenic compositions as disclosed herein. Vesicles for use as antigenic components of such immunogenic compositions include any proteoliposomic vesicle obtained by disrupting a bacterial outer membrane to form vesicles therefrom that include protein components of the outer membrane. Thus the term includes OMVs (sometimes referred to as 'blebs'), microvesicles (MVs, see, e.g., WO02/09643) and 'native OMVs' ('NOMVs' see, e.g., Katial et al. (2002) *Infect. Immun.* 70:702-707). Immunogenic compositions as disclosed herein that include vesicles from one or more pathogenic bacteria can be used in the treatment or prevention of infection by such pathogenic bacteria and related diseases and disorders.

MVs and NOMVs are naturally-occurring membrane vesicles that form spontaneously during bacterial growth and are released into culture medium. MVs can be obtained by culturing bacteria such as *Neisseria* in broth culture medium, separating whole cells from the smaller MVs in the broth culture medium (e.g., by filtration or by low-speed centrifugation to pellet only the cells and not the smaller vesicles), and then collecting the MVs from the cell-depleted medium (e.g., by filtration, by differential precipitation or aggregation of MVs, by high-speed centrifugation to pellet the MVs). Strains for use in production of MVs can generally be selected on the basis of the amount of MVs produced in culture (see, e.g., U.S. Pat. No. 6,180,111 and WO01/34642 describing *Neisseria* with high MV production).

OMVs are prepared artificially from bacteria, and may be prepared using detergent treatment (e.g., with deoxycholate), or by non detergent means (see, e.g., WO04/019977). Methods for obtaining suitable OMV preparations are well known in the art. Techniques for forming OMVs include treating bacteria with a bile acid salt detergent (e.g., salts of lithocholic acid, chenodeoxycholic acid, ursodeoxycholic acid, deoxycholic acid, cholic acid, ursocholic acid, etc., with sodium deoxycholate (EP0011243 and Fredriksen et al. (1991) *NIPH Ann.* 14(2):67-80) being preferred for treating *Neisseria*) at a pH sufficiently high not to precipitate the detergent (see, e.g., WO01/91788). Other techniques may be performed substantially in the absence of detergent (see, e.g., WO04/019977) using techniques such as sonication, homogenisation, microfluidisation, cavitation, osmotic shock, grinding, French press, blending, etc. Methods using no or low detergent can retain useful antigens such as NspA in *Neisserial* OMVs. Thus a method may use an OMV extraction buffer with about 0.5% deoxycholate or lower, e.g., about 0.2%, about 0.1%, <0.05% or zero.

A useful process for OMV preparation is described in WO05/004908 and involves ultrafiltration on crude OMVs, rather than instead of high speed centrifugation. The process may involve a step of ultracentrifugation after the ultrafiltration takes place.

Vesicles can be prepared from any pathogenic strain such as *Neisseria minigtidis* for use with the invention. Vessicles from *Neisserial meningitidis* serogroup B may be of any serotype (e.g., 1, 2a, 2b, 4, 14, 15, 16, etc.), any serosubtype, and any immunotype (e.g., L1; L2; L3; L3,3,7; L10; etc.). The meningococci may be from any suitable lineage, including hyperinvasive and hypervirulent lineages, e.g., any of the following seven hypervirulent lineages: subgroup I; subgroup III; subgroup IV 1; ET 5 complex; ET 37 complex; A4 cluster; lineage 3. These lineages have been defined by multilocus enzyme electrophoresis (MLEE), but multilocus sequence typing (MLST) has also been used to classify meningococci, e.g., the ET 37 complex is the ST 11 complex by MLST, the ET 5 complex is ST-32 (ET-5), lineage 3 is ST 41/44, etc. Vesicles can be prepared from strains having one of the following subtypes: P1.2; P1.2,5; P1.4; P1.5; P1.5,2; P1.5,c; P1.5c,10; P1.7,16; P1.7,16b; P1.7h,4; P1.9; P1.15; P1.9,15; P1.12,13; P1.13; P1.14; P1.21,16; P1.22,14.

Vesicles included in the immunogenic compositions disclosed herein may be prepared from wild type pathogenic strains such as N. meningitidis strains or from mutant strains. By way of example, WO98/56901 discloses preparations of vesicles obtained from N. meningitidis with a modified fur gene. WO02/09746 teaches that nspA expression should be up regulated with concomitant porA and cps knockout. Further knockout mutants of N. meningitidis for OMV production are disclosed in WO02/0974, WO02/062378, and WO04/014417. WO06/081259 discloses vesicles in which fHBP is upregulated. Claassen et al. (1996) 14(10):1001-8, disclose the construction of vesicles from strains modified to express six different PorA subtypes. Mutant *Neisseria* with low endotoxin levels, achieved by knockout of enzymes involved in LPS biosynthesis, may also be used (see, e.g., WO99/10497 and Steeghs et al. (2001) i20:6937-6945). These or others mutants can all be used with the invention.

Thus *N. meningitidis* serogroup B strains included in the immunogenic compositions disclosed herein may in some embodiments express more than one PorA subtype. Six valent and nine valent PorA strains have previously been constructed. The strain may express 2, 3, 4, 5, 6, 7, 8 or 9 of PorA subtypes: P1.7,16; P1.5-1, 2-2; P1,19,15-1; P1.5-2,10; P1.12 1,13; P1.7-2,4; P1.22,14; P1.7-1,1 and/or P1.18-1,3,6. In other embodiments a strain may have been down regulated for PorA expression, e.g., in which the amount of PorA has been reduced by at least 20% (e.g., >30%, >40%, >50%, >60%, >70%, >80%, >90%, >95%, etc.), or even knocked out, relative to wild type levels (e.g., relative to strain H44/76, as disclosed in WO03/105890).

In some embodiments *N. meningitidis* serogroup B strains may over express (relative to the corresponding wild-type strain) certain proteins. For instance, strains may over express NspA, protein 287 (WO01/52885—also referred to as NMB2132 and GNA2132), one or more fHBP (WO06/081259 and U.S. Pat. Pub. 2008/0248065—also referred to as protein 741, NMB1870 and GNA1870), TbpA and/or TbpB (WO00/25811), Cu,Zn-superoxide dismutase (WO00/25811), etc.

In some embodiments *N. meningitidis* serogroup B strains may include one or more of the knockout and/or over expression mutations. Preferred genes for down regulation and/or knockout include: (a) Cps, CtrA, CtrB, CtrC, CtrD, FrpB, GalE, HtrB/MsbB, LbpA, LbpB, LpxK, Opa, Opc, PilC, PorB, SiaA, SiaB, SiaC, SiaD, TbpA, and/or TbpB (WO01/09350); (b) CtrA, CtrB, CtrC, CtrD, FrpB, GalE, HtrB/MsbB, LbpA, LbpB, LpxK, Opa, Opc, PhoP, PilC, PmrE, PmrF, SiaA, SiaB, SiaC, SiaD, TbpA, and/or TbpB (WO02/09746); (c) ExbB, ExbD, rmpM, CtrA, CtrB, CtrD, GalE, LbpA, LpbB, Opa, Opc, PilC, PorB, SiaA, SiaB, SiaC, SiaD, TbpA, and/or TbpB (WO02/062378); and (d) CtrA, CtrB, CtrD, FrpB, OpA, OpC, PilC, PorB, SiaD, SynA, SynB, and/or SynC (WO04/014417).

Where a mutant strain is used, in some embodiments it may have one or more, or all, of the following characteristics: (i) down regulated or knocked-out LgtB and/or GalE to truncate the meningococcal LOS; (ii) up regulated TbpA; (iii) up regulated Hsf; (iv) up regulated Omp85; (v) up regulated LbpA; (vi) up regulated NspA; (vii) knocked-out PorA; (viii) down regulated or knocked-out FrpB; (ix) down regulated or knocked-out Opa; (x) down regulated or knocked-out Opc; (xii) deleted cps gene complex. A truncated LOS can be one that does not include a sialyl-lacto-N-neotetraose epitope, e.g., it might be a galactose-deficient LOS. The LOS may have no a chain.

If LOS is present in a vesicle then it is possible to treat the vesicle so as to link its LOS and protein components ("intra-bleb" conjugation (WO04/014417)).

The immunogenic compositions as disclosed herein may include mixtures of vesicles from different strains. By way of example, WO03/105890 discloses vaccine comprising multivalent meningococcal vesicle compositions, comprising a first vesicle derived from a meningococcal strain with a serosubtype prevalent in a country of use, and a second vesicle derived from a strain that need not have a serosubtype prevent in a country of use. WO06/024946 discloses useful combinations of different vesicles. A combination of vesicles from strains in each of the L2 and L3 immunotypes may be used in some embodiments.

Vesicle-based antigens can be prepared from *N. meningitidis* serogroups other than serogroup B (e.g., WO01/91788 discloses a process for serogroup A). The immunogenic compositions disclosed herein accordingly can include vesicles prepared serogroups other than B (e.g. A, C, W135 and/or Y) and from bacterial pathogens other than *Neisseria*.

Viral Antigens

Viral antigens suitable for use in the immunogenic compositions provided herein include, but are not limited to, inactivated (or killed) virus, attenuated virus, split virus formulations, purified subunit formulations, viral proteins which may be isolated, purified or derived from a virus, Virus Like Particles (VLPs) and polynucleotide antigens which may be isolated, purified or derived from a virus or recombinantly synthesized. In certain embodiments, viral antigens are derived from viruses propagated on cell culture or other substrate. In other embodiments, viral antigens are expressed recombinantly. In certain embodiments, viral antigens preferably include epitopes which are exposed on the surface of the virus during at least one stage of its life cycle. Viral antigens are preferably conserved across multiple serotypes or isolates. Viral antigens suitable for use in the immunogenic compositions provided herein include, but are not limited to, antigens derived from one or more of the viruses set forth below as well as the specific antigens examples identified below.

Orthomyxovirus: Viral antigens include, but are not limited to, those derived from an Orthomyxovirus, such as Influenza A, B and C. In certain embodiments, orthomyxovirus antigens are selected from one or more of the viral proteins, including hemagglutinin (HA), neuraminidase (NA), nucleoprotein (NP), matrix protein (M1), membrane protein (M2), one or more of the transcriptase components (PB1, PB2 and PA). In certain embodiments the viral antigen include HA and NA. In certain embodiments, the influenza antigens are derived from interpandemic (annual) flu strains, while in other embodiments, the influenza antigens are derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens include, but are not limited to, those derived from Paramyxoviridae viruses, such as Pneumoviruses (RSV), Paramyxoviruses (PIV), Metapneumovirus and Morbilliviruses (Measles).

Pneumovirus: Viral antigens include, but are not limited to, those derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. In certain embodiments, pneumovirus antigens are selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. In other embodiments, pneumovirus antigens include F, G and M. In certain embodiments, pneumovirus antigens are also formulated in or derived from chimeric viruses, such as, by way of example only, chimeric RSV/PIV viruses comprising components of both RSV and PIV.

Paramyxovirus: Viral antigens include, but are not limited to, those derived from a Paramyxovirus, such as Parainfluenza virus types 1-4 (PIV), Mumps, Sendai viruses, Simian virus 5, Bovine parainfluenza virus, Nipahvirus, Henipavirus and Newcastle disease virus. In certain embodiments, the Paramyxovirus is PIV or Mumps. In certain embodiments, paramyxovirus antigens are selected from one or more of the following proteins: Hemagglutinin-Neuraminidase (HN), Fusion proteins F1 and F2, Nucleoprotein (NP), Phosphoprotein (P), Large protein (L), and Matrix protein (M). In other embodiments, paramyxovirus proteins include HN, F1 and F2. In certain embodiments, paramyxovirus antigens are also formulated in or derived from chimeric viruses, such as, by way of example only, chimeric RSV/PIV viruses comprising components of both RSV and PIV. Commercially available mumps vaccines include live attenuated mumps virus, in either a monovalent form or in combination with measles and rubella vaccines (MMR). In other embodiments, the Paramyxovirus is Nipahvirus or Henipavirus and the anitgens are selected from one or more of the following proteins: Fusion (F) protein, Glycoprotein (G) protein, Matrix (M) protein, Nucleocapsid (N) protein, Large (L) protein and Phosphoprotein (P).

Poxyiridae: Viral antigens include, but are not limited to, those derived from Orthopoxvirus such as Variola vera, including but not limited to, Variola major and Variola minor.

Metapneumovirus: Viral antigens include, but are not limited to, Metapneumovirus, such as human metapneumovirus (hMPV) and avian metapneumoviruses (aMPV). In certain embodiments, metapneumovirus antigens are selected from one or more of the following proteins, including surface proteins Fusion (F), Glycoprotein (G) and Small Hydrophobic protein (SH), matrix proteins M and M2, nucleocapsid proteins N, P and L. In other embodiments, metapneumovirus antigens include F, G and M. In certain embodiments, metapneumovirus antigens are also formulated in or derived from chimeric viruses.

Morbillivirus: Viral antigens include, but are not limited to, those derived from a Morbillivirus, such as Measles. In certain embodiments, morbillivirus antigens are selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens include, but are not limited to, those derived from Picornaviruses, such as Enteroviruses, Rhinoviruses, Heparnavirus, Cardioviruses and Aphthoviruses. In certain embodiments, the antigens are derived from Enteroviruses, while in other embodiments the enterovirus is Poliovirus. In still other embodiments, the antigens are derived from Rhinoviruses. In certain embodiments, the antigens are formulated into virus-like particles (VLPs).

Enterovirus: Viral antigens include, but are not limited to, those derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In certain embodiments, the antigens are derived from Enteroviruses, while in other embodiments the enterovirus is Poliovirus. In certain embodiments, the enterovirus antigens are selected from one or more of the following Capsid proteins VP0, VP1, VP2, VP3 and VP4. Commercially available polio vaccines include Inactivated Polio Vaccine (IPV) and Oral poliovirus vaccine (OPV). In certain embodiments, the antigens are formulated into virus-like particles.

Bunyavirus: Viral antigens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Rhinovirus: Viral antigens include, but are not limted to, those derived from rhinovirus. In certain embodiments, the rhinovirus antigens are selected from one or more of the following Capsid proteins: VP0, VP1, VP2, VP2 and VP4. In certain embodiments, the antigens are formulated into virus-like particles (VLPs).

Heparnavirus: Viral antigens include, but are not limited to, those derived from a Heparnavirus, such as, by way of example only, Hepatitis A virus (HAV). Commercially available HAV vaccines include inactivated HAV vaccine.

Togavirus: Viral antigens include, but are not limited to, those derived from a Togavirus, such as a Rubivirus, an Alphavirus, or an Arterivirus. In certain embodiments, the antigens are derived from Rubivirus, such as by way of example only, Rubella virus. In certain embodiments, the togavirus antigens are selected from E1, E2, E3, C, NSP-1, NSPO-2, NSP-3 or NSP-4. In certain embodiments, the togavirus antigens are selected from E1, E2 or E3. Commercially available Rubella vaccines include a live cold-adapted virus, typically in combination with mumps and measles vaccines (MMR).

Flavivirus: Viral antigens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus. In certain embodiments, the flavivirus antigens are selected from PrM, M, C, E, NS-1, NS-2a, NS2b, NS3, NS4a, NS4b, and NS5. In certain embodiments, the flavivirus antigens are selected from PrM, M and E. Commercially available TBE vaccine includes inactivated virus vaccines. In certain embodiments, the antigens are formulated into virus-like particles (VLPs).

Pestivirus: Viral antigens include, but are not limited to, those derived from a Pestivirus, such as Bovine viral diarrhea (BVDV), Classical swine fever (CSFV) or Border disease (BDV).

Hepadnavirus: Viral antigens include, but are not limited to, those derived from a Hepadnavirus, such as Hepatitis B virus. In certain embodiments, the hepadnavirus antigens are selected from surface antigens (L, M and S), core antigens (HBc, HBe). Commercially available HBV vaccines include subunit vaccines comprising the surface antigen S protein.

Hepatitis C virus: Viral antigens include, but are not limited to, those derived from a Hepatitis C virus (HCV). In certain embodiments, the HCV antigens are selected from one or more of E1, E2, E1/E2, NS345 polyprotein, NS 345-core polyprotein, core, and/or peptides from the nonstructural regions. In certain embodiments, the Hepatitis C virus antigens include one or more of the following: HCV E1 and or E2 proteins, E1/E2 heterodimer complexes, core proteins and non-structural proteins, or fragments of these antigens, wherein the non-structural proteins can optionally be modified to remove enzymatic activity but retain immunogenicity. In certain embodiments, the antigens are formulated into virus-like particles (VLPs).

Rhabdovirus: Viral antigens include, but are not limited to, those derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens include, but are not limited to, those derived from Calciviridae, such as Norwalk virus, and Norwalk-like Viruses, such as Hawaii Virus and Snow Mountain Virus. In certain embodiments, the antigens are formulated into virus-like particles (VLPs).

Coronavirus: Viral antigens include, but are not limited to, those derived from a Coronavirus, SARS, Human respiratory coronavirus, Avian infectious bronchitis (IBV), Mouse hepatitis virus (MHV), and Porcine transmissible gastroenteritis virus (TGEV). In certain embodiments, the coronavirus antigens are selected from spike (S), envelope (E), matrix (M), nucleocapsid (N), and Hemagglutinin-esterase glycoprotein (HE). In certain embodiments, the coronavirus antigen is derived from a SARS virus. In certain embodiments, the coronavirus is derived from a SARS viral antigen as described in WO 04/92360.

Retrovirus: Viral antigens include, but are not limited to, those derived from a Retrovirus, such as an Oncovirus, a Lentivirus or a Spumavirus. In certain embodiments, the oncovirus antigens are derived from HTLV-1, HTLV-2 or HTLV-5. In certain embodiments, the lentivirus antigens are derived from HIV-1 or HIV-2. In certain embodiments, the antigens are derived from HIV-1 subtypes (or clades), including, but not limited to, HIV-1 subtypes (or clades) A, B, C, D, F, G, H, J. K, O. In other embodiments, the antigens are derived from HIV-1 circulating recombinant forms (CRFs), including, but not limited to, A/B, A/E, A/G, A/G/I, etc. In certain embodiments, the retrovirus antigens are selected from gag, pol, env, tax, tat, rex, rev, nef, vif, vpu, and vpr. In certain embodiments, the HIV antigens are selected from gag (p24gag and p55gag), env (gp160 and gp41), pol, tat, nef, rev vpu, miniproteins, (preferably p55 gag and gp140v delete). In certain embodiments, the HIV antigens are derived from one or more of the following strains: $HIV_{IIIb}$, $HIV_{SF2}$, $HIV_{LAV}$, $HIV_{LAI}$, $HIV_{MN}$, $HIV\text{-}1_{CM235}$, $HIV\text{-}1_{US4}$, $HIV\text{-}1_{SF162}$, $HIV\text{-}1_{TV1}$, $HIV\text{-}1_{MJ4}$. In certain embodiments, the antigens are derived from endogenous human retroviruses, including, but not limited to, HERV-K ("old" HERV-K and "new" HERV-K).

Reovirus: Viral antigens include, but are not limited to, those derived from a Reovirus, such as an Orthoreovirus, a Rotavirus, an Orbivirus, or a Coltivirus. In certain embodiments, the reovirus antigens are selected from structural proteins λ1, λ2, λ3, µ1, µ2, σ1, σ2, or σ3, or nonstructural proteins σNS, µNS, or σ1s. In certain embodiments, the reovirus antigens are derived from a Rotavirus. In certain embodiments, the rotavirus antigens are selected from VP1, VP2, VP3, VP4 (or the cleaved product VP5 and VP8), NSP 1, VP6, NSP3, NSP2, VP7, NSP4, or NSP5. In certain embodiments, the rotavirus antigens include VP4 (or the cleaved product VP5 and VP8), and VP7.

Parvovirus: Viral antigens include, but are not limited to, those derived from a Parvovirus, such as Parvovirus B19. In certain embodiments, the Parvovirus antigens are selected from VP-1, VP-2, VP-3, NS-1 and NS-2. In certain embodiments, the Parvovirus antigen is capsid protein VP1 or VP-2. In certain embodiments, the antigens are formulated into virus-like particles (VLPs).

Delta hepatitis virus (HDV): Viral antigens include, but are not limited to, those derived from HDV, particularly δ-antigen from HDV.

Hepatitis E virus (HEV): Viral antigens include, but are not limited to, those derived from HEV.

Hepatitis G virus (HGV): Viral antigens include, but are not limited to, those derived from HGV.

Human Herpesvirus: Viral antigens include, but are not limited to, those derived from a Human Herpesvirus, such as, by way of example only, Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). In certain embodiments, the Human Herpesvirus antigens are selected from immediate early proteins (α), early proteins (β), and late proteins (γ). In certain embodiments, the HSV antigens are derived from HSV-1 or HSV-2 strains. In certain embodiments, the HSV antigens are selected from glycoproteins gB, gC, gD and gH, fusion protein (gB), or immune escape proteins (gC, gE, or gI). In certain embodiments, the VZV antigens are selected from core, nucleocapsid, tegument, or envelope proteins. A live attenuated VZV vaccine is commercially available. In certain embodiments, the EBV antigens are selected from early antigen (EA) proteins, viral capsid antigen (VCA), and glycoproteins of the membrane antigen (MA). In certain embodiments, the CMV antigens are selected from capsid proteins, envelope glycoproteins (such as gB and gH), and tegument proteins. In other embodiments, CMV antigens may be selected from one or more of the following proteins: pp65, IE1, gB, gD, gH, gL, gM, gN, gO, UL128, UL129, gUL130, UL150, UL131, UL33, UL78, US27, US28, RL5A, RL6, RL10, RL11, RL12, RL13, UL1, UL2, UL4, UL5, UL6, UL7, UL8, UL9, UL10, UL11, UL14, UL15A, UL16, UL17, UL18, UL22A, UL38, UL40, UL41A, UL42, UL116, UL119, UL120, UL121, UL124, UL132, UL147A, UL148, UL142, UL144, UL141, UL140, UL135, UL136, UL138, UL139, UL133, UL135, UL148A, UL148B, UL148C, UL148D, US2, US3, US6, US7, US8, US9, US10, US11, US12, US13, US14, US15, US16, US17, US18, US19, US20, US21, US29, US30 and US34A. CMV antigens may also be fusions of one or more CMV proteins, such as, by way of example only, pp65/IE1 (Reap et al., *Vaccine* (2007) 25:7441-7449). In certain embodiments, the antigens are formulated into virus-like particles (VLPs).

Papovaviruses: Antigens include, but are not limited to, those derived from Papovaviruses, such as Papillomaviruses and Polyomaviruses. In certain embodiments, the Papillomaviruses include HPV serotypes 1, 2, 4, 5, 6, 8, 11, 13, 16, 18, 31, 33, 35, 39, 41, 42, 47, 51, 57, 58, 63 and 65. In certain embodiments, the HPV antigens are derived from serotypes 6, 11, 16 or 18. In certain embodiments, the HPV antigens are selected from capsid proteins (L1) and (L2), or E1-E7, or fusions thereof. In certain embodiments, the HPV antigens are formulated into virus-like particles (VLPs). In certain embodiments, the Polyomyavirus viruses include BK virus and JK virus. In certain embodiments, the Polyomavirus antigens are selected from VP1, VP2 or VP3.

Adenovirus: Antigens include those derived from Adenovirus. In certain embodiments, the Adenovirus antigens are derived from Adenovirus serotype 36 (Ad-36). In certain embodiments, the antigen is derived from a protein or peptide sequence encoding an Ad-36 coat protein or fragment thereof (WO 2007/120362).

Further provided are antigens, compositions, methods, and microbes included in *Vaccines*, 4$^{th}$ Edition (Plotkin and Orenstein ed. 2004); *Medical Microbiology* 4$^{th}$ Edition (Murray et al. ed. 2002); *Virology*, 3rd Edition (W. K. Joklik ed. 1988); *Fundamental Virology*, 2nd Edition (B. N. Fields and D. M. Knipe, eds. 1991), which are contemplated in conjunction with the immunogenic compositions provided herein.

Fungal Antigens

Fungal antigens for use in the immunogenic compositions provided herein include, but are not limited to, those derived from one or more of the fungi set forth below.

Fungal antigens are derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum var. album, var. discoides, var. ochraceum, Trichophyton violaceum,* and/or *Trichophyton faviforme*; and Fungal pathogens are derived from *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In certain embodiments, the process for producing a fungal antigen includes a method wherein a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

Protazoan Antigens/Pathogens

Protazoan antigens/pathogens for use in the immunogenic compositions provided herein include, but are not limited to, those derived from one or more of the following protozoa: *Entamoeba histolytica, Giardia lambli, Cryptosporidium parvum, Cyclospora cayatanensis* and *Toxoplasma*.

Plant Antigens/Pathogens

Plant antigens/pathogens for use in the immunogenic compositions provided herein include, but are not limited to, those derived from *Ricinus communis*.

STD Antigens

In certain embodiments, the immunogenic compositions provided herein include one or more antigens derived from a sexually transmitted disease (STD). In certain embodiments, such antigens provide for prophylactis for STD's such as chlamydia, genital herpes, hepatitis (such as HCV), genital warts, gonorrhea, syphilis and/or chancroid. In other embodiments, such antigens provide for therapy for STD's such as chlamydia, genital herpes, hepatitis (such as HCV), genital warts, gonorrhea, syphilis and/or chancroid. Such antigens are derived from one or more viral or bacterial STD's. In certain embodiments, the viral STD antigens are derived from HIV, herpes simplex virus (HSV-1 and HSV-2), human papillomavirus (HPV), and hepatitis (HCV). In certain embodiments, the bacterial STD antigens are derived from *Neiserria gonorrhoeae, Chlamydia trachomatis, Treponema pallidum, Haemophilus ducreyi, E. coli,* and *Streptococcus agalactiae*. Examples of specific antigens derived from these pathogens are described above.

Respiratory Antigens

In certain embodiments, the immunogenic compositions provided herein include one or more antigens derived from a pathogen which causes respiratory disease. By way of example only, such respiratory antigens are derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). In certain embodiments, the respiratory antigens are derived from a bacteria which causes respiratory disease, such as, by way of example only, *Streptococcus pneumoniae, Pseudomonas aeruginosa, Bordetella pertussis, Mycobacterium tuberculosis, Mycoplasma pneumoniae, Chlamydia*

*pneumoniae, Bacillus anthracis*, and *Moraxella catarrhalis*. Examples of specific antigens derived from these pathogens are described above.

Pediatric Vaccine Antigens

In certain embodiments, the immunogenic compositions provided herein include one or more antigens suitable for use in pediatric subjects. Pediatric subjects are typically less than about 3 years old, or less than about 2 years old, or less than about 1 years old. Pediatric antigens are administered multiple times over the course of 6 months, 1, 2 or 3 years. Pediatric antigens are derived from a virus which may target pediatric populations and/or a virus from which pediatric populations are susceptible to infection. Pediatric viral antigens include, but are not limited to, antigens derived from one or more of Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Cornynebacterium diphtheriae* (Diphtheria), *Haemophilus influenzae* B (Hib), *Pseudomonas aeruginosa, Streptococcus agalactiae* (Group B *Streptococcus*), and *E. coli*. Examples of specific antigens derived from these pathogens are described above.

Antigens Suitable for Use in Elderly or Immunocompromised Individuals

In certain embodiments, the immunogenic compositions provided herein include one or more antigens suitable for use in elderly or immunocompromised individuals. Such individuals may need to be vaccinated more frequently, with higher doses or with adjuvanted formulations to improve their immune response to the targeted antigens. Antigens which are targeted for use in Elderly or Immunocompromised individuals include antigens derived from one or more of the following pathogens: *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Cornynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Chlamydia pneumoniae*, Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV). Examples of specific antigens derived from these pathogens are described above.

Antigens Suitable for Use in Adolescent Vaccines

In certain embodiments, the immunogenic compositions provided herein include one or more antigens suitable for use in adolescent subjects. Adolescents are in need of a boost of a previously administered pediatric antigen. Pediatric antigens which are suitable for use in adolescents are described above. In addition, adolescents are targeted to receive antigens derived from an STD pathogen in order to ensure protective or therapeutic immunity before the beginning of sexual activity. STD antigens which are suitable for use in adolescents are described above.

Tumor Antigens

In certain embodiments, a tumor antigen or cancer antigen is used in conjunction with the immunogenic compositions provided herein. In certain embodiments, the tumor antigens is a peptide-containing tumor antigens, such as a polypeptide tumor antigen or glycoprotein tumor antigens. In certain embodiments, the tumor antigen is a saccharide-containing tumor antigen, such as a glycolipid tumor antigen or a ganglioside tumor antigen. In certain embodiments, the tumor antigen is a polynucleotide-containing tumor antigen that expresses a polypeptide-containing tumor antigen, for instance, an RNA vector construct or a DNA vector construct, such as plasmid DNA.

Tumor antigens appropriate for the use in conjunction with the immunogenic compositions provided herein encompass a wide variety of molecules, such as (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

In certain embodiments, the tumor antigens are, for example, (a) full length molecules associated with cancer cells, (b) homologs and modified forms of the same, including molecules with deleted, added and/or substituted portions, and (c) fragments of the same. In certain embodiments, the tumor antigens are provided in recombinant form. In certain embodiments, the tumor antigens include, for example, class I-restricted antigens recognized by CD8+ lymphocytes or class II-restricted antigens recognized by CD4+ lymphocytes.

In certain embodiments, the tumor antigens include, but are not limited to, (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le$^x$ (associated with, e.g., breast and colorectal cancer) as well as various mucins; glycoproteins are coupled to a carrier protein (e.g., MUC-1 are coupled to KLH); (ii) lipopolypeptides (e.g., MUC-1 linked to a lipid moiety); (iii) polysaccharides (e.g., Globo H synthetic hexasaccharide), which are coupled to a carrier proteins (e.g., to KLH), (iv) gangliosides such as GM2, GM12, GD2, GD3 (associated with, e.g., brain, lung cancer, melanoma), which also are coupled to carrier proteins (e.g., KLH).

In certain embodiments, the tumor antigens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29BCAA), CA 195, CA 242, CA-50, CAM43, CD68KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

Polynucleotide-containing antigens used in conjunction with the immunogenic compositions provided herein include polynucleotides that encode polypeptide cancer antigens such as those listed above. In certain embodiments, the polynucleotide-containing antigens include, but are not limited to, DNA or RNA vector constructs, such as plasmid vectors (e.g., pCMV), which are capable of expressing polypeptide cancer antigens in vivo.

In certain embodiments, the tumor antigens are derived from mutated or altered cellular components. After alteration, the cellular components no longer perform their regulatory functions, and hence the cell may experience uncontrolled growth. Representative examples of altered cellular components include, but are not limited to ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor.

Additionally, bacterial and viral antigens, are used in conjunction with the immunogenic compositions provided herein for the treatment of cancer. In certain embodiments, the carrier proteins, such as $CRM_{197}$, tetanus toxoid, or *Salmonella typhimurium* antigen are used in conjunction/conjugation with compounds provided herein for treatment of cancer. The cancer antigen combination therapies will show increased efficacy and bioavailability as compared with existing therapies.

In certain embodiments, the immunogenic compositions containing at least one compound of Formula (I) include capsular saccharides from at least two of serogroups A, C, W135 and Y of *Neisseria meningitides*. In other embodiments, such vaccines further comprise an antigen from one or more of the following: (a) serogroup B *N. meningitidis*; (b) *Haemophilus influenzae* type B; and/or (c) *Streptococcus pneumoniae*.

In certain embodiments the immunogenic compositions containing at least one compound of Formula (I) include serogroups C, W135 & Y of *N. meningitides*. In certain embodiments the immunogenic compositions containing at least one compound of Formula (I) include serogroups A, C, W135 & Y of *N. meningitides*. In certain embodiments the immunogenic compositions containing at least one compound of Formula (I) include serogroups B, C, W135 & Y of *N. meningitides*. In certain embodiments the immunogenic compositions containing at least one compound of Formula (I) include serogroups A, B, C, W135 & Y of *N. meningitides*. In certain embodiments the immunogenic compositions containing at least one compound of Formula (I) include *H. influenzae* type B and serogroups C, W135 & Y of *N. meningitides*. In certain embodiments the immunogenic compositions containing at least one compound of Formula (I) include *H. influenzae* type B and serogroups A, C, W135 & Y of *N. meningitides*. In certain embodiments the immunogenic compositions containing at least one compound of Formula (I) include *H. influenzae* type B and serogroups B, C, W135 & Y of *N. meningitides*. In certain embodiments the immunogenic compositions containing at least one compound of Formula (I) include *H. influenzae* type B and serogroups A, B, C, W135 & Y of *N. meningitides*. In certain embodiments the immunogenic compositions containing at least one compound of Formula (I) include *S. pneumoniae* and serogroups C, W135 & Y of *N. meningitides*. In certain embodiments the immunogenic compositions containing at least one compound of Formula (I) include *S. pneumoniae* and serogroups A, C, W135 & Y of *N. meningitides*. In certain embodiments the immunogenic compositions containing at least one compound of Formula (I) include *S. pneumoniae* and serogroups B, C, W135 & Y of *N. meningitides*. In certain embodiments the immunogenic compositions containing at least one compound of Formula (I) include *S. pneumoniae* and serogroups A, B, C, W135 & Y of *N. meningitides*. In certain embodiments the immunogenic compositions containing at least one compound of Formula (I) include *H. influenzae* type B, *S. pneumoniae* and serogroups C, W135 & Y of *N. meningitides*. In certain embodiments the immunogenic compositions containing at least one compound of Formula (I) include *H. influenzae* type B, *S. pneumoniae* and serogroups A, C, W135 & Y of *N. meningitides*. In certain embodiments the immunogenic compositions containing at least one compound of Formula (I) include *H. influenzae* type B, *S. pneumoniae* and serogroups B, C, W135 & Y of *N. meningitides*. In certain embodiments the immunogenic compositions containing at least one compound of Formula (I) include *H. influenzae* type B, *S. pneumoniae* and serogroups A, B, C, W135 & Y of *N. meningitidis*.

Kits

Also provided herein are pharmaceutical packs or kits that include one or more containers containing a compound of Formula (I) useful for the treatment or prevention of a disease or disorder associated with toll-like receptors. In other embodiments, the such pharmaceutical packs or kits include one or more containers containing a compound of Formula (I) useful for the treatment or prevention of a disease or disorder associated with toll-like receptors and one or more containers containing an additional therapeutic agent, including but not limited to those listed above. In certain embodiments, such pharmaceutical packs or kits optionally include instructions for its administration of a compound of Formula (I) as disclosed herein. In some embodiments of such kits, the compound of Formula (I) is provided in the form of a vaccine composition as described herein, and optionally includes a syringe for injecting a subject with the vaccine composition Methods of Treatment, Prevention and Administration of Vaccines The immunogenic compositions as disclosed herein may be used in conjunction with vaccines to improve the immunogenicity of the vaccine or where the immunogenic composition includes one or more antigens, the immunogenic composition may be used as a vaccine. Therefore in certain embodiment, the immunogenic compositions disclosed herein may be used in a method for raising or enhancing an immune response in a mammal comprising the step of administering an effective amount of an immunogenic composition as disclosed herein. The immune response is preferably protective and preferably involves antibodies and/or cell-mediated immunity. The method may raise a booster response.

In certain embodiments, the immunogenic compositions disclosed herein may be used as a medicament, e.g., for use in raising or enhancing an immune response in a mammal.

In certain embodiments, the immunogenic compositions disclosed herein may be used in the manufacture of a medicament for raising an immune response in a mammal.

The invention also provides a delivery device pre-filled with an immunogenic composition disclosed herein.

By raising an immune response in the mammal by these uses and methods, the mammal can be infection by pathogens comprising the antigen included in the immunogenic composition or administered in conjunction with the immunogenic composition can be reduced or even prevented. The mammal is preferably a human, but may be, e.g., a cow, a pig, a chicken, a cat or a dog, as the pathogens covered herein may be problematic across a wide range of species. Where the vaccine is for prophylactic use, the human is preferably a child (e.g., a toddler or infant) or a teenager; where the vaccine is for therapeutic use, the human is preferably a teenager or an adult. A vaccine intended for children may also be administered to adults, e.g., to assess safety, dosage, immunogenicity, etc.

One way of checking efficacy of therapeutic treatment involves monitoring pathogen infection after administration of the immunogenic compositions disclosed herein. One way of checking efficacy of prophylactic treatment involves monitoring immune responses, systemically (such as monitoring the level of IgG1 and IgG2a production) and/or mucosally (such as monitoring the level of IgA production), against the antigens included in or administered in conjunction with the immunogenic compositions disclosed herein after administration of the immunogenic composition (and the antigen if administered separately). Typically, antigen-specific serum antibody responses are determined post-immunisation but pre-challenge whereas antigen-specific mucosal antibody responses are determined post-immunisation and post-challenge.

Another way of assessing the immunogenicity of the immunogenic compositions disclosed herein where the antigen is a protein is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the immunogenic compositions can also be determined in vivo by challenging appropriate animal models of the pathogen of interest infection.

The immunogenic compositions disclosed herein will generally be administered directly to a subject. Direct delivery may be accomplished by parenteral injection (e.g., subcutaneously, intraperitoneally, intravenously, intramuscularly, or to the interstitial space of a tissue), or mucosally, such as by rectal, oral (e.g., tablet, spray), vaginal, topical, transdermal or transcutaneous, intranasal, ocular, aural, pulmonary or other mucosal administration.

The immunogenic compositions may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage can be by a single dose schedule or a multiple dose schedule. Multiple doses may be used in a primary immunisation schedule and/or in a booster immunisation schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

The immunogenic compositions disclosed herein that include one or more antigens or are used in conjunction with one or more antigens may be used to treat both children and adults. Thus a human subject may be less than 1 year old, 1-5 years old, 5-15 years old, 15-55 years old, or at least 55 years old. Preferred subjects for receiving such immunogenic compositions are the elderly (e.g., >50 years old, >60 years old, and preferably >65 years), the young (e.g., <5 years old), hospitalised patients, healthcare workers, armed service and military personnel, pregnant women, the chronically ill, or immunodeficient patients. The immunogenic compositions are not suitable solely for these groups, however, and may be used more generally in a population.

The immunogenic compositions disclosed herein that include one or more antigens or are used in conjunction with one or more antigens may be administered to patients at substantially the same time as (e.g., during the same medical consultation or visit to a healthcare professional or vaccination centre) other vaccines, e.g., at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A C W135 Y vaccine), a respiratory syncytial virus vaccine, etc.

Compounds of Formula (I) Formulated with Aluminum-Containing Adjuvants

In certain embodiments, at least one compound of Formula (I) provided herein, or a pharmaceutically acceptable salt or solvate thereof, is combined with an aluminum-containing adjuvant and an effective amount of one or more antigens, resulting in an immunogenic composition. In certain embodiments of such immunogenic compositions the compound of Formula (I) is bound to the aluminum-containing adjuvant. In such immunogenic compositions the antigen is any antigen provided herein. In such immunogenic compositions, the antigen and the compound of Formula (I), a TLR2 agonist, are co-delivered to a desired site.

In certain embodiments of such immunogenic composition, the binding of a compound of Formula (I) to an aluminum-containing adjuvant does not interfere with the binding of the antigen to the aluminum-containing adjuvant.

In certain embodiments, such immunogenic compositions are useful as vaccines. In certain embodiments, such vaccines are prophylactic (i.e. to prevent infection), while in other embodiments, such vaccines are therapeutic (i.e. to treat infection).

The compound(s) of Formula (I) provided herein, or a pharmaceutically acceptable salt or solvate thereof, are TLR2 agonists and are immune potentiators that impart an immunostimulatory effect upon administration when compared to immunogenic formulations that do not contain compound(s) of Formula (I). In certain embodiments, compounds of Formula (I) impart an immunostimulatory effect upon administration when included in an immunogenic composition having one or more immunoregulatory agents, while in other embodiments, compounds of Formula (I) impart an immunostimulatory effect upon administration when included in an immunogenic composition without the presence of other immunoregulatory agents.

In certain embodiments, such immunogenic compositions enhance immune response through the retention of the compound of Formula (I) at the site of injection.

In certain embodiments, such immunogenic compositions include a pharmaceutically acceptable carrier such as, but are not limited to, proteins, polysaccharides, polylactic acids, polyglycolic acids, polymeric amino acids, amino acid copolymers, sucrose, trehalose, lactose, lipid aggregates (such as oil droplets or liposomes), and inactive virus particles. The immunogenic compositions typically also contain diluents, such as water, saline, and glycerol, and optionally contain other excipients, such as wetting or emulsifying agents, and pH buffering substances. In certain embodiments, such immunogenic compositions include one or more additional adjuvants provided herein.

EXAMPLES

The following examples were offered to illustrate, but not to limit, the compounds of Formula (I) provided herein, and the preparation of such compounds.

Synthesis of Starting Compounds

Preparation (5R,9R)-9-(dodecanoyloxy)-1-(9H-fluoren-9-yl)-3,12-dioxo-2,11-dioxa-7-thia-4-azatricosane-5-carboxylic acid (6)

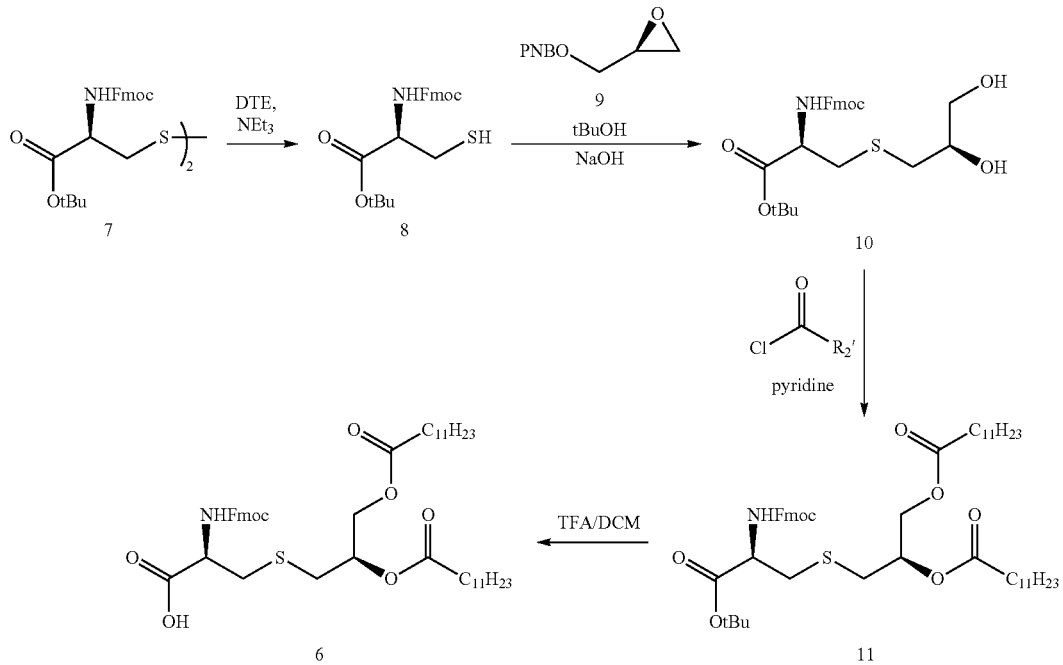

Step 1: (R)-tert-butyl 2-(((9H-fluoren-9-yl)methoxy)carbonylamino)-3-mercaptopropanoate (8)

A solution of (N-Fmoc-Cys-OtBu)$_2$ (7, 1 eq), NEt$_3$ (3 eq) and DTE (1,4-Dithioerythritol, 2.5 eq) in DCM (0.1 M) was stirred at room temperature until complete reduction (1.5 hours). The reaction mixture was diluted in DCM, washed three times with 5% citric acid, twice with water, and once with brine. The organic layer was dried over anhydrous Na$_2$SO$_4$ and concentrated en vaccuo. The resulting crude was purified by flash chromatography on a COMBIFLASH® system (ISCO) using 0-30% EtOAc/Hex to give the title product as colorless viscous oil.

Step 2: (R)-tert-butyl 2-(((9H-fluoren-9-yl)methoxy)carbonylamino)-3-((R)-2,3-dihydroxypropylthio)propanoate (10)

A solution of (2S)-(+)-glycidyl-4-nitrobenzoate (9, 1.1 eq) and 1M NaOH (1.1 eq) in tBuOH (0.1 M) was stirred at room temperature until complete hydrolysis of the nitrobenzoate (30 minutes). To the resulting mixture, a solution of (R)-tert-butyl 2-(((9H-fluoren-9-yl)methoxy)carbonylamino)-3-mercaptopropanoate (8, 1 eq) in tBuOH (1 M) was introduced. The reaction was stirred at room temperature for 15 hours. The reaction mixture was concentrated en vaccuo to remove tBuOH and dissolved in EtOAc. The EtOAc solution was washed three times with water, and once with brine. The resulting crude was purified by flash chromatography on a COMBIFLASH® system (ISCO) using 0-90% EtOAc/Hex to give the title product as colorless viscous oil.

Step 3: (R)-3-((R)-2-(((9H-fluoren-9-yl)methoxy) carbonylamino)-3-tert-butoxy-3-oxopropylthio)propane-1,2-diyl didodecanoate (11)

A solution of (R)-tert-butyl 2-(((9H-fluoren-9-yl)methoxy)carbonylamino)-3-((R)-2,3-dihydroxypropylthio)propanoate (10, 1 eq) in DCM (0.1 M) was cooled in an ice bath. Pyridine (3.7 eq) was added followed by dodecanoyl chloride (3.7 eq). The reaction mixture was stirred for 10 minutes then warmed up to room temperature, and stirred for 2 hours. The reaction mixture was diluted with DCM, washed with saturated aqueous $NH_4Cl$. The aqueous phase was back extracted with DCM. The combined organic phases were washed with $H_2O$, and the aqueous phase was back extracted with DCM. The combined organic phases were washed with brine, dried over anhydrous $Na_2SO_4$ and concentrated en vaccuo. The resulting crude was purified by flash chromatography on a COMBIFLASH® system (ISCO) using 0-30% EtOAc/Hex to give the title product as a white solid.

Step 4: (5R,9R)-9-(dodecanoyloxy)-1-(9H-fluoren-9-yl)-3,12-dioxo-2,11-dioxa-7-thia-4-azatricosane-5-carboxylic acid (6)

A solution of (R)-3-((R)-2-(((9H-fluoren-9-yl)methoxy) carbonylamino)-3-tert-butoxy-3-oxopropylthio)propane-1, 2-diyl didodecanoate (11) in 40% TFA in DCM (0.3 M) was stirred at room temperature until complete deprotection of tert-butyl group (2 hr). The reaction mixture was diluted in MTBE, washed three times with 1M citric acid (adjusted to pH3), and once with 1:2 1N HCl/brine. The organic layer was dried over anhydrous $Na_2SO_4$ and concentrated en vaccuo. The resulting waxy solid was used without further purification.

Synthesis of Example Compounds

Example 1

Synthesis of: (R)-3-((R)-2-amino-3-(1-(hydroxymethyl)cyclopropylamino)-3-oxopropylthio)propane-1,2-diyl didodecanoate

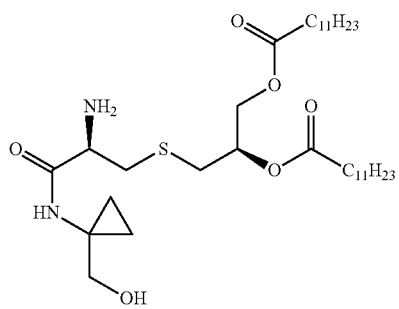

Step 1: (R)-3-((R)-2-(((9H-fluoren-9-yl)methoxy) carbonylamino)-3-(1-(hydroxymethyl)cyclopropylamino)-3-oxopropylthio)propane-1,2-diyl didodecanoate To a solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) and HBTU (1.2 eq) in DCM (0.06 M) was added DIEA (3.5 eq), followed by (1-aminocyclopropyl) methanol hydrochloride (1.2 eq). The reaction was stirred at room temperature for 2 hours. The crude mixture was purified by flash chromatography on a COMBIFLASH® system (ISCO) using 30-50% EtOAc/Hex to give (R)-3-((R)-2-(((9H-fluoren-9-yl)methoxy)carbonylamino)-3-(1-(hydroxymethyl)cyclopropylamino)-3-oxopropylthio)propane-1,2-diyl didodecanoate.

Step 2: (R)-3-((R)-2-amino-3-(1-(hydroxymethyl) cyclopropylamino)-3-oxopropylthio)propane-1,2-diyl didodecanoate To a solution of (R)-3-((R)-2-(((9H-fluoren-9-yl)methoxy)carbonylamino)-3-(1-(hydroxymethyl)-cyclopropylamino)-3-oxopropylthio)propane-1,2-diyl didodecanoate (1 eq) was added 20% piperidine (50 eq) in acetonitrile. The resulting gel was diluted with DCM and sonicated for 3 minutes. The mixture was added to toluene and then concentrated en vaccuo. The crude mixture was purified by flash chromatography on a COMBIFLASH® system (ISCO) using 100% EtOAc then 0-10% MeOH/DCM to give (R)-3-((R)-2-amino-3-(1-(hydroxymethyl)cyclopropylamino)-3-oxopropylthio)propane-1,2-diyl didodecanoate as an off white solid. $^1$H NMR ($CDCl_3$): δ 7.85 (br s, 1H), 5.11-5.18 (m, 1H), 4.36 (dd, 1H), 4.14 (dd, 1H), 4.05 (br s, 1H), 3.59 (q, 2H), 3.50 (dd, 1H), 3.06 (dd, 1H), 2.80 (dd, 1H), 2.68-2.76 (m, 2H), 2.32 (q, 4H), 1.51-1.68 (m, 4H), 1.19-1.35 (m, 32H), 0.90-0.94 (m, 2H), 0.88 (t, 6H), 0.79-0.83 (m, 2H). LRMS [M+H]=629.5.

Example 2

Synthesis of: 3-((R)-2-amino-3-((R)-2,3-bis(dodecanoyloxy)propylthio)propanamido)propylphosphonic acid

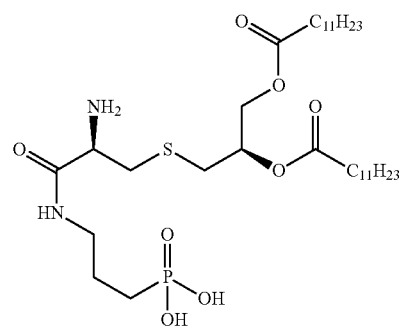

Step 1: diethyl 3-azidopropylphosphonate

To a solution of diethyl 3-bromopropylphosphonate (1 eq) in EtOH (2 M) was added sodium azide (5 eq) in water (4 M). The reaction mixture was heated at reflux overnight. The mixture was then diluted with water, extracted with DCM three times. The combined organic layers are washed with brine, dried over anhydrous $Na_2SO_4$, and concentrated en vaccuo. The crude material was purified by flash chromatography on a COMBIFLASH® system (ISCO) using 80-100% EtOAc/Hex to give the product as a colorless oil.

Step 2: diethyl 3-aminopropylphosphonate

Diethyl 3-azidopropylphosphonate (1 eq) was dissolved in EtOH (0.1 M). Pd(OH)$_2$ (0.02 eq) was added to the reaction. Hydrogen gas was introduced via a balloon and the reaction was stirred for 3 hours. The reaction was stirred for a further 2 hours at room temperature and filtered through Celite and washed with methanol. The solvent was removed en vaccuo and the crude material was purified by flash chromatography on a COMBIFLASH® system (ISCO) using 0-10% MeOH in DCM with 0.5% NH$_3$ in MeOH to give the product as colorless oil.

Step 3: 3-((R)-2-(((9H-fluoren-9-yl)methoxy)carbonylamino)-3-((R)-2,3-bis(dodecanoyloxy)-propylthio)propanamido)propylphosphoryl diethyl ester To a solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) in DCM (0.1M) was added diethyl 3-aminopropylphosphonate (1.3 eq), DIEA (2.5 eq) and HBTU (1.2 eq). The reaction was stirred at room temperature for 2 hours. The crude mixture was purified by flash chromatography on a COMBIFLASH® system (ISCO) using 70-100% EtOAc/Hex to give the product.

Step 4: 3-((R)-2-amino-3-((R)-2,3-bis(dodecanoyloxy)propylthio)propanamido)propyl phosphoryl diethyl ester To a solution of 3-((R)-2-(((9H-fluoren-9-yl)methoxy)carbonylamino)-3-((R)-2,3-bis(dodecanoyloxy)propylthio)propanamido)propylphosphoryl diethyl ester (1 eq) was added 20% piperidine (50 eq) in acetonitrile. The resulting mixture was diluted with dichloromethane and sonicated for 3 minutes. To the mixture was added toluene and then concentrated en vaccuo. The crude mixture was purified by flash chromatography on a COMBIFLASH® system (ISCO) using 100% EtOAc then 0-10% MeOH/DCM to give the product as yellowish oil.

Step 5: 3-((R)-2-amino-3-((R)-2,3-bis(dodecanoyloxy)propylthio)propanamido)propylphosphonic acid To a solution of 3-((R)-2-amino-3-((R)-2,3-bis(dodecanoyloxy)propylthio)-propanamido)propylphosphoryl diethyl ester (1 eq) in DCM (0.1 M) was added trimethylsilyl bromide (10 eq). The reaction mixture was stirred at room temperature overnight and concentrated. The crude mixture was purified by reverse phase high performance liquid chromatography (HPLC) with C4 column eluting with a gradient of 40-100% MeCN/10 mM NH$_4$OAc (95:5) in 10 mM NH$_4$OAc (pH 9) to give the title compound as a white solid.
$^1$H NMR (DMSO d-6): δ 8.51 (t, 1H), 5.10-5.17 (m, 1H), 4.29 (dd, 1H), 4.12 (dd, 1H), 3.86 (t, 1H), 3.08-3.24 (m, 2H), 2.96 (dd, 1H), 2.83 (dd, 2H), 2.74 (dd, 1H), 2.23-2.31 (m, 4H), 1.58-1.70 (m, 2H), 1.44-1.58 (m, 6H), 1.13-1.32 (m, 32H), 0.85 (t, 6H). LRMS [M+H]=681.4.

Example 3

Synthesis of: (8R,12R)-8-amino-12-(dodecanoyloxy)-7,15-dioxo-3,14-dioxa-10-thia-6-azahexacosylphosphonic acid

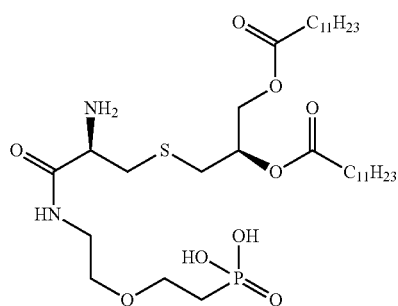

Step 1: diethyl 2-(2-bromoethoxy)ethylphosphonate acid 1-bromo-2-(2-bromoethoxy)ethane (1.0 eq) was mixed with triethyl phosphate (1 eq) then heated to 160° C. for 20 minutes by microwave. The crude mixture was purified by flash chromatography on a COMBIFLASH® system (ISCO) using 70-100% EtOAc/Hex to give the product as a colorless oil.

Step 2: diethyl 2-(2-azidoethoxy)ethylphosphonate

To a solution of diethyl 2-(2-bromoethoxy)ethylphosphonate (1 eq) in EtOH (0.3 M) was added sodium azide (5 eq) in water (2 M). The reaction mixture was heated at reflux overnight. The mixture was then diluted with water, extracted with ethyl acetate. The organic layer was washed with 5% citric acid, saturated NaHCO$_3$, water and brine, dried over anhydrous Na$_2$SO$_4$, and concentrated en vaccuo. The crude material was purified by flash chromatography on a COMBIFLASH® system (ISCO) using 80-100% EtOAc/Hex to give the product as colorless oil.

Step 3: diethyl 2-(2-aminoethoxy)ethylphosphonate

Diethyl 2-(2-azidoethoxy)ethylphosphonate (1 eq) was dissolved in EtOH (0.1 M). Pd(OH)$_2$ (0.05 eq) was added to the reaction. Hydrogen gas was introduced via a balloon; and the reaction was stirred for 2 hours at room temperature. The mixture was filtered through Celite and washed with MeOH. The solvent was removed en vaccuo and the crude material was purified by flash chromatography on a COMBIFLASH® system (ISCO) using 0-10% MeOH/DCM with 2% NH$_3$ in methanol to give the product as colorless oil.

Step 4: (8R,12R)-8-(((9H-fluoren-9-yl)methoxy)carbonylamino)-12-(dodecanoyloxy)-7,15-dioxo-3,14-dioxa-10-thia-6-azahexacosylphosphoryl diethyl ester To a solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) in DCM (0.1M) was added diethyl 2-(2-aminoethoxy)ethylphosphonate (1.3 eq), DIEA (2.5 eq) and HBTU (1.2 eq). The reaction was stirred at room temperature for 2 hours. The crude mixture was purified by flash chromatography by flash chromatography on a COMBIFLASH® system (ISCO) using 50-100% EtOAc/Hex to give the product.

Step 5: ((8R,12R)-8-amino-12-(dodecanoyloxy)-7,15-dioxo-3,14-dioxa-10-thia-6-azahexacosyl phosphoryl diethyl ester To a solution of (8R,12R)-8-(((9H-fluoren-9-yl)methoxy)carbonylamino)-12-(dodecanoyloxy)-7,15-dioxo-3,14-dioxa-10-thia-6-azahexacosylphosphoryl diethyl ester (1 eq) was added 20% piperidine (50 eq) in acetonitrile. The resulting mixture was diluted with DCM and sonicated for 3 minutes. To the mixture was added toluene and then concentrated en vaccuo. The crude mixture was purified by flash chromatography on a COMBIFLASH® system (ISCO) using 100% EtOAc then 0-10% MeOH/DCM to give the product.

Step 6: ((8R,12R)-8-amino-12-(dodecanoyloxy)-7,15-dioxo-3,14-dioxa-10-thia-6-azahexacosylphosphonic acid To a solution of (8R,12R)-8-amino-12-(dodecanoyloxy)-7,15-dioxo-3,14-dioxa-10-thia-6-azahexacosyl phosphoryl diethyl ester (1 eq) in DCM (0.1 M) was added trimethylsilyl bromide (10 eq). The reaction mixture was stirred at room temperature overnight and concentrated. The crude mixture was purified by reverse phase high performance liquid chromatography (HPLC) with C4 column eluting with a gradient of 40-100% MeCN/10 mM $NH_4OAc$ (95:5) in 10 mM $NH_4OAc$ (pH 9) to give the title compound as a white solid. $^1H$ NMR (DMSO d-6): δ 9.16 (br s, 1H), 5.09 (br, 1H), 4.29 (dd, 1H), 4.11 (dd, 1H), 3.44-3.70 (m, 3H), 3.25-3.27 (m, 2H), 3.17-3.25 (m, 1H), 3.03-3.15 (m, 1H), 2.94 (dd, 1H), 2.83 (dd, 1H), 2.61-2.76 (m, 2H), 2.22-2.23 (m, 4H), 1.58-1.75 (m, 2H), 1.45-1.56 (m, 4H), 1.15-1.34 (m, 32H), 0.86 (t, 6H). LRMS [M+H]=711.4.

Example 4

Synthesis of: (12R,16R)-12-amino-16-(dodecanoyloxy)-1,1-difluoro-11,19-dioxo-4,7,18-trioxa-14-thia-10-azatriacontylphosphonic acid

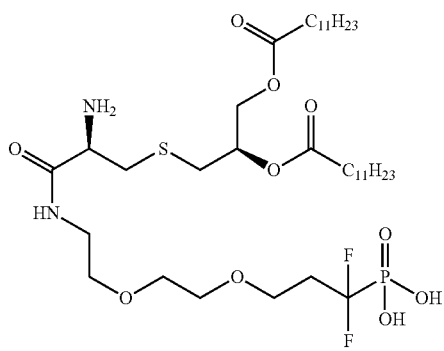

Step 1: diethyl 1,1-difluoro-3-(2-(2-iodoethoxy)ethoxy)propylphosphonate

To a solution of diisopropylamine (1.6 eq) in THF (1.28 M) was slowly added n-butyllithium (1.5 M in cyclohexane, 1.5 eq) dropwise at 0° C. The reaction mixture was stirred at 0° C. for 40 minutes. The mixture was then cooled down to -78° C., and diethyl difluoromethylphosphonate (1 eq) in HMPA (2.1 M) was slowly added to the solution. Then the mixture was stirred at -78° C. for 40 minutes and to the resulting solution was added a cooled solution of 1,2-bis(2-iodoethoxy)ethane (12.8 M in THF, 4 eq) rapidly. After 1.5 hours, the reaction was quenched by pouring into saturated $NH_4Cl$ solution. The aqueous phases were extracted with ethyl acetate three times. The combined organic phases were washed with brine, dried over anhydrous sodium sulfate and concentrated en vaccuo. The resulting crude was purified by flash chromatography on a COMBIFLASH® system (ISCO) using 10-100% EtOAc/Hex to give the product as a yellow oil.

Step 2: diethyl 3-(2-(2-azidoethoxy)ethoxy)-1,1-difluoropropylphosphonate

To a solution of diethyl 1,1-difluoro-3-(2-(2-iodoethoxy)ethoxy)propylphosphonate (1 eq) in DMF (0.5 M) was added sodium azide (3 eq). The reaction mixture was stirred at room temperature for 90 minutes. The mixture was diluted with ethyl acetate, and washed with water. The aqueous phases were back extracted with ethyl acetate. The combined organic phases were washed with brine, dried over anhydrous $Na_2SO_4$, and concentrated en vaccuo. The crude mixture was purified by flash chromatography on a COMBIFLASH® system (ISCO) using 10-50% EtOAc/Hex to give the product as a yellowish oil.

Step 3: diethyl 3-(2-(2-aminoethoxy)ethoxy)-1,1-difluoropropylphosphonate hydrochloride To a solution of diethyl 3-(2-(2-azidoethoxy)ethoxy)-1,1-difluoropropylphosphonate (1 eq) in EtOH (2 M) solution was added palladium hydroxide (0.05 eq) and 2 M HCl in ether (1.1 eq). The reaction mixture was stirred under hydrogen (1 atm) overnight. The palladium was filtered off and the filtrate was concentrated en vaccuo. The crude mixture was used for the next reaction without further purification.

Step 4: diethyl(12R,16R)-12-(((9H-fluoren-9-yl)methoxy)carbonylamino)-16-(dodecanoyloxy)-1,1-difluoro-11,19-dioxo-4,7,18-trioxa-14-thia-10-azatriacontylphosphonate To a solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) in DCM (0.1M) was added diethyl 3-(2-(2-aminoethoxy)ethoxy)-1,1-difluoropropylphosphonate hydrochloride (1.3 eq), DIEA (3.5 eq) and HBTU (1.2 eq). The reaction mixture was then stirred at room temperature for 2 hours. The mixture was purified by flash chromatography on a COMBIFLASH® system (ISCO) using 30-80% EtOAc/Hex to give the product.

Step 5: diethyl(12R,16R)-12-amino-16-(dodecanoyloxy)-1,1-difluoro-11,19-dioxo-4,7,18-trioxa-14-thia-10-azatriacontylphosphonate To a solution of diethyl(12R,16R)-12-(((9H-fluoren-9-yl)methoxy)carbonylamino)-16-(dodecanoyloxy)-1,1-difluoro-11,19-dioxo-4,7,18-trioxa-14-thia-10-azatriacontylphosphonate (1 eq) was added 20% piperidine (50 eq) in acetonitrile The resulting mixture was stirred at 25° C. until the smarting material disappeared. To the mixture was added toluene and then concentrated en vaccuo. The crude mixture was purified by flash chromatography on a COMBIFLASH® system (ISCO) using 100% EtOAc then 0-10% MeOH/DCM to give the product as a colorless oil.

Step 6: (12R,16R)-12-amino-16-(dodecanoyloxy)-1,1-difluoro-1,19-dioxo-4,7,18-trioxa-14-thia-10-azatriacontylphosphonic acid To a solution of diethyl(12R,16R)-12-amino-16-(dodecanoyloxy)-1,1-difluoro-11,19-dioxo-4,7,18-trioxa-14-thia-10-azatriacontylphosphonate (1 eq) in DCM (0.1 M) was added trimethylsilyl bromide (10 eq). The reaction mixture was then stirred at room temperature overnight and concentrated. The crude mixture was purified by reverse phase high performance liquid chromatography (HPLC) with C4 column eluting with a gradient of 40-100% MeCN/10 mM NH$_4$OAc (95:5) in 10 mM NH$_4$OAc (pH 9) to give (12R,16R)-12-amino-16-(dodecanoyloxy)-1,1-difluoro-11,19-dioxo-4,7,18-trioxa-14-thia-10-azatriacontylphosphonic acid. $^1$H NMR (CDCl$_3$): δ 8.47 (br s, 1H), 5.10-5.23 (m, 1H), 4.32 (dd, 1H), 4.18-4.26 (m, 1H), 4.12 (dd, 1H), 3.68-3.86 (m, 2H), 3.44-3.68 (m, 6H), 3.20-3.36 (m, 1H), 2.96-3.16 (m, 2H), 2.76-2.85 (m, 1H), 2.68-2.76 (m, 1H), 2.21-2.38 (m, 4H), 2.12-2.07 (m, 2H), 1.52-1.65 (m, 4H), 1.36-1.15 (m, 32H), 0.87 (t, 6H). LRMS [M+H]=805.5.

Example 5

(11R,15R)-11-amino-15-(dodecanoyloxy)-10,18-dioxo-3,6,17-trioxa-13-thia-9-azanonacosylphosphonic acid

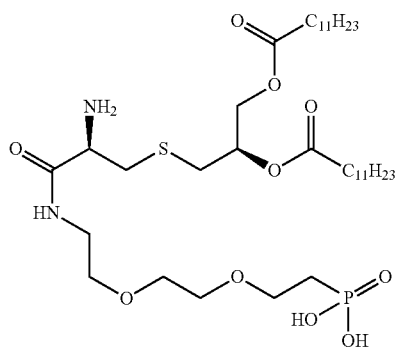

Step 1: diethyl 2-(2-(2-iodoethoxy)ethoxy)ethylphosphonate 1,2-bis(2-iodoethoxy)ethane (1.0 eq) was mixed with triethyl phosphate (1 eq) then heated to 160° C. for 20 minutes by microwave. The crude mixture was purified by flash chromatography on a COMBIFLASH® system (ISCO) using 85-100% EtOAc/Hex to give diethyl 2-(2-(2-iodoethoxy)ethoxy)ethylphosphonate as a colorless oil.

Step 2: diethyl 2-(2-(2-azidoethoxy)ethoxy)ethylphosphonate

To a solution of diethyl 2-(2-(2-iodoethoxy)ethoxy)ethylphosphonate (1 eq) in EtOH (0.2 M) was added sodium azide (5 eq) in water (1.4 M). The reaction mixture was heated at reflux overnight. The mixture was then diluted with water, extracted with EtOAc (3 times). The combined organic layers were washed brine, dried over anhydrous Na$_2$SO$_4$, and concentrated en vaccuo. The crude material was purified by flash chromatography on a COMBIFLASH® system (ISCO) using 0-5% MeOH/DCM to give diethyl 2-(2-(2-azidoethoxy)ethoxy)ethylphosphonate as colorless oil.

Step 3: diethyl 2-(2-(2-aminoethoxy)ethoxy)ethylphosphonate

Diethyl 2-(2-(2-azidoethoxy)ethoxy)ethylphosphonate (1 eq) was dissolved in EtOH (0.1 M). Pd(OH)$_2$ (0.05 eq) was added to the reaction. Hydrogen gas was introduced via a balloon; and the reaction was stirred for 2 hours at room temperature. The mixture was filtered through Celite and washed with MeOH. The solvent was removed en vaccuo and the crude material was purified by flash chromatography on a COMBIFLASH® system (ISCO) using 0-10% MeOH/DCM with 0.5% NH$_3$ to give diethyl 2-(2-(2-aminoethoxy)ethoxy)ethylphosphonate as a colorless oil.

Step 4: (11R,15R)-11-(((9H-fluoren-9-yl)methoxy)carbonylamino)-15-(dodecanoyloxy)-10,18-dioxo-3,6,17-trioxa-13-thia-9-azanonacosylphosphoryl diethyl ester To a solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) in DCM (0.1M) was added diethyl 2-(2-(2-aminoethoxy)ethoxy)ethylphosphonate (1.3 eq), DIEA (2.5 eq) and HBTU (1.2 eq). The reaction was stirred at room temperature for 2 hours. The crude mixture was purified by flash chromatography by flash chromatography on a COMBIFLASH® system (ISCO) using 70-100% EtOAc/Hex to give (11R,15R)-11-(((9H-fluoren-9-yl)methoxy)carbonylamino)-15-(dodecanoyloxy)-10,18-dioxo-3,6,17-trioxa-13-thia-9-azanonacosylphosphoryl diethyl ester.

Step 5: (11R,15R)-1-amino-15-(dodecanoyloxy)-10,18-dioxo-3,6,17-trioxa-13-thia-9-azanonacosyl phosphoryl diethyl ester To a solution of (11R,15R)-11-(((9H-fluoren-9-yl)methoxy)carbonylamino)-15-(dodecanoyloxy)-10,18-dioxo-3,6,17-trioxa-13-thia-9-azanonacosylphosphoryl diethyl ester (1 eq) was added 20% piperidine (50 eq) in acetonitrile. The resulting mixture was diluted with DCM and sonicated for 3 minutes. To the mixture was added to toluene and then concentrated en vaccuo. The crude mixture was purified by flash chromatography on a COMBIFLASH® system (ISCO) using 100% EA followed by 0-10% MeOH in DCM to give (11R,15R)-11-amino-15-(dodecanoyloxy)-10,18-dioxo-3,6,17-trioxa-13-thia-9-azanonacosyl phosphoryl diethyl ester.

Step 6: (11R,15R)-1-amino-15-(dodecanoyloxy)-10,18-dioxo-3,6,17-trioxa-13-thia-9-azanonacosyl phosphonic acid To a solution of (11R,15R)-11-amino-15-(dodecanoyloxy)-10,18-dioxo-3,6,17-trioxa-13-thia-9-azanonacosyl phosphoryl diethyl ester (1 eq) in DCM (0.1 M) was added trimethylsilyl bromide (10 eq). The reaction mixture was stirred at room temperature overnight and concentrated. The crude mixture was purified by reverse phase high performance liquid chromatography (HPLC) with C4 column eluting with a gradient of 40-100% MeCN/10 mM NH$_4$OAc (95:5) in 10 mM NH$_4$OAc (pH 9) to give (11R,15R)-11-amino-15-(dodecanoyloxy)-10,18-dioxo-3,6,17-trioxa-13- thia-9-azanonacosyl phosphonic acid as a white solid. $^1$H NMR (DMSO d-6): δ 8.70 (br t, 1H), 5.05-5.14 (m, 1H), 4.28 (dd, 1H), 4.10 (dd, 1H), 3.79 (t, 2H), 3.20-3.69 (m, 8H), 3.04-3.13 (m, 1H), 2.90 (dd, 1H), 2.83 (dd, 1H), 2.68 (dd, 1H), 2.64-2.72 (m, 1H), 2.21-2.30 (m, 4H), 1.61-1.72 (m, 2H), 1.43-1.55 (m, 4H), 1.15-1.32 (m, 32H), 0.84 (t, 6H). LRMS [M+H]=755.5.

Example 6

(R)-3-((R)-2-amino-3-oxo-3-(2-(pyridin-3-yl)ethylamino)propylthio)propane-1,2-diyl didodecanoate

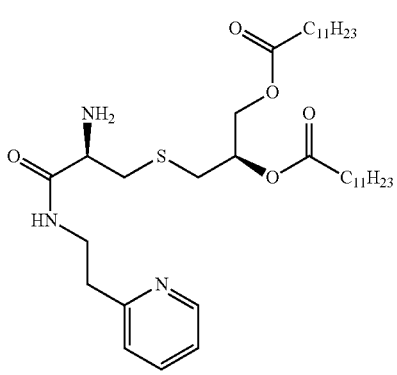

Step 1: (R)-3-((R)-2-(((9H-fluoren-9-yl)methoxy) carbonylamino)-3-oxo-3-(2-pyridin-3-yl)ethylamino) propylthio)propane-1,2-diyl didodecanoate A solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) and HBTU (1.2 eq) were stirred in dry DCM (0.1 M) at room temperature. 3-(2-aminoethyl)pyridine (1.2 eq) was then added followed by diisopropylethylamine (2.0 eq) and the reaction was allowed to stir at room temperature for 2 hours. The crude reaction mixture was then loaded directly onto a silica column and purified by purified by flash chromatography on a COMBIFLASH® system (ISCO) using a 100% Hex, 0-50% EtOAc/Hex, 100% EtOAc gradient to give (R)-3-((R)-2-(((9H-fluoren-9-yl)methoxy)carbonylamino)-3-oxo-3-(2-pyridin-3-yl)ethylamino)propylthio) propane-1,2-diyl didodecanoate.

Step 2: (R)-3-((R)-2-amino-3-oxo-3-(2-(pyridin-3-yl)ethylamino)propylthio)propane-1,2-diyl didodecanoate A solution of (R)-3-((R)-2-(((9H-fluoren-9-yl)methoxy) carbonylamino)-3-oxo-3-(2-pyridin-3-yl)ethylamino)propylthio)propane-1,2-diyl didodecanoate in acetonitrile (0.1M) was stirred at room temperature. Piperidine (final conc. 20%) was then added and the reaction stirred for 30 minutes. After concentration, the crude reaction mixture was purified by flash chromatography on an ISCO COMBIFLASH® system using 0-10% MeOH/DCM (monitored by ninhydrin staining) to afford (R)-3-((R)-2-amino-3-oxo-3-(2-(pyridin-3-yl)ethylamino)propylthio)propane-1,2-diyl didodecanoate. $^1$H NMR (CDCl$_3$): δ 8.49 (m, 2H), 7.53 (m, 2H), 7.24 (m, 1H), 5.18 (m, 1H), 4.36-4.40 (dd, 1H), 4.11-4.19 (dd, 2H), 3.54 (m, 2H), 3.50 (m, 1H), 3.09 (dd, 1H), 2.83 (t, 2H), 2.74 (m, 2H), 2.29-2.38 (q, 4H), 1.60-1.71 (m, 4H), 1.21-1.34 (m, 32H), 0.88 (t, 6H). LRMS [M+H]=664.5.

Example 7

(R)-3-((R)-2-amino-3-(5-aminopentylamino)-3-oxopropylthio)propane-1,2-diyl didodecanoate

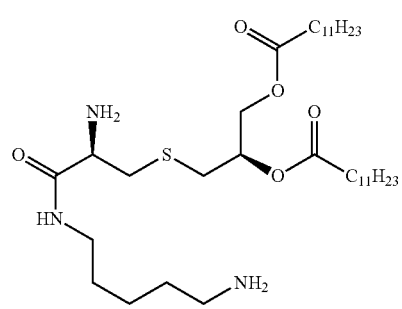

Step 1: (12R,16R)-12-(((9H-fluoren-9-yl)methoxy) carbonylamino)-1-(9H-fluoren-9-yl)-3,11-dioxo-2-oxa-14-thia-4,10-diazaheptadecane-16,17-diyl didodecanoate A solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) and HBTU (1.2 eq) were stirred in dry DCM (0.1 M) at room temperature. Fmoc-1,5-diaminopentane hydrochloride (1.2 eq) was then added followed by diisopropylethylamine (2.0 eq) and the reaction was allowed to stir at room temperature for 2 hr. The crude reaction mixture was then loaded directly onto a silica column and purified by purified by flash chromatography on a COMBIFLASH® system (ISCO) using a 100% Hex, 0-50% EtOAc/Hex, 100% EtOAc gradient to give (12R,16R)-12-(((9H-fluoren-9-yl) methoxy)carbonylamino)-1-(9H-fluoren-9-yl)-3,11-dioxo-2-oxa-14-thia-4,10-diazaheptadecane-16,17-diyl didodecanoate.

Step 2: (R)-3-((R)-2-amino-3-(5-aminopentylamino)-3-oxopropylthio)propane-1,2-diyl didodecanoate A solution of (12R,16R)-12-(((9H-fluoren-9-yl)methoxy) carbonylamino)-1-(9H-fluoren-9-yl)-3,11-dioxo-2-oxa-14-thia-4,10-diazaheptadecane-16,17-diyl didodecanoate in acetonitrile (0.1M) was stirred at room temperature. Piperidine (final conc. 20%) was then added and the reaction stirred for 30 minutes. After concentration, the product was purified by flash chromatography on an ISCO COMBIFLASH® system using a 0-20% MeOH (1% NH$_3$)/DCM gradient to give (R)-3-((R)-2-amino-3-(5-aminopentylamino)-3-oxopropylthio)propane-1,2-diyl didodecanoate. $^1$H NMR (DMSO d-6): δ 7.91 (t, 1H), 5.09 (m, 1H), 4.26-4.32 (dd, 1H), 4.08-4.12 (m, 1H), 3.24-3.36 (m, 8H), 3.05-3.08 (m, 2H), 3.06 (m, 1H), 2.80 (m, 1H), 2.74 (t, 1H), 2.67 (dd, 1H), 2.60 (dd, 1H), 2.29-2.34 (q, 4H), 1.48-1.54 (m, 4H), 1.32-1.40 (m, 4H), 1.21-1.34 (m, 32H), 0.88 (t, 6H). LRMS [M+H]=645.1.

Example 8

((2R,6R)-6,20-diamino-7-oxo-12,17-dioxa-4-thia-8-azaicosane-1,2-diyl didodecanoate

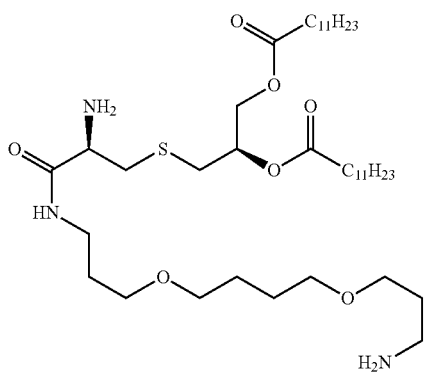

Step 1: (19R,23R)-19-(((9H-fluoren-9-yl)methoxy)carbonylamino)-1-(9H-fluoren-9-yl)-3,18-dioxo-2,8,13-trioxa-21-thia-4,17-diazatetracosane-23,24-diyl didodecanoate A solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) and HBTU (1.2 eq) were stirred in dry DCM (0.1 M) at room temperature. 1-(Fmoc-amino)-4,9-dioxa-12-dodecaneamine hydrochloride (1.2 eq) was then added followed by diisopropylethylamine (2.0 eq) and the reaction was allowed to stir at room temperature for 2 hr. The crude reaction mixture was then loaded directly onto a silica column and purified by purified by flash chromatography on a COMBIFLASH® system (ISCO) using a 100% Hex, 0-50% EtOAc/Hex, 100% EtOAc gradient to give (19R,23R)-19-(((9H-fluoren-9-yl)methoxy)carbonylamino)-1-(9H-fluoren-9-yl)-3,18-dioxo-2,8,13-trioxa-21-thia-4,17-diazatetracosane-23,24-diyl didodecanoate.

Step 2: (R)-3-((R)-2-amino-3-(5-aminopentylamino)-3-oxopropylthio)propane-1,2-diyl didodecanoate A solution of (19R,23R)-19-(((9H-fluoren-9-yl)methoxy)carbonylamino)-1-(9H-fluoren-9-yl)-3,18-dioxo-2,8,13-trioxa-21-thia-4,17-diazatetracosane-23,24-diyl didodecanoate in acetonitrile (0.1M) was stirred at room temperature. Piperidine (final conc. 20%) was then added and the reaction stirred for 30 minutes. After concentration, the product was purified by mass triggered HPLC using a 50-100% MeCN in H$_2$O (0.1% TFA) gradient to give (R)-3-((R)-2-amino-3-(5-aminopentylamino)-3-oxopropylthio)propane-1,2-diyl didodecanoate). $^1$H NMR (DMSO d-6): δ 8.49 (t, 1H), 5.12 (m, 1H), 4.26-4.32 (dd, 1H), 4.08-4.12 (m, 1H), 3.85 (t, 1H), 3.32-3.41 (m, 7H), 3.20 (m, 2H), 3.11 (m, 1H), 2.91 (dd, 1H), 2.82 (m, 4H), 2.73 (m, 1H), 2.52 (m, 2H), 2.29-2.34 (q, 4H), 1.71-1.79 (m, 2H), 1.62-1.68 (m, 2H), 1.49-1.52 (m, 8H), 1.21-1.34 (m, 32H), 1.18-1.21 (t, 2H), 0.88 (t, 6H). LRMS [M+H]=747.1.

Example 9

(20R,24R)-2,20-diamino-1-mercapto-3,19-dioxo-8,11,14-trioxa-22-thia-4,18-diazapentacosane-24,25-diyl didodecanoate

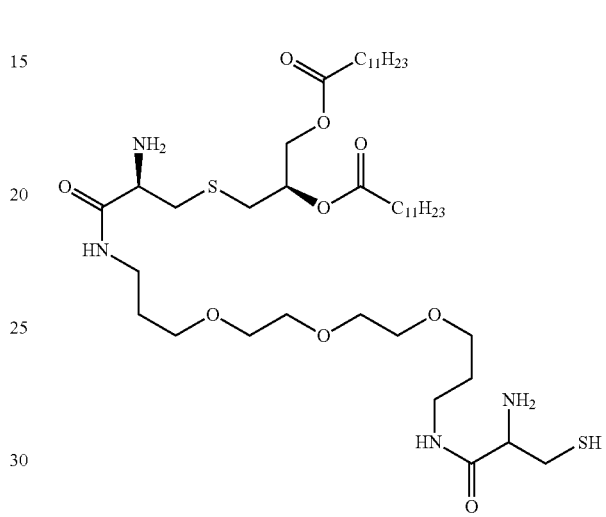

Step 1: (20R,24R)-20-(((9H-fluoren-9-yl)methoxy)carbonylamino)-2,2-dimethyl-4,19-dioxo-3,9,14-trioxa-22-thia-5,18-diazapentacosane-24,25-diyl didodecanoate A solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) and HBTU (1.2 eq) were stirred in dry DCM (0.1 M) at room temperature. Boc-1-amino-4,7,10-trioxa-13-tridecanamine (1.2 eq) was then added followed by diisopropylethylamine (2.0 eq) and the reaction was allowed to stir at room temperature for 2 hr. The crude reaction mixture was then loaded directly onto a silica column and purified by purified by flash chromatography on a COMBIFLASH® system (ISCO) using a 100% Hex, 0-50% EtOAc/Hex, 100% EtOAc gradient to give (20R,24R)-20-(((9H-fluoren-9-yl)methoxy)carbonylamino)-2,2-dimethyl-4,19-dioxo-3,9,14-trioxa-22-thia-5,18-diazapentacosane-24,25-diyl didodecanoate.

Step 2: (2R,6R)-6-(((9H-fluoren-9-yl)methoxy)carbonylamino)-20-amino-7-oxo-12,17-dioxa-4-thia-8-azaicosane-1,2-diyl didodecanoate (20R,24R)-20-(((9H-fluoren-9-yl)methoxy)carbonylamino)-2,2-dimethyl-4,19-dioxo-3,9,14-trioxa-22-thia-5,18-diazapentacosane-24,25-diyl didodecanoate was stirred in 30% TFA/DCM for 4 hours at room temperature. The reaction was then diluted with DCM and washed with 1M citric acid (pH3). The organics were then dried over anhydrous Na$_2$SO$_4$, filtered and concentrated to afford (2R,6R)-6-(((9H-fluoren-9-yl)methoxy)carbonylamino)-20-amino-7-oxo-12,17-dioxa-4-thia-8-azaicosane-1,2-diyl didodecanoate.

Step 3: (23R,27R)-23-(((9H-fluoren-9-yl)methoxy)carbonylamino)-1-(9H-fluoren-9-yl)-3,6,22-trioxo-5-(tritylthiomethyl)-2,11,14,17-tetraoxa-25-thia-4,7,21-triazaoctacosane-27,28-diyl didodecanoate A solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) and HBTU (1.2 eq) were stirred in dry DCM (0.1 M) at room temperature. Fmoc-Cys(Trt)-OH (1.2 eq) was then added followed by diisopropylethylamine (2.0 eq) and the reaction was allowed to stir at room temperature for 2 hr. The crude reaction mixture was then loaded directly onto a silica column and purified by purified by flash chromatography on a COMBIFLASH® system (ISCO) using a 100% Hex, 0-50% EtOAc/Hex, 100% EtOAc gradient to give (23R,27R)-23-(((9H-fluoren-9-yl)methoxy)carbonylamino)-1-(9H-fluoren-9-yl)-3,6,22-trioxo-5-(tritylthiomethyl)-2,11,14,17-tetraoxa-25-thia-4,7,21-triazaoctacosane-27,28-diyl didodecanoate.

Step 4: (22R,26R)-4,22-diamino-5,21-dioxo-1,1,1-triphenyl-10,13,16-trioxa-2,24-dithia-6,20-diazaheptacosane-26,27-diyl didodecanoate A solution of (23R,27R)-23-(((9H-fluoren-9-yl)methoxy)carbonylamino)-1-(9H-fluoren-9-yl)-3,6,22-trioxo-5-(tritylthiomethyl)-2,11,14,17-tetraoxa-25-thia-4,7,21-triazaoctacosane-27,28-diyl didodecanoate in acetonitrile (0.1M) was stirred at room temperature. Piperidine (final conc. 20%) was then added and the reaction stirred for 30 minutes. After concentration, the product was purified by flash chromatography on an ISCO COMBIFLASH® system using an initial gradient of 0-100% EtOAc, then 0-10% MeOH/DCM to give (22R,26R)-4,22-diamino-5,21-dioxo-1,1,1-triphenyl-10,13,16-trioxa-2,24-dithia-6,20-diazaheptacosane-26,27-diyl didodecanoate.

Step 5: (20R,24R)-2,20-diamino-1-mercapto-3,19-dioxo-8,11,14-trioxa-22-thia-4,18-diazapentacosane-24,25-diyl didodecanoate (22R,26R)-4,22-diamino-5,21-dioxo-1,1,1-triphenyl-10,13,16-trioxa-2,24-dithia-6,20-diazaheptacosane-26,27-diyl didodecanoate was stirred in TFA (0.1 M) containing 5% triisopropylsilane at room temperature for 4 hours. The reaction was concentrated and purified by flash chromatography on an ISCO COMBIFLASH® system using a 0-20% MeOH/DCM gradient (20R,24R)-2,20-diamino-1-mercapto-3,19-dioxo-8,11,14-trioxa-22-thia-4,18-diazapentacosane-24,25-diyl didodecanoate. $^1$H NMR (DMSO d-6): δ 8.51 (t, 1H), 8.49 (t, 1H), 5.12 (m, 1H), 4.26-4.32 (dd, 1H), 4.08-4.12 (m, 1H), 3.86 (q, 2H), 3.46-3.52 (m, 8H), 3.40 (t, 4H), 3.35 (br s, 4H), 3.12-3.25 (m, 4H), 2.82-2.94 (m, 6H), 2.72-2.79 (dd, 1H), 2.29-2.34 (q, 4H), 1.68-1.72 (q, 4H), 1.49-1.52 (m, 4H), 1.21-1.34 (m, 32H), 0.86 (t, 6H). LRMS [M+H]=866.3.

Example 10

(4R,7S,10R,14R)-10-amino-4-carbamoyl-7-ethyl-14-(hexadecyloxy)-6,9-dioxo-16-oxa-12-thia-5,8-diazadotriacontan-1-oic acid

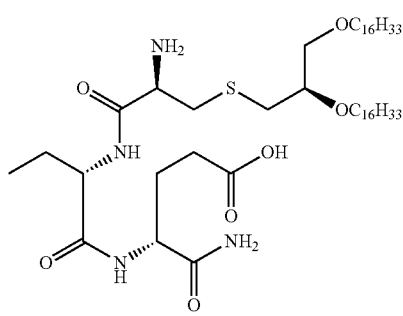

Step 1: (R)-2,3-bis(hexadecyloxy)propyl trifluoromethanesulfonate

To a solution of (S)-2,3-bis(hexadecyloxy)propan-1-ol (1 eq) and pyridine (4 eq) in DCM (0.1 M) at 0° C., was added Tf$_2$O (2 eq). The reaction was stirred at 0° C. for 1 hour and quenched by H$_2$O. The aqueous phase was extracted with DCM. The combined organic phases were washed with H$_2$O, and the aqueous phase was back extracted with DCM. The combined organic phases were washed with saturated NaHCO$_3$ and brine, dried over anhydrous Na$_2$SO$_4$ and concentrated en vaccuo. The resulting crude was purified by flash chromatography on a COMBIFLASH® system (ISCO) using 0-10% EtOAc/Hex to give (R)-2,3-bis(hexadecyloxy)propyl trifluoromethanesulfonate as a colorless oil.

Step 2: (5R,9R)-tert-butyl 1-(9H-fluoren-9-yl)-9-(hexadecyloxy)-3-oxo-2,11-dioxa-7-thia-4-azaheptacosane-5-carboxylate A mixture of (R)-2,3-bis(hexadecyloxy)propyl trifluoromethanesulfonate (1 eq), (R)-tert-butyl 2-(((9H-fluoren-9-yl)methoxy)carbonylamino)-3-mercaptopropanoate (8, 2 eq) and K$_2$CO$_3$ (1 eq) in EtOH (0.1 M) was stirred for 30 minutes at 60° C. The reaction mixture was filtered and washed with DCM. The filtrate was concentrated en vaccuo. The resulting crude was purified by flash chromatography on a COMBIFLASH® system (ISCO) using 0-20% EtOAc/Hex to give (5R,9R)-tert-butyl 1-(9H-fluoren-9-yl)-9-(hexadecyloxy)-3-oxo-2,11-dioxa-7-thia-4-azaheptacosane-5-carboxylate as a colorless oil.

Step 3: (5R,9R)-1-(9H-fluoren-9-yl)-9-(hexadecyloxy)-3-oxo-2,11-dioxa-7-thia-4-azaheptacosane-5-carboxylic acid A solution of (5R,9R)-tert-butyl 1-(9H-fluoren-9-yl)-9-(hexadecyloxy)-3-oxo-2,11-dioxa-7-thia-4-azaheptacosane-5-carboxylate in 40% TFA in DCM (0.3 M) was stirred at room temperature until complete deprotection of tert-butyl group (2 hours). The reaction mixture was diluted in MTBE, washed three times with 1 M citric acid (pH 3), and once with 1:2 HCl (3 M)/brine. The organic layer was dried over anhydrous Na₂SO₄ and concentrated en vaccuo. The resulting waxy solid was used in the next step without further purification.

Step 4: (4R,7S,10R,14R)-benzyl 10-(((9H-fluoren-9-yl)methoxy)carbonylamino)-4-carbamoyl-7-ethyl-14-(hexadecyloxy)-6,9-dioxo-16-oxa-12-thia-5,8-diazadotriacontan-1-oate A solution of (5R,9R)-1-(9H-fluoren-9-yl)-9-(hexadecyloxy)-3-oxo-2,11-dioxa-7-thia-4-azaheptacosane-5-carboxylic acid (1 eq) and HBTU (1.2 eq) were stirred in dry DCM (0.1 M) at room temperature. (R)-benzyl 5-amino-4-((S)-2-aminobutanamido)-5-oxopentanoate hydrochloride (1.2 eq) was then added followed by diisopropylethylamine (2.0 eq) and the reaction was allowed to stir at room temperature for 2 hours. The crude reaction mixture was then loaded directly onto a silica column and purified by purified by flash chromatography on a COMBIFLASH® system (ISCO) using a 100% Hex, 0-50% EtOAc/Hex, 100% EtOAc gradient to give: (4R,7S,10R,14R)-benzyl 10-(((9H-fluoren-9-yl)methoxy)carbonylamino)-4-carbamoyl-7-ethyl-14-(hexadecyloxy)-6,9-dioxo-16-oxa-12-thia-5,8-diazadotriacontan-1-oate.

Step 5: (4R,7S,10R,14R)-10-(((9H-fluoren-9-yl)methoxy)carbonylamino)-4-carbamoyl-7-ethyl-14-(hexadecyloxy)-6,9-dioxo-16-oxa-12-thia-5,8-diazadotriacontan-1-oic acid A mixture of (4R,7S,10R,14R)-benzyl 10-(((9H-fluoren-9-yl)methoxy)carbonylamino)-4-carbamoyl-7-ethyl-14-(hexadecyloxy)-6,9-dioxo-16-oxa-12-thia-5,8-diazadotriacontan-1-oate) and Pd(OH)₂ (1.2 eq) in EtOH (0.1 M) was stirred overnight at 25° C. under H₂ (1 atm). The reaction mixture was filtered and washed with DCM. The filtrate was concentrated en vaccuo. The resulting crude was purified by flash chromatography on a COMBIFLASH® system (ISCO) using 0-10% MeOH/DCM to give (4R,7S,100R,14R)-10-(((9H-fluoren-9-yl)methoxy)carbonylamino)-4-carbamoyl-7-ethyl-14-(hexadecyloxy)-6,9-dioxo-16-oxa-12-thia-5,8-diazadotriacontan-1-oic acid as a white solid.

Step 6: (4R,7S,10R,14R)-10-amino-4-carbamoyl-7-ethyl-14-(hexadecyloxy)-6,9-dioxo-16-oxa-12-thia-5,8-diazadotriacontan-1-oic acid A solution (4R,7S,10R,14R)-10-(((9H-fluoren-9-yl)methoxy)carbonylamino)-4-carbamoyl-7-ethyl-14-(hexadecyloxy)-6,9-dioxo-16-oxa-12-thia-5,8-diazadotriacontan-1-oic acid in acetonitrile (0.1M) was stirred at room temperature. Piperidine (final conc. 20%) was then added and the reaction stirred for 30 min. After concentration, the product was purified by flash chromatography on an ISCO COMBIFLASH® system using a 0-10% MeOH/DCM gradient to give (4R,7S,10R,14R)-10-amino-4-carbamoyl-7-ethyl-14-(hexadecyloxy)-6,9-dioxo-16-oxa-12-thia-5,8-diazadotriacontan-1-oic acid. ¹H NMR (DMSO d-6): δ 12.12 (br, s, 1H), 8.56 (d, 1H), 8.14 (t, 2H), 8.12 (d, 1H), 7.25 (s, 1H), 7.05 (s, 1H), 4.21-4.34 (m, 2H), 3.95-3.97 (m, 1H), 3.44-3.52 (m, 3H), 3.32-3.40 (m, 3H), 2.96 (dd, 1H), 2.66-2.78 (m, 4H), 2.19 (t, 2H), 1.89-1.98 (m, 2H), 1.67-1.76 (m, 4H), 1.56-1.64 (m, 2H), 1.42-1.50 (m, 4H), 1.21-1.28 (m, 48H), 0.83-0.89 (m, 9H). LRMS [M+H]=857.7.

Example 11

N—((R)-1-((R)-2-amino-3-(1-(hydroxymethyl)cyclopropylamino)-3-oxopropylthio)-3-(hexadecyloxy)propan-2-yl)dodecanamide

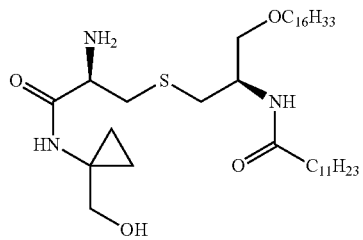

Step 1: (S)-1-(tert-butyldimethylsilyloxy)-3-(hexadecyloxy)propan-2-ol

A solution of (R)-3-(hexadecyloxy)propane-1,2-diol (1 eq), TBDMSCl (1.4 eq), NEt₃ (1.4 eq) and DMAP (0.05 eq) in DCM (0.5 M) was stirred at 25° C. over night. The reaction was diluted with DCM and was with H₂O twice, and the aqueous phase was back extracted with DCM. The combined organic phases were washed with brine, dried over anhydrous sodium sulfate and concentrated en vaccuo. The resulting crude was purified by flash chromatography on a COMBIFLASH® system (ISCO) using 0-20% EtOAc/Hex to give (S)-1-(tert-butyldimethylsilyloxy)-3-(hexadecyloxy)propan-2-ol as a colorless oil.

Step 2: (S)-1-(tert-butyldimethylsilyloxy)-3-(hexadecyloxy)propan-2-yl methanesulfonate To a solution of (S)-1-(tert-butyldimethylsilyloxy)-3-(hexadecyloxy)propan-2-ol (1 eq) in pyridine (0.5 M) at 0° C., was added MsCl (2 eq). The reaction was stirred at 0° C. for 1 h and quenched by H₂O. The aqueous phase was extracted with DCM. The combined organic phases were washed with H₂O, and the aqueous phase was back extracted with DCM. The combined organic phases were washed with saturated NaHCO₃ and brine, dried over anhydrous Na₂SO₄ and concentrated en vaccuo. The resulting crude was purified by flash chromatography on a COMBIFLASH® system (ISCO) using 0-15% EtOAc/Hex to give (S)-1-(tert-butyldimethylsilyloxy)-3-(hexadecyloxy)propan-2-yl methanesulfonate as a colorless oil.

Step 3: (R)-(2-azido-3-(hexadecyloxy)propoxy)(tert-butyl)dimethylsilane

A mixture of (S)-1-(tert-butyldimethylsilyloxy)-3-(hexadecyloxy)propan-2-yl methanesulfonate (1 eq) and NaN₃ (5 eq) in DMF (0.5 M) was stirred at 100° C. over night. The reaction mixture was filtered and washed with DCM. The filtrate was concentrated en vaccuo. The resulting crude was purified by flash chromatography on a COMBIFLASH® system (ISCO) using 0-15% EtOAc/Hex to give (R)-(2-azido-3-(hexadecyloxy)propoxy)(tert-butyl)dimethylsilane as a colorless oil.

Step 4: (S)-2-azido-3-(hexadecyloxy)propan-1-ol

A solution of (R)-(2-azido-3-(hexadecyloxy)propoxy) (tert-butyl)dimethylsilane (1 eq), and 1M TBAF in THF (1.1 eq) in THF (0.2 M) was stirred at 25° C. for 20 minutes. The reaction was diluted with Et$_2$O and washed with saturated NH$_4$Cl, H$_2$O, and brine. The organic phase was dried over anhydrous sodium sulfate and concentrated en vaccuo. The resulting crude was purified by flash chromatography on a COMBIFLASH® system (ISCO) using 0-30% EtOAc/Hex to give (S)-2-azido-3-(hexadecyloxy)propan-1-ol as a colorless oil.

Step 5: (R)-2-azido-3-(hexadecyloxy)propyl trifluoromethanesulfonate

To a solution of (S)-2-azido-3-(hexadecyloxy)propan-1-ol (1 eq) and pyridine (4 eq) in DCM (0.1 M) at 0° C., was added Tf$_2$O (2 eq). The reaction was stirred at 0° C. for 1 hour and quenched by H$_2$O. The aqueous phase was extracted with DCM. The combined organic phases were washed with H$_2$O, and the aqueous phase was back extracted with DCM. The combined organic phases were washed with saturated NaHCO$_3$ and brine, dried over anhydrous Na$_2$SO$_4$ and concentrated en vaccuo. The resulting crude was purified by flash chromatography on a COMBIFLASH® system (ISCO) using 0-10% EtOAc/Hex to give (R)-2-azido-3-(hexadecyloxy) propyl trifluoromethanesulfonate.

Step 6: (5R,9R)-tert-butyl 9-azido-1-(9H-fluoren-9-yl)-3-oxo-2,11-dioxa-7-thia-4-azaheptacosane-5-carboxylate A mixture of (R)-2-azido-3-(hexadecyloxy)propyl trifluoromethanesulfonate (1 eq), (R)-tert-butyl 2-(((9H-fluoren-9-yl)methoxy)carbonylamino)-3-mercaptopropanoate (8, 2 eq) and K$_2$CO$_3$ (1 eq) in EtOH (0.1 M) was stirred for 30 min at 60° C. The reaction mixture was filtered and washed with DCM. The filtrate was concentrated en vaccuo. The resulting crude was purified by flash chromatography on a COMBIFLASH® system (ISCO) using 0-20% EtOAc/Hex to give (5R,9R)-tert-butyl 9-azido-1-(9H-fluoren-9-yl)-3-oxo-2,11-dioxa-7-thia-4-azaheptacosane-5-carboxylate.

Step 7: (5R,9R)-tert-butyl 9-dodecanamido-1-(9H-fluoren-9-yl)-3-oxo-2,11-dioxa-7-thia-4-azaheptacosane-5-carboxylate A mixture of (5R,9R)-tert-butyl 9-azido-1-(9H-fluoren-9-yl)-3-oxo-2,11-dioxa-7-thia-4-azaheptacosane-5-carboxylate (1.0 eq), Pd(OH)$_2$ (0.5 eq), dodecanoyl chloride (2.4 eq), and DIEA (4.8 eq) in EtOAc (0.01 M) was stirred under H$_2$ (1 atm) at 25° C. overnight. The reaction was filtered and washed with DCM. The filtrate was concentrated en vaccuo. The resulting crude was purified by flash chromatography on a COMBIFLASH® system (ISCO) using 0-20% EtOAc/Hex to give (5R,9R)-tert-butyl 9-dodecanamido-1-(9H-fluoren-9-yl)-3-oxo-2,11-dioxa-7-thia-4-azaheptacosane-5-carboxylate as a colorless oil.

Step 8: (5R,9R)-9-dodecanamido-1-(9H-fluoren-9-yl)-3-oxo-2,11-dioxa-7-thia-4-azaheptacosane-5-carboxylic acid A solution of (5R,9R)-tert-butyl 9-dodecanamido-1-(9H-fluoren-9-yl)-3-oxo-2,11-dioxa-7-thia-4-azaheptacosane-5-carboxylate in 40% TFA in DCM (0.3 M) was stirred at room temperature until complete deprotection of tert-butyl group (2 hours). The reaction mixture was diluted in MTBE, washed three times with 1 M citric acid (pH 3), and once with 1:2 HCl (3 M)/brine. The organic layer was dried over anhydrous Na$_2$SO$_4$ and concentrated en vaccuo to give (5R,9R)-9-dodecanamido-1-(9H-fluoren-9-yl)-3-oxo-2,11-dioxa-7-thia-4-azaheptacosane-5-carboxylic acid.

Step 9: (9H-fluoren-9-yl)methyl(R)-3-((R)-2-dodecanamido-3-(hexadecyloxy)propylthio)-1-(1-(hydroxymethyl)cyclopropylamino)-1-oxopropan-2-ylcarbamate To a solution of (5R,9R)-9-dodecanamido-1-(9H-fluoren-9-yl)-3-oxo-2,11-dioxa-7-thia-4-azaheptacosane-5-carboxylic acid (1 eq) and HBTU (1.2 eq) in DCM (0.06 M) was added DIEA (3.5 eq), followed by (1-aminocyclopropyl) methanol hydrochloride (1.2 eq). The reaction was stirred at room temperature for 2 hr. The crude mixture was purified by flash chromatography on a COMBIFLASH® system (ISCO) using 30-50% EtOAc/Hex to give (9H-fluoren-9-yl)methyl (R)-3-((R)-2-dodecanamido-3-(hexadecyloxy)propylthio)-1-(1-(hydroxymethyl)cyclopropylamino)-1-oxopropan-2-ylcarbamate.

Step 10: N—((R)-1-((R)-2-amino-3-(1-(hydroxymethyl)cyclopropylamino)-3-oxopropylthio)-3-(hexadecyloxy)propan-2-yl)dodecanamide To a solution of (9H-fluoren-9-yl)methyl(R)-3-((R)-2-dodecanamido-3-(hexadecyloxy)propylthio)-1-(1-(hydroxymethyl)cyclopropylamino)-1-oxopropan-2-ylcarbamate (1 eq) was added 20% piperidine (50 eq) in acetonitrile. The resulting gel was diluted with DCM and sonicated for 3 minutes. The mixture was added to toluene and then concentrated en vaccuo. The crude mixture was purified by flash chromatography on a COMBIFLASH® system (ISCO) using 100% EtOAc then 0-10% MeOH/DCM to give N—((R)-1-((R)-2-amino-3-(1-(hydroxymethyl)cyclopropylamino)-3-oxopropylthio)-3-(hexadecyloxy)propan-2-yl)dodecanamide. $^1$H NMR (DMSO d-6): δ 8.13 (s, 2H), 7.73 (d, 2H), 4.68 (t, 2H), 3.89-3.97 (m, 2H), 3.35-3.44 (m, 5H), 3.20-3.24 (m, 1H), 2.59-2.74 (m, 4H), 2.32-2.34 (m, 1H), 2.05 (t, 2H), 1.42-1.50 (m, 4H), 1.21-1.28 (m, 40H), 0.85 (t, 6H), 0.67 (dd, 2H), 0.56 (dd, 2H). LRMS [M+H]=670.6.

Example 12

Synthesis of: N,N—((R)-3-((R)-2-amino-3-(1-(hydroxymethyl)cyclopropylamino)-3-oxopropylthio) propane-1,2-diyl)didodecanamide

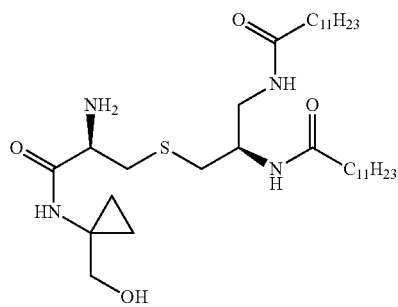

Step 1: (N-Cbz-Cys-OtBu)₂

A solution of (N—H-Cys-OtBu)₂ (1 eq), CbzCl (2.2 eq) and DIEA (5 eq) in DCM (0.1 M) was stirred at 25° C. for 2 hours. The reaction was diluted with DCM then washed successively with 1 M HCl, saturated NaHCO₃, and brine. The organic phase was then dried over anhydrous Na₂SO₄ and concentrated en vaccuo. The resulting crude was purified by flash chromatography on a COMBIFLASH® system (ISCO) using a gradient of 0-60% EtOAc/Hex to afford the title compound as a white gum.

Step 2: (R)-tert-butyl 2-(benzyloxycarbonylamino)-3-mercaptopropanoate

A solution of (N-Cbz-Cys-OtBu)₂ (1 eq), NEt₃ (3 eq) and DTE (1,4-dithioerythritol, 2.5 eq) in DCM (0.1 M) was stirred at room temperature until reduction was complete (1.5 hours). The reaction mixture was then diluted in DCM, washed three times with 5% citric acid, twice with water, and once with brine. The organic layer was dried over anhydrous Na₂SO₄, and concentrated en vaccuo. The resulting crude material was purified by flash chromatography on a COMBIFLASH® system (ISCO) using a gradient of 0-30% EtOAc/Hex to afford the title compound as a colorless viscous oil.

Step 3: (R)-tert-butyl 2-(benzyloxycarbonylamino)-3-((S)-2,3-dihydroxypropylthio)propanoate A solution of (2R)-(−)-glycidyl-4-nitrobenzoate (1.1 eq) and 1M NaOH (1.1 eq) in tBuOH (0.1 M) was stirred at room temperature until complete hydrolysis of nitrobenzoate (30 min) was achieved. To the resulting mixture, a solution of (R)-tert-butyl 2-(benzyloxycarbonylamino)-3-mercaptopropanoate (1 eq) in tBuOH (1 M) was introduced. The reaction was stirred at room temperature for 15 hours, and concentrated en vaccuo to remove tBuOH; then the resulting residue was dissolved in EtOAc. The EtOAc solution was washed three times with H₂O then once with brine. The organic layer was dried over anhydrous Na₂SO₄ then concentrated en vaccuo. The resulting crude material was purified by flash chromatography on a COMBIFLASH® system (ISCO) using a gradient of 0-90% EtOAc/Hex to give the title compound as a colorless viscous oil.

Step 4: (R)-tert-butyl 2-(benzyloxycarbonylamino)-3-((S)-2,3-bis(methylsulfonyloxy)propylthio)-propanoate A solution of (R)-tert-butyl 2-(benzyloxycarbonylamino)-3-((S)-2,3-dihydroxypropylthio)propanoate (1 eq) was stirred in dry DCM (0.1M) in an ice bath (0° C.) under an atmosphere of N₂. Pyridine (8.0 eq) was then carefully added at 0° C. Methanesulfonyl chloride (4.0 eq) and DMAP (0.1 eq) were added with the reaction slowly warming to room temperature, then stirred overnight. The crude reaction mixture was then loaded directly onto a silica column and purified by flash chromatography on a COMBIFLASH® system (ISCO) using a gradient of 100% Hex, 0-20% EtOAc/Hex, 20-50% EtOAc/Hex, 100% EtOAc to afford the title compound as an oil.

Step 5: (R)-tert-butyl 2-(benzyloxycarbonylamino)-3-((R)-2,3-diazidopropylthio)propanoate (R)-tert-butyl 2-(benzyloxycarbonylamino)-3-((S)-2,3-bis(methylsulfonyloxy)propylthio)-propanoate (1 eq) was stirred in DMF (0.05 M) at room temperature in a 40 mL vial. NaN₃ (8.0 eq) was then carefully added. The reaction vessel was then moved to an oil bath and stirred at 50° C. for 16 hours open to atmosphere. The reaction was cooled to room temperature and diluted with DCM. White precipitates were filtered off and the filtrate was concentrated en vaccuo. The resulting crude material was purified by flash chromatography on a COMBIFLASH® system (ISCO) using a gradient of 100% Hex, 0-50% EtOAc/Hex, 100% EtOAc to afford the title compound as an off white solid.

Step 6: (R)-tert-butyl 2-(benzyloxycarbonylamino)-3-((R)-2,3-diaminopropylthio)propanoate (R)-tert-butyl 2-(benzyloxycarbonylamino)-3-((R)-2,3-diazidopropylthio)propanoate (1 eq) was stirred in dry EtOH (0.05 M) under nitrogen at room temperature. Pd(OH)₂ (0.5 eq) was then added in one portion. The reaction was purged with, then stirred under hydrogen atmosphere (1 atm) for 16 hours at room temperature. The crude material was then filtered twice through celite and cotton. The organics were concentrated and used in the next step without further purification.

Step 7: (5R,9R)-tert-butyl 9-dodecanamido-3,12-dioxo-1-phenyl-2-oxa-7-thia-4,11-diazatricosane-5-carboxylate (R)-tert-butyl 2-(benzyloxycarbonylamino)-3-((R)-2,3-diaminopropylthio)propanoate (1 eq) was stirred in dry DCM (0.1 M) in an ice bath (0° C.). Pyridine (3.7 eq) was then added followed by lauroyl chloride (3.7 eq). The reaction was stirred at 0° C. for 5 minutes then warmed to room temperature and stirred for 2 hours. The crude reaction was diluted with DCM then washed with 5% citric acid, saturated NaHCO₃ and brine. The organic layer was dried over anhydrous Na₂SO₄ then concentrated en vaccuo. The crude material was purified by flash chromatography on a COMBIFLASH® system (ISCO) using a gradient of 100% Hex, 0-50% EtOAc/Hex, 100% EtOAc to afford the title compound as a white solid.

Step 8: (5R,9R)-9-dodecanamido-3,12-dioxo-1-phenyl-2-oxa-7-thia-4,11-diazatricosane-5-carboxylic acid (5R,9R)-tert-butyl 9-dodecanamido-3,12-dioxo-1-phenyl-2-oxa-7-thia-4,11-diazatricosane-5-carboxylate was stirred in a 30% TFA/DCM (0.05 M) solution for 2 hours at room temperature. The reaction was then concentrated and diluted with DCM. The organic phase was washed once with 1 M citric acid (pH3) then dried over anhydrous Na₂SO₄, filtered and concentrated to afford the title compound as a viscous oil that was used with no further purification.

Step 9: Benzyl(R)-3-((R)-2,3-didodecanamidopropylthio)-1-(1-(hydroxymethyl)cyclopropylamino)-1-oxopropan-2-ylcarbamate To a solution of (5R,9R)-9-dodecanamido-3,12-dioxo-1-phenyl-2-oxa-7-thia-4,11-diazatricosane-5-carboxylic acid (1 eq) in DCM (0.1 M) was added (1-aminocyclopropyl) methanol hydrochloride (1.3 eq), DIEA (2.5 eq) and HBTU (1.2 eq). The reaction was stirred at room temperature for 2 hours then concentrated and purified by flash chromatography on a COMBIFLASH® system (ISCO) using a gradient of 0-100% EtOAc/Hex, then 0-10% MeOH/DCM to afford the title compound as an off-white solid.

Step 10: N,N'—((R)-3-((R)-2-amino-3-(1-(hydroxymethyl)cyclopropylamino)-3-oxopropylthio) propane-1,2-diyl)didodecanamide Benzyl(R)-3-((R)-2,3-didodecanamidopropylthio)-1-(1-(hydroxymethyl)cyclopropylamino)-1-oxopropan-2-ylcarbamate (1 eq) was stirred in dry EtOH (0.05 M) under N₂ at room temperature. Pd(OH)₂ (2.1 eq) was then added in one portion. The reaction was then stirred under hydrogen atmosphere (1 atm) until complete reduction was observed. The crude reaction was filtered twice through celite and cotton, then the organics concentrated and purified by flash chromatography on a COMBIFLASH® system (ISCO) using a gradient of 0-10% MeOH/DCM to afford N,N'—((R)-3-((R)-2-amino-3-(1-(hydroxymethyl)cyclopropylamino)-3-oxopropylthio)propane-1,2-diyl)didodecanamide as an oil. $^1$H NMR (CDCl₃): δ 8.02 (s, 1H), 6.83 (t, 1H), 6.70 (t, 1H), 3.50-3.71 (m, 6H), 3.00-3.12 (m, 3H), 2.88-2.94 (m, 2H), 2.21 (t, 4H), 1.64 (t, 4H), 1.21-1.35 (m, 32H), 0.93 (m, 4H), 0.82 (t, 6H). LRMS [M+H]=628.0.

Example 13

Synthesis of: (5S,8R,12R)-8-amino-12-(dodecanoyloxy)-5-ethyl-7,15-dioxo-3,14-dioxa-10-thia-6-azahexacosan-1-oic acid

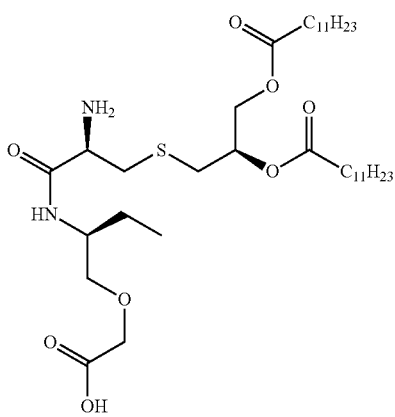

Step 1: (S)-tert-butyl 1-hydroxybutan-2-ylcarbamate

To a solution of (S)-2-aminobutan-1-ol (1 eq) in THF (0.26 M) at 0° C. was added di-tert-butyl carbonate (1 eq) and triethylamine (1 eq). The reaction was stirred at room temperature for 3 hours. The reaction mixture was concentrated en vaccuo; and the residue was diluted in ethyl acetate. The organic solution was washed with water (2×), brine, dried over anhydrous MgSO₄, and concentrated en vaccuo. The material was carried onto the next step without further purification.

Step 2: (S)-tert-butyl 2-(2-(tert-butoxycarbonylamino)butoxy)acetate

To a solution of (S)-tert-butyl 1-hydroxybutan-2-ylcarbamate (1 eq, from the previous step) in THF (0.23 M) at 0° C. was added portionwise 60% wt NaH (2 eq). The reaction was stirred at 0° C. for 30 minutes, and then a solution of tert-butyl 2-bromoacetate (1 eq) in THF (0.12 M) was added dropwise. The reaction was warmed to room temperature and stirred for 1 hour. The reaction was quenched slowly with saturated aqueous NH₄Cl solution and diluted with ether. The organic layer was washed with water, brine, dried over anhydrous MgSO₄, and concentrated en vaccuo. The crude mixture was purified by flash chromatography on a COMBIFLASH® system (ISCO) using a gradient of 0-40% ethyl acetate in hexanes to give the product as an oil.

Step 3: (S)-tert-butyl 2-(2-aminobutoxy)acetate

To a solution of (S)-tert-butyl 2-(2-(tert-butoxycarbonylamino)butoxy)acetate (1 eq, from the previous step) in DCM (0.4 M) at room temperature was added a solution of 4 M HCl in dioxane (10 eq). The reaction was stirred for 2 hours, at which time more 4 M HCl in dioxane (3 eq) was added and stirred for 1 hour. The reaction mixture was concentrated en vaccuo to give the product as an oil. The material was carried onto the next step without further purification.

Step 4: (8S,11R,15R)-11-(((9H-fluoren-9-yl)methoxy)carbonylamino)-8-ethyl-2,2-dimethyl-4,10-dioxo-3,6-dioxa-13-thia-9-azahexadecane-15,16-diyl didodecanoate To a solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) and (S)-tert-butyl 2-(2-aminobutoxy)acetate (1.5 eq, from the previous step) in 2:1 THF/DMF (0.13 M) was added EDCI (1.3 eq), HOBT (1.3 eq), and DIEA (5 eq). The reaction was stirred at room temperature overnight. The reaction mixture was diluted with ethyl acetate. The organic layer was washed with 2:1 saturated aqueous NaHCO₃/water, brine, dried over anhydrous Na₂SO₄, and concentrated en vaccuo. The crude mixture was purified by flash chromatography on a COMBIFLASH® system (ISCO) using a gradient of 0-40% ethyl acetate in hexanes to give the product.

Step 5: (5S,8R,12R)-8-amino-12-(dodecanoyloxy)-5-ethyl-7,15-dioxo-3,14-dioxa-10-thia-6-azahexacosan-1-oic acid A solution of (8S,11R,15R)-11-(((9H-fluoren-9-yl)methoxy)carbonylamino)-8-ethyl-2,2-dimethyl-4,10-dioxo-3,6-dioxa-13-thia-9-azahexadecane-15,16-diyl didodecanoate (1 eq, from the previous step) in 50% TFA in DCM (0.05 M) was stirred in open air at 40° C. for 1.5 hours. The mixture was dried under a stream of air and briefly evaporated under high vacuum. The resulting oil was dissolved in 20% piperidine in THF (0.1 mL) and stirred at room temperature for 1 hour. The reaction mixture was diluted with ethyl acetate. The reaction mixture was concentrated en vaccuo. The crude mixture was purified by flash chromatography on a COMBIFLASH® system (ISCO) using a gradient of 0-10% methanol in DCM to give the product as a solid. $^1$H NMR (DMSO-d₆): δ 8.30 (d, 1H), 5.11 (m, 1H), 4.27 (dd, 1H), 4.09 (dd, 1H), 3.96 (s, 2H), 3.67-3.76 (m, 2H), 3.37-3.48 (m, 2H), 2.71-2.95 (m, 4H), 2.25-2.28 (m, 4H), 1.23-1.62 (m, 41H), 0.83-0.88 (m, 6H). LRMS [M+H]=689.4.

Example 14

Synthesis of: (6S,9R,13R)-9-amino-13-(dodecanoyloxy)-6-methyl-8,16-dioxo-4,15-dioxa-11-thia-7-azaheptacosylphosphonic acid

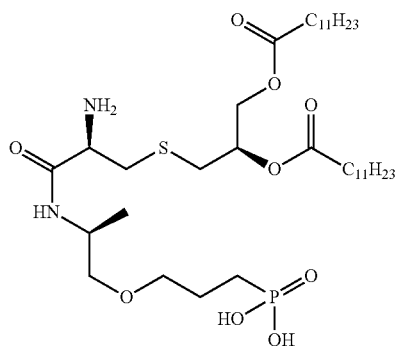

Step 1: (S)-tert-butyl 1-hydroxypropan-2-ylcarbamate

To a solution of (S)-2-aminopropan-1-ol (1 eq) in THF (0.3 M) at room temperature was added di-tert-butyl carbonate (1 eq) and triethylamine (1 eq). The reaction was stirred at room temperature for 3 hours. The reaction mixture was concentrated en vaccuo; and the residue was diluted in ethyl acetate. The organic solution was washed with water (2×), 1:1 saturated aqueous NH$_4$Cl, water and brine, dried over anhydrous MgSO$_4$, and concentrated en vaccuo. The material was carried onto the next step without further purification.

Step 2: (S)-tert-butyl 1-(3-(diethoxyphosphoryl)propoxy)propan-2-ylcarbamate

To a solution of (S)-tert-butyl 1-hydroxypropan-2-ylcarbamate (1 eq, from the previous step) in THF (0.1 M) at room temperature was added KOH (5 eq), tetrabutylammonium bromide (0.1 eq), and diethyl 3-bromopropylphosphonate (2 eq). The reaction was stirred at room temperature overnight. The mixture was concentrated en vaccuo and then taken up in DCM/water. The aqueous layer was extracted with DCM (2×). The combined organic layers were dried over anhydrous MgSO$_4$, and concentrated en vaccuo. The crude mixture was purified by flash chromatography on a COMBIFLASH® system (ISCO) using a gradient of 0-100% ethyl acetate in hexanes and then 100% ethyl acetate to give the product as an oil.

Step 3: (6S,9R,13R)-9-(((9H-fluoren-9-yl)methoxy)carbonylamino)-13-(dodecanoyloxy)-6-methyl-8,16-dioxo-4,15-dioxa-1-thia-7-azaheptacosylphosphonic acid diethyl ester To a solution of (S)-tert-butyl 1-(3-(diethoxyphosphoryl)propoxy)propan-2-ylcarbamate (1.3 eq, from the previous step) in DCM (0.22 M) at room temperature was added a solution of 4 M HCl in dioxane (20 eq). The reaction was stirred for 1.5 hours. The reaction mixture was concentrated en vaccuo to give an oil which was evaporated under high vacuum briefly. This residue was taken up in DCM (0.1M). To this solution was added (5R,9R)-9-(dodecanoyloxy)-1-(9H-fluoren-9-yl)-3,12-dioxo-2,11-dioxa-7-thia-4-azatricosane-5-carboxylic acid (6, 1 eq), HBTU (1.2 eq), and DIEA (4 eq). The reaction was stirred at room temperature for 2 hours. The mixture was purified by flash chromatography on a COMBIFLASH® system (ISCO) using a gradient of 0-100% ethyl acetate in hexanes and then 100% ethyl acetate to give the product as an oil.

Step 4: (6S,9R,13R)-9-amino-13-(dodecanoyloxy)-6-methyl-8,16-dioxo-4,15-dioxa-11-thia-7-azaheptacosylphosphonic acid diethyl ester (6S,9R,13R)-9-(((9H-fluoren-9-yl)methoxy)carbonylamino)-13-(dodecanoyloxy)-6-methyl-8,16-dioxo-4,15-dioxa-11-thia-7-azaheptacosylphosphonic acid diethyl ester (1 eq, from the previous step) in was dissolved in 20% piperidine in THF (0.1 M) and stirred at room temperature for 2 hours. The viscous reaction mixture was diluted in methyl tert-butyl ether and ethyl acetate. The organic layer was washed with 1:1 saturated aqueous NH$_4$Cl/water (2×), brine, dried over anhydrous Na$_2$SO$_4$, and concentrated en vaccuo. The crude mixture was purified by flash chromatography on a COMBIFLASH® system (ISCO) using a gradient of 0-5% methanol in DCM to give the product.

Step 5: (6S,9R,13R)-9-amino-13-(dodecanoyloxy)-6-methyl-8,16-dioxo-4,15-dioxa-11-thia-7-azaheptacosylphosphonic acid A solution of (6S,9R,13R)-9-amino-13-(dodecanoyloxy)-6-methyl-8,16-dioxo-4,15-dioxa-11-thia-7-azaheptacosylphosphonic acid diethyl ester (1 eq, from the previous step) in DCM (0.1 M) was added TMSBr (10 eq) and stirred at room temperature overnight. The reaction mixture was concentrated en vaccuo. The crude mixture was purified by reverse phase high performance liquid chromatography (HPLC) with C4 column eluting with a gradient of 40-80% MeCN/10 mM NH$_4$OAc (95:5) in 10 mM NH$_4$OAc (pH 9). The fractions containing the product were combined and lyophilized to give the desired product as a solid. $^1$H NMR (DMSO-d$_6$): δ 7.97 (d, 1H), 5.09 (m, 1H), 4.27 (dd, 1H), 4.09 (dd, 1H), 3.86 (m, 1H), 3.20-3.43 (m, 5H), 2.59-2.85 (m, 4H), 2.24-2.27 (m, 4H), 1.62-1.69 (m, 2H), 1.23-1.51 (m, 38H), 1.14 (d, 3H), 0.83-0.88 (m, 6H). LRMS [M+H]=739.4.

Example 15

Synthesis of: 3-((1-((R)-2-amino-3-((R)-2,3-bis(dodecanoyloxy)propylthio)propanamido)cyclopropyl)methoxy)propylphosphonic acid

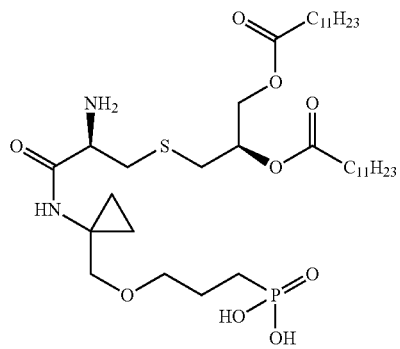

Step 1: tert-butyl 1-(hydroxymethyl)cyclopropylcarbamate

To a solution of ethyl 1-aminocyclopropanecarboxylate hydrochloride (1 eq) in EtOH (0.3 M) at room temperature was added di-tert-butyl carbonate (1.5 eq), triethylamine (2 eq), and DMAP (0.05 eq). The reaction was stirred at room temperature overnight. The reaction mixture was concentrated en vaccuo; and the residue was diluted in ethyl acetate. The organic solution was washed 1:1 saturated aqueous NH$_4$Cl/water, brine, dried over anhydrous MgSO$_4$, and concentrated en vaccuo. The material was taken up in THF (0.3 M) and cooled to 0° C. To this solution was added 2 M LiBH$_4$ in THF (4 eq). The reaction was warmed to room temperature and stirred for 4 hours, at which time more 2 M LiBH$_4$ (1.3 eq) was added, and stirred overnight. The reaction mixture was cooled to 0° C. and slowly quenched with MeOH over 10 minutes and then water. The solution was stirred for 10 minutes; and precipitates appeared. The precipitates were filtered and rinsed with ethyl acetate. The filtrate was washed with water, brine, dried over anhydrous MgSO$_4$, and concentrated en vaccuo. The crude mixture was purified by flash chromatography on a COMBIFLASH® system (ISCO) using a gradient of 0-75% ethyl acetate in hexanes to give the product.

Step 2: tert-butyl 1-((3-(diethoxyphosphoryl)propoxy)methyl)cyclopropylcarbamate To a solution of tert-butyl 1-(hydroxymethyl)cyclopropylcarbamate (1 eq, from the previous step) in THF (0.1 M) at room temperature was added KOH (5 eq), tetrabutylammonium bromide (0.1 eq), and diethyl 3-bromopropylphosphonate (2 eq). The reaction was stirred at room temperature overnight. The mixture was concentrated en vaccuo and then taken up in DCM/water. The aqueous layer was extracted with DCM (2×). The combined organic layers were dried over anhydrous MgSO$_4$, and concentrated en vaccuo. The crude mixture was purified by flash chromatography on a COMBIFLASH® system (ISCO) using a gradient of 0-100% ethyl acetate in hexanes and then 100% ethyl acetate to give the product as an oil.

Step 3: 3-((1-((R)-2-(((9H-fluoren-9-yl)methoxy)carbonylamino)-3-((R)-2,3-bis(dodecanoyloxy)propylthio)propanamido)cyclopropyl)methoxy)propylphosphonic acid diethyl ester The title compound was prepared according to the procedure described in example 14, step 3, but using tert-butyl 1-((3-(diethoxyphosphoryl)propoxy)methyl)cyclopropylcarbamate (from the previous step) as the starting material.

Step 4: 3-((1-((R)-2-amino-3-((R)-2,3-bis(dodecanoyloxy)propylthio)propanamido)cyclopropyl)methoxy)propylphosphonic acid diethyl ester The title compound was prepared according to the procedure described in example 14, step 4, but using 3-((1-((R)-2-(((9H-fluoren-9-yl)methoxy)carbonylamino)-3-((R)-2,3-bis(dodecanoyloxy)propylthio)propanamido)cyclopropyl)methoxy)propylphosphonic acid diethyl ester (from the previous step) as the starting material.

Step 5: 3-((1-((R)-2-amino-3-((R)-2,3-bis(dodecanoyloxy)propylthio)propanamido)cyclopropyl)methoxy)propylphosphonic acid The title compound was prepared according to the procedure described in example 14, step 5, but using 3-((1-((R)-2-amino-3-((R)-2,3-bis(dodecanoyloxy)propylthio)-propanamido)cyclopropyl)methoxy)propylphosphonic acid diethyl ester (from the previous step) as the starting material. $^1$H NMR (DMSO-d$_6$): δ 8.61 (d, 1H), 5.07 (m, 1H), 4.26 (dd, 1H), 4.08 (dd, 1H), 3.14-3.61 (m, 5H), 2.59-2.81 (m, 4H), 2.24-2.27 (m, 4H), 1.23-1.69 (m, 40H), 0.83-0.86 (m, 6H), 0.62-0.63 (m, 4H). LRMS [M+H]=751.4.

Example 16

Synthesis of: 3-(4-(2-((R)-2-amino-3-((R)-2,3 bis(dodecanoyloxy)propylthio)propanamido)ethyl)phenoxy)propylphosphonic acid

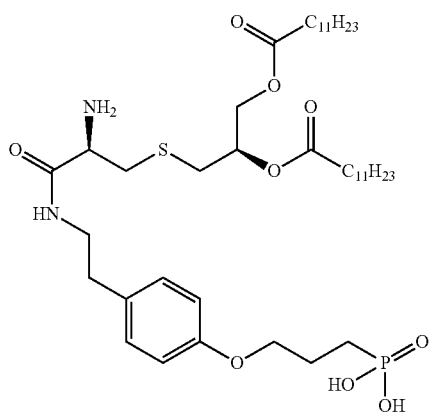

Step 1: tert-butyl 4-(3-(diethoxyphosphoryl)propoxy)phenethylcarbamate

To a solution of tert-butyl 4-hydroxyphenethylcarbamate (1 eq) in DMF (0.17 M) was added cesium carbonate (5 eq). The resulting mixture was stirred at room temperature for 30 minutes, then diethyl 3-bromopropylphosphonate (1.2 eq) was added into the reaction mixture. The resulting mixture was stirred at room temperature for another 4 hours until tert-butyl 4-hydroxyphenethylcarbamate was consumed. The mixture was then diluted with ethyl acetate, and washed with 5% citric acid three times, saturated NaHCO$_3$ solution, water and brine. The organic layer was then dried over anhydrous Na$_2$SO$_4$, and concentrated en vaccuo. The crude material was purified by flash chromatography on a COMBIFLASH® system (ISCO) using 80-100% EtOAc/Hex to give the product as a colorless oil.

Step 2: diethyl 3-(4-(2-aminoethyl)phenoxy)propylphosphonate

To a solution of tert-butyl 4-(3-(diethoxyphosphoryl)propoxy)phenethylcarbamate (1 eq) in DCM (0.14 M) was added 4M HCl in dioxane (50 eq). The resulting mixture was stirred at room temperature for 2 hours. The mixture was concentrated en vaccuo. The crude material was purified by flash chromatography on a COMBIFLASH® system (ISCO) using 0-15% MeOH/DCM to give the product as a yellowish oil.

Step 3: (R)-3-((R)-2-(((9H-fluoren-9-yl)methoxy)carbonylamino)-3-(4-(3-(diethoxyphosphoryl)propoxy)phenethylamino)-3-oxopropylthio)propane-1,2-diyl didodecanoate To a solution of (5R,9R)-9-(dodecanoyloxy)-1-(9H-fluoren-9-yl)-3,12-dioxo-2,11-dioxa-7-thia-4-azatricosane-5- carboxylic acid (6, 1 eq) in DCM (0.1 M) was added diethyl 3-(4-(2-aminoethyl)phenoxy)propylphosphonate (1.1 eq), DIEA (2.5 equiv) and HBTU (1.1 eq). The reaction mixture was then stirred at room temperature for 2 hours. The mixture was diluted with ethyl acetate, and washed with 5% citric acid three times, saturated NaHCO$_3$ solution twice, water and brine. The organic layer was dried over anhydrous Na$_2$SO$_4$, and concentrated en vaccuo. The crude mixture was purified by flash chromatography on a COMBIFLASH® system (ISCO) using 60-100% EtOAc/Hex to give the product.

Step 4: (R)-3-((R)-2-amino-3-(4-(3-(diethoxyphosphoryl)propoxy)phenethylamino)-3-oxopropylthio)propane-1,2-diyl didodecanoate To a solution of (R)-3-((R)-2-(((9H-fluoren-9-yl)methoxy)carbonylamino)-3-(4-(3-(diethoxyphosphoryl)propoxy)phenethylamino)-3-oxopropylthio)propane-1,2-diyl didodecanoate (1 eq) was added 20% piperidine (50 eq) in acetonitrile. The resulting mixture was stirred at 25° C. until the starting material disappeared. To the mixture was added toluene and then concentrated en vaccuo. The crude mixture was purified by flash chromatography on a COMBIFLASH® system (ISCO) using 100% EtOAc then 0-10% MeOH/DCM to give the product as a colorless oil.

Step 5: 3-(4-(2-((R)-2-amino-3-((R)-2,3-bis(dodecanoyloxy)propylthio)propanamido)ethyl)phenoxy)propylphosphonic acid To a solution of (R)-3-((R)-2-amino-3-(4-(3-(diethoxyphosphoryl)propoxy)phenethylamino)-3-oxopropylthio)propane-1,2-diyl didodecanoate (1 eq) in DCM (0.1 M) was added trimethylsilyl bromide (10 eq). The reaction mixture was stirred at room temperature overnight and then concentrated. The crude mixture was purified by reverse phase high performance liquid chromatography (HPLC) with C4 column eluting with a gradient of 50-100% MeCN/10 mM NH$_4$OAc (95:5) in 10 mM NH$_4$OAc (pH 9) to give the product as a white solid. $^1$H NMR (DMSO-d$_6$): δ 7.13 (d, 2H), 6.85 (d, 2H), 5.10-5.19 (m, 2H), 4.28 (dd, 1H), 4.12 (dd, 1H), 3.97 (t, 1H), 3.81-3.90 (m, 1H), 2.93 (dd, 1H), 2.70-2.86 (m, 3H), 2.64-2.70 (m, 2H), 2.31-2.35 (m, 2H), 2.24-2.31 (m, 2H), 2.14-2.21 (m, 2H), 1.82-1.93 (m, 4H), 1.57-1.70 (m, 4H), 1.41-1.57 (m, 4H), 1.07-1.38 (m, 32H), 0.85 (t, 6H). LRMS [M+H]=801.5.

Example 17

Synthesis of: 6-((R)-2-amino-3-((R)-2,3-bis(dodecanoloxypropythio)propanamido)hexanoic acid

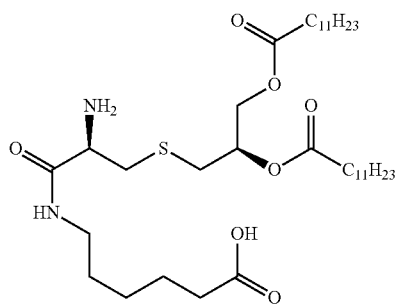

Step 1: benzyl 6-(tert-butoxycarbonylamino)hexanoate

To a solution of 6-(tert-butoxycarbonylamino)hexanoic acid (1 eq) in acetone (0.2 M) was added potassium carbonate (2 eq) and (bromomethyl)benzene (2 eq) in acetone (2 M). The reaction mixture was stirred at room temperature for 1 hour. Additional amount of DMF was then added to the reaction mixture to facilitate the dissolution of potassium carbonate. The reaction mixture was stirred at room temperature for another 30 minutes. The mixture was then diluted with ethyl acetate, and washed with 5% citric acid, water and brine. The organic layer was dried over anhydrous Na$_2$SO$_4$, and concentrated en vaccuo. The crude mixture was purified by flash chromatography on a COMBIFLASH® system (ISCO) using 10-40% EtOAc/Hex to give the product.

Step 2: benzyl 6-aminohexanoate hydrochloride

To a solution of benzyl 6-(tert-butoxycarbonylamino)hexanoate (1 eq) in DCM (0.17 M) was added 4M HCl in dioxane (30 eq). The resulting mixture was stirred at room temperature for 1 hour. The mixture was concentrated en vaccuo. The crude material was dissolved in DCM and precipitated in diethyl ether to give the product as a white solid.

Step 3: (R)-3-((R)-2-(((9H-fluoren-9-yl)methoxy)carbonylamino)-3-(6-(benzyloxy)-6-oxohexylamino)-3-oxopropylthio)propane-1,2-diyl didodecanoate To a solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) in DMF (0.2 M) was added DIEA (5 eq) and EDCI (1.3 eq) and HOBT (1.3 eq). The reaction was stirred at room temperature for 10 minutes, which was followed by adding benzyl 6-aminohexanoate hydrochloride (1.2 eq). The reaction mixture was then stirred at room temperature overnight. The mixture was diluted with ethyl acetate, and washed with saturated NaHCO$_3$ solution, water and brine. The organic layer was dried over anhydrous Na$_2$SO$_4$, and concentrated en vaccuo. The crude mixture was purified by flash chromatography on a COMBIFLASH® system (ISCO) using 0-5% MeOH/DCM to give the title product.

Step 4: (R)-3-((R)-2-amino-3-(6-(benzyloxy)-6-oxohexylamino)-3-oxopropylthio)propane-1,2-diyl didodecanoate To a solution of (R)-3-((R)-2-(((9H-fluoren-9-yl)methoxy)carbonylamino)-3-(6-(benzyloxy)-6-oxohexylamino)-3-oxopropylthio)propane-1,2-diyl didodecanoate (1 eq) was added 20% piperidine (50 eq) in acetonitrile. The resulting mixture was stirred at 25° C. until the deprotection completed. To the mixture was concentrated en vaccuo. The crude mixture was purified by flash chromatography on a COMBIFLASH® system (ISCO) using 100% EtOAc, then 0-10% MeOH/DCM to give the product.

Step 5: 6-((R)-2-amino-3-((R)-2,3-bis(dodecanoyloxy)propylthio)propanamido)hexanoic acid To a solution of (R)-3-((R)-2-amino-3-(6-(benzyloxy)-6-oxohexylamino)-3-oxopropylthio)propane-1,2-diyl didodecanoate in EtOH (0.1 M) was added palladium black (2 eq). The reaction mixture was stirred under hydrogen (1 atm) overnight. The palladium was filtered off and the filtrate was concentrated en vaccuo. The crude mixture was purified by flash chromatography on a COMBIFLASH® system (ISCO) using 0-10% MeOH/DCM to give the product as an off-white solid. $^1$H NMR (CDCl$_3$): δ 7.33 (t, 1H), 5.06-5.15 (m, 1H), 4.30 (dd, 1H), 4.08 (dd, 1H), 3.43 (dd, 1H), 3.20-3.31 (m, 1H), 3.09-3.19 (m, 1H), 3.04 (dd, 1H), 2.61-2.74 (m, 3H), 2.21-2.31 (m, 6H), 1.84-2.06 (m, 3H), 1.40-1.63 (m, 8H), 1.28-1.37 (m, 2H), 1.12-1.28 (m, 32H), 0.81 (t, 6H). LRMS [M+H]=673.5.

Example 18

Synthesis of: (14R,18R)-14-amino-18-(dodecanoyloxy)-13,21-dioxo-3,6,9,20-tetraoxa-16-thia-12-azadotriacontylphosphonic acid

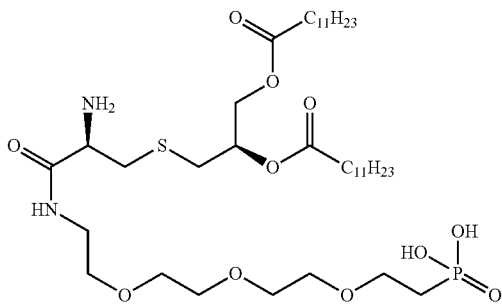

Step 1: 1-iodo-2-(2-(2-(2-iodoethoxy)ethoxy)ethoxy)ethane

To a solution of 1-chloro-2-(2-(2-(2-chloroethoxy)ethoxy)ethoxy)ethane (1 eq) in acetone (0.25 M) was added sodium iodide (4 eq). The mixture was heated at 80° C. in a sealed vial overnight. The reaction mixture was filtered, and the filtrate was concentrated en vaccuo. The crude mixture was suspended in DCM and filtered. The filtrate was then concentrated en vaccuo. The crude mixture was purified by flash chromatography on a COMBIFLASH® system (ISCO) using 0-20% EtOAc/Hex to give the product.

Step 2: diethyl 2-(2-(2-(2-iodoethoxythoxoxy)ethoxy)ethylphosphonate 1-iodo-2-(2-(2-(2-iodoethoxy)ethoxy)ethoxy)ethane (1 eq) was mixed with triethyl phosphate (1 eq) then heated to 160° C. for 20 minutes by microwave. The crude mixture was purified by flash chromatography on a COMBIFLASH® system (ISCO) using 0-10% MeOH/DCM to give the product as a yellow oil.

Step 3: diethyl 2-(2-(2-(2-azidoethoxy)ethoxy)ethoxy)ethylphosphonate

To a solution of diethyl 2-(2-(2-(2-iodoethoxy)ethoxy)ethoxy)ethylphosphonate (1 eq) in DMF (0.5 M) was added sodium azide (3 eq). The reaction mixture was heated at 50° C. overnight. The mixture was then concentrated en vaccuo. The crude material was purified by flash chromatography on a COMBIFLASH® system (ISCO) using 0-5% MeOH/DCM to give the product as a colorless oil.

Step 4: diethyl 2-(2-(2-(2-aminoethoxy)ethoxy)ethoxy)ethylphosphonate

To a solution of diethyl 2-(2-(2-(2-azidoethoxy)ethoxy)ethoxy)ethylphosphonate (1 eq) in EtOH (0.1 M) was added Pd(OH)$_2$ (0.05 eq). The reaction mixture was stirred under hydrogen (1 atm) for 4 hours. The mixture was filtered through Celite and washed with MeOH. The solvent was removed en vaccuo. The crude material was purified by flash chromatography on a COMBIFLASH® system (ISCO) using 0-10% MeOH/DCM with 0.5% NH$_3$ to give the product as a colorless oil.

Step 5: diethyl(14R,18R)-14-(((9H-fluoren-9-yl)methoxy)carbonylamino)-18-(dodecanoyloxy)-13,21-dioxo-3,6,9,20-tetraoxa-16-thia-12-azadotriacontylphosphonate To a solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) in DCM (0.1 M) was added diethyl 2-(2-(2-(2-aminoethoxy)ethoxy)ethoxy)ethylphosphonate (1.2 eq), DIEA (2.5 eq) and HBTU (1.1 eq). The resulting mixture was stirred at room temperature for 2 hours. The crude mixture was purified by flash chromatography on a COMBIFLASH® system (ISCO) using 0-5% MeOH/DCM to give the product.

Step 6: (14R,18R)-14-amino-18-(dodecanoyloxy)-13,21-dioxo-3,6,9,20-tetraoxa-16-thia-12-azadotriacontylphosphonic acid diethyl ester To a solution of diethyl(14R,18R)-14-(((9H-fluoren-9-yl)methoxy)carbonylamino)-18-(dodecanoyloxy)-13,21-dioxo-3,6,9,20-tetraoxa-16-thia-12-azadotriacontylphosphonate (1 eq) was added 20% piperidine (50 eq) in acetonitrile. The resulting mixture was stirred at 25° C. until the deprotection completed. To the mixture was added toluene and then concentrated en vaccuo. The crude mixture was purified by flash chromatography on a COMBIFLASH® system (ISCO) using 100% EtOAc then 0-10% MeOH/DCM to give the product as colorless oil.

Step 7: (14R,18R)-14-amino-18-(dodecanoyloxy)-13,21-dioxo-3,6,9,20-tetraoxa-16-thia-12-azadotriacontylphosphonic acid To a solution of (14R,18R)-14-amino-18-(dodecanoyloxy)-13,21-dioxo-3,6,9,20-tetraoxa-16-thia-12-azadotriacontylphosphonic acid diethyl ester (1 eq) in DCM (0.1 M) was added trimethylsilyl bromide (10 eq). The reaction mixture was stirred at room temperature overnight and then concentrated. The crude mixture was purified by reverse phase high performance liquid chromatography (HPLC) with C4 column eluting with a gradient of 40-100% MeCN/10 mM NH$_4$OAc (95:5) in 10 mM NH$_4$OAc (pH 9) to give the title compound as a white solid. $^1$H NMR (CDCl$_3$): δ 8.80 (br s, 1H), 5.13-5.24 (m, 1H), 4.35 (dd, 1H), 4.15 (dd, 1H), 3.45-3.88 (m, 15H), 3.31-3.45 (m, 2H), 3.03-3.17 (m, 2H), 2.82-

2.96 (m, 1H), 2.76 (dd, 1H), 2.30 (q, 4H), 1.78-2.00 (m, 2H), 1.51-1.66 (m, 4H), 1.17-1.37 (m, 32H), 0.86 (t, 6H). LRMS [M+H]=799.5.

Example 19

Synthesis of: 4-((R)-2-amino-3-((R)-2,3-bis(dodecanoyloxy)propylthio)propanamido)-1,1-difluorobutylphosphonic acid

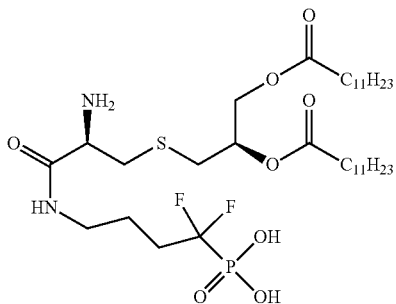

Step 1: diethyl 1,1-difluoro-4-iodobutylphosphonate

To a solution of diisopropylamine (1.6 eq) in THF (1.28 M) was slowly added n-butyllithium (1.5 M in cyclohexane, 1.5 eq) dropwise at 0° C. The reaction mixture was stirred at 0° C. for 40 minutes. The mixture was then cooled down to −78° C., and diethyl difluoromethylphosphonate (1 eq) in HMPA (2.1 M) was slowly added to the reaction. Then the mixture was stirred at −78° C. for 40 minutes and to the resulting solution was added a cooled solution of 1,3-diiodopropane (12.8 M in THF, 4 eq) rapidly. After 1.5 hours, the reaction was quenched by pouring into saturated $NH_4Cl$ solution. The aqueous phase was extracted with ethyl acetate three times. The combined organic phases were washed with brine, dried over anhydrous sodium sulfate and concentrated en vaccuo. The resulting crude was purified by flash chromatography on a COMBIFLASH® system (ISCO) using 10-100% EtOAc/Hex to give the product as a yellow oil.

Step 2: diethyl 4-azido-1,1-difluorobutylphosphonate

To a solution of diethyl 1,1-difluoro-4-iodobutylphosphonate (1 eq) in DMF (0.27 M) was added sodium azide (3 eq). The reaction mixture was stirred at room temperature for 90 minutes. The mixture was diluted with ethyl acetate and washed with water. The aqueous phase was back extracted with ethyl acetate. The combined organic phases were washed with brine, dried over anhydrous $Na_2SO_4$, and concentrated en vaccuo. The crude mixture was purified by flash chromatography on a COMBIFLASH® system (ISCO) using 10-50% EtOAc/Hex to give the product as a yellowish oil.

Step 3: diethyl 4-amino-1,1-difluorobutylphosphonate hydrochloride

To a solution of diethyl 4-azido-1,1-difluorobutylphosphonate (1 eq) in EtOH (2 M) was added palladium hydroxide (0.05 eq) and 2 M HCl in ether (1.1 eq). The reaction mixture was stirred under hydrogen (1 atm) overnight. The palladium was filtered off and the filtrate was concentrated en vaccuo. The crude mixture was used for the next reaction without further purification.

Step 4: diethyl 4-((R)-2-(((9H-fluoren-9-yl)methoxy)carbonylamino)-3-((R)-2,3-bis(dodecanoyloxy)propylthio)propanamido)-1,1-difluorobutylphosphonate To a solution of (5R,9R)-9-(dodecanoyloxy)-1-(9H-fluoren-9-yl)-3,12-dioxo-2,11-dioxa-7-thia-4-azatricosane-5-carboxylic acid (6, 1 eq) in DCM (0.1 M) was added diethyl 4-amino-1,1-difluorobutylphosphonate hydrochloride (1.1 eq), DIEA (3.5 eq) and HBTU (1.1 eq). The reaction mixture was then stirred at room temperature for 2 hours. The mixture was purified by flash chromatography on a COMBIFLASH® system (ISCO) using 30-70% EtOAc/Hex to give the product.

Step 5: diethyl 4-((R)-2-amino-3-((R)-2,3-bis(dodecanoyloxy)propylthio)propanamido)-1,1-difluorobutylphosphonate To a solution of diethyl(4-((R)-2-(((9H-fluoren-9-yl)methoxy)carbonylamino)-3-((R)-2,3-bis(dodecanoyloxy)propylthio)propanamido)-1,1-difluorobutylphosphonate (1 eq) was added 20% piperidine (50 eq) in acetonitrile. The resulting mixture was stirred at 25° C. until the deprotection completed. To the mixture was added toluene and then concentrated en vaccuo. The crude mixture was purified by flash chromatography on a COMBIFLASH® system (ISCO) using 100% EtOAc then 0-10% MeOH/DCM to give the product as a colorless oil.

Step 6: 4-((R)-2-amino-3-((R)-2,3-bis(dodecanoyloxy)propylthio)propanamido)-1,1-difluorobutylphosphonic acid To a solution of diethyl 4-((R)-2-amino-3-((R)-2,3-bis(dodecanoyloxy)propylthio)propanamido)-1,1-difluorobutylphosphonate (1 eq) in DCM (0.1 M) was added trimethylsilyl bromide (10 eq). The reaction mixture was stirred at room temperature overnight and concentrated. The crude mixture was purified by reverse phase high performance liquid chromatography (HPLC) with C4 column eluting with a gradient of 30-80% MeCN/10 mM $NH_4OAc$ (95:5) in 10 mM $NH_4OAc$ (pH 9) to give the title compound as a white solid. $^1H$ NMR ($CDCl_3$): δ 8.74 (br s, 1H), 5.07-5.17 (m, 1H), 4.29 (dd, 1H), 4.19 (dd, 1H), 3.66-3.78 (m, 1H), 2.25-3.51 (m, 4H), 2.66-2.98 (m, 4H), 2.23-2.36 (m, 4H), 1.05-1.84 (m, 2H), 1.60-1.84 (m, 2H), 1.44-1.58 (m, 4H), 1.17-1.34 (m, 32H), 0.85 (t, 6H). LRMS [M+H]=731.4.

Example 20

Synthesis of: (14R,18R)-14-amino-18-(dodecyloxy)-13-oxo-3,6,9,20-tetraoxa-16-thia-12-azadotriacontylphosphonic acid

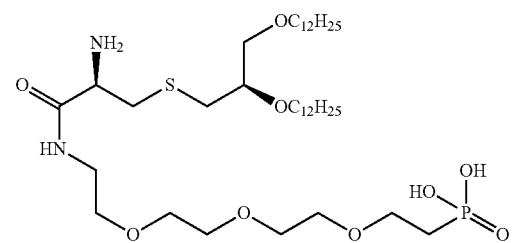

Step 1: (R)-((2,3-bis(dodecyloxy)propoxy)methyl)benzene

To a solution of (R)-3-(benzyloxy)propane-1,2-diol (1 eq) in THF (0.3 M) was added n-tetrabutylammonium bromide (0.2 eq), 1-bromododecane (4 eq) and potassium hydroxide (5 eq). The reaction mixture was stirred at room temperature overnight. The mixture was diluted with ethyl ether, washed with water, 1 N hydrochloric acid, water, and brine, dried over anhydrous $Na_2SO_4$, and concentrated en vaccuo. The crude mixture was purified by flash chromatography on a COMBIFLASH® system (ISCO) using 0-10% EtOAc/Hex to give the product.

Step 2: (S)-2,3-bis(dodecyloxy)propan-1-ol

To a solution of (R)-((2,3-bis(dodecyloxy)propoxy)methyl)benzene (1 eq) in EtOH (0.1 M) was added palladium hydroxide (1.1 eq). The reaction mixture was stirred under hydrogen (1 atm) overnight. The palladium was filtered off and the filtrate was concentrated en vaccuo. The crude mixture was purified by flash chromatography on a COMBIFLASH® system (ISCO) using 0-10% EtOAc/Hex to give the product.

Step 3: (R)-2,3-bis(dodecyloxy)propyl trifluoromethanesulfonate

To a solution of (S)-2,3-bis(dodecyloxy)propan-1-ol (1 eq) in DCM (0.12 M) was added pyridine (4 eq) and trifluoromethanesulfonic anhydride slowly (2 eq) at 0° C. The reaction mixture was stirred at 0° C. for 20 minutes. The mixture was diluted with DCM, washed with water, saturated copper sulfate solution, water and brine, dried over anhydrous $Na_2SO_4$, and concentrated en vaccuo. The crude mixture was purified by flash chromatography on a COMBIFLASH® system (ISCO) using 0-5% EtOAc/Hex to give the product (silica gel was deactivated using MeOH before flash chromatography).

Step 4: (5R,9R)-tert-butyl 9-(dodecyloxy)-1-(9H-fluoren-9-yl)-3-oxo-2,11-dioxa-7-thia-4-azatricosane-5-carboxylate To a solution of (R)-2,3-bis(dodecyloxy)propyl trifluoromethanesulfonate (1 eq) in ethanol (0.15 M) was added (R)-tert-butyl 2-(((9H-fluoren-9-yl)methoxy)carbonylamino)-3-mercaptopropanoate (8, 1.5 eq) and potassium carbonate (1 eq). The reaction mixture was stirred at 60° C. for 30 minutes. The salt from the reaction was filtered off and the filtrate was concentrated en vaccuo. The crude mixture was purified by flash chromatography on a COMBIFLASH® system (ISCO) using 0-40% EtOAc/Hex to give the product.

Step 5: (R)-2-((((9H-fluoren-9-yl)methoxy)carbonyl)amino)-3-(((R)-2,3-bis(dodecyloxy)propyl)thio)propanoic acid A solution of (5R,9R)-tert-butyl 9-(dodecyloxy)-1-(9H-fluoren-9-yl)-3-oxo-2,11-dioxa-7-thia-4-azatricosane-5-carboxylate in 50% TFA in DCM (0.3 M) was stirred at room temperature until complete deprotection of tert-butyl group (30 minutes). The reaction mixture was diluted in MTBE, washed three times with 1M citric acid (adjusted to pH3), and once with 1:2 1N HCl/brine. The organic layer was dried over anhydrous $Na_2SO_4$ and concentrated en vaccuo. The resulting waxy solid was used for the next step without further purification.

Step 6: diethyl(14R,18R)-14-(((9H-fluoren-9-yl)methoxy)carbonylamino)-18-(dodecyloxy)-13-oxo-3,6,9,20-tetraoxa-16-thia-12-azadotriacontylphosphonate To a solution of (R)-2-((((9H-fluoren-9-yl)methoxy)carbonyl)amino)-3-(((R)-2,3-bis(dodecyloxy)propyl)thio)propanoic acid (1 eq) in DCM (0.1 M) was added diethyl 2-(2-(2-(2-aminoethoxy)ethoxy)ethoxy)ethylphosphonate (1.3 eq, from example 18, step 4), DIEA (2.5 eq) and HBTU (1.2 eq). The reaction mixture was then stirred at room temperature for 2 hours. The mixture was purified by flash chromatography on a COMBIFLASH® system (ISCO) using 0-10% MeOH/DCM to give the product.

Step 7: diethyl(14R,18R)-14-amino-18-(dodecyloxy)-13-oxo-3,6,9,20-tetraoxa-16-thia-12-azadotriacontylphosphonate To a solution of diethyl(14R,18R)-14-(((9H-fluoren-9-yl)methoxy)carbonylamino)-18-(dodecyloxy)-13-oxo-3,6,9,20-tetraoxa-16-thia-12-azadotriacontylphosphonate (1 eq) was added 20% piperidine (50 eq) in acetonitrile. The resulting mixture was stirred at 25° C. until the deprotection completed. To the mixture was added toluene and then concentrated en vaccuo. The crude mixture was purified by flash chromatography on a COMBIFLASH® system (ISCO) using 100% EtOAc then 0-10% MeOH/DCM to give the product as a colorless oil.

Step 8: (14R,18R)-14-amino-18-(dodecyloxy)-13-oxo-3,6,9,20-tetraoxa-16-thia-12-azadotriacontylphosphonic acid To a solution of diethyl(14R,18R)-14-amino-18-(dodecyloxy)-13-oxo-3,6,9,20-tetraoxa-16-thia-12-azadotriacontylphosphonate (1 eq) in DCM (0.1 M) was added trimethylsilyl bromide (20 eq). The reaction mixture was stirred at room temperature overnight and then concentrated. The crude mixture was purified by reverse phase high performance liquid chromatography (HPLC) with C4 column eluting with a gradient of 50-100% MeCN/10 mM $NH_4OAc$ (95:5) in 10 mM $NH_4OAc$ (pH 9) to give the title compound as a white solid. $^1H$ NMR ($CDCl_3$): δ 8.73 (br s, 1H), 4.17 (br s, 1H), 3.70-3.83 (m, 3H), 3.57-3.70 (m, 10H), 3.50-3.57 (m, 4H), 3.45-3.50 (m, 2H), 3.33-3.45 (m, 4H), 3.02-3.16 (m, 2H), 2.65-2.79 (m, 2H), 1.90 (dd, 2H), 1.47-1.61 (m, 4H), 1.16-1.36 (m, 36H), 0.88 (t, 6H). LRMS [M+H]=771.5.

Example 21

Synthesis of: (9R,13R)-9-amino-13-(dodecanoyloxy)-1,1-difluoro-8,16-dioxo-4,15-dioxa-11-thia-7-azaheptacosylphosphonic acid

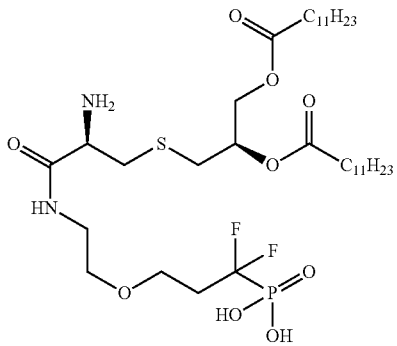

Step 1: diethyl 3-(2-bromoethoxy)-1,1-difluoropropylphosphonate

A solution of diisopropylamine (2 eq) in dry THF (1 M) was cooled in an acetone-dry ice bath. To the solution was added n-butyllithium (1.5 M in cyclohexane, 1.6 eq) in dropwised fashion via syringe. The reaction mixture was warmed up in an ice-water bath upon completion of the addition, and stirred for 30 minutes. The reaction mixture was then cooled back down to −78° C. in the dry ice-acetone bath, and was treated with a solution of diethyl difluoromethylphosphonate (1 eq) in HMPA (1:1 v/v) via syringe. The reaction turned dark brown from pale yellow instantly. The stirring was allowed to proceed for an hour. To the above reaction mixture, a cooled solution of 1-bromo-2-(2-bromoethoxy)ethane (3 eq) in THF (0.6 M) was added quickly through a syringe, and the reaction was allowed to stir for another 3 hours before quenching with 1 N HCl. The reaction mixture was warmed to room temperature, and pH was adjusted to <4 with 1 N HCl, and was extracted with ethyl acetate three times. The combined organic phases were washed with brine, dried over anhydrous $Na_2SO_4$, and concentrated en vaccuo. The mixture was purified by flash chromatography on a COMBIFLASH® system (ISCO) using 0-70% EtOAc/Hex followed by reverse phase high performance liquid chromatography (HPLC) with C18 column eluting with a gradient of 20-50% MeCN (0.035% TFA) in $H_2O$ (0.05% TFA) to afford the product as a pale yellow oil.

Step 2-3: diethyl 3-(2-aminoethoxy)-1,1-difluoropropylphosphonate hydrochloride The title product was prepared from diethyl 3-(2-bromoethoxy)-1,1-difluoropropylphosphonate by following the procedure described for example 4, step 2-3.

Step 4-6: (9R,13R)-9-amino-13-(dodecanoyloxy)-1,1-difluoro-8,16-dioxo-4,15-dioxa-11-thia-7-azaheptacosylphosphonic acid The title product was prepared from (5R,9R)-9-(dodecanoyloxy)-1-(9H-fluoren-9-yl)-3,12-dioxo-2,11-dioxa-7-thia-4-azatricosane-5-carboxylic acid (6, 1 eq) and diethyl 3-(2-aminoethoxy)-1,1-difluoropropylphosphonate hydrochloride (1.2 eq) by following the procedure described for example 19, step 4-6. $^1$H NMR (CDCl$_3$): δ 8.08 (br s, 1H), 5.11-5.24 (m, 1H), 4.31 (dd, 1H), 4.08-4.25 (m, 2H), 3.64-3.80 (m, 3H), 3.48-3.64 (m, 2H), 2.99-3.19 (m, 3H), 2.82 (dd, 1H), 2.72 (dd, 1H), 2.23-2.37 (m, 6H), 1.51-1.64 (m, 4H), 1.16-1.36 (m, 32H), 0.88 (t, 6H). LRMS [M+H]=761.4.

Example 22

Synthesis of: (12R,16R)-12-amino-16-(dodecyloxy)-1,1-difluoro-11-oxo-4,7,18-trioxa-14-thia-10-azatriacontylphosphonic acid

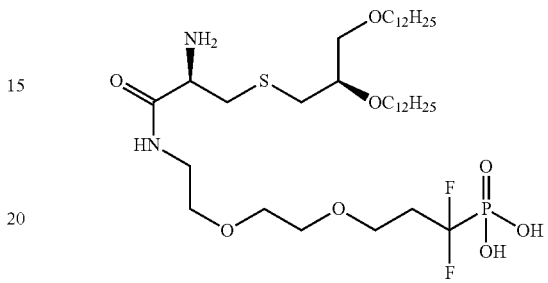

Step 1-3: diethyl 3-(2-(2-aminoethoxy)ethoxy)-1,1-difluoropropylphosphonate hydrochloride The product was prepared from 1,2-bis(2-iodoethoxy)ethane by following the procedure described for example 19, step 1-3.

Step 4-6: (12R,16R)-12-amino-16-(dodecyloxy)-1,1-difluoro-1-oxo-4,7,18-trioxa-14-thia-10-azatriacontylphosphonic acid The title product was prepared from (R)-2-((((9H-fluoren-9-yl)methoxy)carbonyl)amino)-3-(((R)-2,3-bis(dodecyloxy)propyl)thio)propanoic acid (1 eq, from example 20, step 5) and diethyl 3-(2-(2-aminoethoxy)ethoxy)-1,1-difluoropropylphosphonate hydrochloride (1.2 eq) by following the procedure described for example 19, step 4-6. $^1$H NMR (CDCl$_3$): δ 9.15 (br s, 1H), 4.16 (br s, 1H), 3.48-3.77 (m, 9H), 3.34-3.48 (m, 4H), 3.07-3.17 (m, 2H), 2.93-3.07 (m, 2H), 2.67-2.82 (m, 2H), 2.25-2.41 (m, 2H), 1.62-1.71 (m, 2H), 1.45-1.60 (m, 4H), 1.04-1.35 (m, 36H), 0.87 (t, 6H). LRMS [M+H]=777.5.

Example 23

Synthesis of: (14R,18R)-14-amino-18-(octanoyloxy)-13,21-dioxo-3,6,9,20-tetraoxa-16-thia-12-azaoctacosylphosphonic acid

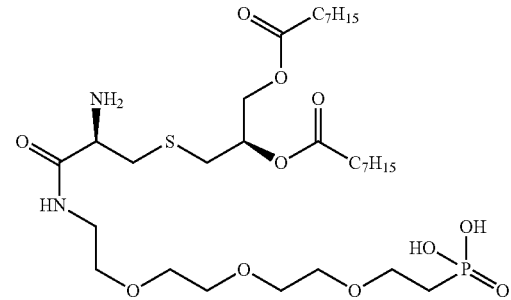

Step 1: (R)-3-((R)-2-(((9H-fluoren-9-yl)methoxy) carbonylamino)-3-tert-butoxy-3-oxopropylthio)propane-1,2-diyl dioctanoate The product was prepared from (R)-tert-butyl 2-(((9H-fluoren-9-yl)methoxy)carbonylamino)-3-((R)-2,3-dihydroxypropylthio)propanoate (10, 1 eq) and octanoyl chloride (3.7 eq) by following the procedure described for compound 11.

Step 2: (5R,9R)-1-(9H-fluoren-9-yl)-9-(octanoyloxy)-3,12-dioxo-2,11-dioxa-7-thia-4-azanonadecane-5-carboxylic acid The product was prepared from (R)-3-((R)-2-(((9H-fluoren-9-yl)methoxy)carbonylamino)-3-tert-butoxy-3-oxopropylthio)propane-1,2-diyl dioctanoate by following the procedure described for compound 6.

Step 3-5: (14R,18R)-14-amino-18-(octanoyloxy)-13,21-dioxo-3,6,9,20-tetraoxa-16-thia-12-azaoctacosylphosphonic acid The title product was prepared from (5R,9R)-1-(9H-fluoren-9-yl)-9-(octanoyloxy)-3,12-dioxo-2,11-dioxa-7-thia-4-azanonadecane-5-carboxylic acid (1 eq) and diethyl 2-(2-(2-(2-aminoethoxy)ethoxy)ethoxy)ethylphosphonate (1.3 eq, from example 18, step 4) by following the procedure described for example 20, step 6-8. $^1$H NMR (DMSO-d$_6$): δ 8.18 (t, 1H), 5.04-5.11 (m, 1H), 4.27 (dd, 1H), 4.10 (dd, 1H), 3.46-3.56 (m, 8H), 3.38-3.56 (m, 4H), 3.27-3.36 (m, 1H), 3.18-3.25 (m, 2H), 2.74-2.83 (m, 2H), 2.68 (dd, 1H), 2.57 (dd, 1H), 2.21-2.33 (m, 4H), 1.55-1.67 (m, 2H), 1.44-1.55 (m, 4H), 1.16-1.32 (m, 16H), 0.85 (t, 6H). LRMS [M+H]=687.4.

Example 24

Synthesis of: (14R,18R)-14-amino-18-(decanoyloxy)-13,21-dioxo-3,6,9,20-tetraoxa-16-thia-12-azatriacontylphosphonic acid

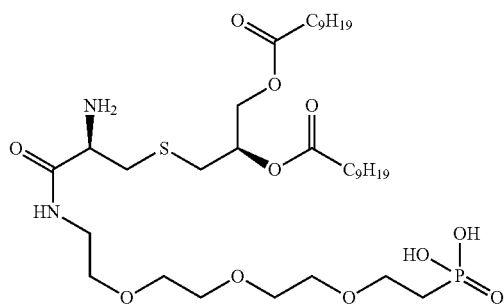

Step 1: (R)-3-((R)-2-(((9H-fluoren-9-yl)methoxy) carbonylamino)-3-tert-butoxy-3-oxopropylthio)propane-1,2-diyl bis(decanoate)

The product was prepared from (R)-tert-butyl 2-(((9H-fluoren-9-yl)methoxy)carbonylamino)-3-((R)-2,3-dihydroxypropylthio)propanoate (10, 1 eq) and decanoyl chloride (3.7 eq) by following the procedure described for compound 11.

Step 2: (5R,9R)-9-(decanoyloxy)-1-(9H-fluoren-9-yl)-3,12-dioxo-2,11-dioxa-7-thia-4-azahenicosane-5-carboxylic acid The product was prepared from (R)-3-((R)-2-(((9H-fluoren-9-yl)methoxy)carbonylamino)-3-tert-butoxy-3-oxopropylthio)propane-1,2-diyl bis(decanoate) by following the procedure described for compound 6.

Step 3-5: (14R,18R)-14-amino-18-(decanoyloxy)-13,21-dioxo-3,6,9,20-tetraoxa-16-thia-12-azatriacontylphosphonic acid The title product was prepared from (5R,9R)-9-(decanoyloxy)-1-(9H-fluoren-9-yl)-3,12-dioxo-2,11-dioxa-7-thia-4-azahenicosane-5-carboxylic acid (1 eq) and diethyl 2-(2-(2-(2-aminoethoxy)ethoxy)ethoxy)ethylphosphonate (1.3 eq, from example 18, step 4) by following the procedure described for example 20, step 6-8. $^1$H NMR (CDCl$_3$): δ 8.67 (br s, 1H), 5.07-5.16 (m, 1H), 3.29 (dd, 1H), 4.08 (dd, 1H), 3.40-3.73 (m, 13H), 3.26-3.38 (m, 2H), 3.02 (dd, 1H), 2.87-2.97 (m, 1H), 2.78 (dd, 1H), 2.68 (dd, 1H), 2.18-2.29 (m, 4H), 1.75-1.89 (m, 2H), 1.46-1.59 (m, 4H), 1.10-1.31 (m, 24H), 0.81 (t, 6H). LRMS [M+H]=743.5.

Example 25

Synthesis of: (14R,18R)-14-amino-13,21-dioxo-18-(tetradecanoyloxy)-3,6,9,20-tetraoxa-16-thia-12-azatetratriacontylphosphonic acid

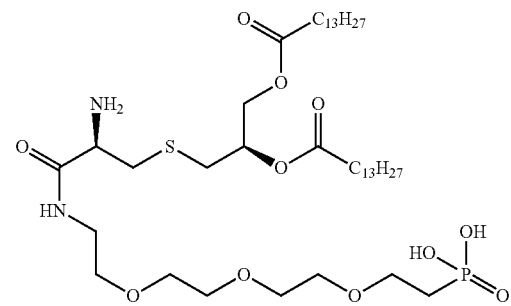

Step 1: (R)-3-((R)-2-(((9H-fluoren-9-yl)methoxy) carbonylamino)-3-tert-butoxy-3-oxopropylthio)propane-1,2-diyl ditetradecanoate The product was prepared from (R)-tert-butyl 2-(((9H-fluoren-9-yl)methoxy)carbonylamino)-3-((R)-2,3-dihydroxypropylthio)propanoate (10, 1 eq) and tetradecanoyl chloride (3.7 eq) following the procedure described for compound 11.

Step 2: (5R,9R)-1-(9H-fluoren-9-yl)-3,12-dioxo-9-(tetradecanoyloxy)-2,11-dioxa-7-thia-4-azapentacosane-5-carboxylic acid The product was prepared from (R)-3-((R)-2-(((9H-fluoren-9-yl)methoxy)carbonylamino)-3-tert-butoxy-3-oxopropylthio)propane-1,2-diyl ditetradecanoate by following the procedure described for compound 6.

131

Step 3-5: (14R,18R)-14-amino-13,21-dioxo-18-(tetradecanoyloxy)-3,6,9,20-tetraoxa-16-thia-12-azatetratriacontylphosphonic acid The title product was prepared from (5R,9R)-1-(9H-fluoren-9-yl)-3,12-dioxo-9-(tetradecanoyloxy)-2,11-dioxa-7-thia-4-azapentacosane-5-carboxylic acid (1 eq) and diethyl 2-(2-(2-(2-aminoethoxy)ethoxy)ethoxy)ethylphosphonate (1.3 eq, from example 18, step 4) by following the procedure described for example 20, step 6-8. $^1$H NMR (CDCl$_3$): δ 7.30 (br s, 1H), 5.13-5.23 (m, 2H), 4.30-4.43 (m, 2H), 4.07-4.20 (m, 2H), 3.44-3.87 (m, 11H), 2.92-3.13 (m, 3H), 2.68-2.92 (m, 4H), 2.22-2.38 (m, 4H), 1.69-2.17 (m, 8H), 1.52-1.67 (m, 4H), 1.10-1.36 (m, 32H), 0.88 (t, 6H). LRMS [M+H]=855.6.

Example 26

Synthesis of: ((14R,18R)-14-amino-18-dodecanamido-13-oxo-3,6,9,20-tetraoxa-16-thia-12-azadotriacontyl)phosphonic acid

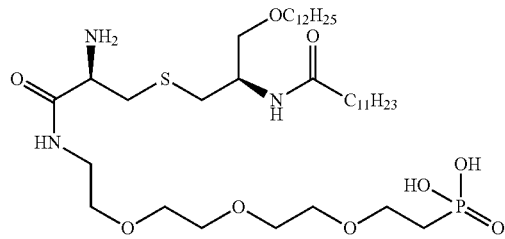

Step 1-8: (R)-2-((((9H-fluoren-9-yl)methoxy)carbonyl)amino)-3-(((R)-2-dodecanamido-3-(dodecyloxy)propyl)thio)propanoic acid The title product was prepared from (R)-3-(dodecyloxy)propane-1,2-diol by following the procedure described for example 11, step 1-8.

Step 9: (9H-fluoren-9-yl)methyl((14R,18R)-1-(diethoxyphosphoryl)-18-dodecanamido-13-oxo-3,6,9,20-tetraoxa-16-thia-12-azadotriacontan-14-yl)carbamate To a solution of (R)-2-((((9H-fluoren-9-yl)methoxy)carbonyl)amino)-3-(((R)-2-dodecanamido-3-(dodecyloxy)propyl)thio)propanoic acid (1 eq) and HBTU (1.2 eq) in DCM (0.06 M) was added DIEA (3.5 eq), followed by diethyl(2-(2-(2-(2-aminoethoxy)ethoxy)ethoxy)ethyl)phosphonate (1.2 eq, from example 18, step 4). The reaction was stirred at room temperature for 2 hours. The crude mixture was purified by flash chromatography on a COMBIFLASH® system (ISCO) using 0-5% MeOH/DCM to give the title product as a white solid.

Step 10: diethyl((14R,18R)-14-amino-18-dodecanamido-13-oxo-3,6,9,20-tetraoxa-16-thia-12-azadotriacontyl)phosphonate To a solution of ((9H-fluoren-9-yl)methyl((14R,18R)-1-(diethoxyphosphoryl)-18-dodecanamido-13-oxo-3,6,9,20-tetraoxa-16-thia-12-azadotriacontan-14-yl)carbamate (1 eq) was added 20% piperidine (50 eq) in 4:1 THF/DMF. The resulting solution was stirred for 15 minutes at 25° C. and then concentrated en vaccuo. The crude mixture was purified by flash chromatography on a COMBIFLASH® system (ISCO) using 0-10% MeOH/DCM to give the title product as a white solid.

Step 11: ((14R,18R)-14-amino-18-dodecanamido-13-oxo-3,6,9,20-tetraoxa-16-thia-12-azadotriacontyl) phosphonic acid To a solution of diethyl((14R,18R)-14-amino-18-dodecanamido-13-oxo-3,6,9,20-tetraoxa-16-thia-12-azadotriacontyl)phosphonate (1 eq) in DCM (0.1 M) was added trimethylsilyl bromide (10 eq). The reaction mixture was stirred at 25° C. overnight and concentrated. The crude mixture was purified by reverse phase high performance liquid chromatography (HPLC) with C4 column eluting with a gradient of 40-100% MeCN/10 mM NH$_4$OAc (95:5) in 10 mM NH$_4$OAc (pH 9) to give ((14R,18R)-14-amino-18-dodecanamido-13-oxo-3,6,9,20-tetraoxa-16-thia-12-azadotriacontyl)phosphonic acid as a white solid after lyophilizing. $^1$H NMR (CDCl$_3$): δ 8.84 (s, 2H), 6.54 (d, 2H), 4.20 (t, 2H), 4.07-4.11 (m, 2H), 3.49-3.70 (m, 12H), 3.31-3.36 (m, 4H), 3.00-3.02 (m, 4H), 2.72 (d, 4H), 2.15 (t, 2H), 1.43-1.55 (m, 6H), 1.16-1.22 (m, 32H), 0.80 (t, 6H). LRMS [M+H]=784.5.

Example 27

Synthesis of: ((14R,18R)-14-amino-18-(dodecanoyloxy)-13-oxo-3,6,9,20-tetraoxa-16-thia-12-azadotriacontyl)phosphonic acid

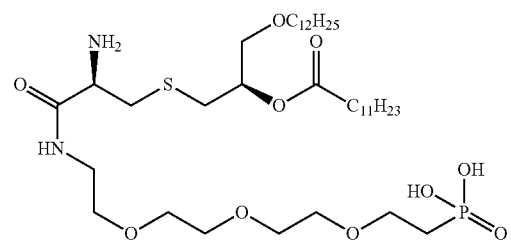

Step 1: (S)-2-((dodecyloxy)methyl)oxirane

A solution of (S)-3-(dodecyloxy)propane-1,2-diol (1 eq) in HBr/AcOH (33 wt %, 0.4 M) was stirred at 35° C. for 30 minutes. The reaction mixture was cooled down to 0° C., diluted with DCM and tuned to pH 7 by adding saturated Na$_2$CO$_3$. The organic layer was separated, dried over Na$_2$SO$_4$ and concentrated en vaccuo. The residue was dissolved in MeOH (0.5 M), cooled down to 0° C. and treated with NaOH (3N in MeOH, 2.5 eq). The reaction mixture was stirred for 30 minutes and diluted with Et$_2$O. The organic layer was separated, washed with H$_2$O and brine, dried over Na$_2$SO$_4$ and concentrated en vaccuo to give the title product as a colorless viscous oil without further purification.

Step 2: (R)-tert-butyl 2-((((9H-fluoren-9-yl)methoxy)carbonyl)amino)-3-(((R)-3-(dodecyloxy)-2-hydroxypropyl)thio)propanoate A solution of (S)-2-((dodecyloxy)methyl)oxirane (1.1 eq), (R)-tert-butyl 2-(((9H-fluoren-9-yl)methoxy)carbonylamino)-3-mercaptopropanoate (8, 1 eq) and 1M K$_2$CO$_3$ (1.1 eq) in tBuOH (0.1 M) was stirred at 25° C. for 15 hours. The reaction mixture was concentrated en vaccuo to remove tBuOH and dissolved in EtOAc. The EtOAc solution was washed three times with water, and once with brine. The resulting crude was purified by flash chromatography on a COMBIFLASH® system (ISCO) using 0-30% EtOAc/Hex to give the title product as a colorless viscous oil.

Step 3: (5R,9R)-5-(tert-butoxycarbonyl)-1-(9H-fluoren-9-yl)-3-oxo-2,11-dioxa-7-thia-4-azatricosan-9-yl dodecanoate A solution (R)-tert-butyl 2-((((9H-fluoren-9-yl)methoxy)carbonyl)amino)-3-(((R)-3-(dodecyloxy)-2-hydroxypropyl)thio)propanoate (1 eq) in DCM (0.1 M) was cooled in an ice bath. Pyridine (3.0 eq) was added followed by dodecanoyl chloride (3.0 eq). The reaction mixture was stirred for 10 minutes then warmed up to room temperature, and stirred for 2 hours. The reaction mixture was diluted with DCM, and washed with saturated aqueous $NH_4Cl$. The aqueous phase was back extracted with DCM. The combined organic phases were washed with brine, dried over anhydrous $Na_2SO_4$ and concentrated en vaccuo. The resulting crude was purified by flash chromatography on a COMBIFLASH® system (ISCO) using 0-30% EtOAc/Hex to give the title product as a white solid.

Step 4: (R)-2-((((9H-fluoren-9-yl)methoxy)carbonyl)amino)-3-(((R)-2-(dodecanoyloxy)-3-(dodecyloxy)propyl)thio)propanoic acid A solution of ((5R,9R)-5-(tert-butoxycarbonyl)-1-(9H-fluoren-9-yl)-3-oxo-2,11-dioxa-7-thia-4-azatricosan-9-yl dodecanoate in 40% TFA in DCM (0.3 M) was stirred at room temperature until complete deprotection of tert-butyl group (2 hours). The reaction mixture was diluted in MTBE, washed three times with 1M citric acid (adjusted to pH3), and once with 1:2 1N HCl/brine. The organic layer was dried over anhydrous $Na_2SO_4$ and concentrated en vaccuo. The resulting waxy solid was used without further purification.

Step 5-7: ((14R,18R)-14-amino-18-(dodecanoyloxy)-13-oxo-3,6,9,20-tetraoxa-16-thia-12-azadotriacontyl)phosphonic acid The title product was prepared from (R)-2-((((9H-fluoren-9-yl)methoxy)carbonyl)amino)-3-(((R)-2-(dodecanoyloxy)-3-(dodecyloxy)propyl)thio)propanoic acid by following the procedure described for example 26, step 9-11. $^1$H NMR (DMSO-$d_6$): δ 8.82 (t, 2H), 7.11 (br s, 4H), 5.00-5.05 (m, 2H), 3.76 (t, 2H), 3.16-3.60 (m, 12H), 2.92 (dd, 2H), 2.73-2.81 (m, 2H), 2.62-2.67 (m, 2H), 2.32-2.34 (m, 1H), 2.28 (t, 2H), 1.68-1.77 (m, 3H), 1.43-1.54 (m, 5H), 1.23-1.27 (m, 32H), 0.85 (t, 6H). LRMS [M+H]=785.5.

Example 28

Synthesis of: ((11S,14R,18R)-14-amino-18-dodecanamido-11-methyl-13-oxo-3,6,9,20-tetraoxa-16-thia-12-azadotriacontyl)phosphonic acid

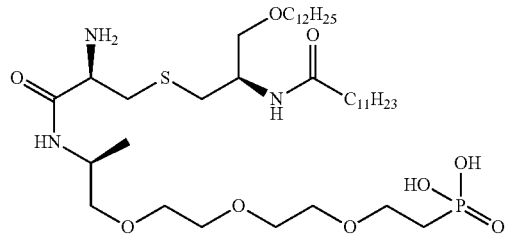

Step 1: (S)-tert-butyl(1-(2-(2-(2-(diethoxyphosphoryl)ethoxy)ethoxy)propan-2-yl)carbamate A suspension of (S)-tert-butyl(1-hydroxypropan-2-yl)carbamate (1 eq, from example 14, step 1), diethyl(2-(2-(2-iodoethoxy)ethoxy)ethyl)phosphonate (1.2 eq, from example 5, step 1), KOH (3 eq) and $Bu_4NBr$ (0.11 eq) in THF (0.1 M) was stirred at 25° C. overnight. The reaction mixture was diluted with EtOAc. The organic layer was separated, washed with $H_2O$, saturated $NH_4Cl$ and brine, dried over $Na_2SO_4$ and concentrated en vaccuo. The resulting crude was purified by flash chromatography on a COMBIFLASH® system (ISCO) using 0-10% EtOAc/Hex to give the title product as a colorless viscous oil.

Step 2: (S)-diethyl(2-(2-(2-(2-aminopropoxy)ethoxy)ethoxy)ethyl)phosphonate

A solution of (S)-tert-butyl(1-(2-(2-(2-(diethoxyphosphoryl)ethoxy)ethoxy)ethoxy)propan-2-yl)carbamate (1 eq) in 4N HCl/dioxane (0.4 M) was stirred at 25° C. for 1 hour. The reaction mixture was concentrated en vaccuo to give the title product as a colorless viscous oil.

Step 3: (9H-fluoren-9-yl)methyl((11S,14R,18R)-1-(diethoxyphosphoryl)-18-dodecanamido-11-methyl-13-oxo-3,6,9,20-tetraoxa-16-thia-12-azadotriacontan-14-yl)carbamate To a solution of (R)-2-((((9H-fluoren-9-yl)methoxy)carbonyl)amino)-3-(((R)-2-dodecanamido-3-(dodecyloxy)propyl)thio)propanoic acid (1 eq, from example 26, step 8) and HBTU (1.2 eq) in DCM (0.06 M) was added DIEA (3.5 eq), followed by (S)-diethyl(2-(2-(2-(2-aminopropoxy)ethoxy)ethoxy)ethyl)phosphonate (1.2 eq). The reaction was stirred at room temperature for 2 hours. The crude mixture was purified by flash chromatography on a COMBIFLASH® system (ISCO) using 0-5% MeOH/DCM to give the title product as a white solid.

Step 4-5: ((11S,14R,18R)-14-amino-18-dodecanamido-11-methyl-13-oxo-3,6,9,20-tetraoxa-16-thia-12-azadotriacontyl)phosphonic acid The title product was prepared from (9H-fluoren-9-yl)methyl((11S,14R,18R)-1-(diethoxyphosphoryl)-18-dodecanamido-11-methyl-13-oxo-3,6,9,20-tetraoxa-16-thia-12-azadotriacontan-14-yl)carbamate by following the procedure described for example 26, step 10-11. $^1$H NMR (CDCl$_3$): 8.63 (s, 2H), 6.59 (d, 2H), 4.04-4.13 (m, 4H), 3.45-3.72 (m, 11H), 3.43 (d, 2H), 3.32-3.36 (m, 4H), 3.00-3.13 (m, 4H), 2.72 (d, 2H), 2.13 (t, 2H), 1.44-1.55 (m, 6H), 1.17-1.22 (m, 32H), 1.12 (d, 3H), 0.81 (t, 6H). LRMS [M+H]=798.5.

Example 29

Synthesis of: ((11S,14R,18R)-14-amino-18-(dodecyloxy)-11-methyl-13-oxo-3,6,9,20-tetraoxa-16-thia-12-azadotriacontyl)phosphonic acid

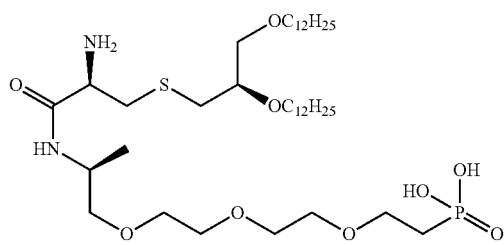

Step 1-3: ((11S,14R,18R)-14-amino-18-(dodecyloxy)-11-methyl-13-oxo-3,6,9,20-tetraoxa-16-thia-12-azadotriacontyl)phosphonic acid The title product was prepared from (R)-2-((((9H-fluoren-9-yl)methoxy)carbonyl)amino)-3-(((R)-2,3-bis(dodecyloxy)propyl)thio)propanoic acid (1 eq, from example 20, step 5) and (S)-diethyl(2-(2-(2-(2-aminopropoxy)ethoxy)ethoxy)ethyl)phosphonate (1.2 eq, from example 28, step 2) by following the procedure described for example 28, step 3-5. $^1$H NMR (CDCl$_3$): δ 8.21 (br s, 1H), 4.10-4.16 (m, 3H), 3.36-3.82 (m, 18H), 3.06 (dd, 2H), 2.91 (dd, 2H), 2.02-2.06 (m, 4H), 1.84-1.89 (m, 2H), 1.51-1.58 (m, 8H), 1.13-1.23 (m, 32H), 1.17 (d, 3H), 0.81 (t, 6H). LRMS [M+H]=785.5.

Example 30

Synthesis of: ((11S,14R,18R)-14-amino-18-(dodecyloxy)-11-methyl-10,13-dioxo-3,6,20-trioxa-16-thia-9,12-diazadotriacontyl)phosphonic acid

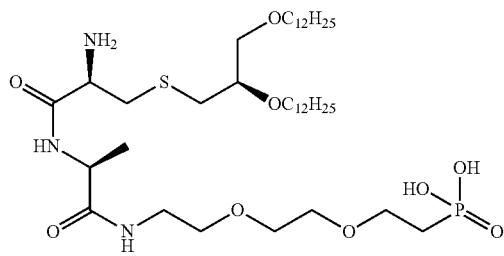

Step 1: (S)-tert-butyl(1-((2-(2-(2-(diethoxyphosphoryl)ethoxy)ethoxy)ethyl)amino)-1-oxopropan-2-yl)carbamate To a solution of (S)-2-((tert-butoxycarbonyl)amino)propanoic acid (1 eq) and HBTU (1.2 eq) in DCM (0.06 M) was added DIEA (3.5 eq), followed by diethyl(2-(2-(2-aminoethoxy)ethoxy)ethyl)phosphonate (1.2 eq, from example 5, step 3). The reaction was stirred at room temperature for 2 hours. The crude mixture was purified by flash chromatography on a COMBIFLASH® system (ISCO) using 0-5% MeOH/DCM to give the title product as a colorless viscous oil.

Step 2: (S)-diethyl(2-(2-(2-(2-aminopropanamido)ethoxy)ethoxy)ethyl)phosphonate

A solution of (S)-tert-butyl(1-((2-(2-(2-(diethoxyphosphoryl)ethoxy)ethoxy)ethyl)amino)-1-oxopropan-2-yl)carbamate (1 eq) in 4N HCl/dioxane (0.4 M) was stirred at 25° C. for 1 hour. The reaction mixture was concentrated en vaccuo to give the title product as a colorless viscous oil.

Step 3-5: (9H-fluoren-9-yl)methyl((11S,14R,18R)-1-(diethoxyphosphoryl)-18-(dodecyloxy)-11-methyl-10,13-dioxo-3,6,20-trioxa-16-thia-9,12-diazadotriacontan-14-yl)carbamate The title product was prepared from (R)-2-((((9H-fluoren-9-yl)methoxy)carbonyl)amino)-3-(((R)-2,3-bis(dodecyloxy)propyl)thio)propanoic acid (1 eq, from example 20, step 5) and (S)-diethyl(2-(2-(2-(2-aminopropoxy)ethoxy)ethoxy)ethyl)phosphonate (1.2 eq) by following the procedure described for example 28, step 3-5. $^1$H NMR (DMSO-d$_6$): δ 9.28 (br s, 1H), 8.16 (t, 1H), 4.18-4.25 (m, 1H), 3.08-3.65 (m, 16H), 2.93 (dd, 2H), 2.76 (dd, 2H), 2.59-2.67 (m, 4H), 2.32-2.34 (m, 2H), 1.66-1.75 (m, 4H), 1.43-1.48 (m, 4H), 1.21-1.29 (m, 35H), 0.85 (t, 6H). LRMS [M+H]=798.5.

Example 31

Synthesis of: ((11S,14R,18R)-14-amino-18-dodecanamido-11-methyl-10,13-dioxo-3,6,20-trioxa-16-thia-9,12-diazadotriacontyl)phosphonic acid

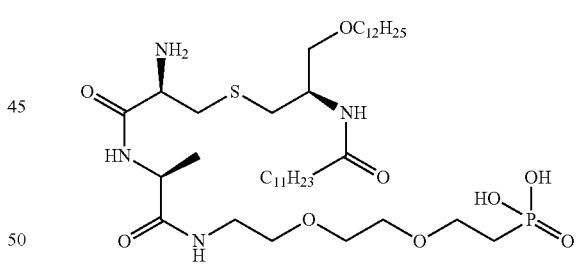

Step 1-3: ((11S,14R,18R)-14-amino-18-dodecanamido-11-methyl-10,13-dioxo-3,6,20-trioxa-16-thia-9,12-diazadotriacontyl)phosphonic acid The title product was prepared from (R)-2-((((9H-fluoren-9-yl)methoxy)carbonyl)amino)-3-(((R)-2-dodecanamido-3-(dodecyloxy)propyl)thio)propanoic acid (1 eq, from example 26, step 8) and (S)-diethyl(2-(2-(2-(2-aminopropoxy)ethoxy)ethoxy)ethyl)phosphonate (1.2 eq, from example 30, step 2) by following the procedure described for example 28, step 3-5. $^1$H NMR (DMSO-d$_6$): δ 9.38 (br s, 1H), 8.14 (t, 2H), 4.18-4.25 (m, 1H), 3.92-4.00 (m, 1H), 3.06-3.67 (m, 15H), 2.92 (dd, 2H), 2.79 (dd, 2H), 2.59-2.73 (m, 4H), 2.07 (t, 2H), 1.65-1.75 (m, 2H), 1.42-1.50 (m, 4H), 1.21-1.28 (m, 35H), 0.85 (t, 6H). LRMS [M+H]=811.5.

Example 32

Synthesis of: (15R,19R)-15-amino-19-(dodecyloxy)-14-oxo-4,7,10,21-tetraoxa-17-thia-13-azatritriacontan-1-oic acid

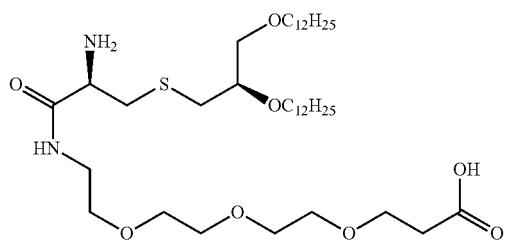

Step 1: (15R,19R)-tert-butyl 15-((((9H-fluoren-9-yl)methoxy)carbonyl)amino)-19-(dodecyloxy)-14-oxo-4,7,10,21-tetraoxa-17-thia-13-azatritriacontan-1-oate To a solution of (R)-2-((((9H-fluoren-9-yl)methoxy)carbonyl)amino)-3-(((R)-2,3-bis(dodecyloxy)propyl)thio)propanoic acid (1 eq, from example 20, step 5) and HBTU (1.2 eq) in DCM (0.06 M) was added DIEA (3.5 eq), followed by tert-butyl 3-(2-(2-(2-aminoethoxy)ethoxy)ethoxy)propanoate (1.2 eq). The reaction was stirred at room temperature for 2 hours. The crude mixture was purified by flash chromatography on a COMBIFLASH® system (ISCO) using 0-5% MeOH/DCM to give the title product as a white solid.

Step 2: (15R,19R)-tert-butyl 15-amino-19-(dodecyloxy)-14-oxo-4,7,10,21-tetraoxa-17-thia-13-azatritriacontan-1-oate To a solution of (15R,19R)-tert-butyl 15-((((9H-fluoren-9-yl)methoxy)carbonyl)amino)-19-(dodecyloxy)-14-oxo-4,7,10,21-tetraoxa-17-thia-13-azatritriacontan-1-oate (1 eq) was added 20% piperidine (50 eq) in 4:1 THF/DMF. The resulting solution was stirred for 15 minutes at 25° C. and then concentrated en vaccuo. The crude mixture was purified by flash chromatography on a COMBIFLASH® system (ISCO) using 0-10% MeOH/DCM to give the title product as a white solid.

Step 3: (15R,19R)-15-amino-19-(dodecyloxy)-14-oxo-4,7,10,21-tetraoxa-17-thia-13-azatritriacontan-1-oic acid A solution of (15R,19R)-tert-butyl 15-amino-19-(dodecyloxy)-14-oxo-4,7,10,21-tetraoxa-17-thia-13-azatritriacontan-1-oate in 1:1 TFA/DCM (0.1 M) was stirred at 25° C. for 1 hour. The reaction mixture was concentrated en vaccuo. The crude mixture was purified by reverse phase high performance liquid chromatography (HPLC) with C4 column eluting with a gradient of 40-100% MeCN/10 mM NH$_4$OAc (95:5) in 10 mM NH$_4$OAc (pH 9) to give the title product as a white solid after lyophilizing. $^1$H NMR (DMSO-d$_6$): δ 8.04 (t, 1H), 7.36 (s, 1H), 5.04 (d, 2H), 3.58 (t, 2H), 3.19-3.50 (m, 20H), 2.77 (dd, 2H), 2.59 (dd, 2H), 2.40 (t, 2H), 1.43-1.48 (m, 4H), 1.21-1.28 (m, 36H), 0.85 (t, 6H). LRMS [M+H]=735.6.

Example 33

Synthesis of: (15R,19R)-15-amino-19-dodecanamido-14-oxo-4,7,10,21-tetraoxa-17-thia-13-azatritriacontan-1-oic acid

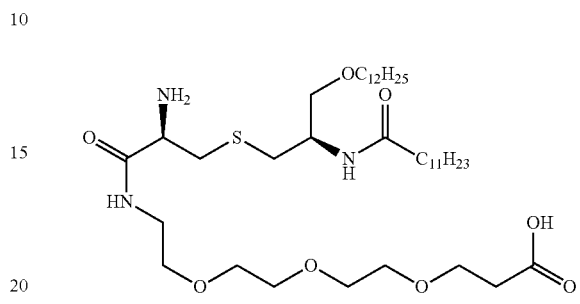

Step 1-3: (15R,19R)-15-amino-19-dodecanamido-14-oxo-4,7,10,21-tetraoxa-17-thia-13-azatritriacontan-1-oic acid The title product was prepared from (R)-2-((((9H-fluoren-9-yl)methoxy)carbonyl)amino)-3-(((R)-2-dodecanamido-3-(dodecyloxy)propyl)thio)propanoic acid (1 eq, from example 26, step 8) and tert-butyl 3-(2-(2-(2-aminoethoxy)ethoxy)ethoxy)propanoate (1.2 eq) by following the procedure described for example 32, step 1-3. $^1$H NMR (DMSO-d$_6$): δ 8.06 (t, 1H), 7.78 (d, 1H), 5.05 (br s, 2H), 3.90-3.98 (m, 1H), 3.58 (t, 2H), 3.19-3.50 (m, 15H), 2.77 (dd, 2H), 2.62 (dd, 2H), 2.39 (t, 2H), 2.05 (t, 2H), 1.42-1.48 (m, 4H), 1.21-1.29 (m, 36H), 0.85 (t, 6H). LRMS [M+H]=748.5.

Example 34

Synthesis of: ((14R,18R)-18-(dodecanoyloxy)-13,21-dioxo-14-palmitamido-3,6,9,20-tetraoxa-16-thia-12-azadotriacontyl)phosphonic acid

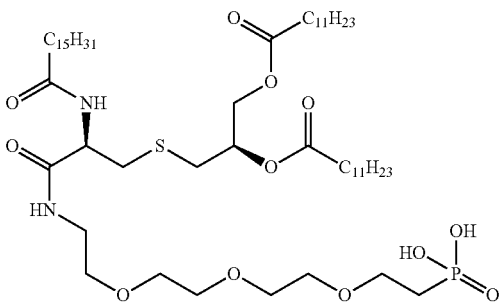

Step 1: (14R,18R)-1-(diethoxyphosphoryl)-13-oxo-14-palmitamido-3,6,9-trioxa-16-thia-12-azanonadecane-18,19-diyl didodecanoate A solution of (14R,18R)-14-amino-18-(dodecanoyloxy)-13,21-dioxo-3,6,9,20-tetraoxa-16-thia-12-azadotriacontylphosphonic acid diethyl ester (1 eq, from example 18, step 6) in DCM (0.1 M) was cooled in an ice bath. Pyridine (1.2 eq)

was added followed by palmitoyl chloride (1.1 eq). The reaction mixture was stirred for 10 minutes then warmed up to room temperature, and stirred for 2 hours. The reaction mixture was diluted with DCM, washed with saturated aqueous NH$_4$Cl. The aqueous phase was back extracted with DCM. The combined organic phases were washed with brine, dried over anhydrous Na$_2$SO$_4$ and concentrated en vaccuo. The resulting crude was purified by flash chromatography on a COMBIFLASH® system (ISCO) using 0-10% MeOH/DCM to give the title product as a white solid.

Step 2: ((14R,18R)-18-(dodecanoyloxy)-13,21-dioxo-14-palmitamido-3,6,9,20-tetraoxa-16-thia-12-azadotriacontyl)phosphonic acid To a solution of (14R,18R)-1-(diethoxyphosphoryl)-13-oxo-14-palmitamido-3,6,9-trioxa-16-thia-12-azanonadecane-18,19-diyl didodecanoate (1 eq) in DCM (0.1 M) was added trimethylsilyl bromide (10 eq). The reaction mixture was stirred at 25° C. overnight and concentrated. The crude mixture was purified by reverse phase high performance liquid chromatography (HPLC) with C4 column eluting with a gradient of 40-100% MeCN/10 mM NH$_4$OAc (95:5) in 10 mM NH$_4$OAc (pH 9) to give the title product as a white solid after lyophilizing. $^1$H NMR (CDCl$_3$): δ 8.09 (br s, 2H), 5.18 (d, 2H), 4.62-4.70 (m, 2H), 4.36 (d, 2H), 4.13 (dd, 2H), 3.40-3.80 (m, 13H), 2.70-3.05 (m, 8H), 2.27-2.32 (m, 6H), 1.54-1.62 (m, 6H), 1.20-1.32 (m, 56H), 0.88 (t, 9H). LRMS [M+H]=1037.7.

Example 35

Synthesis of: (12R,16R)-12-amino-16-dodecanamido-1,1-difluoro-11-oxo-4,7,18-trioxa-14-thia-10-azatriacontylphosphonic acid

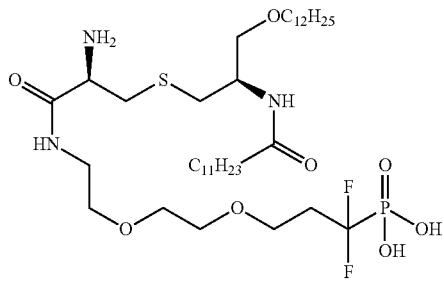

Step 1: (12R,16R)-12-(((9H-fluoren-9-yl)methoxy)carbonylamino)-16-dodecanamido-1,1-difluoro-11-oxo-4,7,18-trioxa-14-thia-10-azatriacontylphosphonic acid diethyl ester The title compound was prepared from (R)-2-(((9H-fluoren-9-yl)methoxy)carbonylamino)-3-((R)-2-dodecanamido-3-(dodecyloxy)propylthio)propanoic acid (1.0 eq, from example 26, step 8) and diethyl 3-(2-(2-aminoethoxy)ethoxy)-1,1-difluoropropylphosphonate (1.2 eq, from example 22, step 3) by following the procedure described for example 26, step 9.

Step 2: diethyl((12R,16R)-12-amino-16-dodecanamido-1,1-difluoro-11-oxo-4,7,18-trioxa-14-thia-10-azatriacontyl)phosphonate A solution of (12R,16R)-12-(((9H-fluoren-9-yl)methoxy)carbonylamino)-16-dodecanamido-1,1-difluoro-11-oxo-4,7, 18-trioxa-14-thia-10-azatriacontylphosphonic acid diethyl ester in acetonitrile (0.1M) was stirred at room temperature. Piperidine (final conc. 20%) was then added and the reaction stirred for 30 minutes. After concentration, the crude material was by flash chromatography on a COMBIFLASH® system (ISCO) using a gradient of 0-100% EtOAc/Hex, then 0-10% MeOH/DCM to give the title compound as an off-white solid.

Step 3: (12R,16R)-12-amino-16-dodecanamido-1,1-difluoro-1-oxo-4,7,18-trioxa-14-thia-10-azatriacontylphosphonic acid The title compound was prepared using diethyl((12R,16R)-12-amino-16-dodecanamido-1,1-difluoro-11-oxo-4,7,18-trioxa-14-thia-10-azatriacontyl)phosphonate (1 eq) by following the procedure described in example 14, step 5. $^1$H NMR (DMSO-d$_6$): δ 8.53 (t, 1H), 8.01 (d, 1H), 3.98 (m, 1H), 3.62 (t, 2H), 3.55 (t, 2H), 3.20-3.50 (m, 14H), 2.76 (dd, 1H), 2.62 (m, 2H), 2.58 (m, 1H), 2.52 (m, 2H), 2.02-2.20 (m, 3H), 1.49 (m, 4H), 1.21-1.42 (m, 34H), 0.82 (t, 6H). LRMS [M+H]=790.5.

Example 36

Synthesis of: (14R,18R)-14-amino-18-(decylcarbamoyloxy)-13,21-dioxo-3,6,9,20-tetraoxa-16-thia-12,22-diazadotriacontylphosphonic acid

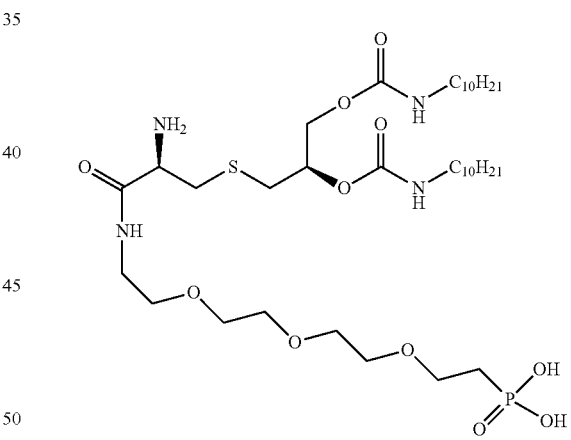

Preparation of starting compound: (R)-2-(benzyloxycarbonylamino)-3-((R)-2,3-bis(decylcarbamoyloxy)propylthio propanoic acid (15)

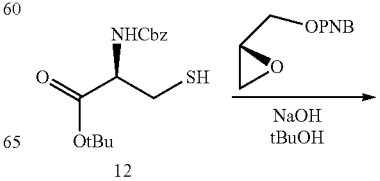

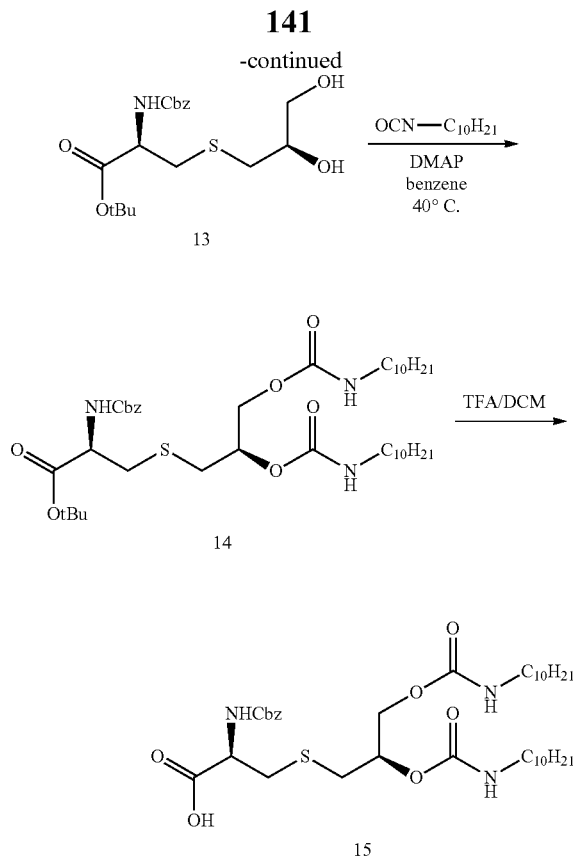

Step 1: (R)-tert-butyl 2-(benzyloxycarbonylamino)-3-((R)-2,3-dihydroxypropylthio)propanoate (13)

A solution of (2S)-(+)-glycidyl-4-nitrobenzoate (1.1 eq) and 1M NaOH (1.1 eq) in tBuOH (0.1 M) was stirred at room temperature until complete hydrolysis of the nitrobenzoate was observed (30 minutes). To the resulting mixture, a solution of (R)-tert-butyl 2-(benzyloxycarbonylamino)-3-mercaptopropanoate (12, 1 eq) in tBuOH (1 M) was introduced and the reaction stirred at room temperature for 15 hours. The reaction mixture was concentrated en vaccuo to remove tBuOH then dissolved in EtOAc. The EtOAc solution was washed three times with water, once with brine, then dried over $Na_2SO_4$ and concentrated. The crude material was purified by flash chromatography on a COMBIFLASH® system (ISCO) using a gradient of 0-90% EtOAc/Hex to give the title product as a colorless viscous oil.

Step 2: (R)-tert-butyl 2-(benzyloxycarbonylamino)-3-((R)-2,3-bis(decylcarbamoyloxy)propylthio)propanoate (14)

A solution of (R)-tert-butyl 2-(benzyloxycarbonylamino)-3-((R)-2,3-dihydroxypropylthio)propanoate (13) was stirred in anhydrous benzene (0.1 M) under nitrogen at room temperature. Decyl isocyanate (2.02 eq) and DMAP (dimethylaminopyridine, 2.02 eq) were added and the resulting mixture heated to 40° C. and stirred overnight. The reaction mixture was concentrated to remove benzene then reconstituted in DCM and purified on a COMBIFLASH® system (ISCO) using a gradient of 0-50% EtOAc/Hex to give the title product as a colorless oil.

Step 3: (R)-2-(benzyloxycarbonylamino)-3-((R)-2,3-bis(decylcarbamoyloxy)propylthio)propanoic acid (15)

A solution of (R)-tert-butyl 2-(benzyloxycarbonylamino)-3-((R)-2,3-bis(decylcarbamoyloxy)propylthio)propanoate (14) in 30% TFA in DCM (0.3 M) was stirred at room temperature until complete deprotection of the tert-butyl group (4 hours). The reaction was diluted with DCM and concentrated with a stream of nitrogen. The residue was then diluted in MTBE and washed once with 1M citric acid (adjusted to pH3). The organic layer was dried over anhydrous $Na_2SO_4$ and concentrated en vaccuo to afford (R)-2-(benzyloxycarbonylamino)-3-((R)-2,3-bis(decylcarbamoyloxy)propylthio)propanoic acid (15) as a waxy solid that was used without further purification.

Step 1: (14R,18R)-14-(benzyloxycarbonylamino)-18-(decylcarbamoyloxy)-13,21-dioxo-3,6,9,20-tetraoxa-16-thia-12,22-diazadotriacontylphosphonic acid diethyl ester To a solution of (R)-2-(benzyloxycarbonylamino)-3-((R)-2,3-bis(decylcarbamoyloxy)propylthio)propanoic acid (15, 1 eq) and HBTU (1.2 eq) in DCM (0.06 M) was added DIEA (2.4 eq), followed by diethyl 2-(2-(2-(2-aminoethoxy)ethoxy)ethoxy)ethylphosphonate (1.2 eq, from example 18, step 4). The reaction was stirred at room temperature for 4 hours. The crude mixture was purified by flash chromatography on a COMBIFLASH® system (ISCO) using a gradient of 0-10% MeOH/DCM to afford the title compound as a clear viscous oil.

Step 2: (14R,18R)-14-amino-18-(decylcarbamoyloxy)-13,21-dioxo-3,6,9,20-tetraoxa-16-thia-12,22-diazadotriacontylphosphonic acid To a solution of (14R,18R)-14-(benzyloxycarbonylamino)-18-(decylcarbamoyloxy)-13,21-dioxo-3,6,9,20-tetraoxa-16-thia-12,22-diazadotriacontylphosphonic acid diethyl ester (1 eq) in DCM at 0° C. (0.1 M) was added trimethylsilyl bromide (10 eq). The reaction mixture was stirred at 32° C. overnight then cooled to room temperature, diluted with DCM and concentrated. The crude material was dried under high vacuum for 2 hours then purified by reverse phase high performance liquid chromatography (HPLC) with a C4 column eluting with a gradient of 40-100% MeCN/10 mM $NH_4OAc$ (95:5) in 10 mM $NH_4OAc$ (pH 9) to afford (14R,18R)-14-amino-18-(decylcarbamoyloxy)-13,21-dioxo-3,6,9,20-tetraoxa-16-thia-12,22-diazadotriacontylphosphonic acid as a white solid. $^1$H NMR (DMSO-$d_6$): δ 8.49 (t, 1H), 7.32 (m, 2H), 4.78 (m, 1H), 4.01 (m, 2H), 3.0-3.6 (m, 18H), 2.88 (m, 4H), 2.52-2.81 (m, 5H), 1.54 (m, 2H), 1.34 (m, 4H), 1.12-1.24 (m, 28H), 0.81 (t, 6H). LRMS [M+H]=801.5.

Example 37

Synthesis of: (15R,19R)-15-amino-19-(decylcarbamoyloxy)-14,22-dioxo-4,7,10,21-tetraoxa-17-thia-13, 23-diazatritriacontan-1-oic acid

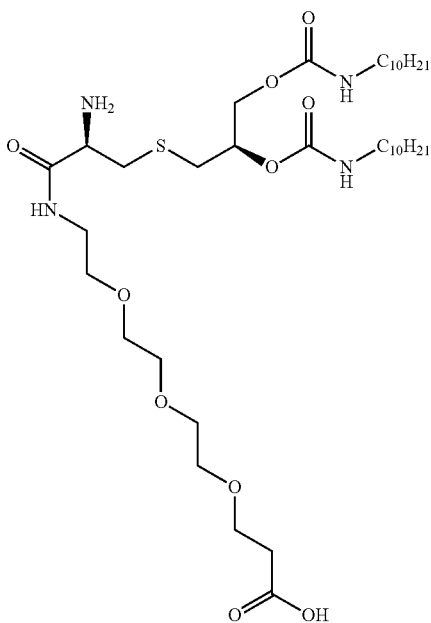

Step 1: (15R,19R)-tert-butyl 15-(benzyloxycarbonylamino)-19-(decylcarbamoyloxy)-14,22-dioxo-4,7, 10,21-tetraoxa-17-thia-13,23-diazatritriacontan-1-oate To a solution of (R)-2-(benzyloxycarbonylamino)-3-((R)-2,3-bis(decylcarbamoyloxy)propylthio)propanoic acid (15, 1 eq) and HBTU (1.2 eq) in DCM (0.06 M) was added DIEA (2.4 eq), followed by tert-butyl 3-(2-(2-(2-aminoethoxy)ethoxy)ethoxy)propanoate (1.2 eq). The reaction was stirred at room temperature for 4 hours. The crude mixture was purified by flash chromatography on a COMBIFLASH® system (ISCO) using a gradient of 0-100% EtOAc/Hex to afford the title compound as an off-white solid.

Step 2: (15R,19R)-tert-butyl 15-amino-19-(decylcarbamoyloxy)-14,22-dioxo-4,7,10,21-tetraoxa-17-thia-13,23-diazatritriacontan-1-oate A solution of (15R,19R)-tert-butyl 15-(benzyloxycarbonylamino)-19-(decylcarbamoyloxy)-14,22-dioxo-4,7,10,21-tetraoxa-17-thia-13,23-diazatritriacontan-1-oate in MeOH (0.1 M) was stirred under nitrogen at room temperature. A small scoop (catalytic) of Pd/C was then added and stirred. A solution of ammonium formate (8 eq) in 9:1 MeOH/water was then added, the reaction vessel purged with nitrogen and heated to 40° C. for 4 hours. The reaction was then cooled to room temperature and diluted with EtOAc. The reaction mixture was filtered through celite then Na$_2$SO$_4$ and concentrated to afford the title compound as a light yellow oil. The concentrated material was used with no further purification.

Step 3: (15R,19R)-15-amino-19-(decylcarbamoyloxy)-14,22-dioxo-4,7,10,21-tetraoxa-17-thia-13,23-diazatritriacontan-1-oic acid A solution of (15R,19R)-tert-butyl 15-amino-19-(decylcarbamoyloxy)-14,22-dioxo-4,7,10,21-tetraoxa-17-thia-13, 23-diazatritriacontan-1-oate in 30% TFA in DCM (0.3 M) was stirred at room temperature until complete deprotection of the tert-butyl group (4 hours). The reaction was diluted with DCM and concentrated with a stream of nitrogen then purified by flash chromatography on a COMBIFLASH® system (ISCO) using a gradient of 0-10% MeOH/DCM with 0.5% AcOH to afford (15R,19R)-15-amino-19-(decylcarbamoyloxy)-14,22-dioxo-4,7,10,21-tetraoxa-17-thia-13,23-diazatritriacontan-1-oic acid as a clear oil. $^1$H NMR (DMSO-d$_6$): δ 12.21 (br s, 1H), 8.22 (t, 1H), 7.23 (m, 2H), 4.92 (m, 1H), 4.18 (dd, 2H), 3.94 (m, 1H), 3.57 (t, 2H), 3.30-3.54 (m, 12H), 3.37 (t, 2H), 2.90-3.08 (m, 4H), 2.60-2.82 (m, 4H), 2.48 (t, 2H), 1.32 (m, 4H), 1.22-1.28 (m, 28H), 0.79 (t, 6H). LRMS [M+H]=765.5.

Example 38

Synthesis of: (14R,18R)-14-amino-18-(octylcarbamoyloxy)-13,21-dioxo-3,6,9,20-tetraoxa-16-thia-12, 22-diazatriacontylphosphonic acid

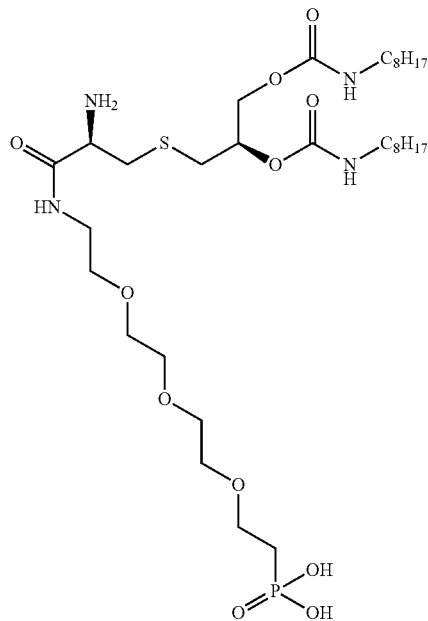

Step 1: (R)-tert-butyl 2-(benzyloxycarbonylamino)-3-((R)-2,3-bis(octylcarbamoyloxy)propylthio)propanoate A solution of (R)-tert-butyl 2-(benzyloxycarbonylamino)-3-((R)-2,3-dihydroxypropylthio)propanoate (13) was stirred in anhydrous benzene (0.1 M) under nitrogen at room temperature. Octyl isocyanate (2.02 eq) and DMAP (dimethylaminopyridine, 2.02 eq) were added and the resulting mixture heated to 40° C. and stirred overnight. The reaction mixture was concentrated to remove benzene then reconstituted in DCM and purified by flash chromatography on a COMBIFLASH® system (ISCO) using a gradient of 0-50% EtOAc/Hex to afford the title product as a colorless oil.

Step 2: (R)-2-(benzyloxycarbonylamino)-3-((R)-2,3-bis(octylcarbamoyloxy)propylthio)propanoic acid A solution of (R)-tert-butyl 2-(benzyloxycarbonylamino)-3-((R)-2,3-bis(octylcarbamoyloxy)propylthio)propanoate in 30% TFA in DCM (0.3 M) was stirred at room temperature until complete deprotection of the tert-butyl group (4 hours). The reaction was diluted with DCM and concentrated with a stream of nitrogen. The reaction mixture was then diluted in MTBE and washed once with 1M citric acid (adjusted to pH3). The organic layer was dried over anhydrous $Na_2SO_4$ and concentrated en vaccuo. The resulting waxy solid was used without further purification.

Step 3: (14R,18R)-14-(benzyloxycarbonylamino)-18-(octylcarbamoyloxy)-13,21-dioxo-3,6,9,20-tetraoxa-16-thia-12,22-diazatriacontylphosphonic acid diethyl ester To a solution of (R)-2-(benzyloxycarbonylamino)-3-((R)-2,3-bis(decylcarbamoyloxy)propylthio)propanoic acid (1 eq) and HBTU (1.2 eq) in DCM (0.06 M) was added DIEA (2.4 eq), followed by diethyl 2-(2-(2-(2-aminoethoxy)ethoxy)ethoxy)ethylphosphonate (1.2 eq, from example 18, step 4). The reaction was stirred at room temperature for 4 hours. The crude mixture was purified by flash chromatography on a COMBIFLASH® system (ISCO) using a gradient of 0-10% MeOH/DCM to afford the title compound as an opaque oil.

Step 4: (14R,18R)-14-amino-18-(octylcarbamoyloxy)-13,21-dioxo-3,6,9,20-tetraoxa-16-thia-12,22-diazatriacontylphosphonic acid To a solution of (14R,18R)-14-(benzyloxycarbonylamino)-18-(octylcarbamoyloxy)-13,21-dioxo-3,6,9,20-tetraoxa-16-thia-12,22-diazatriacontylphosphonic acid diethyl ester (1 eq) in DCM (0.1 M) was added trimethylsilyl bromide (10 eq). The reaction mixture was stirred at 32° C. overnight then cooled to room temperature, diluted with DCM and concentrated. The crude material was dried under high vacuum for 2 hours then purified by reverse phase high performance liquid chromatography (HPLC) with a C4 column eluting with a gradient of 40-100% MeCN/10 mM $NH_4OAc$ (95:5) in 10 mM $NH_4OAc$ (pH 9) to afford (14R,18R)-14-amino-18-(octylcarbamoyloxy)-13,21-dioxo-3,6,9,20-tetraoxa-16-thia-12,22-diazatriacontyl phosphonic acid as a white solid. $^1$H NMR (DMSO-$d_6$): δ 8.57 (t, 1H), 7.42 (m, 2H), 4.78 (m, 1H), 4.01 (m, 2H), 3.0-3.6 (m, 18H), 2.88 (m, 4H), 2.52-2.81 (m, 5H), 1.68 (m, 2H), 1.54 (m, 2H), 1.40 (m, 2H), 1.12-1.24 (m, 20H), 0.82 (t, 6H). LRMS [M+H]=745.4.

Example 39

Synthesis of: (14R,18R)-18-(decylcarbamoyloxy)-13,21-dioxo-14-palmitamido-3,6,9,20-tetraoxa-16-thia-12,22-diazadotriacontylphosphonic acid

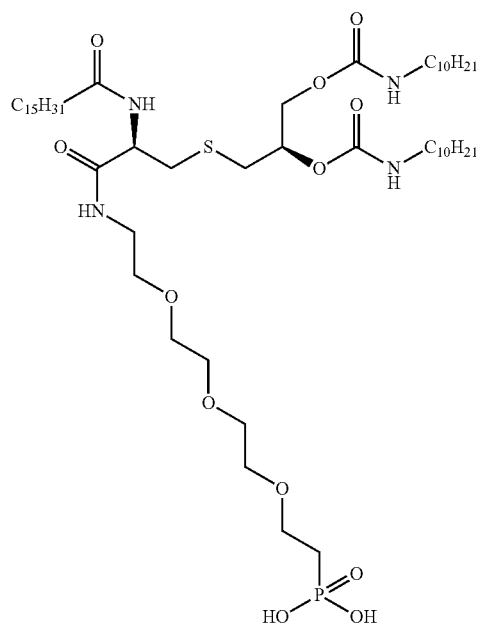

Step 1: (R)-tert-butyl 2-amino-3-((R)-2,3-bis(decylcarbamoyloxy)propylthio)propanoate A solution of (R)-tert-butyl 2-(benzyloxycarbonylamino)-3-((R)-2,3-bis(decylcarbamoyloxy)propylthio)propanoate (14) in MeOH (0.1 M) was stirred under nitrogen at room temperature. A small scoop (catalytic) of Pd/C was then added and stirred. A solution of ammonium formate (8 eq) in 9:1 MeOH/water was then added, the reaction vessel purged with nitrogen and heated to 40° C. for 4 hours. The reaction was then cooled to room temperature and diluted with EtOAc. The reaction mixture was filtered through celite then $Na_2SO_4$ and concentrated. The crude material was purified by flash chromatography on a COMBIFLASH® system (ISCO) using a gradient of 0-60% EtOAc/Hex to afford the title compound as a colorless oil.

Step 2: (R)-tert-butyl 3-((R)-2,3-bis(decylcarbamoyloxy)propylthio)-2-palmitamidopropanoate To a solution of (R)-tert-butyl 2-amino-3-((R)-2,3-bis(decylcarbamoyloxy)propylthio)propanoate in dry DCM (0.1 M) at 0° C. was added DIEA (1.2 eq) and palmitoyl chloride (1.1 eq). The reaction was allowed to warm to room temperature then stirred for 16 hours. The crude reaction was then concentrated and purified by flash chromatography on a COMBIFLASH® system (ISCO) using a gradient 0-60% EtOAc/Hex to afford the title compound as a white solid.

Step 3: (R)-3-((R)-2,3-bis(decylcarbamoyloxy)propylthio)-2-palmitamidopropanoic acid A solution of (R)-tert-butyl 3-((R)-2,3-bis(decylcarbamoyloxy)propylthio)-2-palmitamido propanoate in 30% TFA in DCM (0.3 M) was stirred at room temperature until complete deprotection of the tert-butyl group (4 hours). The reaction was diluted with DCM and concentrated with a stream of nitrogen. The reaction mixture was then diluted in MTBE and washed once with 1M citric acid (adjusted to pH3). The organic layer was dried over $Na_2SO_4$ and concentrated. The resulting compound was used without further purification.

Step 4: (14R,18R)-18-(decylcarbamoyloxy)-13,21-dioxo-14-palmitamido-3,6,9,20-tetraoxa-16-thia-12,22-diazadotriacontylphosphonic acid diethyl ester To a solution of (R)-3-((R)-2,3-bis(decylcarbamoyloxy) propylthio)-2-palmitamidopropanoic acid and HBTU (1.2 eq) in DCM (0.06 M) was added DIEA (2.4 eq), followed by diethyl 2-(2-(2-(2-aminoethoxy)ethoxy)ethoxy)ethylphosphonate (1.2 eq, from example 18, step 4). The reaction was stirred at room temperature for 4 hours. The crude mixture was purified by flash chromatography on a COMBIFLASH® system (ISCO) using a gradient of 0-10% MeOH/DCM to afford the title compound as an off-white oil.

Step 4: (14R,18R)-18-(decylcarbamoyloxy)-13,21-dioxo-14-palmitamido-3,6,9,20-tetraoxa-16-thia-12,22-diazadotriacontylphosphonic acid A solution of (14R,18R)-18-(decylcarbamoyloxy)-13,21-dioxo-14-palmitamido-3,6,9,20-tetraoxa-16-thia-12,22-diazadotriacontylphosphonic acid diethyl ester (1 eq) in DCM (0.1 M) was stirred at 0° C. Trimethylsilyl bromide (10 eq) was added and allowed to warm to room temperature. The reaction was then heated to 32° C. and stirred overnight. The reaction was then diluted with DCM and concentrated with a stream of nitrogen then purified by flash chromatography on a COMBIFLASH® system (ISCO) using a gradient of 0-10% MeOH/DCM with 0.5% AcOH to afford (14R,18R)-18-(decylcarbamoyloxy)-13,21-dioxo-14-palmitamido-3,6,9,20-tetraoxa-16-thia-12,22-diazadotriacontylphosphonic acid as a colorless oil. $^1$H NMR (DMSO-$d_6$): δ 7.32 (t, 1H), 6.65 (t, 1H), 5.63 (t, 1H), 5.24 (t, 1H), 5.16 (t, 1H), 4.68 (m, 1H), 4.48 (m, 1H), 3.46-3.78 (m, 15H), 3.17 (m, 4H), 2.75-2.95 (m, 4H), 2.15-2.35 (m, 4H), 1.56 (m, 4H), 1.49 (m, 4H), 1.20-1.45 (m, 52H), 0.87 (t, 9H). LRMS [M+H]=1039.7.

In Table 1, the compounds of Formula (I) showing corresponding physical data and assay data were obtained, using appropriate starting materials, by repeating the procedures described in the above examples.

Compounds of Formula (I) provided herein were assayed to measure their capacity to modulate toll-like receptor 2.

Human Peripheral Blood Mononuclear Cell Assay

The bioactivity of the compounds of Formula (I) provided herein were tested in the human peripheral blood assay (human PBMC) using a panel of independent normal human donors according to approved guidelines by the institutional review committee. Human PBMC were isolated from freshly peripheral blood using a Ficoll density gradient (GE healthcare 17-1440-03). 30-35 mLs of peripheral human blood were layered onto 15 mLs of Ficoll in 50 ml conical tubes, followed by centrifugation at 1800 rpm (Eppendorf Centrifuge 5810R with biohazard caps over the tube buckets) at room temperature for 30 minutes with no acceleration and no brake. The buffy layers were then collected and transferred onto new 50 ml conical tubes and washed twice in complete media consisting of RPMI 1640 (11875085 from Invitrogen Corporation, Carlsbad, Calif.) supplemented with 10% heat inactivated fetal bovine serum (Gibco 10099-141), 1% Pen-Strep (Gibco#15140-122), 1 mM non essential amino acids (Gibco#11140-050), 1 mM sodium pyruvate (Gibco#11360-070), 2 mM L-Glutamine (Gibco#25030-081) and 1 mM HEPES (Gibco#15630-080). Viable cells were then counted using trypan blue staining, plated in 96 well flat bottom plates (Becton Dickinson #353070) at $2\times10^5$ cells per well in 200 μl total volume of complete media. Compounds were then added in a 10 point dose response format starting at 100 mM, 3 fold dilution. Negative controls wells received equal concentration of DMSO. Culture supernatants were collected after 18-24 hours incubation at 37° C., 5% $CO_2$, stored at −20° C. until further use.

IL-6 levels in the culture supernatants were measured using a Luminex kit (Biorad). Data analysis is performed using Prism software from GraphPad (San Diego, Calif.). Dose response curves are generated for each compound and $EC_{50}$ values were determined as the concentration that gives 50% of the maximal signal.

Reporter Gene Assay

Human embryonic kidney 293 (HEK 293) cells were stably transfected with human TLR2 and an NF-kB-driven luciferase reporter vector (pNifty-Luciferase). As a control assay, normal Hek293 transfected with pNifty-Luc were used. Cells were cultured in DMEM supplemented with 2 mM L-glutamine, 10% heart inactivated FBS, 1% penicillin and streptomycin, 2 μg/ml puromycin (InvivoGen #ant-pr-5) and 5 μg/ml of blasticidin (Invitrogen #46-1120). Bright-Glo™ Luciferase assay buffer and substrate were supplied by Promega #E263B and #E264B (assay substrate and buffer respectively). 384 well clear-bottom plates were supplied by Greiner bio-one (#789163-G) and were custom bar-coded plates.

Cells were plated at 25,000 cells/well in 384-well plates in a final volume of 50 μl of media. Cells were allowed to adhere to the plates after overnight (18 hours) culture at 37° C. and 5% $CO_2$. Serially diluted experimental and positive control compounds were then dispensed to each well and incubated for 7 hours at 37° C. and 5% $CO_2$. Cells stimulated with DMSO alone also serve as negative controls. After the incubation, 30 μl of the pre-mix assay buffer and substrate buffer were added to each well according to manufacturer's instructions. The luminescence signal was read on a CLIPR machine with an integration time of 20 seconds per plate.

Dose response curves are generated for each compound and $EC_{50}$ values were determined as the concentration that gives 50% of the maximal signal. $EC_{50}$ values are obtained relative to the activity of resiquimod set to 100%. The $EC_{50}$ and % Efficacy for TLR2 stimulation by compounds of Formula (I) are also given in Table 1.

TABLE 1
| Example Number | Structure | Physical Data MS (m/z) [M + H] | Hek-TLR2 μM (% Eff)* |
|---|---|---|---|
| 1 | 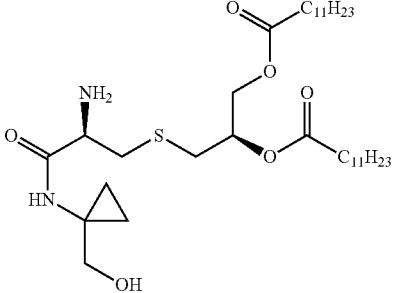 | 629.5 | 0.265 (74%) |
| 2 | 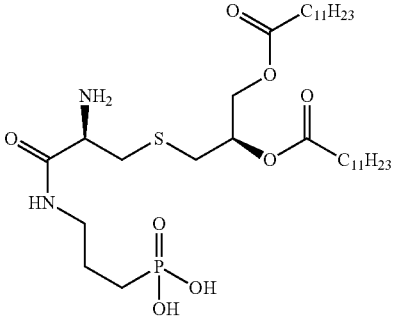 | 681.4 | 0.44 (90%) |
| 3 | 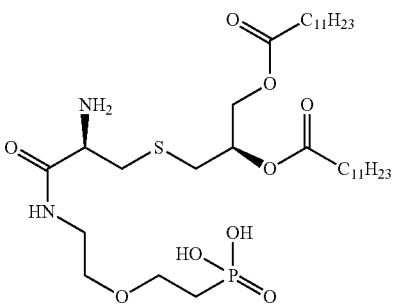 | 711.4 | 0.119 (103%) |
| 4 | 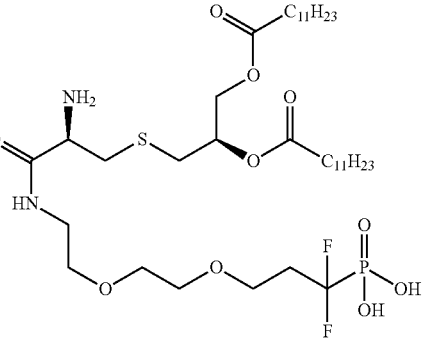 | 806.0 | 0.031 (101%) |

TABLE 1-continued
| Example Number | Structure | Physical Data MS (m/z) [M + H] | Hek-TLR2 μM (% Eff)* |
|---|---|---|---|
| 5 | 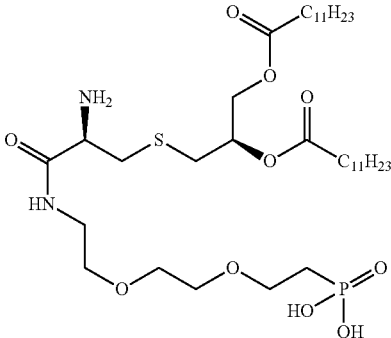 | 755.5 | 0.051 (101%) |
| 6 | 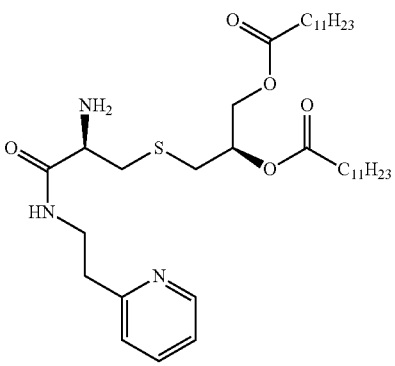 | 664.5 | 1.31 (113%) |
| 7 | 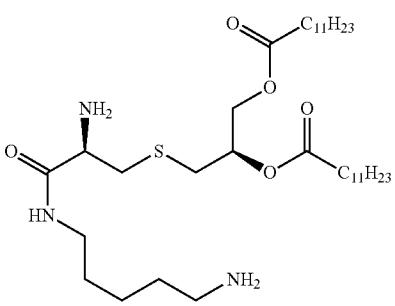 | 644.5 | 1.22 (113%) |
| 8 | 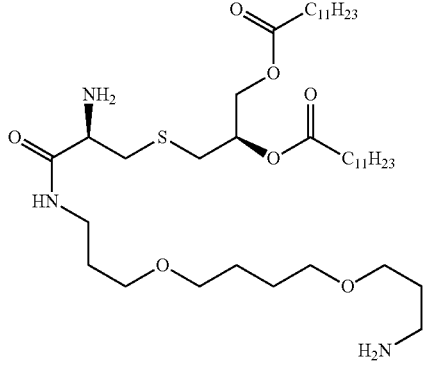 | 746.6 | 0.81 (98%) |

TABLE 1-continued

| Example Number | Structure | Physical Data MS (m/z) [M + H] | Hek-TLR2 μM (% Eff)* |
|---|---|---|---|
| 9 | 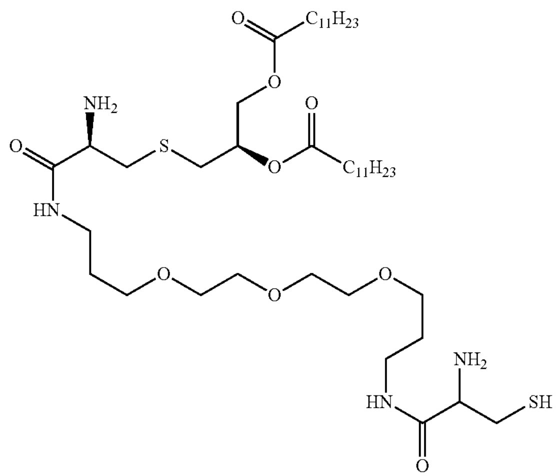 | 865.6 | 0.247 (73%) |
| 10 | 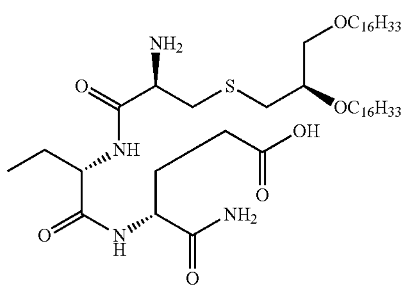 | 857.7 | 14.1 (72%) |
| 11 | 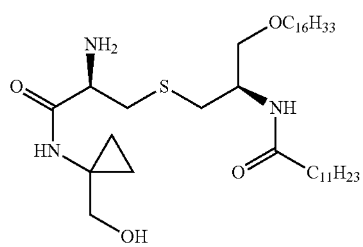 | 671.1 | >100 (3.6%) |
| 12 | 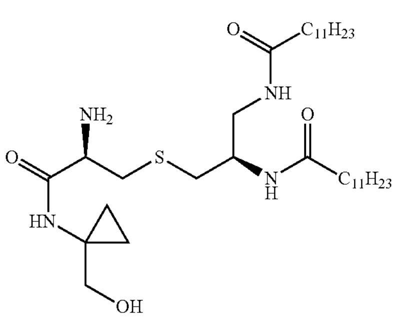 | 628.0 | >100 (3.5%) |

TABLE 1-continued
| Example Number | Structure | Physical Data MS (m/z) [M + H] | Hek-TLR2 μM (% Eff)* |
|---|---|---|---|
| 13 | 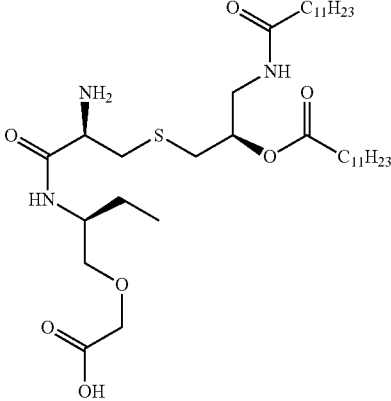 | 689.4 | 6.5 (118%) |
| 14 | 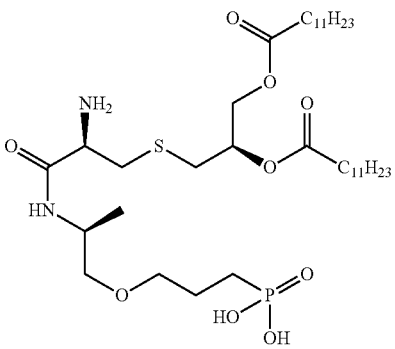 | 739.4 | 0.0192 (153%) |
| 15 | 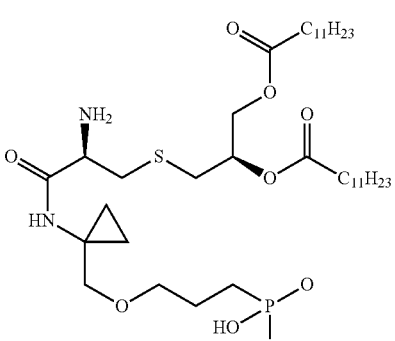 | 751.4 | 0.165 (96%) |
| 16 | 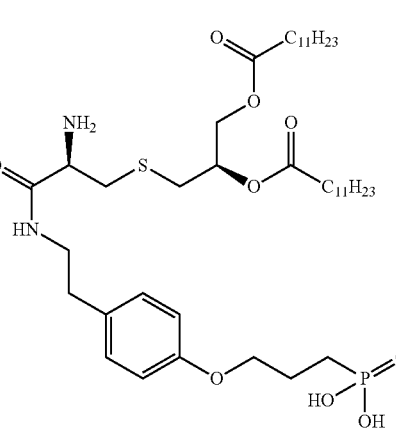 | 801.5 | 0.41 (107%) |

TABLE 1-continued

| Example Number | Structure | Physical Data MS (m/z) [M + H] | Hek-TLR2 μM (% Eff)* |
|---|---|---|---|
| 17 | 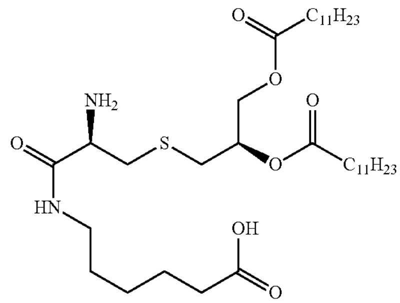 | 673.5 | 0.108 (121%) |
| 18 | 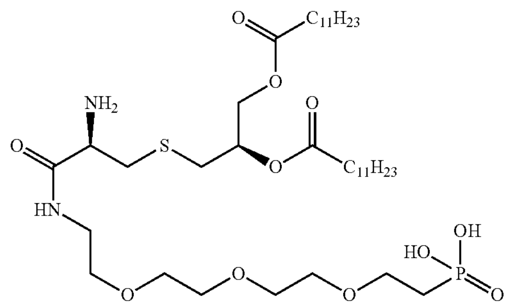 | 799.5 | 0.27 (96%) |
| 19 | 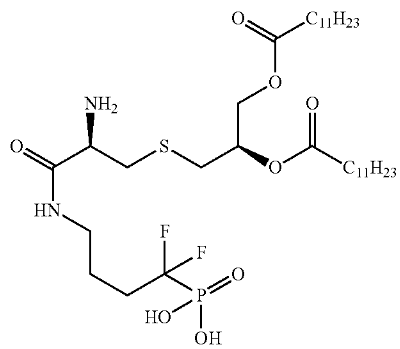 | 731.5 | 0.25 (110%) |
| 20 | 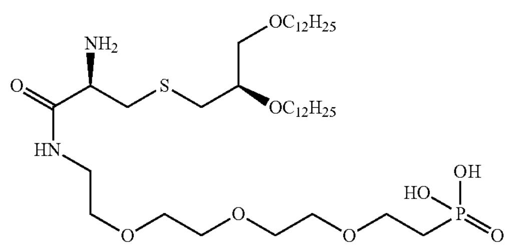 | 771.5 | 0.552 (84%) |
| 21 | 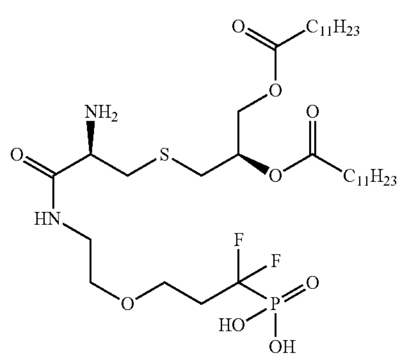 | 761.4 | 0.014 (122%) |

TABLE 1-continued

| Example Number | Structure | Physical Data MS (m/z) [M + H] | Hek-TLR2 μM (% Eff)* |
|---|---|---|---|
| 22 | 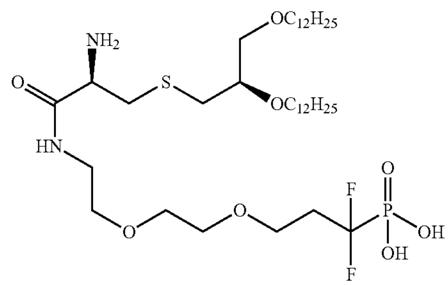 | 777.5 | 2.45 (60%) |
| 23 | 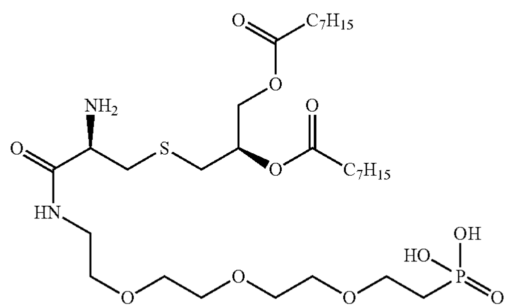 | 687.4 | 3.04 (73%) |
| 24 | 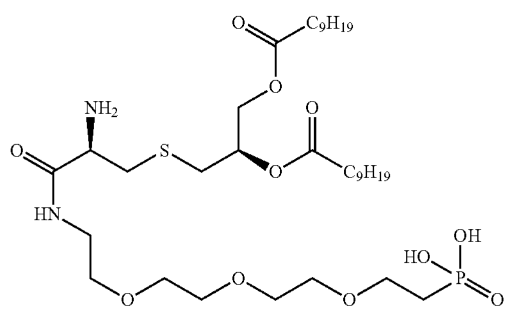 | 743.4 | 1.45 (66%) |
| 25 | 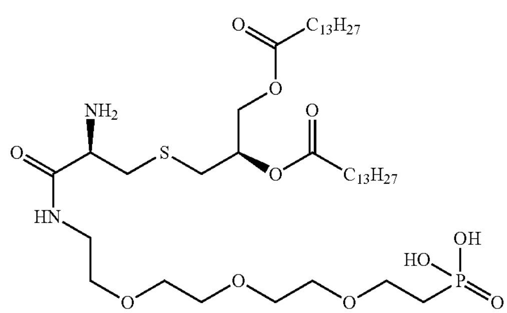 | 855.6 | 0.0063 (99%) |
| 26 | 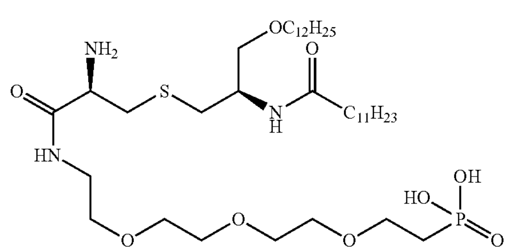 | 784.5 | 1.75 (28%) |

TABLE 1-continued

| Example Number | Structure | Physical Data MS (m/z) [M + H] | Hek-TLR2 μM (% Eff)* |
|---|---|---|---|
| 27 | 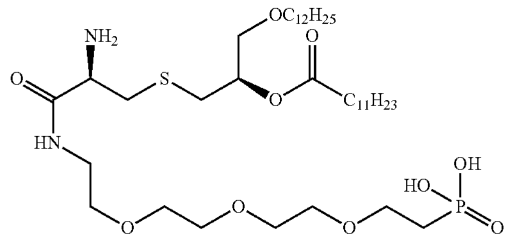 | 785.5 | 0.61 (77%) |
| 28 | 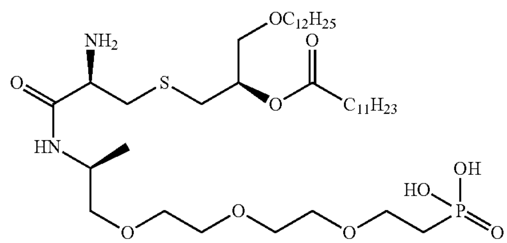 | 798.5 | 0.99 (37%) |
| 29 | 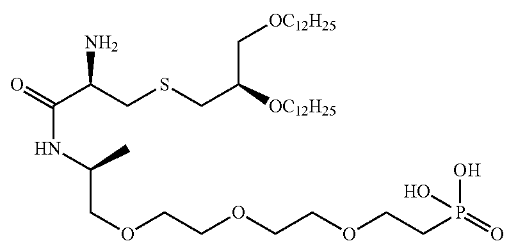 | 785.5 | 1.85 (74%) |
| 30 | 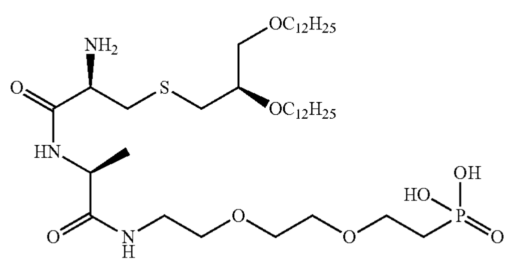 | 798.5 | 0.92 (59%) |
| 31 | 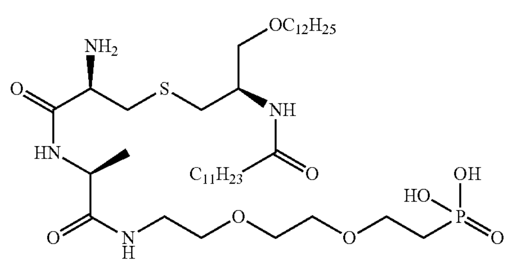 | 811.5 | 2.91 (35%) |
| 32 | 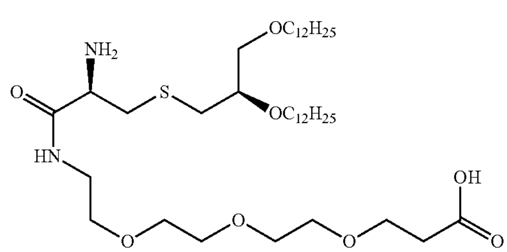 | 735.6 | 9.13 (78%) |

TABLE 1-continued

| Example Number | Structure | Physical Data MS (m/z) [M + H] | Hek-TLR2 μM (% Eff)* |
|---|---|---|---|
| 33 | 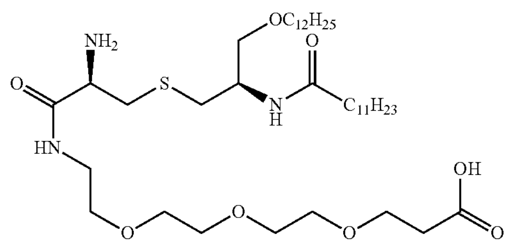 | 748.5 | 3.85 (48%) |
| 34 | 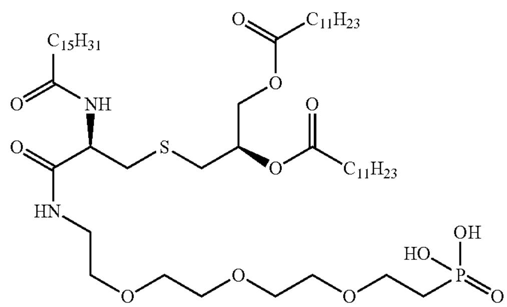 | 1037.7 | >100 (47%) |
| 35 | 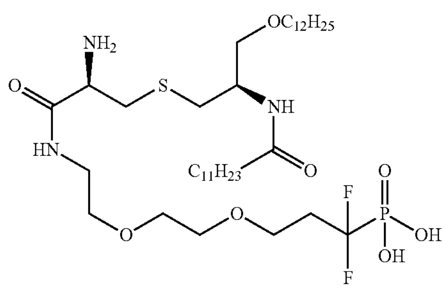 | 790.5 | 0.77 (15%) |
| 36 | 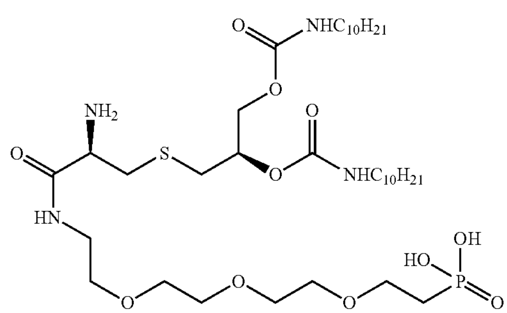 | 801.5 | 0.822 (76%) |
| 37 | 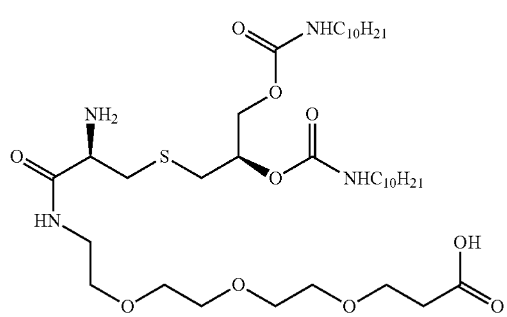 | 765.5 | 6.21 (7%) |

TABLE 1-continued

| Example Number | Structure | Physical Data MS (m/z) [M + H] | Hek-TLR2 μM (% Eff)* |
|---|---|---|---|
| 38 | 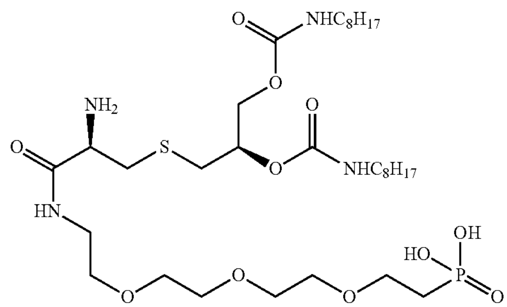 | 745.4 | 7.03 (107%) |
| 39 | 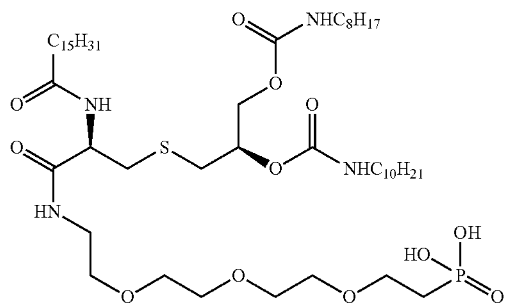 | 1039.7 | 2.64 (92%) |
| 40 | 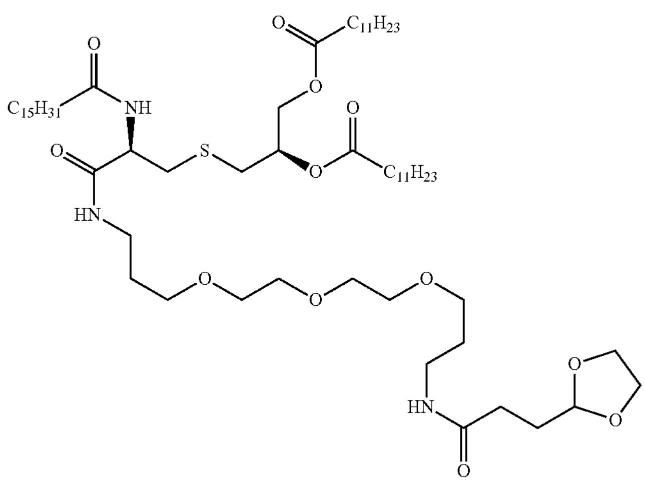 | 1128.8 | 0.096 (25%) |
| 41 | 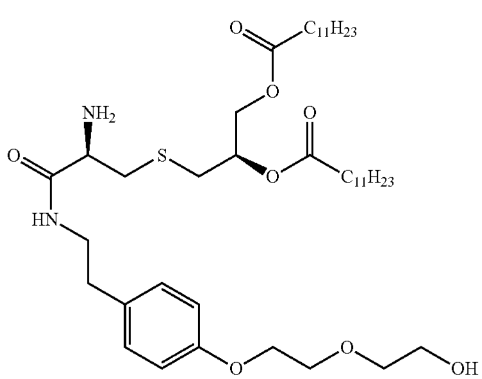 | 767.5 | 15.3 (61%) |

TABLE 1-continued

| Example Number | Structure | Physical Data MS (m/z) [M + H] | Hek-TLR2 μM (% Eff)* |
|---|---|---|---|
| 42 | 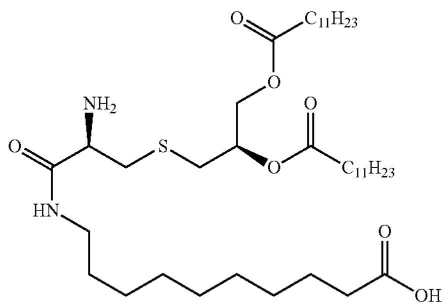 | 729.5 | 4.40 (101%) |
| 43 | 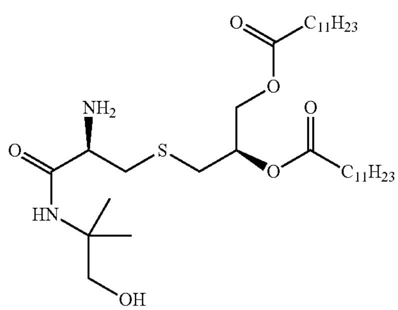 | 631.5 | 15.5 (54%) |
| 44 | 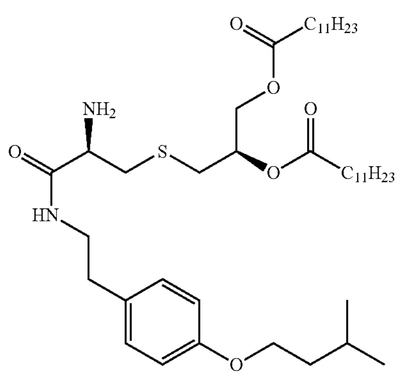 | 749.5 | 8.17 (72%) |
| 45 | 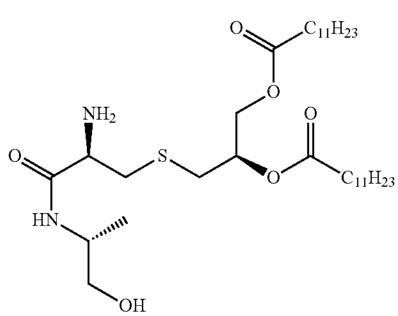 | 617.5 | 22.2 (50%) |

TABLE 1-continued

| Example Number | Structure | Physical Data MS (m/z) [M + H] | Hek-TLR2 μM (% Eff)* |
|---|---|---|---|
| 46 | 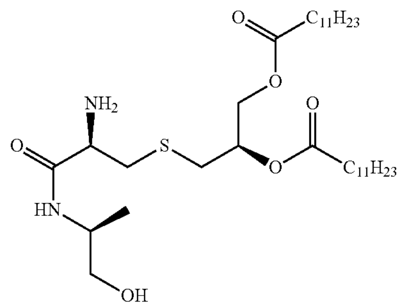 | 617.5 | 1.56 (116%) |
| 47 | 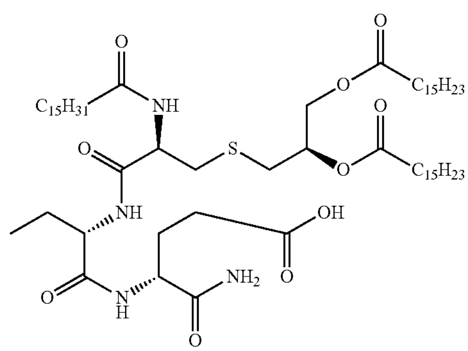 | 1107.7 | 0.565 (88%) |
| 48 | 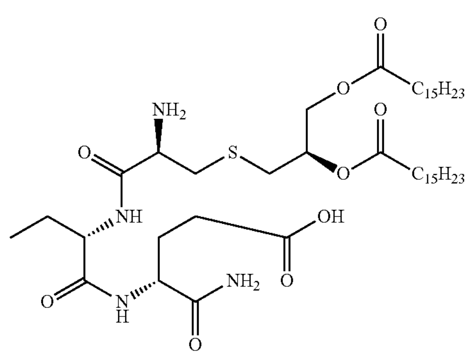 | 869.5 | 1.36 (106%) |
| 49 | 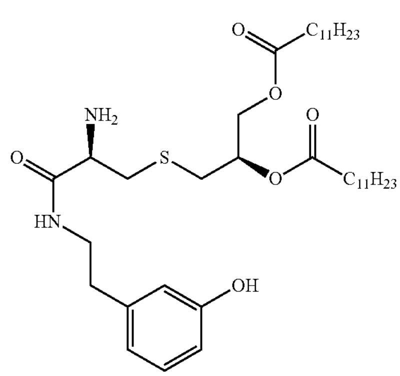 | 679.5 | >21 (51%) |

TABLE 1-continued

| Example Number | Structure | Physical Data MS (m/z) [M + H] | Hek-TLR2 μM (% Eff)* |
|---|---|---|---|
| 50 | 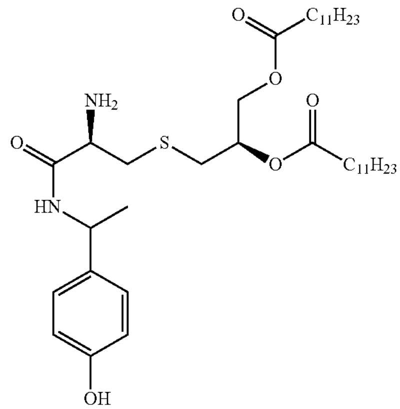 | 679.5 | 2.09 (118%) |
| 51 | 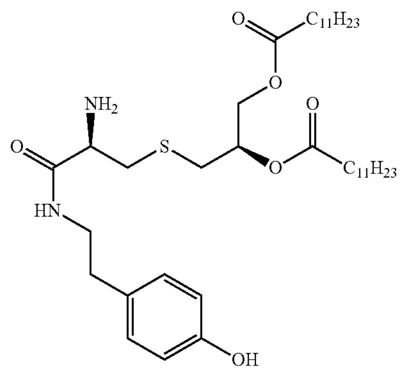 | 679.5 | 4.69 (102%) |
| 52 | 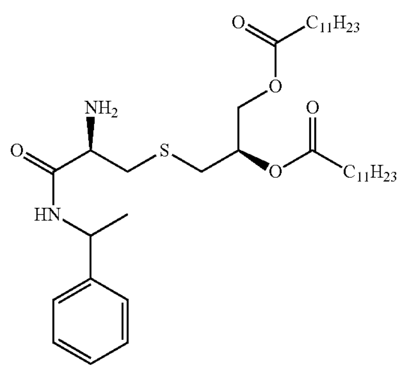 | 663.5 | 9.9 (57%) |
| 53 | 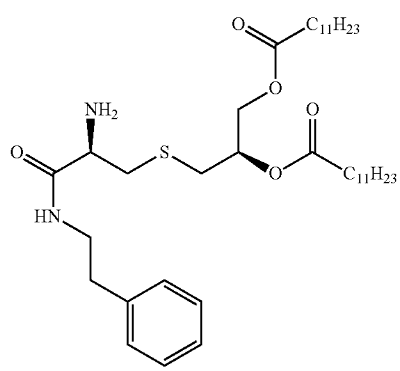 | 663.5 | 1.37 (93%) |

TABLE 1-continued

| Example Number | Structure | Physical Data MS (m/z) [M + H] | Hek-TLR2 μM (% Eff)* |
|---|---|---|---|
| 54 | 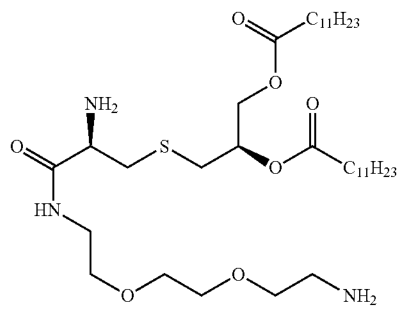 | 690.5 | 1.29 (101%) |
| 55 | 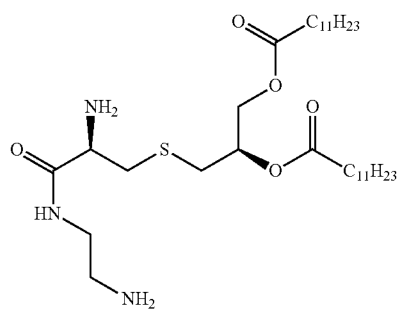 | 602.5 | 5.24 (66%) |
| 56 | 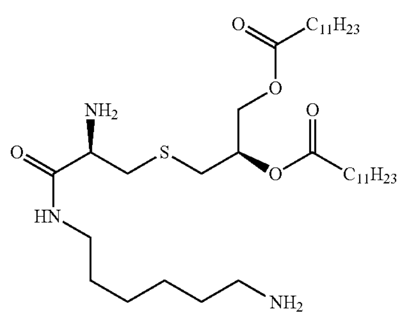 | 658.5 | 1.22 (107%) |
| 57 | 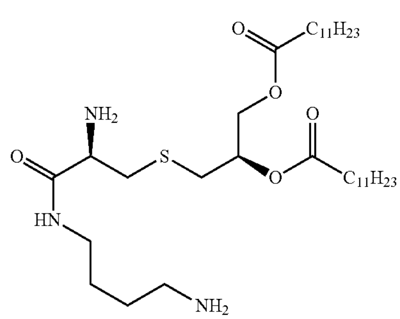 | 630.5 | 1.04 (111%) |

TABLE 1-continued

| Example Number | Structure | Physical Data MS (m/z) [M + H] | Hek-TLR2 μM (% Eff)* |
|---|---|---|---|
| 58 | 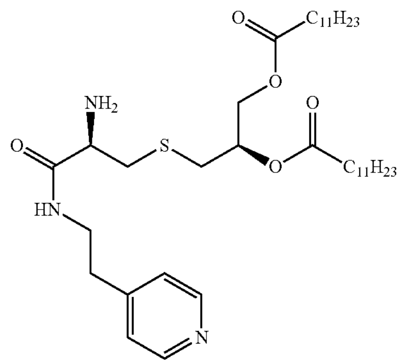 | 664.5 | 0.145 (117%) |
| 59 | 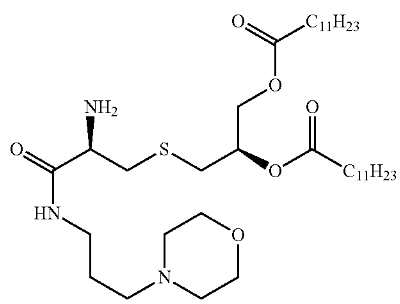 | 686.5 | 0.71 (121%) |
| 60 | 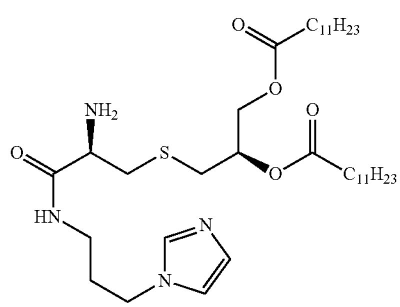 | 666.5 | 0.41 (119%) |
| 61 | 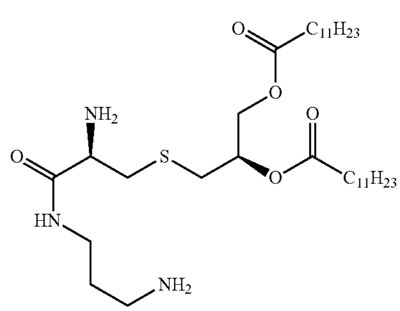 | 616.5 | 1.96 (55%) |

TABLE 1-continued

| Example Number | Structure | Physical Data MS (m/z) [M + H] | Hek-TLR2 µM (% Eff)* |
|---|---|---|---|
| 62 | 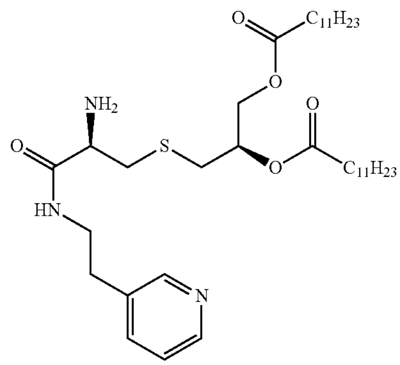 | 664.5 | 0.0044 (102%) |
| 63 | 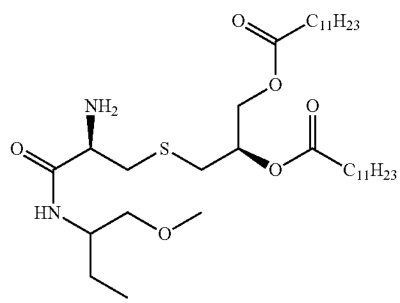 | 645.5 | 0.0718 (96%) |
| 64 | 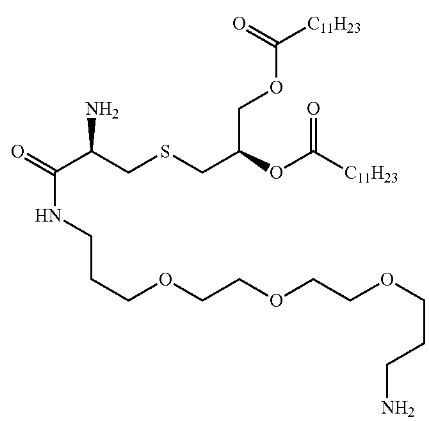 | 762.6 | 0.498 (124%) |
| 65 | 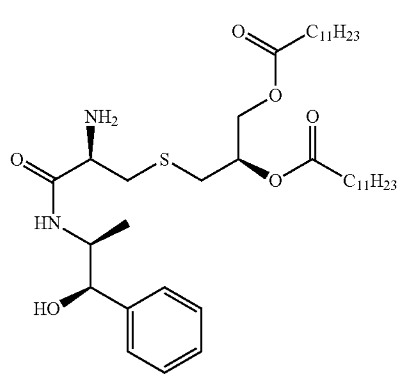 | 692.5 | 0.04 (91%) |

TABLE 1-continued

| Example Number | Structure | Physical Data MS (m/z) [M + H] | Hek-TLR2 μM (% Eff)* |
|---|---|---|---|
| 66 | 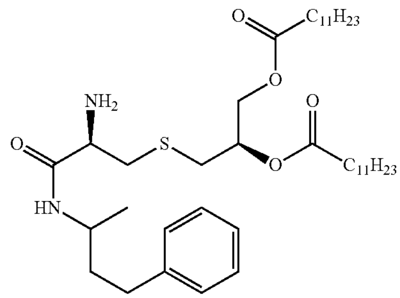 | 691.5 | 0.16 (93%) |
| 67 | 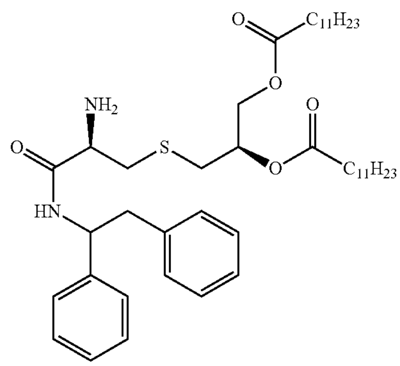 | 739.5 | 0.068 (64%) |
| 68 | 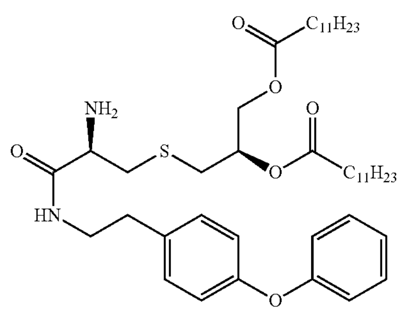 | 755.5 | 4.08 (77%) |
| 69 | 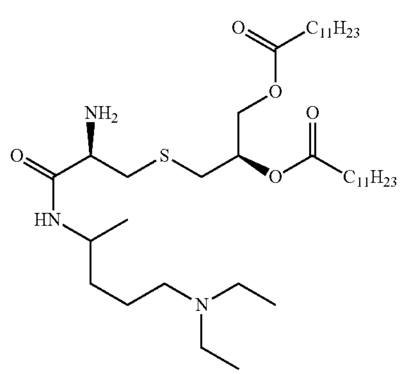 | 700.6 | 0.257 (118%) |

TABLE 1-continued

| Example Number | Structure | Physical Data MS (m/z) [M + H] | Hek-TLR2 μM (% Eff)* |
|---|---|---|---|
| 70 | 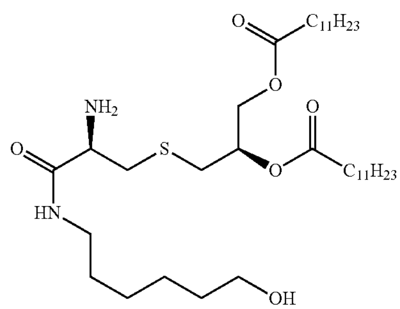 | 659.5 | 0.033 (92%) |
| 71 | 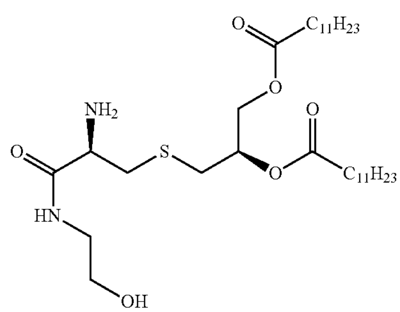 | 603.4 | 0.024 (95%) |
| 72 | 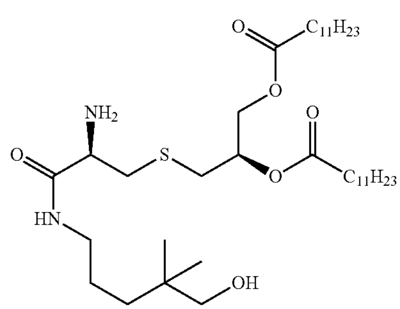 | 673.5 | 30.7 (49%) |
| 73 | 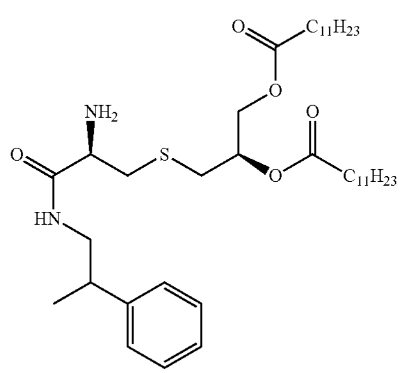 | 677.5 | 0.81 (115%) |

TABLE 1-continued

| Example Number | Structure | Physical Data MS (m/z) [M + H] | Hek-TLR2 μM (% Eff)* |
|---|---|---|---|
| 74 | 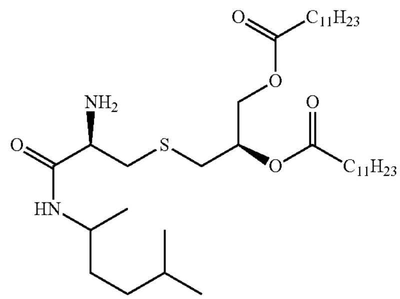 | 657.5 | 0.19 (105%) |
| 75 | 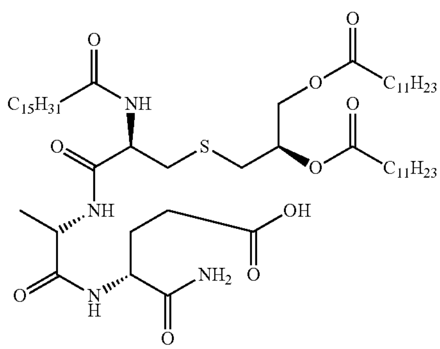 | 997.7 | 0.96 (58%) |
| 76 | 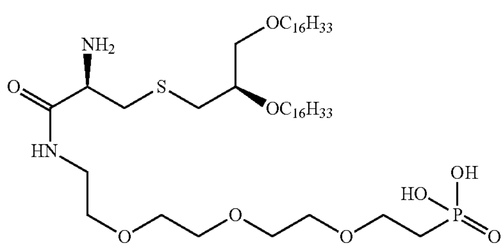 | 883.7 | 3.45 (109%) |
| 77 | 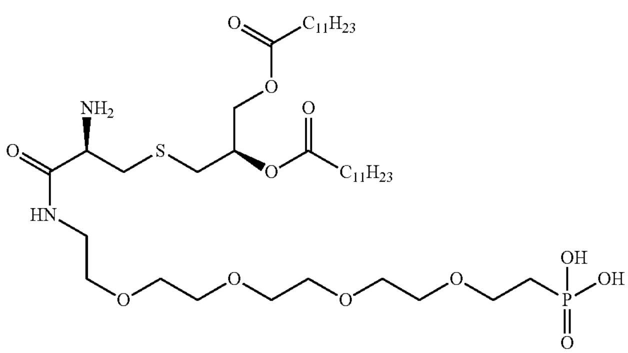 | 843.5 | 0.038 (100%) |
| 78 | 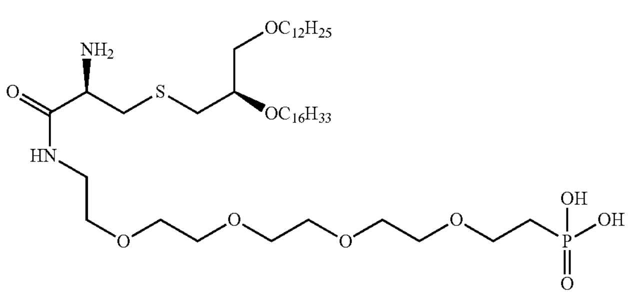 | 815.6 | 1.43 (35%) |

TABLE 1-continued
| Example Number | Structure | Physical Data MS (m/z) [M + H] | Hek-TLR2 μM (% Eff)* |
|---|---|---|---|
| 79 | 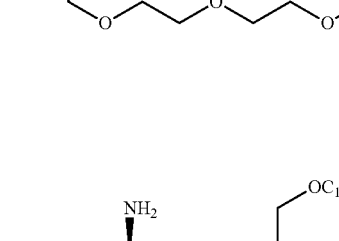 | 828.6 | 1.86 (20%) |
| 80 | 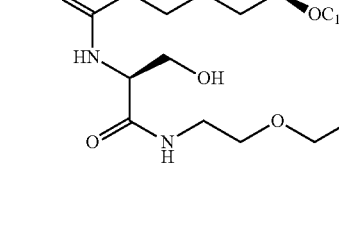 | 814.5 | 1.91 (52%) |
| 81 | 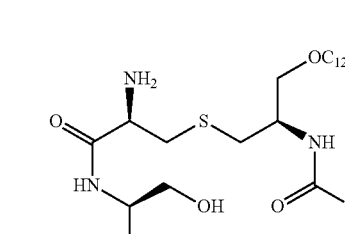 | 827.5 | 1.97 (30%) |
| 82 | 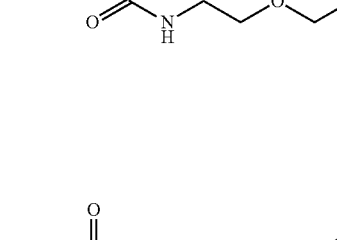 | 844.1 | 0.83 (84%) |

TABLE 1-continued

| Example Number | Structure | Physical Data MS (m/z) [M + H] | Hek-TLR2 μM (% Eff)* |
|---|---|---|---|
| 83 | 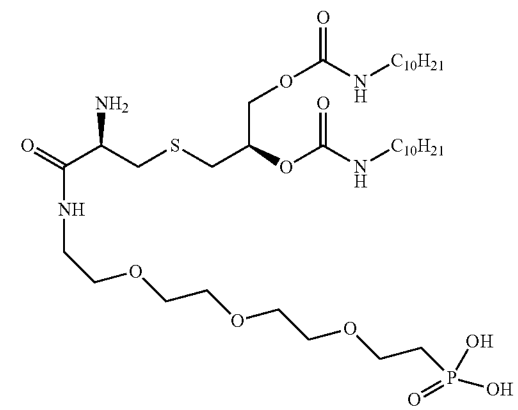 | 802.0 | 0.82 (76%) |
| 84 | 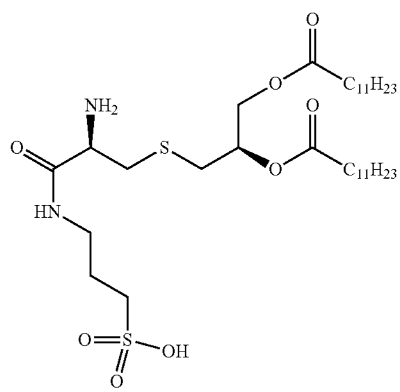 | 682.0 | 5.56 (72%) |
| 85 | 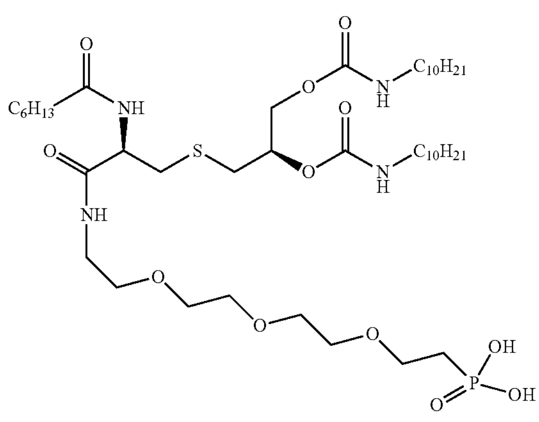 | 914.2 | 2.17 (71%) |
| 86 | 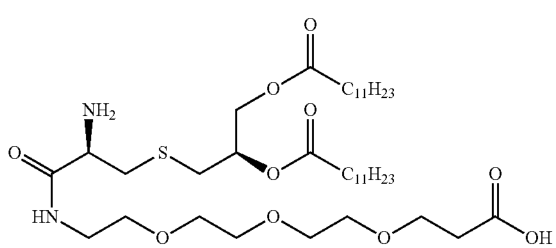 | 763.5 | 0.90 (84%) |

TABLE 1-continued
| Example Number | Structure | Physical Data MS (m/z) [M + H] | Hek-TLR2 μM (% Eff)* |
|---|---|---|---|
| 87 | 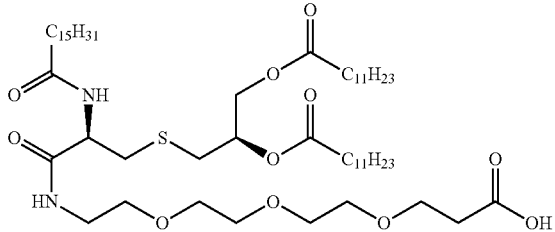 | 1001.7 | 38 (30%) |
| 88 | 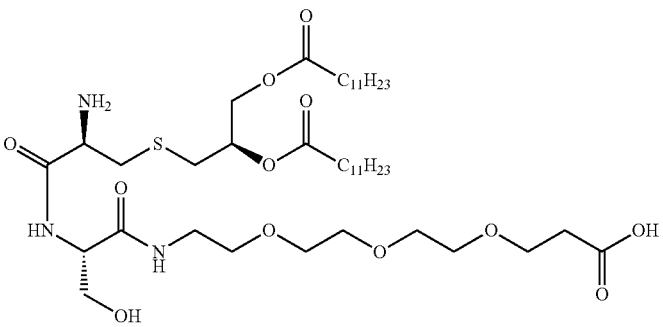 | 850.5 | 0.0092 (145%) |
| 89 | 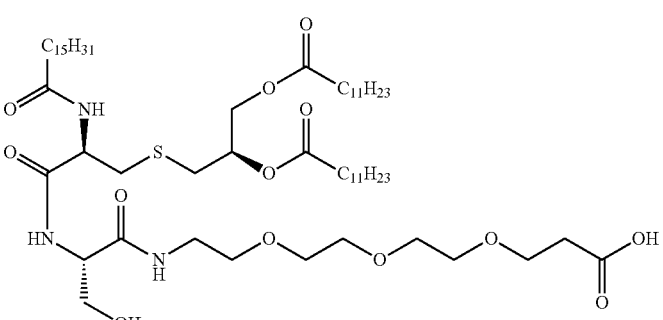 | 1088.8 | 4.94 (104%) |
| 90 | 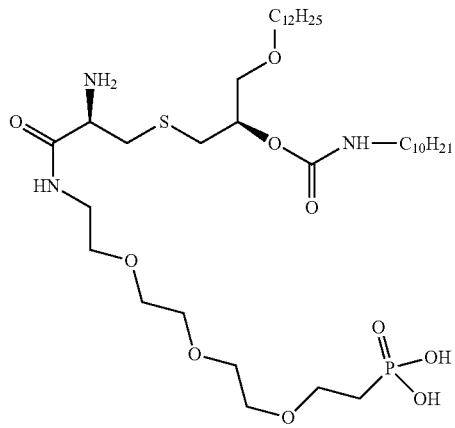 | 787.1 | >100 (47%) |

TABLE 1-continued

| Example Number | Structure | Physical Data MS (m/z) [M + H] | Hek-TLR2 μM (% Eff)* |
|---|---|---|---|
| 91 | 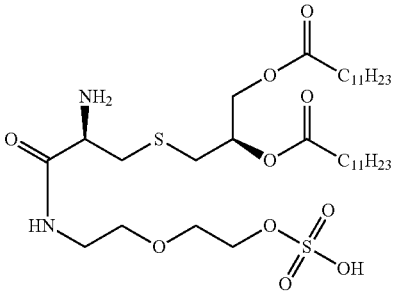 | 727.5 | 0.061 (120%) |
| 92 | 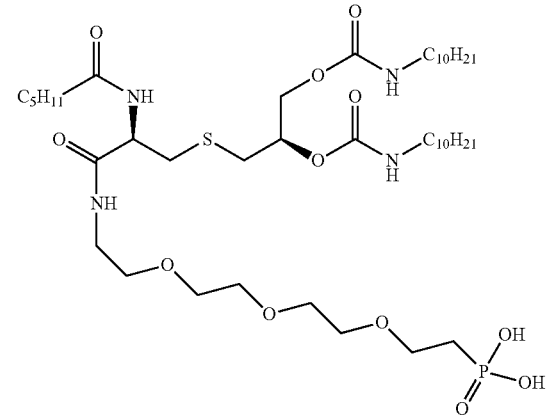 | 900.2 | 0.28 (99%) |

*% Eff relative to Pam$_3$CSK$_4$.

Evaluation of % Alum Binding

The binding of certain compounds of Formula (I) to aluminum-containing adjuvants at pH 6.5 was evaluated using HPLC-MS/MS to monitor the presence of the compound of Formula (I) in the supernatant.

Evaluation of Binding at pH 6.5

To a mixture of compound (4 mg/mL) in Endotox free water was added 1 M NaOH (2.1 eq) to achieve a clear solution. A mixture of the resulting solution (0.5 mL), Endotox free water (0.86 mL), 100 mM Histidine buffer (0.2 mL) and aluminum hydroxide adjuvant (13.78 mg/mL, 0.44 mL) was stirred at 25° C. overnight to result in a 1 mg/mL formulation. An additional 1 mg/mL formulation was prepared as control in 10 mM Histidine buffer without aluminum hydroxide.

Three 50 uL aliquots of each formulation (in Histidine buffer with and without aluminum hydroxide) were centrifuged at 14,000 rpm for 10 minutes at 4° C. The supernatant was diluted, treated with an internal standard and analyzed by HPLC-MS/MS using a ballistic gradient (from 50% CH$_3$CN-1.0% NH$_4$OH to 95% CH$_3$CN-1.0% NH$_4$OH in 1.5 minutes) on a C8 (50 cm×2.1 mm) Waters XBridge column at ambient temperature. The supernatant concentration was determined for each formulation. The fraction in the aluminum hydroxide formulation bound to alum was calculated as follows:

$$\text{Alum binding \%} = 100\% - \frac{\text{(concentration in alum formulation supernatant)}}{\text{(concentration in histidine buffer supernatant)}}$$

The % of alum binding for certain representative examples of the phosphonate compounds provided herein are given in Table 2.

TABLE 2

| Example Number | Structure | Alum Binding % |
|---|---|---|
| 3 | 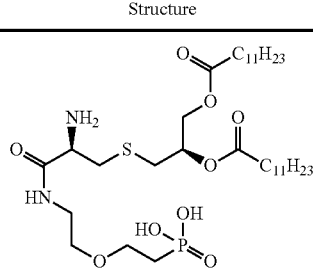 | >80% |

TABLE 2-continued

| Example Number | Structure | Alum Binding % |
|---|---|---|
| 5 | 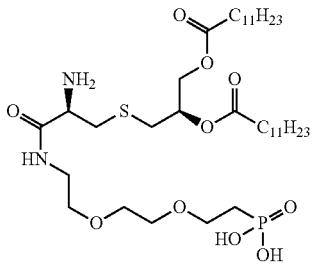 | >80% |
| 15 | 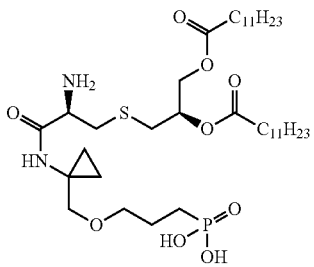 | >80% |
| 18 | 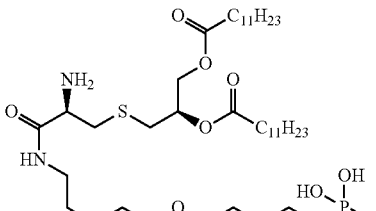 | >80% |
| 19 | 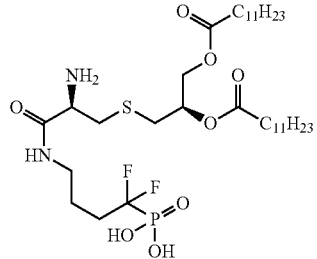 | >80% |
| 20 | 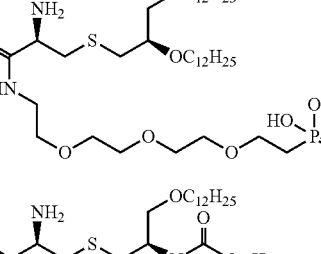 | >80% |
| 26 | 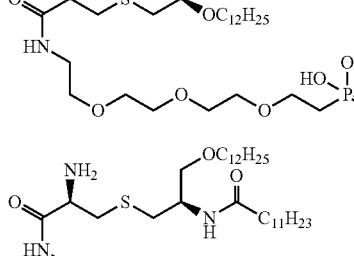 | >80% |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula (I), or pharmaceutically acceptable salt thereof:

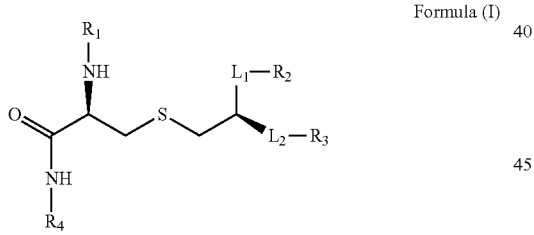

Formula (I)

wherein:
$R^1$ is H, —C(O)—$C_7$-$C_{18}$alkyl or —C(O)—$C_1$-$C_6$alkyl;
$R^2$ is $C_7$-$C_{18}$alkyl;
$R^3$ is $C_7$-$C_{18}$alkyl;
$L_1$ is —$CH_2$OC(O)—;
$L_2$ is —OC(O)—;
$R^4$ is -$L_3R^5$ or -$L_4R^5$;
$R^5$ is —P(O)(OR$^7$)$_2$, —NR$^7$C(O)L$_3$R$^8$, —NR$^7$C(O)L$_4$R$^8$, —OL$_3$R$^6$, —C(O)NR$^7$L$_3$R$^8$, —C(O)NR$^7$L$_4$R$^8$, —S(O)$_2$OR$^7$, —OS(O)$_2$OR$^7$, $C_1$-$C_6$alkyl, a $C_6$aryl, a $C_{10}$aryl, a $C_{14}$aryl, 5 to 14 ring membered heteroaryl containing 1 to 3 heteroatoms selected from O, S and N, $C_3$-$C_8$cycloalkyl or a 5 to 6 ring membered heterocycloalkyl containing 1 to 3 heteroatoms selected from O, S and N, wherein the aryl, heteroaryl, cycloalkyl and heterocycloalkyl of R$^5$ are each unsubstituted or the aryl, heteroaryl, cycloalkyl and heterocycloalkyl of R$^5$ are each substituted with 1 to 3 substituents independently selected from —OR$^9$, —OL$_3$R$^6$, —OL$_4$R$^6$, —OR$^7$, and —C(O)OR$^7$;
$L_3$ is a $C_1$-$C_{10}$alkylene, wherein the $C_1$-$C_{10}$alkylene of $L_3$ is substituted with 1 to 4 R$^6$ groups, or the $C_1$-$C_{10}$alkylene of $L_3$ is substituted with 2 $C_1$-$C_6$alkyl groups on the same carbon atom which together, along with the carbon atom they are attached to, form a $C_3$-$C_8$cycloakyl;
$L_4$ is —((CR$^7$R$^7$)$_p$O)$_q$(CR$^{10}$R$^{10}$)$_p$— or —(CR$^{11}$R$^{11}$)((CR$^7$R$^7$)$_p$O)$_q$(CR$^{10}$R$^{10}$)$_p$—, wherein each R$^{11}$ is a $C_1$-$C_6$alkyl groups which together, along with the carbon atom they are attached to, form a $C_3$-$C_8$cycloakyl;
each R$^6$ is independently selected from halo, —OR$^7$, —N(R$^7$)$_2$, —C(O)N(R$^7$)$_2$, —P(O)(OR$^7$)$_2$, a $C_6$aryl, a $C_{10}$aryl and a $C_{14}$aryl;
each R$^7$ is independently selected from H and $C_1$-$C_6$alkyl;
R$^8$ is —SR$^7$, —C(O)OH, —P(O)(OR$^7$)$_2$, or a 5 to 6 ring membered heterocycloalkyl containing 1 to 3 heteroatoms selected from O and N;
R$^9$ is phenyl;
each R$^{19}$ is independently selected from H and halo;
each p is independently selected from 1, 2, 3, 4, 5 and 6, and
q is 1, 2, 3 or 4.

2. The compound of claim 1, or pharmaceutically acceptable salt thereof, wherein R$^1$ is H.

3. The compound of claim 1, or pharmaceutically acceptable salt thereof, wherein R$^1$ is —C(O)—$C_{15}$alkyl.

4. The compound of claim 1, or pharmaceutically acceptable salt thereof, wherein:
R$^2$ is —$C_{11}$alkyl and R$^3$ is —$C_{11}$alkyl;
or R$^2$ is —$C_{10}$alkyl and R$^3$ is —$C_{10}$alkyl;

or R² is —C₁₀alkyl and R³ is —C₁₁alkyl;
or R² is —C₁₂alkyl and R³ is —C₁₂alkyl;
or R² is —C₇alkyl and R³ is —C₇alkyl;
or R² is —C₉alkyl and R³ is —C₉alkyl;
or R² is —C₈alkyl and R³ is —C₈alkyl;
or R² is —C₁₃alkyl and R³ is —C₁₃alkyl;
or R² is —C₁₂alkyl and R³ is —C₁₁alkyl;
or R² is —C₁₀alkyl and R³ is —C₁₀alkyl;
or R² is —C₁₅alkyl and R³ is —C₁₅alkyl.

5. The compound of claim 1, or pharmaceutically acceptable salt thereof, wherein R² is —C₁₁alkyl and R³ is —C₁₁alkyl.

6. The compound of claim 1, or pharmaceutically acceptable salt thereof, wherein R⁵ is —P(O)(OH)₂—S(O)₂OH, —OS(O)₂OH, —NHC(O)L₃R⁸, —OL₃R⁶, —C(O)NHL₄R⁸ or —C(O)NHL₃R⁸.

7. The compound of claim 6, or pharmaceutically acceptable salt thereof, wherein R⁵ is —P(O)(OH)₂—NHC(O)L₃R⁸, —S(O)₂OH, —OS(O)₂OH or —OL₃R⁶.

8. The compound of claim 1, wherein R⁵ is C₁-C₆alkyl, phenyl, pyridinyl, imidazolyl or morpholinyl, each of which is unsubstituted or substituted with 1 to 3 substituents independently selected from —OR⁹, —OL₃R⁶, —OL₄R⁶ and —OH.

9. The compound of claim 1, wherein R⁸ is —SH, —C(O)OH, —P(O)(OH)₂, or a 5-6 membered heterocycloalkyl containing 1 to 2 heteroatoms selected from O.

10. The compound of claim 1, wherein L₃ is a C₁-C₁₀alkylene substituted with 1 to 4 R⁶ groups.

11. The compound of claim 1, wherein:
L₄ is —((CR⁷R⁷)ₚO)ᵩ(CR¹⁰R¹⁰)ₚ—, each R¹⁰ is independently selected from H and F;
each p is independently selected from 2, 3, and 4, and
q is 1, 2, 3 or 4.

12. The compound of claim 1, wherein each R⁶ is independently selected from —OH, —F, —NH₂, —C(O)NH₂, —P(O)(OH)₂ and phenyl.

13. The compound of claim 1, wherein each R⁷ is independently selected from H, methyl and ethyl.

14. The compound of claim 1, wherein the compound is selected from:
(R)-3-(((R)-2-amino-3-((1-(hydroxymethyl)cyclopropyl)amino)-3-oxopropyl)thio)propane-1,2-diyl didodecanoate;
(3-((R)-2-amino-3-(((R)-2,3-bis(dodecanoyloxy)propyl)thio)propanamido)propyl)phosphonic acid;
((8R,12R)-8-amino-12-(dodecanoyloxy)-7,15-dioxo-3,14-dioxa-10-thia-6-azahexacosyl)phosphonic acid;
((12R,16R)-12-amino-16-(dodecanoyloxy)-1,1-difluoro-11,19-dioxo-4,7,18-trioxa-14-thia-10-azatriacontyl)phosphonic acid;
((11R,15R)-11-amino-15-(dodecanoyloxy)-10,18-dioxo-3,6,17-trioxa-13-thia-9-azanonacosyl)phosphonic acid;
(R)-3-(((R)-2-amino-3-oxo-3-((2-(pyridin-2-yl)ethyl)amino)propyl)thio)propane-1,2-diyl didodecanoate;
(20R,24R)-2,20-diamino-1-mercapto-3,19-dioxo-8,11,14-trioxa-22-thia-4,18-diazapentacosane-24,25-diyl didodecanoate;
((6S,9R,13R)-9-amino-13-(dodecanoyloxy)-6-methyl-8,16-dioxo-4,15-dioxa-11-thia-7-azaheptacosyl)phosphonic acid;
(3-((1-((R)-2-amino-3-(((R)-2,3-bis(dodecanoyloxy)propyl)thio)propanamido)cyclopropyl)methoxy)propyl)phosphonic acid;
(3-(4-(2-((R)-2-amino-3-(((R)-2,3-bis(dodecanoyloxy)propyl)thio)propanamido)ethyl)phenoxy)propyl)phosphonic acid;
((14R,18R)-14-amino-18-(dodecanoyloxy)-13,21-dioxo-3,6,9,20-tetraoxa-16-thia-12-azadotriacontyl)phosphonic acid;
(4-((R)-2-amino-3-(((R)-2,3-bis(dodecanoyloxy)propyl)thio)propanamido)-1,1-difluorobutyl)phosphonic acid;
((9R,13R)-9-amino-13-(dodecanoyloxy)-1,1-difluoro-8,16-dioxo-4,15-dioxa-11-thia-7-azaheptacosyl)phosphonic acid;
((14R,18R)-14-amino-18-(octanoyloxy)-13,21-dioxo-3,6,9,20-tetraoxa-16-thia-12-azaoctacosyl)phosphonic acid;
((14R,18R)-14-amino-18-(decanoyloxy)-13,21-dioxo-3,6,9,20-tetraoxa-16-thia-12-azatriacontyl)phosphonic acid;
((14R,18R)-14-amino-13,21-dioxo-18-(tetradecanoyloxy)-3,6,9,20-tetraoxa-16-thia-12-azatetratriacontyl)phosphonic acid;
((14R,18R)-18-(dodecanoyloxy)-13,21-dioxo-14-palmitamido-3,6,9,20-tetraoxa-16-thia-12-azadotriacontyl)phosphonic acid;
(20R,24R)-1-(1,3-dioxolan-2-yl)-3,19-dioxo-20-palmitamido-8,11,14-trioxa-22-thia-4,18-diazapentacosane-24,25-diyl didodecanoate;
(R)-3-(((R)-2-amino-3-((4-(2-(2-hydroxyethoxy)ethoxy)phenethyl)amino)-3-oxopropyl)thio)propane-1,2-diyl didodecanoate;
(R)-3-(((R)-2-amino-3-((4-(isopentyloxy)phenethyl)amino)-3-oxopropyl)thio)propane-1,2-diyl didodecanoate;
(R)-3-(((R)-2-amino-3-((3-hydroxyphenethyl)amino)-3-oxopropyl)thio)propane-1,2-diyl didodecanoate;
(R)-3-(((R)-2-amino-3-((4-hydroxyphenethyl)amino)-3-oxopropyl)thio)propane-1,2-diyl didodecanoate;
(R)-3-(((R)-2-amino-3-oxo-3-(phenethylamino)propyl)thio)propane-1,2-diyl didodecanoate;
(R)-3-(((R)-2-amino-3-oxo-3-((2-(pyridin-4-yl)ethyl)amino)propyl)thio)propane-1,2-diyl didodecanoate;
(R)-3-(((R)-2-amino-3-((3-morpholinopropyl)amino)-3-oxopropyl)thio)propane-1,2-diyl didodecanoate;
(R)-3-(((R)-3-((3-(1H-imidazol-1-yl)propyl)amino)-2-amino-3-oxopropyl)thio)propane-1,2-diyl didodecanoate;
(R)-3-(((R)-2-amino-3-oxo-3-((2-(pyridin-3-yl)ethyl)amino)propyl)thio)propane-1,2-diyl didodecanoate;
(2R)-3-(((2R)-2-amino-3-((1,2-diphenylethyl)amino)-3-oxopropyl)thio)propane-1,2-diyl didodecanoate;
(R)-3-(((R)-2-amino-3-oxo-3-((4-phenoxyphenethyl)amino)propyl)thio)propane-1,2-diyl didodecanoate;
((14R,18R)-14-amino-18-(hexadecyloxy)-13-oxo-3,6,9,20-tetraoxa-16-thia-12-azahexatriacontyl)phosphonic acid;
((17R,21R)-17-amino-21-(dodecanoyloxy)-16,24-dioxo-3,6,9,12,23-pentaoxa-19-thia-15-azapentatriacontyl)phosphonic acid;
3-((R)-2-amino-3-(((R)-2,3-bis(dodecanoyloxy)propyl)thio)propanamido)propane-1-sulfonic acid; and
(R)-3-(((R)-2-amino-3-oxo-3-((2-(2-(sulfooxy)ethoxy)ethyl)amino)propyl)thio)propane-1,2-diyldidodecanoate.

15. A compound selected from:
(R)-3-(((R)-2-amino-3-((5-aminopentyl)amino)-3-oxopropyl)thio)propane-1,2-diyl didodecanoate;
(2R,6R)-6,20-diamino-7-oxo-12,17-dioxa-4-thia-8-azaicosane-1,2-diyl didodecanoate;
(5S,8R,12R)-8-amino-12-(dodecanoyloxy)-5-ethyl-7,15-dioxo-3,14-dioxa-10-thia-6-azahexacosan-1-oic acid;

6-(((R)-2-amino-3-(((R)-2,3-bis(dodecanoyloxy)propyl)thio)propanamido)hexanoic acid;
10-((R)-2-amino-3-(((R)-2,3-bis(dodecanoyloxy)propyl)thio)propanamido)decanoic acid;
(R)-3-(((R)-2-amino-3-((1-hydroxy-2-methylpropan-2-yl)amino)-3-oxopropyl)thio)propane-1,2-diyl didodecanoate;
(R)-3-(((R)-2-amino-3-(((R)-1-hydroxypropan-2-yl)amino)-3-oxopropyl)thio)propane-1,2-diyl didodecanoate;
(R)-3-(((R)-2-amino-3-(((S)-1-hydroxypropan-2-yl)amino)-3-oxopropyl)thio)propane-1,2-diyl didodecanoate;
(4R,7S,10R,14R)-4-carbamoyl-7-ethyl-6,9,17-trioxo-10-palmitamido-14-(palmitoyloxy)-16-oxa-12-thia-5,8-diazadotriacontan-1-oic acid;
(4R,7S,10R,14R)-10-amino-4-carbamoyl-7-ethyl-6,9,17-trioxo-14-(palmitoyloxy)-16-oxa-12-thia-5,8-diazadotriacontan-1-oic acid;
(2R)-3-(((2R)-2-amino-3-((1-(4-hydroxyphenyl)ethyl)amino)-3-oxopropyl)thio)propane-1,2-diyl didodecanoate;
(2R)-3-(((2R)-2-amino-3-oxo-3-((1-phenylethyl)amino)propyl)thio)propane-1,2-diyl didodecanoate;
(11R,15R)-1,11-diamino-10-oxo-3,6-dioxa-13-thia-9-azahexadecane-15,16-diyl didodecanoate;
(R)-3-4(R)-2-amino-3-((2-aminoethyl)amino)-3-oxopropyl)propane-1,2-diyl didodecanoate;
(R)-3-(((R)-2-amino-3-((6-aminohexyl)amino)-3-oxopropyl)thio)propane-1,2-diyl didodecanoate;
(R)-3-(((R)-2-amino-3-((4-aminobutyl)amino)-3-oxopropyl)thio)propane-1,2-diyl didodecanoate;
(R)-3-(((R)-2-amino-3-((3-aminopropyl)amino)-3-oxopropyl)thio)propane-1,2-diyl didodecanoate;
(2R)-3-(((2R)-2-amino-3-((1-methoxybutan-2-yl)amino)-3-oxopropyl)thio)propane-1,2-diyldidodecanoate;
(16R,20R)-1,16-diamino-15-oxo-4,7,10-trioxa-18-thia-14-azahenicosane-20,21-diyl didodecanoate;
(R)-3-(((R)-2-amino-3-(((1R,2S)-1-hydroxy-1-phenylpropan-2-yl)amino)-3-oxopropyl)thio)propane-1,2-diyl didodecanoate;
(2R)-3-(((2R)-2-amino-3-oxo-3-((4-phenylbutan-2-yl)amino)propyl)thio)propane-1,2-diyl didodecanoate;
(2R)-3-(((2R)-2-amino-3-((5-(diethylamino)pentan-2-yl)amino)-3-oxopropyl)thio)propane-1,2-diyl didodecanoate;
(R)-3-(((R)-2-amino-3-((6-hydroxyhexyl)amino)-3-oxopropyl)thio)propane-1,2-diyl didodecanoate;
(R)-3-(((R)-2-amino-3-((2-hydroxyethyl)amino)-3-oxopropyl)thio)propane-1,2-diyl didodecanoate;
(R)-3-(((R)-2-amino-3-((5-hydroxy-4,4-dimethylpentyl)amino)-3-oxopropyl)thio)propane-1,2-diyl didodecanoate;
(2R)-3-(((2R)-2-amino-3-oxo-3-((2-phenylpropyl)amino)propyl)thio)propane-1,2-diyl didodecanoate;
(2R)-3-(((2R)-2-amino-3-((5-methylhexan-2-yl)amino)-3-oxopropyl)thio)propane-1,2-diyl didodecanoate;
(4R,7S,10R,14R)-4-carbamoyl-14-(dodecanoyloxy)-7-methyl-6,9,17-trioxo-10-palmitamido-16-oxa-12-thia-5,8-diazaoctacosan-1-oic acid;
(15R,19R)-15-amino-19-(dodecanoyloxy)-14,22-dioxo-4,7,10,21-tetraoxa-17-thia-13-azatritriacontan-1-oic acid;
(15R,19R)-19-(dodecanoyloxy)-14,22-dioxo-15-palmitamido-4,7,10,21-tetraoxa-17-thia-13-azatritriacontan-1-oic acid;
(15S,18R,22R)-18-amino-22-(dodecanoyloxy)-15-(hydroxymethyl)-14,17,25-trioxo-4,7,10,24-tetraoxa-20-thia-13,16-diazahexatriacontan-1-oic acid;
(15S,18R,22R)-22-(dodecanoyloxy)-15-(hydroxymethyl)-14,17,25-trioxo-18-palmitamido-4,7,10,24-tetraoxa-20-thia-13,16-diazahexatriacontan-1-oic acid;
((17R,21R)-17-amino-21-(dodecyloxy)-16-oxo-3,6,9,12,23-pentaoxa-19-thia-15-azapentatriacontyl)phosphonic acid;
((17R,21R)-17-amino-21-dodecanamido-16-oxo-3,6,9,12,23-pentaoxa-19-thia-15-azapentatriacontyl)phosphonic acid;
((11S,14R,18R)-14-amino-18-(dodecyloxy)-11-(hydroxymethyl)-10,13-dioxo-3,6,20-trioxa-16-thia-9,12-diazadotriacontyl)phosphonic acid;
((11S,14R,18R)-14-amino-18-dodecanamido-11-(hydroxymethyl)-10,13-dioxo-3,6,20-trioxa-16-thia-9,12-diazadotriacontyl)phosphonic acid, and
((14R,18R)-14-amino-18-((decylcarbamoyl)oxy)-13,21-dioxo-3,6,9,20-tetraoxa-16-thia-12,22-diazadotriacontyl)phosphonic acid.

16. A pharmaceutical composition comprising a therapeutically effective amount a compound of claim 1 and a pharmaceutically acceptable carrier.

17. A method for treating a disease where modulation of TLR2 receptor is implicated, wherein the method comprises administering to a system or subject in need of such treatment an effective amount of a compound of claim 1, wherein the compound of Formula (I) is a TLR2 receptor agonist and the disease is selected from an infectious disease, an inflammatory disease, a respiratory disease, a dermatological disease and an autoimmune disease.

18. The method of claim 17, wherein the disease is asthma, chronic obstructive pulmonary disease (COPD), adult respiratory distress syndrome (ARDS), ulcerative colitis, Crohns disease, bronchitis, dermatitis, actinic keratosis, basal cell carcinoma, allergic rhinitis, psoriasis, scleroderma, urticaria, rheumatoid arthritis, multiple sclerosis, cancer, breast cancer, HIV or lupus.

* * * * *

SEQUENCE LISTING

```
<160> NUMBER OF SEQ ID NOS: 6

<210> SEQ ID NO 1
<211> LENGTH: 248
<212> TYPE: PRT
<213> ORGANISM: Neisseria meningitidis

<400> SEQUENCE: 1

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110
```

```
Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
        130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
                180                 185                 190

Pro Asp Gly Lys Arg His Ala Val Ile Ser Gly Ser Val Leu Tyr Asn
                195                 200                 205

Gln Ala Glu Lys Gly Ser Tyr Ser Leu Gly Ile Phe Gly Gly Lys Ala
        210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 2
<211> LENGTH: 247
<212> TYPE: PRT
<213> ORGANISM: Neisseria meningitidis

<400> SEQUENCE: 2

Val Ala Ala Asp Ile Gly Ala Gly Leu Ala Asp Ala Leu Thr Ala Pro
1               5                   10                  15

Leu Asp His Lys Asp Lys Ser Leu Gln Ser Leu Thr Leu Asp Gln Ser
                20                  25                  30

Val Arg Lys Asn Glu Lys Leu Lys Leu Ala Ala Gln Gly Ala Glu Lys
            35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Ile Tyr Lys Gln Asp His
                85                  90                  95

Ser Ala Val Val Ala Leu Gln Ile Glu Lys Ile Asn Asn Pro Asp Lys
                100                 105                 110

Ile Asp Ser Leu Ile Asn Gln Arg Ser Phe Leu Val Ser Gly Leu Gly
        115                 120                 125

Gly Glu His Thr Ala Phe Asn Gln Leu Pro Asp Gly Lys Ala Glu Tyr
        130                 135                 140

His Gly Lys Ala Phe Ser Ser Asp Asp Ala Gly Gly Lys Leu Thr Tyr
145                 150                 155                 160

Thr Ile Asp Phe Ala Ala Lys Gln Gly His Gly Lys Ile Glu His Leu
                165                 170                 175

Lys Thr Pro Glu Gln Asn Val Glu Leu Ala Ala Ala Glu Leu Lys Ala
                180                 185                 190

Asp Glu Lys Ser His Ala Val Ile Leu Gly Asp Thr Arg Tyr Gly Ser
                195                 200                 205

Glu Glu Lys Gly Thr Tyr His Leu Ala Leu Phe Gly Asp Arg Ala Gln
        210                 215                 220

Glu Ile Ala Gly Ser Ala Thr Val Lys Ile Gly Glu Lys Val His Glu
```

```
                225                 230                 235                 240
Ile Gly Ile Ala Gly Lys Gln
                245

<210> SEQ ID NO 3
<211> LENGTH: 250
<212> TYPE: PRT
<213> ORGANISM: Neisseria meningitidis

<400> SEQUENCE: 3

Val Ala Ala Asp Ile Gly Thr Gly Leu Ala Asp Ala Leu Thr Ala Pro
1               5                   10                  15

Leu Asp His Lys Asp Lys Gly Leu Lys Ser Leu Thr Leu Glu Asp Ser
                20                  25                  30

Ile Pro Gln Asn Gly Thr Leu Thr Leu Ser Ala Gln Gly Ala Glu Lys
            35                  40                  45

Thr Phe Lys Ala Gly Asp Lys Asp Asn Ser Leu Asn Thr Gly Lys Leu
        50                  55                  60

Lys Asn Asp Lys Ile Ser Arg Phe Asp Phe Val Gln Lys Ile Glu Val
65                  70                  75                  80

Asp Gly Gln Thr Ile Thr Leu Ala Ser Gly Glu Phe Gln Ile Tyr Lys
                85                  90                  95

Gln Asn His Ser Ala Val Val Ala Leu Gln Ile Glu Lys Ile Asn Asn
            100                 105                 110

Pro Asp Lys Thr Asp Ser Leu Ile Asn Gln Arg Ser Phe Leu Val Ser
        115                 120                 125

Gly Leu Gly Gly Glu His Thr Ala Phe Asn Gln Leu Pro Gly Gly Lys
130                 135                 140

Ala Glu Tyr His Gly Lys Ala Phe Ser Ser Asp Asp Pro Asn Gly Arg
145                 150                 155                 160

Leu His Tyr Ser Ile Asp Phe Thr Lys Lys Gln Gly Tyr Gly Arg Ile
                165                 170                 175

Glu His Leu Lys Thr Leu Glu Gln Asn Val Glu Leu Ala Ala Ala Glu
            180                 185                 190

Leu Lys Ala Asp Glu Lys Ser His Ala Val Ile Leu Gly Asp Thr Arg
        195                 200                 205

Tyr Gly Ser Glu Glu Lys Gly Thr Tyr His Leu Ala Leu Phe Gly Asp
    210                 215                 220

Arg Ala Gln Glu Ile Ala Gly Ser Ala Thr Val Lys Ile Gly Glu Lys
225                 230                 235                 240

Val His Glu Ile Gly Ile Ala Gly Lys Gln
                245                 250

<210> SEQ ID NO 4
<211> LENGTH: 644
<212> TYPE: PRT
<213> ORGANISM: Neisseria meningitidis

<400> SEQUENCE: 4

Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
                20                  25                  30

Gln Ala Gly Ser Gln Gly Gln Gly Ala Pro Ser Ala Gln Gly Gly Gln
            35                  40                  45

Asp Met Ala Ala Val Ser Glu Glu Asn Thr Gly Asn Gly Gly Ala Ala
```

```
                50                  55                  60
Ala Thr Asp Lys Pro Lys Asn Glu Asp Glu Gly Ala Gln Asn Asp Met
 65                  70                  75                  80

Pro Gln Asn Ala Ala Asp Thr Asp Ser Leu Thr Pro Asn His Thr Pro
                    85                  90                  95

Ala Ser Asn Met Pro Ala Gly Asn Met Glu Asn Gln Ala Pro Asp Ala
                100                 105                 110

Gly Glu Ser Glu Gln Pro Ala Asn Gln Pro Asp Met Ala Asn Thr Ala
                115                 120                 125

Asp Gly Met Gln Gly Asp Pro Ser Ala Gly Glu Asn Ala Gly
                130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
                180                 185                 190

Gly Pro Ser Gln Asn Ile Thr Leu Thr His Cys Lys Gly Asp Ser Cys
                195                 200                 205

Ser Gly Asn Asn Phe Leu Asp Glu Glu Val Gln Leu Lys Ser Glu Phe
210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
                260                 265                 270

Pro Thr Ser Phe Ala Arg Phe Arg Arg Ser Ala Arg Ser Arg Arg Ser
                275                 280                 285

Leu Pro Ala Glu Met Pro Leu Ile Pro Val Asn Gln Ala Asp Thr Leu
                290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
                340                 345                 350

Gly Glu Met Leu Ala Gly Thr Ala Val Tyr Asn Gly Glu Val Leu His
                355                 360                 365

Phe His Thr Glu Asn Gly Arg Pro Ser Pro Ser Arg Gly Arg Phe Ala
                370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
                420                 425                 430

Ser Gly Lys Phe Tyr Gly Pro Ala Gly Glu Glu Val Ala Gly Lys Tyr
                435                 440                 445

Ser Tyr Arg Pro Thr Asp Ala Glu Lys Gly Gly Phe Gly Val Phe Ala
                450                 455                 460

Gly Lys Lys Glu Gln Asp Gly Ser Gly Gly Gly Ala Thr Tyr Lys
465                 470                 475                 480
```

```
Val Asp Glu Tyr His Ala Asn Ala Arg Phe Ala Ile Asp His Phe Asn
            485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
            515                 520                 525

Ala Asn Leu Gln Ser Gly Ser Gln His Phe Thr Asp His Leu Lys Ser
            530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
            565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
            595                 600                 605

Asp Phe Ser Thr Thr Ile Asp Arg Thr Lys Trp Gly Val Asp Tyr Leu
            610                 615                 620

Val Asn Val Gly Met Thr Lys Ser Val Arg Ile Asp Ile Gln Ile Glu
625                 630                 635                 640

Ala Ala Lys Gln

<210> SEQ ID NO 5
<211> LENGTH: 434
<212> TYPE: PRT
<213> ORGANISM: Neisseria meningitidis

<400> SEQUENCE: 5

Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
            20                  25                  30

Leu Arg Ile Glu Thr Thr Ala Arg Ser Tyr Leu Arg Gln Asn Asn Gln
        35                  40                  45

Thr Lys Gly Tyr Thr Pro Gln Ile Ser Val Val Gly Tyr Asn Arg His
    50                  55                  60

Leu Leu Leu Leu Gly Gln Val Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
        115                 120                 125

Ala Thr Gln Ala Arg Val Lys Ile Val Thr Tyr Gly Asn Val Thr Tyr
    130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
        195                 200                 205
```

```
Gly Leu Gln Ser Leu Thr Leu Asp Gln Ser Val Arg Lys Asn Glu Lys
            210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
                245                 250                 255

Phe Ile Arg Gln Ile Glu Val Asp Gly Gln Leu Ile Thr Leu Glu Ser
                260                 265                 270

Gly Glu Phe Gln Val Tyr Lys Gln Ser His Ser Ala Leu Thr Ala Phe
            275                 280                 285

Gln Thr Glu Gln Ile Gln Asp Ser Glu His Ser Gly Lys Met Val Ala
        290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
                325                 330                 335

Gly Ser Asp Asp Ala Gly Gly Lys Leu Thr Tyr Thr Ile Asp Phe Ala
            340                 345                 350

Ala Lys Gln Gly Asn Gly Lys Ile Glu His Leu Lys Ser Pro Glu Leu
        355                 360                 365

Asn Val Asp Leu Ala Ala Ala Asp Ile Lys Pro Asp Gly Lys Arg His
    370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
                405                 410                 415

Ala Glu Val Lys Thr Val Asn Gly Ile Arg His Ile Gly Leu Ala Ala
            420                 425                 430

Lys Gln

<210> SEQ ID NO 6
<211> LENGTH: 327
<212> TYPE: PRT
<213> ORGANISM: Neisseria meningitidis

<400> SEQUENCE: 6

Ala Thr Asn Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu
                20                  25                  30

Thr Ile Tyr Asp Ile Asp Glu Asp Gly Thr Ile Thr Lys Lys Asp Ala
            35                  40                  45

Thr Ala Ala Asp Val Glu Ala Asp Phe Lys Gly Leu Gly Leu Lys
        50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
    130                 135                 140
```

```
Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
            195                 200                 205

Glu Ala Ala Gly Thr Ala Asn Thr Ala Ala Asp Lys Ala Glu Ala
    210             215             220

Val Ala Ala Lys Val Thr Asp Ile Lys Ala Asp Ile Ala Thr Asn Lys
225             230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
        275                 280                 285

His Asp Thr Arg Leu Asn Gly Leu Asp Lys Thr Val Ser Asp Leu Arg
    290                 295                 300

Lys Glu Thr Arg Gln Gly Leu Ala Glu Gln Ala Ala Leu Ser Gly Leu
305             310                 315                 320

Phe Gln Pro Tyr Asn Val Gly
                325
```